(12) United States Patent
Marban et al.

(10) Patent No.: US 11,759,482 B2
(45) Date of Patent: Sep. 19, 2023

(54) METHODS AND COMPOSITIONS FOR TREATING SKELETAL MUSCULAR DYSTROPHY

(71) Applicants: Cedars-Sinai Medical Center, Los Angeles, CA (US); Capricor, Inc, Beverly Hills, CA (US)

(72) Inventors: Eduardo Marban, Los Angeles, CA (US); Mark Amin Aminzadeh, Los Angeles, CA (US); Russell Rogers, Los Angeles, CA (US); Jennifer Moseley, Los Angeles, CA (US); Luis Rodriguez-Borlado, Los Angeles, CA (US); Saravana Kanagavelu, Los Angeles, CA (US); Christopher Stewart Sakoda, Los Angeles, CA (US)

(73) Assignees: Cedars-Sinai Medical Center, Los Angeles, CA (US); Capricor, Inc., Beverly Hills, CA (US)

( * ) Notice: Subject to any disclaimer, the term of this patent is extended or adjusted under 35 U.S.C. 154(b) by 685 days.

(21) Appl. No.: 16/605,489

(22) PCT Filed: Apr. 18, 2018

(86) PCT No.: PCT/US2018/028184
§ 371 (c)(1),
(2) Date: Oct. 15, 2019

(87) PCT Pub. No.: WO2018/195210
PCT Pub. Date: Oct. 25, 2018

(65) Prior Publication Data
US 2020/0121727 A1    Apr. 23, 2020

Related U.S. Application Data

(60) Provisional application No. 62/614,753, filed on Jan. 8, 2018, provisional application No. 62/569,440, filed on Oct. 6, 2017, provisional application No. 62/535,672, filed on Jul. 21, 2017, provisional application No. 62/487,402, filed on Apr. 19, 2017, provisional application No. 62/487,393, filed on Apr. 19, 2017, provisional application No. 62/487,408, filed on Apr. 19, 2017.

(51) Int. Cl.
| | |
|---|---|
| *A61K 35/34* | (2015.01) |
| *A61P 25/14* | (2006.01) |
| *A61P 21/00* | (2006.01) |
| *A61K 31/7105* | (2006.01) |
| *C12N 15/113* | (2010.01) |
| *A61K 9/00* | (2006.01) |

(52) U.S. Cl.
CPC .......... *A61K 35/34* (2013.01); *A61K 31/7105* (2013.01); *A61P 21/00* (2018.01); *A61P 25/14* (2018.01); *C12N 15/113* (2013.01); *A61K 9/0019* (2013.01)

(58) Field of Classification Search
None
See application file for complete search history.

(56) References Cited

U.S. PATENT DOCUMENTS

| | | |
|---|---|---|
| 3,470,876 A | 10/1969 | Barchilon |
| 3,964,468 A | 6/1976 | Schulz |
| 4,106,488 A | 8/1978 | Gordon |
| 4,659,839 A | 4/1987 | Nicolotti et al. |
| 4,921,482 A | 5/1990 | Hammerslag et al. |
| 4,960,134 A | 10/1990 | Webster, Jr. |
| 5,028,588 A | 7/1991 | Hoffman et al. |
| 5,052,402 A | 10/1991 | Bencini et al. |
| 5,104,787 A | 4/1992 | Lindstrom et al. |

(Continued)

FOREIGN PATENT DOCUMENTS

| | | |
|---|---|---|
| CA | 2488346 | 12/2003 |
| CN | 1537646 | 10/2004 |

(Continued)

OTHER PUBLICATIONS

Aminzadeh and Marban. Circulation Research Dec. 4, 2015 117(12):E125, abstract No. 22919 (Year: 2015).*
Agrahari et al., "How Are We Improving the Delivery to Back of the Eye? Advances and Challenges of Novel Therapeutic Approaches", Expert Opinion on Drug Delivery, 2017, vol. 14, No. 10, pp. 1145-1162.
Aminzadeh et al., "Exosome-Mediated Benefits of Cell Therapy in Mouse and Human Models of Duchenne Muscular Dystrophy", Stem Cell Reports, Mar. 13, 2018, vol. 10, No. 3, pp. 942-955.

(Continued)

*Primary Examiner* — Marcia S Noble
(74) *Attorney, Agent, or Firm* — Knobbe, Martens, Olson & Bear, LLP

(57) ABSTRACT

Some embodiments provide a method of treating skeletal muscular myopathy, e.g., Duchenne muscular dystrophy (DMD), with cardiosphere-derived cells (CDCs), wherein a therapeutically effective amount of CDCs is delivered to a targeted dystrophic skeletal muscle. Some embodiment enable delivery of a therapeutically effective amount of CDCs via intramuscular injection directly at a skeletal muscle or systemic administration, intravenous injection, in a single dose or multiple doses, to treat a targeted dystrophic skeletal muscle. Some embodiments provide a method for improving exercise capabilities in DMD patients. Additional embodiments relate to exosome, mediated transfer of non-coding RNAs ameliorates Duchenne muscular dystrophy by restoring dystrophin in heart and skeletal muscle. Delivery of noncoding RNA species found in CDC-derived exosomes mimics the ability of CDCs and CDC-derived exosomes to increase dystrophin protein levels.

20 Claims, 117 Drawing Sheets
Specification includes a Sequence Listing.

(56) References Cited

U.S. PATENT DOCUMENTS

| | | |
|---|---|---|
| 5,175,004 A | 12/1992 | Matsumura |
| 5,199,950 A | 4/1993 | Schmitt |
| 5,228,441 A | 7/1993 | Lundquist |
| 5,243,167 A | 9/1993 | Lundquist |
| 5,287,857 A | 2/1994 | Mann |
| 5,315,996 A | 5/1994 | Lundquist |
| 5,322,064 A | 6/1994 | Lundquist |
| 5,329,923 A | 7/1994 | Lundquist |
| 5,334,145 A | 8/1994 | Lundquist et al. |
| 5,383,852 A | 1/1995 | Stevens-Wright |
| 5,436,128 A | 7/1995 | Harpold et al. |
| 5,454,787 A | 10/1995 | Lundquist |
| 5,477,856 A | 12/1995 | Lundquist |
| 5,492,825 A | 2/1996 | Jan et al. |
| 5,507,725 A | 4/1996 | Savage et al. |
| 5,616,568 A | 4/1997 | Prestwich et al. |
| 5,618,294 A | 4/1997 | Aust et al. |
| 5,670,335 A | 9/1997 | Jan et al. |
| 5,685,868 A | 11/1997 | Lundquist |
| 5,702,433 A | 12/1997 | Taylor et al. |
| 5,702,905 A | 12/1997 | Takahashi et al. |
| 5,762,069 A | 6/1998 | Kelleher et al. |
| 5,782,748 A | 7/1998 | Palmer et al. |
| 5,824,031 A | 10/1998 | Cookston et al. |
| 5,840,502 A | 11/1998 | Van Vlasselaer |
| 5,851,212 A | 12/1998 | Zirps et al. |
| 5,856,155 A | 1/1999 | Li |
| 5,872,109 A | 2/1999 | Akima et al. |
| 5,874,417 A | 2/1999 | Prestwich et al. |
| 5,938,603 A | 8/1999 | Ponzi |
| 5,955,275 A | 9/1999 | Kamb |
| 5,957,863 A | 9/1999 | Koblish et al. |
| 5,981,165 A | 11/1999 | Weiss et al. |
| 6,004,295 A | 12/1999 | Langer et al. |
| 6,074,408 A | 6/2000 | Freeman |
| 6,077,287 A | 6/2000 | Taylor et al. |
| 6,086,582 A | 7/2000 | Altman et al. |
| 6,099,832 A | 8/2000 | Mickle et al. |
| 6,102,887 A | 8/2000 | Altman |
| 6,132,390 A | 10/2000 | Cookston et al. |
| 6,153,582 A | 11/2000 | Skelnik |
| 6,165,164 A | 12/2000 | Hill et al. |
| 6,193,763 B1 | 2/2001 | Mackin |
| 6,203,487 B1 | 3/2001 | Consigny |
| 6,224,587 B1 | 5/2001 | Gibson |
| 6,296,630 B1 | 10/2001 | Altman et al. |
| RE37,463 E | 12/2001 | Altman |
| 6,326,198 B1 | 12/2001 | Emerson et al. |
| 6,337,387 B1 | 1/2002 | Sakano et al. |
| 6,338,942 B2 | 1/2002 | Kraus et al. |
| 6,346,099 B1 | 2/2002 | Altman |
| 6,358,247 B1 | 3/2002 | Altman et al. |
| 6,361,997 B1 | 3/2002 | Huss |
| 6,387,369 B1 | 5/2002 | Pittenger et al. |
| 6,408,203 B2 | 6/2002 | Mackin |
| 6,416,510 B1 | 7/2002 | Altman et al. |
| 6,443,949 B2 | 9/2002 | Altman |
| 6,478,776 B1 | 11/2002 | Rosenman et al. |
| 6,488,659 B1 | 12/2002 | Rosenman |
| 6,500,167 B1 | 12/2002 | Webster, Jr. |
| 6,511,471 B2 | 1/2003 | Rosenman et al. |
| 6,511,477 B2 | 1/2003 | Altman et al. |
| 6,514,481 B1 | 2/2003 | Prasad et al. |
| 6,530,944 B2 | 3/2003 | West et al. |
| 6,540,725 B1 | 4/2003 | Ponzi |
| 6,547,787 B1 | 4/2003 | Altman et al. |
| 6,569,144 B2 | 5/2003 | Altman |
| 6,572,611 B1 | 6/2003 | Falwell |
| 6,577,895 B1 | 6/2003 | Altman |
| 6,585,716 B2 | 7/2003 | Altman |
| 6,716,242 B1 | 4/2004 | Altman |
| 6,726,654 B2 | 4/2004 | Rosenman |
| 6,726,662 B2 | 4/2004 | Altman |
| 6,739,342 B1 | 5/2004 | Fredriksson et al. |
| 6,783,510 B1 | 8/2004 | Gibson et al. |
| 6,796,963 B2 | 9/2004 | Carpenter et al. |
| 6,805,860 B1 | 10/2004 | Alt |
| 6,818,757 B2 | 11/2004 | Lee et al. |
| 6,866,117 B2 | 3/2005 | Moss et al. |
| 6,866,843 B2 | 3/2005 | Habener et al. |
| 6,905,827 B2 | 6/2005 | Wohlgemuth et al. |
| 6,925,327 B2 | 8/2005 | Altman |
| 6,971,998 B2 | 12/2005 | Rosenman et al. |
| 6,997,863 B2 | 2/2006 | Handy et al. |
| 7,026,121 B1 | 4/2006 | Wohlgemuth et al. |
| 7,029,466 B2 | 4/2006 | Altman |
| 7,034,008 B2 | 4/2006 | Donahue et al. |
| 7,037,648 B1 | 5/2006 | Marbán et al. |
| 7,048,711 B2 | 5/2006 | Rosenman et al. |
| 7,074,175 B2 | 7/2006 | Handy et al. |
| 7,104,988 B2 | 9/2006 | Altman et al. |
| 7,138,275 B2 | 11/2006 | Kremer et al. |
| 7,156,824 B2 | 1/2007 | Rosenman et al. |
| 7,220,582 B2 | 5/2007 | Epstein et al. |
| 7,259,011 B2 | 8/2007 | Lucas et al. |
| 7,280,863 B2 | 10/2007 | Shachar |
| 7,329,638 B2 | 2/2008 | Yang et al. |
| 7,351,237 B2 | 4/2008 | Altman |
| 7,402,151 B2 | 7/2008 | Rosenman et al. |
| 7,452,532 B2 | 11/2008 | Alt |
| 7,468,276 B2 | 12/2008 | Hariri |
| 7,470,425 B2 | 12/2008 | Vacanti et al. |
| 7,500,970 B2 | 3/2009 | Altman |
| 7,514,074 B2 | 4/2009 | Pittenger et al. |
| 7,517,686 B2 | 4/2009 | Kremer et al. |
| 7,531,354 B2 | 5/2009 | Stice et al. |
| 7,547,301 B2 | 6/2009 | Altman et al. |
| 7,547,674 B2 | 6/2009 | Anversa et al. |
| 7,553,663 B2 | 6/2009 | Kremer et al. |
| 7,592,177 B2 | 9/2009 | Chen et al. |
| 7,625,581 B2 | 12/2009 | Laredo et al. |
| 7,659,118 B2 | 2/2010 | Furcht et al. |
| 7,686,799 B2 | 3/2010 | Leonhardt et al. |
| 7,731,648 B2 | 6/2010 | Ivkov |
| 7,745,113 B2 | 6/2010 | Evans et al. |
| 7,780,873 B2 | 8/2010 | Mora-Gutierrez et al. |
| 7,794,702 B2 | 9/2010 | Rosen et al. |
| 7,837,631 B2 | 11/2010 | Diamond et al. |
| 7,862,810 B2 | 1/2011 | Anversa |
| 7,875,451 B2 | 1/2011 | Murray et al. |
| 7,971,592 B2 | 7/2011 | Ochi |
| 7,999,025 B2 | 8/2011 | Shumaker-Parry et al. |
| 8,008,254 B2 | 8/2011 | Anversa |
| 8,017,389 B2 | 9/2011 | Phillips et al. |
| 8,119,123 B2 | 2/2012 | Anversa et al. |
| 8,193,161 B2 | 6/2012 | Hosoda |
| 8,232,102 B2 | 7/2012 | Dobson et al. |
| 8,258,113 B2 | 9/2012 | Dimmeler et al. |
| 8,268,619 B2 | 9/2012 | Giacomello et al. |
| 8,562,972 B2 | 10/2013 | Edinger et al. |
| 8,772,030 B2 | 7/2014 | Giacomello et al. |
| 8,846,396 B2 | 9/2014 | Giacomello et al. |
| 8,945,558 B2 | 2/2015 | Kobara |
| 9,249,392 B2 | 2/2016 | Marbán et al. |
| 9,828,603 B2 | 11/2017 | Marbán et al. |
| 9,845,457 B2 | 12/2017 | Marbán et al. |
| 9,884,076 B2 | 2/2018 | Kreke et al. |
| 10,457,942 B2 | 10/2019 | Marbán et al. |
| 11,220,687 B2 | 1/2022 | Marbán et al. |
| 11,253,551 B2 | 2/2022 | Marbán et al. |
| 11,351,200 B2 | 6/2022 | Marbán et al. |
| 11,357,799 B2 * | 6/2022 | Marban .................. A61P 9/10 |
| 2001/0024824 A1 | 9/2001 | Moss et al. |
| 2002/0022259 A1 | 2/2002 | Lee et al. |
| 2002/0061587 A1 | 5/2002 | Anversa |
| 2002/0098167 A1 | 7/2002 | Anversa et al. |
| 2002/0155101 A1 | 10/2002 | Donahue et al. |
| 2002/0156383 A1 | 10/2002 | Altman et al. |
| 2002/0177772 A1 | 11/2002 | Altman et al. |
| 2003/0054973 A1 | 3/2003 | Anversa |
| 2003/0129221 A1 | 7/2003 | Semple et al. |
| 2003/0135113 A1 | 7/2003 | Altman et al. |
| 2003/0161817 A1 | 8/2003 | Young et al. |
| 2003/0195432 A1 | 10/2003 | Kortenbach et al. |

(56) References Cited

U.S. PATENT DOCUMENTS

| | | |
|---|---|---|
| 2003/0229386 A1 | 12/2003 | Rosenman et al. |
| 2004/0014209 A1 | 1/2004 | Lassar et al. |
| 2004/0018174 A1 | 1/2004 | Palasis |
| 2004/0030286 A1 | 2/2004 | Altman |
| 2004/0033214 A1 | 2/2004 | Young et al. |
| 2004/0076619 A1 | 4/2004 | Anversa et al. |
| 2004/0087016 A1 | 5/2004 | Keating et al. |
| 2004/0102759 A1 | 5/2004 | Altman et al. |
| 2004/0110287 A1 | 6/2004 | Clarke et al. |
| 2004/0126879 A1 | 7/2004 | Schneider et al. |
| 2004/0136966 A1 | 7/2004 | Anversa et al. |
| 2004/0137621 A1 | 7/2004 | Rosen et al. |
| 2004/0153139 A1 | 8/2004 | Altman |
| 2004/0158313 A1 | 8/2004 | Altman |
| 2004/0168341 A1 | 9/2004 | Petersen et al. |
| 2004/0214182 A1 | 10/2004 | Sharma et al. |
| 2004/0254134 A1 | 12/2004 | Marbán et al. |
| 2005/0031854 A1 | 2/2005 | Lorenz et al. |
| 2005/0058630 A1 | 3/2005 | Harris et al. |
| 2005/0074880 A1 | 4/2005 | Sang et al. |
| 2005/0090732 A1 | 4/2005 | Ivkov |
| 2005/0176620 A1 | 8/2005 | Prestwich et al. |
| 2005/0214938 A1 | 9/2005 | Gold et al. |
| 2005/0215991 A1 | 9/2005 | Altman et al. |
| 2005/0255588 A1 | 11/2005 | Young et al. |
| 2005/0260748 A1 | 11/2005 | Chang et al. |
| 2005/0260750 A1 | 11/2005 | Kerr-Conte et al. |
| 2005/0271745 A1 | 12/2005 | Gruettner et al. |
| 2006/0018897 A1 | 1/2006 | Lee et al. |
| 2006/0020158 A1 | 1/2006 | Altman |
| 2006/0025713 A1 | 2/2006 | Rosengart et al. |
| 2006/0041182 A1 | 2/2006 | Forbes et al. |
| 2006/0078496 A1 | 4/2006 | Altman et al. |
| 2006/0083712 A1 | 4/2006 | Anversa |
| 2006/0084089 A1 | 4/2006 | Fort et al. |
| 2006/0084943 A1 | 4/2006 | Rosenman et al. |
| 2006/0142749 A1 | 6/2006 | Ivkov |
| 2006/0165805 A1 | 7/2006 | Steinhoff |
| 2006/0198829 A1 | 9/2006 | Rosen et al. |
| 2006/0205071 A1 | 9/2006 | Hasson et al. |
| 2006/0224111 A1 | 10/2006 | Rosenman et al. |
| 2006/0233712 A1 | 10/2006 | Penades et al. |
| 2006/0234375 A1 | 10/2006 | Doronin et al. |
| 2006/0239980 A1 | 10/2006 | Miana et al. |
| 2006/0239983 A1 | 10/2006 | Anversa |
| 2006/0281791 A1 | 12/2006 | Keating et al. |
| 2007/0003528 A1 | 1/2007 | Consigny et al. |
| 2007/0014869 A1 | 1/2007 | Matheny |
| 2007/0048383 A1 | 3/2007 | Helmus |
| 2007/0053839 A1 | 3/2007 | Zhang |
| 2007/0054397 A1 | 3/2007 | Ott et al. |
| 2007/0072291 A1 | 3/2007 | Kremer et al. |
| 2007/0088244 A1 | 4/2007 | Miller et al. |
| 2007/0099268 A1 | 5/2007 | Cohen et al. |
| 2007/0129296 A1 | 6/2007 | Zhou |
| 2007/0134210 A1 | 6/2007 | Heidaran |
| 2007/0142774 A1 | 6/2007 | Rosenman |
| 2007/0166288 A1 | 7/2007 | Murray et al. |
| 2007/0196281 A1 | 8/2007 | Jin et al. |
| 2007/0196918 A1 | 8/2007 | Sayre et al. |
| 2007/0197891 A1 | 8/2007 | Shachar et al. |
| 2007/0231393 A1 | 10/2007 | Ritter et al. |
| 2007/0248580 A1 | 10/2007 | Garcia Castro et al. |
| 2007/0286848 A1 | 12/2007 | Louis-Georges et al. |
| 2007/0292353 A1 | 12/2007 | Levy et al. |
| 2008/0006281 A1 | 1/2008 | Ou et al. |
| 2008/0027313 A1 | 1/2008 | Shachar |
| 2008/0031854 A1 | 2/2008 | Prestwich et al. |
| 2008/0076176 A1 | 3/2008 | Dominko et al. |
| 2008/0089874 A1 | 4/2008 | Li et al. |
| 2008/0103536 A1 | 5/2008 | Xiao |
| 2008/0138416 A1 | 6/2008 | Rauh et al. |
| 2008/0187514 A1 | 8/2008 | Anversa |
| 2008/0213230 A1 | 9/2008 | Phillips et al. |
| 2008/0213812 A1 | 9/2008 | Andrews et al. |
| 2008/0260704 A1 | 10/2008 | Riordan et al. |
| 2008/0267921 A1 | 10/2008 | Marbán et al. |
| 2008/0268061 A1 | 10/2008 | Jordan et al. |
| 2008/0274998 A1 | 11/2008 | Cohen et al. |
| 2008/0287918 A1 | 11/2008 | Rosenman et al. |
| 2008/0297287 A1 | 12/2008 | Shachar et al. |
| 2008/0319420 A1 | 12/2008 | Rosenman et al. |
| 2009/0011004 A1 | 1/2009 | Lutz et al. |
| 2009/0074728 A1 | 3/2009 | Gronthos et al. |
| 2009/0081170 A1 | 3/2009 | Riley |
| 2009/0081276 A1 | 3/2009 | Alsberg et al. |
| 2009/0099611 A1 | 4/2009 | Sigg et al. |
| 2009/0123366 A1 | 5/2009 | Dobson et al. |
| 2009/0136582 A1 | 5/2009 | Albrecht et al. |
| 2009/0143296 A1 | 6/2009 | Anversa et al. |
| 2009/0143748 A1 | 6/2009 | Mickley et al. |
| 2009/0148415 A1 | 6/2009 | de la Fuente et al. |
| 2009/0148421 A1 | 6/2009 | Anversa et al. |
| 2009/0157046 A1 | 6/2009 | Anversa |
| 2009/0162329 A1 | 6/2009 | Anversa et al. |
| 2009/0169525 A1 | 7/2009 | Anversa et al. |
| 2009/0177152 A1 | 7/2009 | Altman |
| 2009/0180998 A1 | 7/2009 | Anversa et al. |
| 2009/0226521 A1 | 9/2009 | Smyth et al. |
| 2009/0317369 A1 | 12/2009 | Hosoda et al. |
| 2010/0010073 A1 | 1/2010 | Thum et al. |
| 2010/0012880 A1 | 1/2010 | Rampersaud et al. |
| 2010/0040587 A1 | 2/2010 | Haag et al. |
| 2010/0068811 A1 | 3/2010 | Marbán et al. |
| 2010/0081200 A1 | 4/2010 | Rajala et al. |
| 2010/0233216 A1 | 9/2010 | Cantaluppi et al. |
| 2010/0239538 A9 | 9/2010 | Anversa et al. |
| 2010/0255034 A1 | 10/2010 | Meinke et al. |
| 2010/0303716 A1 | 12/2010 | Jin et al. |
| 2010/0303722 A1 | 12/2010 | Jin et al. |
| 2010/0303909 A1 | 12/2010 | Oh et al. |
| 2010/0310534 A1 | 12/2010 | Oved et al. |
| 2011/0003003 A1 | 1/2011 | Goldberg et al. |
| 2011/0003008 A1 | 1/2011 | Lim |
| 2011/0034753 A1 | 2/2011 | Dobson et al. |
| 2011/0064675 A1 | 3/2011 | Hadjipanayis et al. |
| 2011/0070153 A1 | 3/2011 | Hyde et al. |
| 2011/0070154 A1 | 3/2011 | Hyde et al. |
| 2011/0091428 A1 | 4/2011 | Anversa |
| 2011/0091448 A1 | 4/2011 | Moon et al. |
| 2011/0092961 A1 | 4/2011 | Hyde et al. |
| 2011/0110897 A1 | 5/2011 | Schwarz et al. |
| 2011/0111412 A1 | 5/2011 | Tai et al. |
| 2011/0123500 A1 | 5/2011 | Anversa et al. |
| 2011/0135577 A1 | 6/2011 | Wu et al. |
| 2011/0152835 A1 | 6/2011 | Anversa |
| 2011/0165068 A1 | 7/2011 | Liu et al. |
| 2011/0177054 A1 | 7/2011 | Gibbings et al. |
| 2011/0256105 A1 | 10/2011 | Marbán et al. |
| 2011/0256621 A1 | 10/2011 | Albrecht et al. |
| 2011/0258716 A1 | 10/2011 | Baltimore et al. |
| 2011/0280834 A1 | 11/2011 | Forrester et al. |
| 2011/0300111 A1 | 12/2011 | White et al. |
| 2011/0300112 A1 | 12/2011 | Marbán et al. |
| 2012/0021019 A1 | 1/2012 | Giacomello et al. |
| 2012/0034156 A1 | 2/2012 | Hyde et al. |
| 2012/0034157 A1 | 2/2012 | Hyde et al. |
| 2012/0039857 A1 | 2/2012 | Smith et al. |
| 2012/0093879 A1 | 4/2012 | Giacomello et al. |
| 2012/0093885 A1 | 4/2012 | Sahoo et al. |
| 2012/0165392 A1 | 6/2012 | Olson et al. |
| 2012/0171291 A1 | 7/2012 | Rademacher et al. |
| 2012/0177574 A1 | 7/2012 | Gho et al. |
| 2012/0183528 A1 | 7/2012 | Ebert et al. |
| 2012/0201795 A1 | 8/2012 | Ware et al. |
| 2012/0238619 A1 | 9/2012 | Dimmeler et al. |
| 2012/0253102 A1 | 10/2012 | Marbán et al. |
| 2012/0258093 A1 | 10/2012 | Butler-Browne et al. |
| 2012/0315252 A1 | 12/2012 | Marbán et al. |
| 2013/0059006 A1 | 3/2013 | Schmuck et al. |
| 2013/0177593 A1 | 7/2013 | Gunn et al. |
| 2013/0189780 A1 | 7/2013 | Shoemaker et al. |
| 2013/0266543 A1 | 10/2013 | Nadal-Ginard |
| 2013/0280205 A1 | 10/2013 | Mozaffari et al. |

(56) References Cited

U.S. PATENT DOCUMENTS

| | | |
|---|---|---|
| 2013/0288962 A1 | 10/2013 | Anversa et al. |
| 2013/0295060 A1 | 11/2013 | Yang et al. |
| 2013/0309304 A1 | 11/2013 | Nadal-Ginard |
| 2014/0031256 A1 | 1/2014 | Lim |
| 2014/0120066 A1 | 5/2014 | Yeghiazarians et al. |
| 2014/0121171 A1 | 5/2014 | Muñoz-Cánoves et al. |
| 2014/0156200 A1 | 6/2014 | Verhaegh et al. |
| 2014/0235526 A1 | 8/2014 | Srivastava et al. |
| 2014/0275976 A1 | 9/2014 | Moro |
| 2015/0010640 A1 | 1/2015 | Marbán et al. |
| 2015/0140658 A1 | 5/2015 | Kamp et al. |
| 2015/0246030 A1 | 9/2015 | Armer et al. |
| 2015/0273113 A1 | 10/2015 | Marbán et al. |
| 2015/0328263 A1 | 11/2015 | Kaushal |
| 2016/0158291 A1 | 6/2016 | Kreke et al. |
| 2016/0194631 A1 | 7/2016 | Yuan et al. |
| 2016/0237500 A1 | 8/2016 | Trabucchi et al. |
| 2016/0244723 A1 | 8/2016 | Giacomello et al. |
| 2017/0037375 A1 | 2/2017 | Palecek et al. |
| 2017/0049793 A1 | 2/2017 | Moon et al. |
| 2017/0087087 A1 | 3/2017 | Leonard et al. |
| 2017/0102397 A1 | 4/2017 | Zhang |
| 2017/0290860 A1 | 10/2017 | Marbán et al. |
| 2017/0304368 A1 | 10/2017 | Marbán et al. |
| 2018/0100149 A1 | 4/2018 | Marbán et al. |
| 2019/0000888 A1 | 1/2019 | Marbán et al. |
| 2019/0062740 A1 | 2/2019 | Zhu |
| 2019/0160111 A1 | 5/2019 | Marbán et al. |
| 2019/0194662 A1 | 6/2019 | Dalby et al. |
| 2019/0203259 A1 | 7/2019 | Korennykh et al. |
| 2019/0255119 A1 | 8/2019 | Marbán et al. |
| 2020/0024604 A1 | 1/2020 | Marbán et al. |
| 2020/0199555 A1 | 6/2020 | Zhang |
| 2020/0316226 A1 | 10/2020 | Marbán et al. |
| 2021/0032598 A1 | 2/2021 | Ibrahim et al. |
| 2021/0085724 A1 | 3/2021 | Marbán et al. |
| 2021/0207145 A1 | 7/2021 | Marbán et al. |
| 2021/0401896 A1 | 12/2021 | Marbán et al. |
| 2022/0072062 A1 | 3/2022 | Marbán et al. |
| 2022/0119813 A1 | 4/2022 | Marbán et al. |
| 2022/0218757 A1 | 7/2022 | Marbán et al. |
| 2022/0273729 A1 | 9/2022 | Marbán et al. |

FOREIGN PATENT DOCUMENTS

| | | |
|---|---|---|
| CN | 1772300 | 5/2006 |
| CN | 1785430 | 6/2006 |
| EP | 1 254 952 | 11/2002 |
| EP | 1 857 544 | 11/2007 |
| EP | 1 970 446 | 9/2008 |
| EP | 2 182 053 | 5/2010 |
| EP | 2 228 444 | 9/2010 |
| EP | 1 631 318 | 11/2010 |
| EP | 1 650 293 | 12/2010 |
| EP | 2 371 370 | 10/2011 |
| EP | 2 385 120 | 11/2011 |
| EP | 2 446 929 | 5/2012 |
| EP | 1 945 256 | 7/2012 |
| EP | 2 094 869 | 7/2012 |
| EP | 2 486 944 | 8/2012 |
| EP | 2 277 548 | 1/2013 |
| EP | 2 687 219 | 1/2014 |
| JP | 2005-506845 | 3/2005 |
| JP | 2005-110565 | 4/2005 |
| JP | 2006-006125 | 1/2006 |
| JP | 2008-504816 | 2/2008 |
| JP | 2008-518730 | 6/2008 |
| JP | 2015-524844 | 8/2015 |
| KR | 100830889 | 5/2008 |
| KR | 10-1818560 | 1/2018 |
| WO | WO 97/005265 | 2/1997 |
| WO | WO 97/012912 | 4/1997 |
| WO | WO 98/004708 | 2/1998 |
| WO | WO 98/032866 | 7/1998 |
| WO | WO 99/011809 | 3/1999 |
| WO | WO 99/039624 | 8/1999 |
| WO | WO 99/049015 | 9/1999 |
| WO | WO 99/051297 | 10/1999 |
| WO | WO 00/009185 | 2/2000 |
| WO | WO 00/024452 | 5/2000 |
| WO | WO 01/010482 | 2/2001 |
| WO | WO 01/026585 | 4/2001 |
| WO | WO 01/026706 | 4/2001 |
| WO | WO 01/026727 | 4/2001 |
| WO | WO 01/048151 | 7/2001 |
| WO | WO 01/076679 | 10/2001 |
| WO | WO 01/076682 | 10/2001 |
| WO | WO 02/009650 | 2/2002 |
| WO | WO 02/013760 | 2/2002 |
| WO | WO 02/051489 | 7/2002 |
| WO | WO 03/004626 | 1/2003 |
| WO | WO 03/006950 | 1/2003 |
| WO | WO 03/008535 | 1/2003 |
| WO | WO 03/049626 | 6/2003 |
| WO | WO 03/064463 | 8/2003 |
| WO | WO 03/103611 | 12/2003 |
| WO | WO 03/103764 | 12/2003 |
| WO | WO 2004/044142 | 5/2004 |
| WO | WO 2005/012510 | 2/2005 |
| WO | WO 2006/007529 | 1/2006 |
| WO | WO 2006/052925 | 5/2006 |
| WO | WO 2006/065949 | 6/2006 |
| WO | WO 2006/081190 | 8/2006 |
| WO | WO 2007/019398 | 2/2007 |
| WO | WO 2007/069666 | 6/2007 |
| WO | WO 2007/100530 | 9/2007 |
| WO | WO 2007/106175 | 9/2007 |
| WO | WO 2008/036776 | 3/2008 |
| WO | WO 2008/043521 | 4/2008 |
| WO | WO 2008/058216 | 5/2008 |
| WO | WO 2008/058273 | 5/2008 |
| WO | WO 2008/118820 | 10/2008 |
| WO | WO 2008/124133 | 10/2008 |
| WO | WO 2009/032456 | 3/2009 |
| WO | WO 2009/056116 | 5/2009 |
| WO | WO 2009/058818 | 5/2009 |
| WO | WO 2009/062143 | 5/2009 |
| WO | WO 2009/062169 | 5/2009 |
| WO | WO 2009/067644 | 5/2009 |
| WO | WO 2009/073518 | 6/2009 |
| WO | WO 2009/073594 | 6/2009 |
| WO | WO 2009/073616 | 6/2009 |
| WO | WO 2009/073618 | 6/2009 |
| WO | WO 2009/100137 | 8/2009 |
| WO | WO 2009/103818 | 8/2009 |
| WO | WO 2009/149956 | 12/2009 |
| WO | WO 2009/152111 | 12/2009 |
| WO | WO 2010/015665 | 2/2010 |
| WO | WO 2010/028090 | 3/2010 |
| WO | WO 2010/033285 | 3/2010 |
| WO | WO 2010/059806 | 5/2010 |
| WO | WO 2010/083466 | 7/2010 |
| WO | WO 2010/118059 | 10/2010 |
| WO | WO 2010/135570 | 11/2010 |
| WO | WO 2011/029092 | 3/2011 |
| WO | WO 2011/029903 | 3/2011 |
| WO | WO 2011/053901 | 5/2011 |
| WO | WO 2011/056685 | 5/2011 |
| WO | WO 2011/057249 | 5/2011 |
| WO | WO 2011/057251 | 5/2011 |
| WO | WO 2011/062244 | 5/2011 |
| WO | WO 2011/064354 | 6/2011 |
| WO | WO 2011/084460 | 7/2011 |
| WO | WO 2011/121120 | 10/2011 |
| WO | WO 2011/127625 | 10/2011 |
| WO | WO 2011/138328 | 11/2011 |
| WO | WO 2011/143499 | 11/2011 |
| WO | WO 2012/019103 | 2/2012 |
| WO | WO 2012/020307 | 2/2012 |
| WO | WO 2012/020308 | 2/2012 |
| WO | WO 2012/055971 | 5/2012 |
| WO | WO 2012/065027 | 5/2012 |
| WO | WO 2012/125471 | 9/2012 |
| WO | WO 2012/135253 | 10/2012 |

(56) References Cited

FOREIGN PATENT DOCUMENTS

| | | |
|---|---|---|
| WO | WO 2012/149557 | 11/2012 |
| WO | WO 2012/162741 | 12/2012 |
| WO | WO 2013/048734 | 4/2013 |
| WO | WO 2013/170170 | 11/2013 |
| WO | WO 2013/184527 | 12/2013 |
| WO | WO 2014/013258 | 1/2014 |
| WO | WO 2014/028493 | 2/2014 |
| WO | WO 2014/114465 | 7/2014 |
| WO | WO 2014/152211 | 9/2014 |
| WO | WO 2014/160153 | 10/2014 |
| WO | WO 2015/022545 | 2/2015 |
| WO | WO 2015/055857 | 4/2015 |
| WO | WO 2015/085096 | 6/2015 |
| WO | WO 2015/092020 | 6/2015 |
| WO | WO 2015/120150 | 8/2015 |
| WO | WO 2016/054569 | 4/2016 |
| WO | WO 2016/054591 | 4/2016 |
| WO | WO 2016/057560 | 4/2016 |
| WO | WO 2016/090183 | 6/2016 |
| WO | WO 2016/152786 | 9/2016 |
| WO | WO 2017/136652 | 8/2017 |
| WO | WO 2017/160884 | 9/2017 |
| WO | WO 2017/173034 | 10/2017 |
| WO | WO 2019/015702 | 1/2019 |
| WO | WO 2019/028223 | 2/2019 |
| WO | WO 2019/050071 | 3/2019 |
| WO | WO 2019/126068 | 6/2019 |
| WO | WO 2019/152549 | 8/2019 |
| WO | WO 2020/131986 | 6/2020 |
| WO | WO 2020/227489 | 11/2020 |
| WO | WO 2021/178514 | 9/2021 |
| WO | WO 2021/188899 | 9/2021 |
| WO | WO 2021/237238 | 11/2021 |

OTHER PUBLICATIONS

Aminzadeh et al., "Mitigation of Skeletal Myopathy After Intramyocardial Injection of Cardiosphere-derived Cells in the Mdx Mouse Model of Duchenne Muscular Dystrophy", Circulation Research, Dec. 4, 2015, No. 22919, pp. e122-e127.

Bryan et al., "Implications of Protein Fold Switching", Current Comments, posted Feb. 4, 2013, printed in 4 pages. https://web.archive.org/web/20160628060217/http://www.elsevierblogs.com/currentcomments/?p=962.

Cheng et al., "Focus on Mesenchymal Stem Cell-Derived Exosomes: Opportunities and Challenges in Cell-Free Therapy", Hindawi, Stem Cells International, 2017, Article ID 6305295, pp. 10.

Cooper et al., "Immunobiological Barriers to Xenotransplantation", International Journal of Surgery, 2015, vol. 23, pp. 211-216.

Dib et al., "Cell Therapy for Cardiovascular Disease: A Comparison of Methods of Delivery", Journal of Cardiovascular Translational Research, 2011, vol. 4, pp. 177-181.

Edelberg et al., "Platelet-Derived Growth Factor-AB Limits the Extent of Myocardial Infarction in a Rat Model: Feasibility of Restoring Impaired Angiogenic Capacity in the Aging Heart", Circulation, 2002, vol. 150, No. 5, pp. 608-613.

Fernandez-Aviles et al., "Experimental and Clinical Regenerative Capability of Human Bone Marrow Cells After Myocardial Infarction", Circulation Research, 2004, vol. 95, pp. 742-748.

Gallet et al, "Cardiosphere-Derived Cells Reverse Heart Failure with Preserved Ejection Fraction in Rats by Decreasing Fibrosis and Inflammation", JACC: Basic to Translational Science, Jan. 1, 2016, vol. 1, No. 1-2, pp. 14-28.

Gallet et al, "Exosomes Secreted by Cardiosphere-Derived Cells Reduce Scarring, Attenuate Adverse Remodeling, and Improve Function in Acute and Chronic Porcine Myocardial Infarction", European Heart Journal, Jan. 14, 201,7, vol. 38, pp. 201-211.

Heng et al., "Strategies for Directing the Differentiation of Stem Cells into the Cardiomyogenic Lineage in Vitro", Cardiovascular Research, 2004, vol. 62, pp. 34-42.

Hoppe et al., "Distinct Gene-Specific Mechanisms of Arrhythmia Revealed by Cardiac Gene Transfer of Two Long QT Disease Genes, HERG and KCNE1", Proceedings of the National Academy of Sciences of the United States of America, Apr. 24, 2001, vol. 98, No. 9, pp. 5335-5340.

Ikehara et al., "Grand Challenges in Stem Cell Treatments", Frontiers in Cell and Developmental Biology, Oct. 10, 2013, vol. 1, No. 2, pp. 2.

International Preliminary Report on Patentability and Written Opinion received in PCT/US2018/028184, dated Oct. 31, 2019 in 15 pages.

Kobashigawa et al., "A Randomized Active-Controlled Trial of Mycophenolate Mofetil in Heart Transplant Recipients", Transplantation, Aug. 27, 1998, vol. 66, No. 4, pp. 507-515.

Li et al., "IL-6 Contributes to the Defective Osteogenesis of Bone Marrow Stromal Cells from the Vertebral Body of the Glucocorticoid-Induced Osteoporotic Mouse", PLoS One, Apr. 29, 2016, vol. 11, No. 4, pp. 19.

Limana et al., "Exogenous High-Mobility Group Box 1 Protein Induces Myocardial Regeneration after Infarction via Enhanced Cardiac C-Kit+ Cell Proliferation and Differentiation", Circulation Research, Oct. 14, 2005, vol. 97, No. 8, pp. 73-83.

Liu et al., "The Immunogenicity and Immune Tolerance of Pluripotent Stem Cell Derivatives", Frontiers in Immunology, Jun. 2017, vol. 3, No. 645, pp. 1-6.

Makkar et al., "Intracoronary Cardiosphere-Derived Cells for Heart Regeneration After Myocardial Infarction (CADUCEUS): A Prospective, Randomised Phase 1 Trial", Lancet, Mar. 10, 2012, vol. 379, pp. 895-904.

Malliaras et al., "Intracoronary Cardiosphere-Derived Cells After Myocardial Infarction", Journal of the American College of Cardiology, 2014, vol. 63, No. 2, pp. 110-121.

Maqbool et al., The Substrate-Binding Protein in Bacterial ABC Transporters: Dissecting Roles in the Evolution of Substrate Specificity, Biochemical Society Transactions, 2015, vol. 43, Part 5, pp. 1011-1017.

Matsumura, Tsuyoshi, "Cardiaphal Association in Muscular Dystrophy", Nanbyo to Zaitaku Care (Intractable Diseases and Home Care), 2013, vol. 19, No. 8, pp. 55-57.

Menasché et al., "Autologous Skeletal Myoblast Transplantation for Severe Postinfarction Left Ventricular Dysfunction", Journal of the American College of Cardiology, vol. 41, No. 7, Apr. 2, 2003, pp. 1078-1083.

North et al., "The Intersection Between Aging and Cardiovascular Disease", Circulation Research, Apr. 13, 2012, pp. 1097-1108.

Pfeffer et al., "Myocardial Infarct Size and Ventricular Function in Rats", Circulation Research, Apr. 1979, vol. 44, No. 4, pp. 503-512.

Rogers et al., "Intravenous Delivery of Cardiosphere-Derived Cells Improves Striated Muscle Function and Structure in a Murine Model of Duchenne Muscular Dystrophy", The FASEB Journal, Apr. 22-26, 2017, vol. 31, No. S1, pp. 3.

Schächinger et al., "Transplantation of Progenitor Cells and Regeneration Enhancement in Acute Myocardial Infarction: Final One-Year Results of the TOPCARE-AMI Trial", Journal of the American College of Cardiology, Oct. 19, 2004, vol. 44, No. 8, pp. 1690-1699.

Shi et al., "3,3'-Diindolylmethane Stimulates Exosomal Wnt11 Autocrine Signaling in Human Umbilical Cord Mesenchymal Stem Cells to Enhance Wound Healing", Theranostics, 2017, vol. 7, No. 6, pp. 1674-1688.

Shimasaki et al., "Exosome Research and Co-culture Study", Biological and Pharmaceutical Bulletin, vol. 40, No. 9, 2018, pp. 1311-1321.

Siminiak et al., "Autologous Skeletal Myoblast Trans plantation for the Treatment of Postinfarction Myocardial Injury: Phase I Clinical Study with 12 Months of Follow-Up", American Heart Journal, Sep. 2004, vol. 148, No. 3, pp. 531-537.

Smits et al., "Catheter-Based Intramyocardial Injection of Autologous Skeletal Myoblasts as a Primary Treatment of Ischemic Heart Failure: Clinical Experience with Six-Month Follow-Up", Journal of the American College of Cardiology, 2003, vol. 42, No. 12, pp. 2063-2069.

(56) References Cited

OTHER PUBLICATIONS

Strauer et al., "Repair of infarcted Myocardium by Autologous Intracoronary Mononuclear Bone Marrow Cell Transplantation in Humans", Circulation, Oct. 8, 2002, vol. 106, No. 15, pp. 1913-1918.
Takeda et al., "Induced Pluripotant Stem (IPS) Cell-Based Cell Therapy for Duchenne Muscular Dystrophy", History of Medicine, Dec. 31, 2011, vol. 239, No. 14, pp. 1440-1444.
Taylor et al., "A Randomized, Multicenter Comparison of Tacrolimus and Cyclosporine Immunosuppressive Regimens in Cardiac Transplantation: Decreased Hyperlipidemia and Hypertension with Tacrolimus", Journal Heart Lung Transplant, Apr. 1, 1999, vol. 18, No. 4, pp. 336-345.
Tsutsui, Hiroyuki, "Cardiomyopathy: Progress in Diagnosis and Treatments Topics: 1. New classification based on etiology of cardiomyopathy; 1. Classification of cardiomyopathy—its past and present status", The Japanese Society of Internal Medicine, Feb. 2014, vol. 103, No. 2, pp. 277-284.
Bioptome.com, Scholten Surgical Instruments, Inc., downloaded from http://www.bioptome.com, 2001, first date of publication unknown, printed on Nov. 1, 2005, pp. 2.
Wu et al., "Cell Delivery in Cardiac Regenerative Therapy", Ageing Research Reviews, 2012, vol. 11, pp. 32-40.
Zeger et al., "Longitudinal Data Analysis for Discrete and Continuous Outcomes", Biometrics, Mar. 1986, vol. 42, No. 1, pp. 121-130.
Abdel-Latif et al., "Adult Bone Marrow-Derived Cells for Cardiac Repair: A Systematic Review and Meta-Analysis", Archives of Internal Medicine, vol. 167, May 28, 2007, pp. 989-997.
Abela et al., "A New Method for Isolation of Cardiac Myocytes by Percutaneous Endomyocardial Biopsy", Catheterization and Cardiovascular Diagnosis, 1996, vol. 37, pp. 227-230.
Ajijola et al., "Ventricular Tachycardia in Ischemic Heart Disease Substrates", Indian Heart Journal, 2014, pp. S24-S34, S28 & S30, vol. 66, Supplement 1.
Albini et al., "A Rapid in Vitro Assay for Quantitating the Invasive Potential of Tumor Cells", Cancer Research, Jun. 15, 1987, pp. 3239-3245, vol. 47.
Ames et al., "Oxidants, Antioxidants, and the Degenerative Diseases of Aging", Proceedings of the National Academy of Sciences of the United States of America, Sep. 1993, vol. 90, pp. 7915-7922.
Aminzadeh et al., "Heart-Derived Cell Therapy for Duchenne Cardiomyopathy: Cardiosphere-Derived Cells and their Exosomes Improve Function, Restore Mitochondrial Integrity and Reverse Degenerative Changes in the Hearts of Mdx Mice", Circulation Research, Dec. 5, 2014, vol. 115, No. 12, 24248, pp. E90-E91.
Andersen et al., "Murine 'Cardiospheres' Are Not a Source of Stem Cells with Cardiomyogenic Potential," Stem Cells, 2009, vol. 27, No. 7, pp. 1571-1581.
Anversa et al., "Primitive Cells and Tissue Regeneration", Circulation Research, 2003, vol. 92, pp. 579-582.
Assmus et al., "Transplantation of Progenitor Cells and Regeneration Enhancement in Acute Myocardial Infarction (TOPCARE-AMI)", Circulation, Dec. 10, 2002, vol. 106, pp. 3009-3017.
"ATS/ACCP Statement on Cardiopulmonary Exercise Testing", American Thoracic Society/American College of Chest Physicians, American Journal of Respiratory and Critical Care Medicine, 2003, vol. 167, pp. 211-277.
Ausma et al., "Dedifferentiation of Atrial Cardiomyocytes: From in Vivo to In Vitro", Cardiovascular Research, Jul. 2002, vol. 55, No. 1, pp. 9-12.
Baker et al. "Adaptation to Culture of Human Embryonic Stem Cells and Oncogenesis in Vivo" Nature Biotechnology, Feb. 2007, vol. 25, No. 2, pp. 207-215.
Balser et al., "Global Parameter Optimization for Cardiac Potassium Channel Gating Models", Biophysical Journal, Mar. 1990, vol. 57, pp. 433-444.
Balser et al., "Local Anesthetics as Effectors of Allosteric Gating", Journal of Clinical Investigation, Dec. 1996, vol. 98, No. 12, pp. 2874-2886.
Barbash et al., "Systemic Delivery of Bone-Marrow-Derived Mesenchymal Stem Cells to the Infarcted Myocardium Feasibility, Cell Migration, and Body Distribution," Circulation, Apr. 19, 2003, vol. 108, pp. 863-868.
Barile et al., "Cardiac Stem Cells: Isolation, Expansion and Experimental use for Myocardial Regeneration", Nature Clinical Practice Cardiovascular Medicine, Feb. 2007, vol. 4, No. 1, pp. S9-S14.
Barile et al., "Endogenous Cardiac Stem Cells", Progress in Cardiovascular Diseases, Jul.-Aug. 2007, vol. 50, No. 1, pp. 31-48.
Barile et al., "Human Cardiospheres as a Source of Multipotent Stem and Progenitor Cells", Hindawi Publishing Corporation, Stem Cells International, 2013, vol. 2013, pp. 10.
Barr et al., "Efficient Catheter-Mediated Gene Transfer Into the Heart Using Replication-Defective Adenovirus", Gene Therapy, Jan. 1994, vol. 1, No. 1, pp. 51-58.
Barry et al., "Differential Expression of Voltage-Gated $K^+$ Channel Subunits in Adult Rat Heart", Circulation Research, 1995, vol. 77, pp. 361-369.
Barth et al., "Lentiviral Vectors Bearing the Cardiac Promoter of the $Na^+$—$Ca^{2+}$ Exchanger Report Cardiogenic Differentiation in Stem Cells", Molecular Therapy, May 2008, vol. 16, No. 5, pp. 957-964.
Bearzi et al., "Human Cardiac Stem Cells", Proceedings of the National Academy of Sciences of the United States of America (PNAS), Aug. 28, 2007, pp. 14068-14073, vol. 104, No. 35.
Beltrami et al., "Adult Cardiac Stem Cells are Multipotent and Support Myocardial Regeneration", Cell, Sep. 19, 2003, vol. 114, No. 6, pp. 763-776.
Beltrami et al., "Evidence That Human Cardiac Myocytes Divide After Myocardial Infarction", The New England Journal of Medicine, Jun. 7, 2001, vol. 344, pp. 1750-1757.
Beltrami et al., "Multipotent Cells Can be Generated In Vitro from Several Adult Human Organs (Heart, Liver and Bone Marrow)", Stem Cells in Hematology, Blood, 2007, pp. 3438-3446, vol. 110, No. 9.
Bénardeau et al., "Primary Culture of Human Atrial Myocytes is Associated with the Appearance of Structural and Functional Characteristics of Immature Myocardium", Journal of Molecular and Cellular Cardiology, 1997, vol. 29, pp. 1307-1320.
Bergmann et al., "Evidence for Cardiomyocyte Renewal in Humans", Science, Apr. 3, 2009, vol. 324, pp. 98-102.
Bernanke et al., "Effects of Hyaluronic Acid on Cardiac Cushion Tissue Cells in Collagen Matrix Cultures", Texas Reports on Biology and Medicine, 1979, pp. 271-285, vol. 39.
"Bioptome.com", Scholten Surgical Instruments, Inc., downloaded from <http://www.bioptome.com/pages.php?page=Products>, 2001, first date of publication unknown, printed on Nov. 1, 2005, pp. 2.
Bird et al., "The Human Adult Cardiomyocyte Phenotype", Cardiovascular Research, May 1, 2003, vol. 58, No. 2, pp. 423-434.
Birks et al., "Left Ventricular Assist Device and Drug Therapy for the Reversal of Heart Failure", The New England Journal of Medicine, 2006, vol. 355, No. 18, pp. 1873-1884.
Bjelakovic et al., "Mortality in Randomized Trials of Antioxidant Supplements for Primary and Secondary Prevention: Systematic Review and Meta-Analysis", JAMA, 2007, vol. 297, pp. 842-857.
Bosnali et al., "Generation of Transducible Versions of Transcription Factors Oct4 and Sox2", Biological Chemistry, Jul. 2008, vol. 389, pp. 851-861.
Bredemeyer et al., "ATM Stabilizes DNA Double-Strand-Break Complexes During V(D)J Recombination", Nature, Jul. 27, 2006, vol. 442, pp. 466-470.
Burstein et al., "Systemic and Coronary Delivery of Marrow Stromal Cells for Cellular Cardiomyoplasty: Advantages and Precautions", Basic and Applied Myology, 2003, vol. 13, No. 1, pp. 7-10.
Cai et al., "Injectable Glycosaminoglycan Hydrogels for Controlled Release of Human Basic Fibroblast Growth Factor," Biomaterials, 2005, vol. 26, pp. 6054-6067.
Cambier et al., "Y RNA Fragment in Extracellular Vesicles Confers Cardioprotection via Modulation of IL-10 Expression and Secretion", EMBO Molecular Medicine, 2017, vol. 9, No. 3, pp. 337-352.
"CArdiosphere-Derived aUtologous StemCElls to Reverse ventricUlar dySfunction (CADUCEUS)", ClinicalTrials.gov, Identifier NCT00893360, 2009, pp. 6.

(56) References Cited

OTHER PUBLICATIONS

Chambers et al., "Functional Expression Cloning of Nanog, a Pluripotency Sustaining Factor in Embryonic Stem Cells", Cell, May 30, 2003, vol. 113, No. 5, pp. 643-655.
Chen et al., "Enhanced Tumorigenesis in p53 Knockout Mice Exposed in Utero to High-Dose Vitamin E", Carcinogenesis, 2006, vol. 27, No. 7, pp. 1358-1368.
Chen et al., "Mesenchymal Stem Cell Secretes Microparticles Enriched in Pre-MicroRNAs", Nucleic Acids Research, 2010, vol. 38, No. 1, pp. 215-224.
Chen et al., "Reduced Tumorigenesis in p53 Knockout Mice Exposed in Utero to Low-Dose Vitamin E", Cancer, Apr. 1, 2009, vol. 115, pp. 1563-1575.
Chen et al., "The Role of Notch 1 Activation in Cardiosphere Derived Cell Differentiation", Stem Cells and Development, 2012, pp. 2122-2129, vol. 21, No. 12.
Chen et al., "Vascular Endothelial Growth Factor Promotes Cardiomyocyte Differentiation of Embryonic Stem Cells", American Journal of Physiology-Heart and Circulatory Physiology, Oct. 2006, vol. 291, No. 4, pp. H1653-H1658.
Cheng et al., "Functional Performance of Human Cardiosphere-Derived Cells Delivered in an in situ Polymerizable Hyaluronan-Gelatin Hydrogel", Biomaterials, 2012, pp. 8.
Cheng et al., "Magnetic Targeting Enhances Engraftment and Functional Benefit of Iron-Labeled Cardiosphere-Derived Cells in Myocardial Infarction", Circulation Research, 2010, pp. 1570-1581, vol. 106.
Cheng et al., "Relative Roles of CD90 and c-Kit to the Regenerative Efficacy of Cardiosphere-Derived Cells in Humans and in a Mouse Mode of Myocardial Infarction", Journal of the American Heart Association, Oct. 9, 2014, pp. 1-10, vol. 3, No. 5.
Cheng et al., "Transplantation of Platelet Gel Spike with Cardiosphere-Derived Cells Boosts Structural and Functional Benefits Relative to Gel Transplantation Alone in Rats with Myocardial Infarction", Biomaterials, 2012, vol. 33, pp. 2872-2879.
Chimenti et al., "Abstract 3182: Paracrine Contribution versus Direct Regeneration in Cardiosphere-Derived Cell Therapy for Acute Myocardial Infarction", Circulation, 2009, vol. 120, p. S756.
Chimenti et al., "Relative Roles of Direct Regeneration Versus Paracrine Effects of Human Cardiosphere-Derived Cells Transplanted Into Infarcted Mice", Circulation Research, Mar. 19, 2010, vol. 106, pp. 971-980.
Chlopčí'ková et al., "Neonatal Rat Cardiomyocytes—A Model for the Study of Morphological Biochemical and Electrophysiological Characteristics of the Heart", Biomedical Papers, 2001, vol. 145, No. 2, pp. 49-55.
Cho et al., "Secondary Sphere Formation Enhances the Functionality of Cardiac Progenitor Cells", Molecular Therapy, Sep. 2012, vol. 20, No. 9, pp. 1750-1766.
Christman et al., "Biomaterials for the Treatment of Myocardial Infarction", Journal of the American College of Cardiology, 2006, vol. 48, No. 5, pp. 907-913.
Conkright et al., "A Gene Encoding an Intestinal-Enriched Member of the Kruppel-Like Factor Family Expressed in Intestinal Epithelia Cells", Nucleic Acids Research, 1999, vol. 27, No. 5, pp. 1263-1270.
Crisostomo et al., "Embryonic Stem Cells Attenuate Myocardial Dysfunction and Inflammation After Surgical Global Ischemia Via Paracrine Actions", American Journal of Physiology-Heart and Circulatory Physiology, 2008, vol. 295, pp. H1726-H1735.
Csete, Marie, "Oxygen in the Cultivation of Stem Cells", Annals New York Academy of Sciences, 2005, vol. 1049, pp. 1-8.
"Culture Media Database", EGM-2 (Endothelial Growth Medium 2)—ID 63, downloaded from <http://bio.lonza.com/3018.html#ext-comp-1003:tab_63:change>, printed on Jan. 14, 2013, p. 1.
Davis et al., "Isolation and Expansion of Functionally-Competent Cardiac Progenitor Cells Directly from Heart Biopsies", Journal of Molecular and Cellular Cardiology, Aug. 2010, vol. 49, No. 2, pp. 312-321.
Davis et al., "Validation of the Cardiosphere Method to Culture Cardiac Progenitor Cells from Myocardial Tissue", PLoS One, 2009, vol. 4, No. 9, e7195, pp. 1-8.
Davis et al., "Human Cardiospheres are a Source of Stem Cells with Cardiomyogenic Potential", Stem Cells, 2010, vol. 28, No. 5, pp. 903-904.
De Bakker et al, "Slow Conduction in the Infarcted Human Heart 'Zigzag' Course of Activation", Circulation, Sep. 1993, pp. 915-926, vol. 88, No. 3.
De Couto et al., "Macrophages Mediate Cardioprotective Cellular Postconditioning in Acute Myocardial Infarction", The Journal of Clinical Investigation, Jul. 27, 2015, vol. 125, No. 8, pp. 3147-3162.
De Pomerai et al., "Influence of Serum Factors on the Prevalence of 'Normal' and 'Foreign' Differentiation Pathways in the Cultures of Chick Embryo Neuroretinal Cells", Journal of Embryology and Experimental Morphology, 1981, pp. 291-308, vol. 62.
Deal et al., "Molecular Physiology of Cardiac Potassium Channels", Physiological Reviews, Jan. 1996, vol. 76, No. 1, pp. 49-67.
Del Monte et al., "Abrogation of Ventricular Arrhythmias in a Model of Ischemia and Reperfusion by Targeting Myocardial Calcium Cycling", Proceedings of the National Academy of Sciences of the United States of America (PNAS), Apr. 13, 2004, vol. 101, No. 15, pp. 5622-5627.
Deregibus et al., "Endothelial Progenitor Cell-Derived Microvesicles Activate an Angiogenic Program in Endothelial Cells by a Horizontal Transfer of mRNA", Blood, Oct. 1, 2007, vol. 110, No. 7, pp. 2440-2448.
Derossi et al., "The Third Helix of the Antennapedia Homeodomain Translocates through Biological Membranes", The Journal of Biological Chemistry, Apr. 8, 1994, vol. 269, No. 14, pp. 10444-10450.
Di Meglio et al., "In Vitro Cultured Progenitors and Precursors of Cardiac Cell Lineages from Human Normal and Post-Ischemic Hearts", European Journal of Histochemistry, Oct.-Dec. 2007, vol. 51, No. 4, pp. 275-285.
Dispersyn et al., "Adult Rabbit Cardiomyocytes Undergo Hibernation-Like Dedifferentiation When Co-Cultured with Cardiac Fibroblasts", Cardiovascular Research, 2001, vol. 51, pp. 230-240.
Dispersyn et al., "Dissociation of Cardiomyocyte Apoptosis and Dedifferentiation in Infarct Border Zones", European Heart Journal, 2002, vol. 23, pp. 849-857.
Dixon et al., "Quantitative Analysis of Potassium Channel mRNA Expression in Atrial and Ventricular Muscle of Rats", Circulation Research, Aug. 1994, vol. 75, No. 2, pp. 252-260.
Dixon et al., "Role of the Kv4.3 K$^+$ Channel in Ventricular Muscle", Circulation Research, 1996, vol. 79, pp. 659-668.
Djokic et al., "Post-Transplant Lymphoproliferative Disorder Subtypes Correlate with Different Recurring Chromosomal Abnormalities", Genes, Chromosomes & Cancer, 2006, vol. 45, pp. 313-318.
Donahue et al., "Ultrarapid, Highly Efficient Viral Gene Transfer to the Heart", Proceedings of the National Academy of Sciences of the United States of America, Apr. 1997, vol. 94, pp. 4664-4668.
Dong et al., "Islet Cell and Extrapancreatic Expression of the LIM Domain Homeobox Gene is/-1", Molecular Endocrinology, 1991, vol. 5, No. 11, pp. 1633-1641.
Drakos et al., "Impact of Mechanical Unloading on Microvasculature and Associated Central Remodeling Features of the Failing Human Heart", Journal of the American College of Cardiology, Jul. 27, 2010, vol. 56, No. 5, pp. 382-391.
Driesen et al., "Structural Adaptation in Adult Rabbit Ventricular Myocytes: Influence of Dynamic Physical Interaction With Fibroblasts", Cell Biochemistry and Biophysics, 2006, vol. 44: 119-128.
Driesen et al., "Structural Remodeling of Cardiomyocytes in the Border Zone of Infarcted Rabbit Heart", Molecular and Cellular Biochemistry, 2007, pp. 225-232, vol. 302.
Duff et al., "CD105 is Important for Angiogenesis: Evidence and Potential Applications," FASEB Journal, Jun. 2003, vol. 17, No. 9, pp. 984-992.
Eguchi, Masakatsu, "Recent Advances in Selective Opioid Receptor Agonists and Antagonists", Medicinal Research Reviews, 2004, vol. 24, No. 2, pp. 182-212.
Elliott et al., "Intercellular Trafficking and Protein Delivery by a Herpesvirus Structural Protein", Cell, Jan. 24, 1997, vol. 88, pp. 223-233.

(56) References Cited

OTHER PUBLICATIONS

Elliott et al., "Intercellular Trafficking of VP22-GFP Fusion Proteins", Gene Therapy, 1999, vol. 6, pp. 149-151.

Engel et al., FGF1/p38 MAP Kinase Inhibitor Therapy Induces Cardiomyocyte Mitosis, Reduces Scarring, and Rescues Function after Myocardial Infarction, Proceedings of the National Academy of Sciences of the United States of America (PNAS), Oct. 17, 2006, vol. 103, No. 42, pp. 15546-15551.

Engel et al. "p38 MAP Kinase Inhibition Enables Proliferation of Adult Mammalian Cardiomyocytes", Genes & Development, May 2005, vol. 19, No. 10, pp. 1175-1187.

Eppenberger-Eberhardt et al., "Reexpression of α-Smooth Muscle Acting Isoform in Cultured Adult Rat Cardiomyocytes", Developmental Biology, Jun. 1990, vol. 139, No. 2, pp. 269-278.

Eschenhagen et al., "Engineering Myocardial Tissue", Circulation Research, 2005, vol. 97, pp. 1220-1231.

Falck et al., "Conserved Modes of Recruitment of ATM, ATR and DNA-PKcs to Sites of DNA Damage", Nature, Mar. 31, 2005, vol. 434, pp. 605-611.

Fehrer et al., "Reduced Oxygen Tension Attenuates Differentiation Capacity of Human Mesenchymal Stem Cells and Prolongs their Lifespan", Aging Cell, 2007, vol. 6, pp. 745-757.

Fiset et al., Shal-Type Channels Contribute to the $Ca^{2+}$-Independent Transient Outward $K^+$ Current in Rat Ventricle, Journal of Physiology, 1997, vol. 500, No. 1, pp. 51-64.

Foreman et al., "Reactive Oxygen Species Produced by NADPH Oxidase Regulate Plant Cell Growth", Nature, Mar. 27, 2003, vol. 422, pp. 442-446.

Frankel et al., "Cellular Uptake of the Tat Protein from Human Immunodeficiency Virus", Cell, vol. 55, Dec. 23, 1988, pp. 1189-1193.

Freyman et al., "A Quantitative, Randomized Study Evaluating Three Methods of Mesenchymal Stem Cell Delivery Following Myocardial Infarction", European Heart Journal, 2006, vol. 27, pp. 1114-1122.

Furlani et al., "A Transformed Cell Population Derived From Cultured Mesenchymal Stem Cells Has no Functional Effect After Transplantation Into the Injured Heart", Cell Transplantation, 2009, vol. 18, pp. 319-331.

Gallet et al, "Intracoronary Delivery of Self-Assembling Heart-Derived Microtissues (Cardiospheres) for Prevention of Adverse Remodeling in a Pig Model of Convalescent Myocardial Infarction", <http://circinterventions.ahajournals.org>, Dec. 8, 2015, pp. 21.

Galli et al., "Neural Stem Cells: An Overview", Circulation Research, 2003, vol. 92, No. 6, pp. 598-608.

Gatti et al., Microvesicles Derived from Human Adult Mesenchymal Stem Cells Protect Against Ischaemia-Reperfusion-Induced Acute and Chronic Kidney Injury, Nephrology Dialysis Transplantation, 2011, vol. 26, No. 5, pp. 1474-1483.

George et al, "Echocardiographic Assessment of Flow Across Continuous-Flow Ventricular Assist Devices at Low Speeds", The Journal of Heart and Lung Transplantation, Nov. 2010, vol. 29, No. 11, pp. 1245-1252.

Gibco, "Insulin-Transferrin-Selenium", Product Sheet, 2014.

Gibco, "Insulin-Transferrin-Selenium: 100X (For General Tissue Culture Applications)", Product Sheet, Form No. 2672, Jun. 2001, p. 1.

Gidh-Jain et al., Differential Expression of Voltage-Gated $K^+$ Channel Genes in Left Ventricular Remodeled Myocardium After Experimental Myocardial Infarction, Circulation Research, 1996, vol. 79, pp. 669-675.

Glover et al., "Reduction of Infarct Size and Postischemic Inflammation from ATL-146e, a Highly Selective Adenosine $A_{2A}$ Receptor Agonist in Reperfused Canine Myocardium", American Journal of Physiology-Heart and Circulatory Physiology, Apr. 2005, vol. 288, No. 4, pp. H1851-H1858.

Gómez-Márquez et al., "Thymosin-β4 Gene: Preliminary Characterization and Expression in Tissues, Thymic Cells, and Lymphocytes", The Journal of Immunology, Oct. 15, 1989, vol. 143, No. 8, pp. 2740-2744.

Good et al., "β-Amyloid Peptide Blocks the Fast-Inactivating $K^+$ Current in Rat Hippocampal Neurons", Biophysical Journal, Jan. 1996, vol. 70, pp. 296-304.

Goumans et al., "TGF-β1 Induces Efficient Differentiation of Human Cardiomyocyte Progenitor Cells into Functional Cardiomyocytes In Vitro", Stem Cell Research, 2008, vol. 1, pp. 138-149.

Grayson et al. "Hypoxia Enhances Proliferation and Tissue Formation of Human Mesenchymal Stem Cells", Biochemical and Biophysical Research Communications, 2007, vol. 358, pp. 948-953.

Green et al, "Autonomous Functional Domains of Chemically Synthesized Human Immunodeficiency Virus Tat Trans-Activator Protein", Dec. 23, 1988, Cell, vol. 55, pp. 1179-1188.

Grigorian-Shamagian et al., "Cardiac and Systemic Rejuvenation After Cardiosphere-Derived Cell Therapy in Senescent Rats", European Heart Journal, Oct. 14, 2017, vol. 38, No. 39, pp. 2957-2967.

Grigorian-Shamagian et al., "Harnessing the Heart's Resistance to Malignant Tumors; Cardiac-Derived Extracellular Vesicles Decrease Fibrosarcoma Growth and Leukemia-Related Mortality in Rodents", Oncotarget, 2017, vol. 8, No. 59, pp. 99624-99636.

Grossman et al., "Contractile State of the Left Ventricle in Man as Evaluated from End-Systolic Pressure-Volume Relations", Circulation, vol. 56, No. 5, Nov. 1977, pp. 845-852.

Gu, Yiping, "Bispecific Antibody Targeted Stem Cell Therapy for Myocardial Repair", Dissertation, University of California San Francisco and University of California Berkeley, 2008, pp. 94.

Gubbay et al., "A Gene Mapping to the Sex-Determining Region of the Mouse Y Chromosome is a Member of a Novel Family of Embryonically Expressed Genes", Nature, Jul. 19, 1990, vol. 346, pp. 245-250.

Hacein-Bey-Abina et al., "LMO2-Associated Clonal T Cell Proliferation in Two Patients after Gene Therapy for SCID-X1", Science, Oct. 17, 2003, vol. 302, pp. 415-419 with Erratum in 1 page.

Haderk et al., "Tumor-Derived Exosomes Modulate PD-L1 Expression in Monocytes", Science Immunology, Jul. 28, 2017, vol. 2, No. 13, pp. 1-11.

Hagège, MD, PhD, et al., "Skeletal Myoblast Transplantation in Ischemic Heart Failure: Long-Term Follow-Up of the First Phase I Cohort of Patients", Circulation, Jul. 4, 2006, vol. 114, No. 1, pp. I108-I113.

Haider et al., "Bone Marrow Stem Cell Transplantation for Cardiac Repair", American Journal of Physiology-Heart and Circulatory Physiology, 2005, H2557-H2567, vol. 288.

Hainsworth et al., "The Nitrone Disodium 2,4-Sulphophenyl-N-Tert-Butylnitrone is Without Cytoprotective Effect on Sodium Nitroprusside-Induced Cell Death In N1E-115 Neuroblastoma Cells in vitro", Journal of Cerebral Blood Flow & Metabolism, 2008, vol. 28, pp. 24-28.

Haj-Yahia et al., "Limited Surgical Approach for Explanting the HeartMate II Left Ventricular Assist Device after Myocardial Recovery", The Journal of Thoracic and Cardiovascular Surgery, 2008, vol. 135, No. 2, pp. 453-454.

Harvey, "Molecular Determinants of Cardiac Development and Congenital Disease," Mouse Development, Patterning, Morphogenesis, and Organogensis, 2002, pp. 331-370, Chapter 16.

Heng et al., "Incorporating Protein Transduction Domains (PTD) Within Recombinant 'Fusion' Transcription Factors. A Novel Strategy for Directing Stem Cell Differentiation?" Biomedicine and Pharmacotherapy, Apr. 1, 2005, vol. 59, No. 3, pp. 132-134.

Hergenreider et al., "Atheroprotective Communication Between Endothelial Cells and Smooth Muscle Cells Through miRNAs", Nature Cell Biology, Mar. 2012, vol. 14, No. 3, pp. 249-256.

Herrera et al., "Human Liver Stem Cell-Derived Microvesicles Accelerate Hepatic Regeneration in Hepatectomized Rats", Journal of Cellular and Molecular Medicine, 2010, vol. 14, No. 6B, pp. 1605-1618.

Hierlihy et al., "The Post-Natal Heart Contains a Myocardial Stem Cell Population", FEBS Letters, 2002, vol. 530, No. 1-3, pp. 239-243.

(56) References Cited

OTHER PUBLICATIONS

Hine et al., "NRF2 and the Phase II Response in Acute Stress Resistance Induced by Dietary Restriction", Journal ofClinical & Experimental Pathology, Jun. 19, 2012, vol. S4, No. 4, pp. 1-33.
Hochedlinger et al., "Nuclear Reprogramming and Pluripotency", Nature, Jun. 29, 2006, vol. 441, pp. 1061-1067.
Hu et al., "MicroRNA-210 as a Novel Therapy for Treatment of Ischemic Heart Disease", Circulation, Sep. 14, 2010, vol. 122, Supplement 11, S124-S131, pp. 17.
Hullinger et al., Inhibition of miR-15 Protects Against Cardiac Ischemic Injury, Circulation Research, Jan. 6, 2012, vol. 110, No. 1, pp. 71-81.
Ibrahim et al., "Exosomes as Critical Agents of Cardiac Regeneration Triggered by Cell Therapy", Stem Cell Reports, May 6, 2014, vol. 2, pp. 606-619.
Ibrahim et al., "Exosomes: Fundamental Biology and Roles in Cardiovascular Physiology", Annual Review of Physiology, 2016, vol. 78, pp. 67-83.
Ibrahim et al., "Microrna-Containing Exosomes from Cardiosphere-Derived Cells Stimulate Cardiomyocyte Proliferation and Angiogenesis in Vitro, and Improve Functional Recovery after Myocardial Infarction in Mice", Circulation, 2012, vol. 126, Abs. 14697, pp. 4.
Ibrahim et al., "Role of Exosomes and Their MicroRNA Constituents in Mediating the Therapeutic Benefits of Human Cardiosphere-Derived Cells in Vitro and in Mice with Myocardial Infarction", Circulation, Nov. 26, 2013, vol. 128, No. 22, Abs. 19186, pp. 2.
International Search Report and Written Opinion received in PCT Application No. PCT/US2018/028184, dated Aug. 30, 2018 in 20 pages.
Invitation to Pay Additional Fees received in PCT Application No. PCT/US2018/028184, dated Jul. 2, 2018 in 2 pages.
Ivanovic, Zoran, "Hypoxia or In Situ Normoxia: The Stem Cell Paradigm", Journal of Cellular Physiology, 2009, vol. 219, pp. 271-275.
Jackson et al., "Regeneration of Ischemic Cardiac Muscle and Vascular Endothelium by Adult Stem Cells", The Journal ofClinical Investigation, Jun. 2001, pp. 1395-1402, vol. 107, No. 11.
Jayawardena et al., MicroRNA-Mediated In Vitro and In Vivo Direct Reprogramming of Cardiac Fibroblasts to Cardiomyocytes, Circulation Research, 2012, vol. 110, No. 11, pp. 1465-1473.
Johnston, MD, et al., "Engraftment, Differentiation, and Functional Benefits of Autologous Cardiosphere-Derived Cells in Porcine Ischemic Cardiomyopathy", Circulation, Sep. 22, 2009, vol. 120, pp. 1075-1083.
Jutkiewicz, Emily, The Antidepressant-Like Effects of Delta-Opioid Receptor Agonists, Molecular Interventions, 2006, vol. No. 3, pp. 162-169.
Kääb et al., "Ionic Mechanism of Action Potential Prolongation in Ventricular Myocytes From Dogs With Pacing-Induced Heart Failure", Circulation Research, 1996, vol. 78, No. 2, pp. 262-273.
Kamdar et al., "Dystrophin-Deficient Cardiomyopathy", Journal of the American College of Cardiology, 2016, vol. 67, No. 21, pp. 2533-2546.
Karlsson et al., "Insulin Gene Enhancer Binding Protein Isl-1 is a Member of a Novel Class of Proteins Containing Both a Homeo- and a Cys-His Domain", Nature, Apr. 26, 1990, vol. 344, pp. 879-882.
Karoubi et al., "Single-Cell Hydrogel Encapsulation for Enhanced Survival of Human Marrow Stromal Cells", Biomaterials, 2009, vol. 30, pp. 5445-5455.
Kaspar et al., "Current Understanding and Management of Dilated Cardiomyopathy in Duchenne and Becker Muscular Dystrophy", Journal of the American Association of Nurse Practitioners, May 2009, vol. 21, No. 5, pp. 241-249.
Kawaguchi et al., "Cell Shape and Cardiosphere Differentiation: A Revelation by Proteomic Profiling", Hindawi Publishing Corporation, Biochemistry Research International, vol. 2013, Article ID 730874, pp. 1-9.
Kim et al., "Generation of Human Induced Pluripotent Stem Cells by Direct Delivery of Reprogramming Proteins", Cell Stem Cell, Jun. 5, 2009, vol. 4, No. 6, pp. 472-476.
Kisselbach et al., "CD90 Expression on Human Primary Cells and Elimination of Contaminating Fibroblasts from Cell Cultures", Cytotechnology, 2009, pp. 31-44, vol. 59.
Kooijmans et al., "PEGylated and Targeted Extracellular Vesicles Display Enhanced Cell Specificity and Circulation Time", Journal of Controlled Release, 2016, vol. 224, pp. 77-85.
Kühn et al., "Periostin Induces Proliferation of Differentiated Cardiomyocytes and Promotes Cardiac Repair", Nature Medicine, Aug. 2007, vol. 13, No. 8, pp. 962-969.
Kutschka et al., "Collagen Matrices Enhance Survival of Transplanted Cardiomyoblasts and Contribute to Functional Improvement of Ischemic Rat Hearts", Circulation, Jul. 4, 2006, vol. 114, pp. I167-I173.
Kwon et al., "Cellular Manipulation of Human Embryonic Stem Cells by TAT-PDX1 Protein Transduction," Molecular Therapy, Jul. 1, 2005, vol. 12, No. 1, pp. 28-32.
Kyrtatos et al., "Magnetic Tagging Increases Delivery of Circulating Progenitors in Vascular Injury", Journal of the American College of Cardiology: Cardiovascular Interventions, 2009, pp. 794-802, vol. 2, No. 8.
LaFlamme et al., "Cardiomyocytes Derived from Human Embryonic Stem Cells in Pro-Survival Factors Enhance Function of Infarcted Rat Hearts", Nature Biotechnology, Sep. 2007, vol. 25, No. 9, pp. 1015-1024.
Lai et al., "Exosome Secreted by MSC Reduces Myocardial Ischemia/Reperfusion Injury", Stem Cell Research, 2010, vol. 4, pp. 214-222.
Lapchak et al., "Intravenous Xenogeneic Human Cardiosphere-Derived Cell Extracellular Vesicles (Exosomes) Improves Behavioral Function in Small-Clot Embolized Rabbits", Experimental Neurology, vol. 307, Sep. 2018, pp. 109-117.
Landázuri et al., "Complexation of Retroviruses with Charged Polymers Enhances Gene Transfer by Increasing the Rate that Viruses are Delivered to Cells", The Journal of Gene Medicine, 2004, vol. 6, pp. 12, pp. 1304-1319.
Lavon et al., "Derivation of Euploid Human Embryonic Stem Cells from Aneuploid Embryos", Stem Cells, 2008, vol. 26, pp. 1874-1882.
Lee et al., "Antibody Targeting of Stem Cells to Infarcted Myocardium", Stem Cells: Translational and Clinical Research, 2007, pp. 712-717, vol. 25.
Lee et al., "Cardiac Gene Transfer by Intracoronary Infusion of Adenovirus Vector-Mediated Reporter Gene in the Transplanted Mouse Heart", The Journal of Thoracic and Cardiovascular Surgery, 1996, pp. 246-252, vol. 111.
Lee et al., "Intramyocardial Injection of Autologous Cardiospheres or Cardiosphere-Derived Cells Preserves Function and Minimizes Adverse Ventricular Remodeling in Pigs With Heart Failure Post-Myocardial Infarction", Journal of the American College of Cardiology, Jan. 25, 2011, vol. 57, No. 4, pp. 455-465.
Leferovich et al., "Heart Regeneration in Adult MRL Mice", Proceedings of the National Academy of Sciences of the United States of America (PNAS), Aug. 14, 2001, vol. 98, No. 17, pp. 9830-9835.
Leor, MD, et al., "Transplantation of Fetal Myocardial Tissue Into the Infarcted Myocardium of Rat", Circulation, Nov. 1, 1996, vol. 94, No. 9, II-332-II-336.
Levenberg at al., "Endothelial Cells Derived from Human Embryonic Stem Cells", Proceedings of the National Academy of Sciences of the United States of America (PNAS), Developmental Biology, Apr. 2, 2002, pp. 4391-4396, vol. 99, No. 7.
Levine et al., "Vitamin C Pharmacokinetics in Healthy Volunteers: Evidence for a Recommended Dietary Allowance", Proceedings of the National Academy of Sciences of the United States of America, Apr. 1996, vol. 93, pp. 3704-3709.
Li et al., "Cardiospheres Recapitulate a Niche-Like Microenvironment Rich in Stemness and Cell-Matrix Interactions, Rationalizing Their Enhanced Functional Potency for Myocardial Repair", Stem Cells: Translational and Clinical Research, 2010, pp. 2088-2098, vol. 28.
Li et al., "Direct Comparison of Different Stem Cell Types and Subpopulations Reveals Superior Paracrine Potency and Myocar-

(56) References Cited

OTHER PUBLICATIONS dial Repair Efficacy with Cardiosphere-Derived Cells", Journal of American College of Cardiology, 2012, vol. 59, No. 10, pp. 942-953.
Li et al., "Expansion of Human Cardiac Stem Cells in Physiological Oxygen Improves Cell Production Efficiency and Potency for Myocardial Repair", Cardiovascular Research, Jul. 29, 2010, pp. 1-9.
Li et al., "Late-Breaking Basic Science Abstracts From the American Heart Association's Scientific Sessions 2009", Late-Breaking Basic Science Oral Abstracts: Translational Studies, Molecular, Cellular, and Functional Phenotypes of Human Cardiac Stem Cells Dependent Upon Monolayer Versus Three-Dimensional Culture Conditions, Abstract 5173, Circulation Research, Dec. 4, 2009, vol. 105, No. 12, pp. e56-e62.
Li et al., "Molecular, Cellular, and Functional Phenotypes of Human Cardiac Stem Cells Dependent Upon Monolayer Versus Three-Dimensional Culture Conditions", Circulation Research, Dec. 4, 2009, Abs. 5173, vol. 105, No. 12, p. e58.
Li et al., "Physiological Levels of Reactive Oxygen Species Are Required to Maintain Genomic Stability in Stem Cells", Stem Cell, Stem Cell Technology: Epigenetics, Genomics, Proteomics, and Metabonomics, May 4, 2010, vol. 28, pp. 1178-1185.
Li, MD, PhD et al., "Imaging Survival and Function of Transplanted Cardiac Resident Stem Cells", Journal of the American College of Cardiology, Apr. 7, 2009, vol. 53, No. 14, pp. 1229-1240.
Liao et al., "Enhanced Efficiency of Generating Induced Pluripotent Stem (iPS) Cells from Human Somatic Cells by a Combination of Six Transcription Factors", Cell Research, 2008, vol. 18, pp. 600-603.
Lin et al., "Accelerated Growth and Prolonged Lifespan of Adipose Tissue-Derived Human Mesenchymal Stem Cells in a Medium Using Reduced Calcium and Antioxidants", Stem Cells and Development, 2005, vol. 14, pp. 92-102.
Lindsay, Mark A., "Peptide-Mediated Cell Delivery: Application in Protein Target Validation", Current Opinion in Pharmacology, 2002, vol. 2, pp. 587-594.
Lindsley et al., "The PI3K/Akt Pathway: Recent Progress in the Development of ATP-Competitive and Allosteric Akt Kinase Inhibitors", Current Cancer Drug Targets, 2008, vol. 8, pp. 7-18.
Lipinski et al., "Impact of Intracoronary Cell Therapy on Left Ventricular Function in the Setting of Acute Myocardial Infarction: A Collaborative Systematic Review and Meta-Analysis of Controlled Clinical Trials", Journal of the American College of Cardiology, 2007, vol. 50, No. 18, pp. 1761-1767.
Liu et al. "Autologous Stem Cell Transplantation for Myocardial Repair", American Journal of Physiology, Heart and Circulatory Physiology, 2004, pp. H501-H511, vol. 287.
Liu et al., "Osteochondral Defect Repair with Autologous Bone Marrow-Derived Mesenchymal Stem Cells in an Injectable, In Situ, Cross-Linked Synthetic Extracellular Matrix", Tissue Engineering, 2006, pp. 3405-3416, vol. 12, No. 12.
Lowry et al., "Generation of Human Induced Pluripotent Stem Cells from Dermal Fibroblasts", Proceedings of the National Academy of Sciences of the United States of America (PNAS), Feb. 26, 2008, vol. 105, No. 8, pp. 2883-2888.
Lum et al., "The New Face of Bispecific Antibodies: Targeting Cancer and Much More", Experimental Hematology, 2006, pp. 1-6, vol. 34.
Lyngbaek et al., "Cardiac Regeneration by Resident Stem and Progenitor Cells in the Adult Heart", Basic Research in Cardiology, 2007, vol. 102, pp. 101-114.
Maitra et al, Genomic Alterations in Cultured Human Embryonic Stem Cells, Nature Genetics, Oct. 2005, vol. 37, No. 10, pp. 1099-1103.
Maletic-Savatic et al., "Differential Spatiotemporal Expression of $K^+$ Channel Polypeptides in Rat Hippocampal Neurons Developing In Situ and In Vitro", The Journal of Neuroscience, May 1995, vol. 15, No. 5, pp. 3840-3851.

Mangi et al., "Mesenchymal Stem Cells Modified with Akt Prevent Remodeling and Restore Performance of Infarcted Hearts," Nature Medicine, Sep. 2003, vol. 9, No. 9, pp. 1195-1201.
Marbán, Eduardo, "Big Cells, Little Cells, Stem Cells: Agents of Cardiac Plasticity", Circulation Research, 2007, vol. 100, No. 4, pp. 445-446.
Marshall et al., "The Jellyfish Green Fluorescent Protein: A New Tool for Studying Ion Channel Express and Function", Neuron, Feb. 1995, vol. 14, pp. 211-215.
Martens et al., "Percutaneous Cell Delivery Into the Heart Using Hydrogels Polymerizing In Situ", Cell Transplantation, 2009, vol. 18, No. 3, pp. 297-304.
Matsuura et al., "Adult Cardiac Sca-1-positive Cells Differentiate into Beating Cardiomyocytes", The Journal of Biological Chemistry, Mar. 19, 2004, vol. 279, No. 12, pp. 11384-11391.
McGann et al., "Mammalian Myotube Dedifferentiation Induced by Newt Regeneration Extract", Proceedings of the National Academy of Sciences of the United States of America (PNAS), Nov. 20, 2001, vol. 98, No. 24, pp. 13699-13704.
Mehmel et al., "The Linearity of the End-Systolic Pressure-Volume Relationship in Man and its Sensitivity for Assessment of Left Ventricular Function", Circulation, 1981, vol. 63, pp. 1216-1222.
Messina et al., "Isolation and Expansion of Adult Cardiac Stem Cells from Human and Murine Heart", Oct. 29, 2004, Circulation Research, Cellular Biology, American Heart Association, vol. 95, pp. 911-921.
Middleton et al., "Newt Cells Secrete Extracellular Vesicles with Therapeutic Bioactivity in Mammalian Cardiomyocytes", Journal of Extracellular Vesicles, 2018, vol. 7, pp. 1-15.
Miller III, et al., Meta-Analysis: High-Dosage Vitamin E Supplementation May Increase All-Cause Mortality, Annals of Internal Medicine, 2005, vol. 142, pp. 37-46.
Miltenyi et al., "High Gradient Magnetic Cell Separation With MACS$^1$", Cytometry, 1990, pp. 231-238, vol. 11.
Mitsui et al., "The Homeoprotein Nanog is Required for Maintenance of Pluripotency in Mouse Epiblast and ES Cells", Cell, May 30, 2003, vol. 113, No. 5, pp. 631-642.
Miyazono et al. "Latent High Molecular Weight Complex of Transforming Growth Factor β1", May 5, 1988, vol. 263, No. 13, pp. 6407-6415.
Montessuit et al., "Regulation of Glucose Transporter Expression in Cardiac Myocytes: p38 MAPK is a Strong Inducer of GLUT4", Cardiovascular Research, Oct. 1, 2004, vol. 64, No. 1, pp. 94-104.
Montessuit et al., "Retinoic Acids Increase Expression of GLUT4 in Dedifferentiated and Hypertrophied Cardiac Myocytes", Basic Research in Cardiology, Jan. 1, 2006, vol. 101, No. 1, pp. 27-35.
Moss et al., "Conservation of the Heterochronic Regulator Lin-28, its Developmental Expression and MicroRNA Complementary Sites", Developmental Biology, 2003, vol. 258, No. 2, pp. 432-442.
Moss, M.D., et al., Prophylactic Implantation of a Defibrillator in Patients with Myocardial Infarction and Reduced Ejection Fraction, The New England Journal of Medicine, Mar. 21, 2002, vol. 346, No. 12, pp. 877-883.
Murata et al., "C4d Deposition and Cellular Infiltrates as Markers of Acute Rejection in Rat Models of Orthotopic Lung Transplantation", Transplantation, Jul. 15, 2008, vol. 86, No. 1, pp. 123-129.
Nadal-Ginard et al, "Myocyte Death, Growth, and Regeneration in Cardiac Hypertrophy and Failure", Circulation Research, 2003, vol. 92, pp. 139-150.
Nadal-Ginard et al., "A Matter of Life and Death: Cardiac Myocyte Apoptosis and Regeneration", Journal of Clinical Investigation, May 2003, vol. 111, No. 10, pp. 1457-1459.
Naito-Matsui, Yuko, "Lack of Neu5Gc Expression Contributes to the Severity of Duchenne Muscular Dystrophy in Humans", Trends in Glycoscience and Glycotechnology, 2011, vol. 23, No. 132, pp. 194-196.
Naka et al., "Regulation of Reactive Oxygen Species and Genomic Stability in Hematopoietic Stem Cells", Antioxidants & Redox Signaling, 2008, vol. 10, No. 11, pp. 1883-1894.
Nakagawa et al., "Generation of Induced Pluripotent Stem Cells without Myc from Mouse and Human Fibroblasts", Nature Biotechnology, Jan. 2008, vol. 26, No. 1, pp. 101-106.

(56) References Cited

OTHER PUBLICATIONS

Nakasa et al., "Acceleration of Muscle Regeneration by Local Injection of Muscle-Specific MicroRNAs in Rat Skeletal Muscle Injury Model", Journal of Cellular and Molecular Medicine, 2010, vol. 14, No. 10, pp. 2495-2505.
Nelson et al., "CXCR4+/FLK-1+ Biomarkers Select a Cardiopoietic Lineage from Embryonic Stem Cells", Stem Cells, 2008, vol. 26, pp. 1464-1473.
Nelson, MD, PhD et al., "Repair of Acute Myocardial Infarction with iPS Induced by Human Sternness Factors", Circulation, Aug. 4, 2009, vol. 120, No. 5, pp. 408-416.
Niethammer et al., "A Tissue-Scale Gradient of Hydrogen Peroxide Mediates Rapid Wound Detection in Zebrafish", Nature, Jun. 18, 2009, vol. 459, pp. 996-999.
Noguchi et al., "Protein Transduction Technology: A Novel Therapeutic Perspective", Acta Medica Okayama, 2006, vol. 60, No. 1, pp. 1-11.
Nussbaum et al., "Transplantation of Undifferentiated Murine Embryonic Stem Cells in the Heart: Teratoma Formation and Immune Response", The FASEB Journal, Research Communication, May 2007, vol. 21, No. 7, pp. 1345-1357.
Odelberg et al., "Dedifferentiation of Mammalian Myotubes Induced by msx1", Cell, Dec. 22, 2000, vol. 103, No. 7, pp. 1099-1109.
Odelberg, Shannon J., Inducing Cellular Dedifferentiation: A Potential Method for Enhancing Endogenous Regeneration in Mammals., Seminars in Cell & Developmental Biology, 2002, vol. 13, No. 5, pp. 335-343.
Offord et al., "Photoprotective Potential of Lycopene, -Carotene, Vitamin E, Vitamin C and Carnosic in UVA-Irradiated Human Skin Fibroblasts", Free Radical Biology & Medicine, 2002, vol. 32, No. 12, pp. 1293-1303.
Oh et al., "Cardiac Muscle Plasticity in Adult and Embryo by Heart-Derived Progenitor Cells", Annals of the New York Academy of Sciences, 2004, vol. 1015, pp. 182-189.
Oh et al., "Cardiac Progenitor Cells from Adult Myocardium: Homing, Differentiation, and Fusion After Infarction", Proceedings of the National Academy of Sciences of the United States of America (PNAS), Oct. 14, 2003, pp. 12313-12318, vol. 100, No. 21.
Okita et al., Generation of Mouse Induced Pluripotent Stem Cells Without Viral Vectors, Nov. 7, 2008, Science, vol. 322, pp. 949-953.
Ousaka et al., "Abstract 13881: Cardiac Progenitor Cell Infusion in Patients With Univentricular Heart Diseases in Heart Failure With Preserved Ejection Fraction", Circulation, Abstract 13881, 2015, vol. 132, <http://circ.ahajournals.org/content/132/Suppl_3/A13881.short>.
Owusu-Ansah et al., "Reactive Oxygen Species Prime *Drosophila* Haematopoietic Progenitors for Differentiation", Nature, Sep. 24, 2009, vol. 461, pp. 537-541.
Park et al., "Reprogramming of Human Somatic Cells to Pluripotency with Defined Factors", Nature, Jan. 10, 2008, vol. 451, pp. 141-146.
Passier et al., "Stem-Cell-Based Therapy and Lessons from the Heart", May 15, 2008, Nature, vol. 453, pp. 322-329.
Passier et al., "Origin and Use of Embryonic and Adult Stem Cells in Differentiation and Tissue Repair", Cardiovascular Research, 2003, vol. 58, No. 2, pp. 324-335.
Payne, Anthony G., "Using Immunomagnetic Technology and Other Means to Facilitate Stem Cell Homing", Medical Hypotheses, 2004, pp. 718-720, vol. 62.
Peterson, MD, MPH, et al., "Risk Stratification After Myocardial Infarction", Annals of Internal Medicine, 1997, vol. 126, No. 7, pp. 561-582.
Pike et al., "Heparin-Regulated Release of Growth Factors In Vitro and Angiogenic Response In Vivo to Implanted Hyaluronan Hydrogels Containing VEGF and bFGF," Biomaterials, 2006, vol. 27, pp. 5242-5241.
Piper et al. "Determinants of Cardiomyocyte Development in Long-Term Primary Culture", Journal of Molecular and Cellular Cardiology, 1988, vol. 20, pp. 825-835.

Plotnikov et al., "Biological Pacemaker Implanted in Canine Left Bundle Branch Provides Ventricular Escape Rhythms that Have Physiologically Acceptable Rates", Circulation, 2004, vol. 109, pp. 506-512.
Potapova et al., "Enhanced Recovery of Mechanical Function in the Canine Heart by Seeding an Extracellular Matrix Patch with Mesenchymal Stem Cells Committed to a Cardiac Lineage", American Journal of Physiology-Heart and Circulatory Physiology, 2008, vol. 295, pp. H2257-H2263.
Prestwich et al., "The Translational Imperative: Making Cell Therapy Simple and Effective", Acta Biomaterialia, 2012, vol. 8, pp. 4200-4207.
Prunier et al., "Delayed Erythropoietin Therapy Reduces Post-MI Cardiac Remodeling Only at a Dose that Mobilizes Endothelial Progenitor Cells", American Journal of Physiology-Heart and Circulatory Physiology, 2007, vol. 292, pp. H522-H529.
Puceat, Michel, "Role of Rac-GTPase and Reactive Oxygen Species in Cardiac Differentiation of Stem Cell", Antioxidants & Redox Signaling, 2005, vol. 7, No. 11 & 12, pp. 1435-1439.
Qin et al., "ATM-Mediated Transcriptional Elevation of Prion in Response to Copper-Induced Oxidative Stress", The Journal of Biological Chemistry, Feb. 13, 2009, vol. 284, No. 7, pp. 4582-4593.
Quaini et al., "Chimerism of the Transplanted Heart", The New England Journal of Medicine, Jan. 3, 2002, vol. 346, No. 1, pp. 5-15.
Quevedo et al., "Allogeneic Mesenchymal Stem Cells Restore Cardiac Function in Chronic Ischemic Cardiomyopathy via Trilineage Differentiating Capacity", Proceedings of the National Academy of Sciences of the United States of America (PNAS), Aug. 18, 2009, vol. 106, No. 33, pp. 14022-14027.
Rajasekaran et al., "Human αB-Crystallin Mutation Causes Oxido-Reductive Stress and Protein Aggregation Cardiomyopathy in Mice", Cell, 2007, vol. 130, No. 3, pp. 427-439.
Ranghino et al., "Endothelial Progenitor Cell-Derived Microvesicles Improve Neovascularization in a Murine Model of Hindlimb Ischemia", International Journal of Immunopathology and Pharmacology, 2012, vol. 25, No. 1, pp. 75-85.
Reiffel, James A., MD, FACC, "Ten Pearls for the Use of Antiarrhythmic Drugs for Atrial Fibrillation", Aug. 17, 2012, Retrieved from <http://www.acc.org/latest-in-cardiology/articles/2014/07/18/15/12/ten-pearls-for-the-use-of-antiarrhythmic-drugs-for-atrial-fibrillation>, pp. 17.
Riazifar et al., "Stem Cell Extracellular Vesicles: Extended Messages of Regeneration", Reviews in Advance, Oct. 19, 2016, vol. 14, No. 1, pp. 1-30.
Ribera, Angeles B., "Homogeneous Development of Electrical Excitability via Heterogeneous Ion Channel Expression", The Journal of Neuroscience, Feb. 1, 1996, vol. 16, No. 3, pp. 1123-1130.
Risebro et al., "Hand1 Regulates Cardiomyocyte Proliferation Versus Differentiation in the Developing Heart", Development, Nov. 2006, vol. 133, No. 22, pp. 4595-4606.
Rossi et al., "Deficiencies in DNA Damage Repair Limit the Function of Haematopoietic Stem Cells with Age", Nature, Jun. 7, 2007, vol. 447, pp. 725-729.
Rotwein et al., "Organization and Sequence of the Human Insulin-Like Growth Factor I Gene", The Journal of Biological Chemistry, Apr. 15, 1986, vol. 261, No. 11, pp. 4828-4832.
Rubio et al., "Spontaneous Human Adult Stem Cell Transformation", Cancer Research, 2005, vol. 65, pp. 3035-3039.
Rucker-Martin et al., "Dedifferentiation of Atrial Myocytes During Atrial Fibrillation: Role of Fibroblast Proliferation in Vitro", Cardiovascular Research, 2002, vol. 55, pp. 38-52.
Rudy, B. "Diversity and Ubiquity of K Channels", Neuroscience, 1988, vol. 25, No. 3, pp. 729-749.
Saito et al., "Cell Death Caused by Selenium Deficiency and Protective Effect of Antioxidants", The Journal of Biological Chemistry, Oct. 10, 2003, vol. 278, No. 41, pp. 39428-39434.
Sareen et al., Chromosome 7 and 19 Trisomy in Cultured Human Neural Progenitor Cells, PLoS One, Oct. 2009, vol. 4, No. 10, e7630, pp. 12.
Sasano et al., "Molecular Ablation of Ventricular Tachycardia after Myocardial Infarction", Natural Medicine, 2006, vol. 12, No. 11, pp. 1256-1258.

(56) References Cited

OTHER PUBLICATIONS

Sasano et al., "Ventricular Tachycardia from the Healed Myocardial Infarction Scar: Validation of an Animal Model and Utility of Gene Therapy", Heart Rhythm, Aug. 2009, vol. 6, No. 8, pp. S91-S97.
Scaria et al., "Host-Virus Genome Interactions: Marco Roles for MicroRNAs", Cellular Microbiology, 2007, vol. 9, No. 12, pp. 2784-2794.
Seifried et al., "A Review of the Interaction Among Dietary Antioxidants and Reactive Oxygen Species", Journal of Nutritional Biochemistry, 2007, vol. 18, pp. 567-579.
Sempere et al., Expression Profiling of Mammalian MicroRNAs Uncovers a Subset of Brain-Expressed MicroRNAs with Possible Roles in Murine and Human Neuronal Differentiation, Genome Biology, 2004, vol. 5, No. 3, pp. R13.1-R13.11.
Serôdio et al., "Cloning of a Novel Component of A-Type K+ Channels Operating at Subthreshold Potentials With Unique Expression in Heart and Brain", Journal of Neurophysiology, May 1996, vol. 75, No. 5, pp. 2174-2179.
Sert et al., "The Radioprotective Effect of Vitamins C, E and Vitamin E + Glutathione on the Small Intestine and the Thyroid Gland in Rats Irradiated with X-Rays", Turkish Journal of Medical Sciences, 2000, vol. 30, pp. 417-425.
Sesso, ScD, MPH, et al., "Vitamins E and C in the Prevention of Cardiovascular Disease in Men: The Physicians' Health Study II Randomized Controlled Trial", The Journal of the American Medical Association (JAMA), 2008, vol. 300, pp. 2123-2133.
Sharkey et al., "Stage-Specific Expression of Cytokine and Receptor Messenger Ribonucleic Acids in Human Preimplantation Embryos", 1995, Biology of Reproduction, 1995, vol. 53, pp. 955-962.
Sharma et al., "Cardiosphere Derived Cells from Pediatric End-Stage Heart Failure Patients Have Enhanced Functional Activity due to the Heat Shock Response Regulating the Secretome", Stem Cells, Apr. 2015, pp. 1213-1229, vol. 33, No. 4.
Shen et al. "Isolation of an Insulin-Like Growth Factor II cDNA with a Unique 5' Untranslated Region from Human Placenta", Mar. 1988, Proceedings of the National Academy of Sciences of the United States of America (PNAS), vol. 85, pp. 1947-1951.
Shenje et al., "Lineage Tracing of Cardiac Explant Derived Cells", PLoS One, Apr. 2008, vol. 3, No. 4, e1929, pp. 10.
Shimizu et al., "Fabrication of Pulsatile Cardiac Tissue Grafts Using a Novel 3-D Cell Sheet Manipulation Techniques and Temperature-Responsive Cell Culture Surfaces", Circulation Research, 2002, vol. 90, No. 3, pp. 1-10.
Shu et al., "Disulfide-Crosslinked Hyaluronan-Gelatin Hydrogel Films: A Covalent Mimic of the Extracellular Matrix for In Vitro Cell Growth", Biomaterials, 2003, vol. 24, pp. 3825-3834.
Sigma-Aldrich, Inc., "Nutrient Mixture F12 Ham Kaighn's Modification (F12K)", Product Description, May 2007, pp. 2.
Simpson et al., "A Tissue Engineering Approach to Progenitor Cell Delivery Results in Significant Cell Engraftment and Improved Myocardial Remodeling", Stem Cells, Sep. 2007, vol. 25, No. 9, pp. 2350-2357.
Singh, PhD, Jai Pal, "Enabling Technologies for Homing and Engraftment of Cells for Therapeutic Applications", JACC: Cardiovascular Interventions, Aug. 2009, vol. 2, No. 8, pp. 803-804.
Singh, et al. "High-Dose α-Tocopherol Therapy Does Not Affect HDL Subtractions in Patients with Coronary Artery Disease on Statin Therapy", Clinical Chemistry, 2007, vol. 53, No. 3, pp. 525-528.
Slaughter, MD et al., "Clinical Management of Continuous-Flow Left Ventricular Assist Devices in Advanced Heart Failure", The Journal of Heart and Lung Transplantation, Apr. 2010, vol. 29, No. 4S, pp. S1-39.
Smart et al., "De Novo Cardiomyocytes from Within the Activated Adult Heart After Injury", Nature, Jun. 30, 2011, vol. 474, pp. 640-646.
Smith, PhD et al., "Stem Cells in the Heart: What's the Buzz all About? Part 1: Preclinical Considerations", Heart Rhythm, May 2008, vol. 5, No. 5, pp. 749-757.
Smith, PhD et al., "Stem Cells in the Heart: What's the Buzz all About? Part 2: Arrhythmic Risks and Clinical Studies", Heart Rhythm, Jun. 2008, vol. 5, No. 6, pp. 880-887.
Smith et al., "Regenerative Potential of Cardiosphere-Derived Cells Expanded From Percutaneous Endomyocardial Biopsy Specimens", Circulation, Feb. 5, 2007, pp. 896-908, vol. 115.
Smith et al., "Unique Phenotype of Cardiospheres Derived from Human Endomyocardial Biopsies", Circulation, Supplement II, Oct. 25, 2005, pp. 2, vol. 112, No. 17.
Smith et al., "Unselected Human Cardiosphere-derived Cells are Functionally Superior to c-Kit- or CD90-Purified Cardiosphere-Derived Cells", Circulation, Supplement 2, Oct. 28, 2008, vol. 118, No. 17, p. 1.
Smits, Anke Maria, "Cell-Based Cardiac Repair", Thesis, Utrecht University, The Netherlands, 2009, pp. 180.
Srivastava et al., "Thymosin β4 Is Cardioprotective after Myocardial Infarction", Annals of the New York Academy of Sciences, Sep. 2007, vol. 1112, pp. 161-170. Abstract only.
Stańczyk, et al., "The Effect of Vitamin C and Glutathione on Ethanol Cytotoxicity and Selected Parameters of Pro- and Antioxidative Processes in Mouse Fibroblasts 3T3-L1", Polish Journal of Environmental Studies, 2005, vol. 15, No. 1, pp. 131-137.
Stewart et al. "Revision of the 1990 Working Formulation for the Standardization of Nomenclature in the Diagnosis of Heart Rejection", The Journal of Heart and Lung Transplantation, 2005, vol. 24, No. 11, pp. 1710-1720.
Stull et al., "Chronic Treatment With Allopurinol Boosts Survival and Cardiac Contractility in Murine Postischemic Cardiomyopathy", Circulation Research, Cellular Biology, Nov. 12, 2004, pp. 1005-1011.
Sussman, Mark A., "Myocardial Aging and Senescence: Where Have the Stem Cells Gone?" Annual Review of Physiology, 2004, vol. 66, pp. 29-48.
Takahashi et al., "Induction of Pluripotent Stem Cells from Adult Human Fibroblasts by Defined Factors," Cell, vol. 131, Nov. 30, 2007, pp. 861-872.
Takahashi et al., "Induction of Pluripotent Stem Cells from Fibroblast Cultures, Nature Protocols", 2007, vol. 2 No. 12, pp. 3081-3089.
Takeda et al., "Human Oct3 Gene Family: cDNA Sequences, Alternative Splicing, Gene Organization, Chromosomal Location, and Expression at Low Levels in Adult Tissues", Nucleic Acids Research, 1992, vol. 20, No. 17, pp. 4613-4620.
Takehara, MD, PhD, et al., "Controlled Delivery of Basic Fibroblast Growth Factor Promotes Human Cardiosphere-Derived Cell Engraftment to Enhance Cardiac Repair for Chronic Myocardial Infarction" Journal of the American College of Cardiology, 2008, vol. 52, No. 23, pp. 1858-1865.
Takeshita et al. "Osteoblast-Specific Factor 2: Cloning of a Putative Bone Adhesion Protein with Homology with the Insect Protein Fasciclin I", Biochemical Journal, 1993, vol. 294, pp. 271-278.
Tateishi et al., "Clonally Amplified Cardiac Stem Cells are Regulated by Sca-1 Signaling for Efficient Cardiovascular Regeneration", Journal of Cell Science, 2007, vol. 120, No. 10, pp. 1791-1800.
Ten Duke et al. "Identification of Another Member of the Transforming Growth Factor Type β Gene Family", Proceedings of the National Academy of Sciences of the United States of America (PNAS), 1988, vol. 85, pp. 4715-4719.
Terrovitis, MD, et al., "Assessment and Optimization of Cell Engraftment after Transplantation into the Heart", Circulation Research, Feb. 19, 2010, vol. 106, No. 3, pp. 479-494.
Terrovitis, MD, et al., "Noninvasive Quantification and Optimization of Acute Cell Retention by In Vivo Positron Emission Tomography after Intramyocardial Cardiac-Derived Stem Cell Delivery", Journal of the American College of Cardiology, Oct. 20, 2009, vol. 54, No. 17, pp. 1619-1626.
The Exosomes Derived from CDCs Experimental Data to Show that Unexpectedly Improved Characteristics are Exhibited, p. 1.
Tomita et al., "Cardiac Neural Crest Cells Contribute to the Dorman Multipotent Stem Cell in the Mammalian Heart", Journal of Cell Biology, Sep. 26, 2005, vol. 170, No. 7, pp. 1135-1148.

(56) References Cited

OTHER PUBLICATIONS

Torella et al., "Cardiac Stem Cell and Myocyte Aging, Heart Failure, and Insulin-Like Growth Factor-1 Overexpression", Circulation Research, 2004, vol. 95, pp. 514-524.
Torella et al., Resident Human Cardiac Stem Cells: Role in Cardiac Cellular Homeostasis and Potential for Myocardial Regeneration, Nature Clinical Practice: Cardiovascular Medicine, Mar. 2006, vol. 3, No. 1, pp. S8-S13.
Trevethick et al., "Treating Lung Inflammation with Agonists from the Adenosine A2A Receptor: Promises, Problems and Potential Solutions", British Journal of Pharmacology, 2008, vol. 155, pp. 463-474.
Tsagalou, MD, et al., "Depressed Coronary Flow Reserve is Associated with Decreased Myocardial Capillary Density in Patients with Heart Failure Due to Idiopathic Dilated Cardiomyopathy", Journal of the American College of Cardiology, 2008, vol. 52, No. 17, pp. 1391-1398.
Tseliou et al., "Abstract 15925: Newt Exosomes are Bioactive on Mammalian Heart, Enhancing Proliferation of Rat Cardiomyocytes and Improving Recovery After Myocardial Infarction", Circulation, Nov. 10, 2015, vol. 132, No. 3, pp. 2.
Tseliou et al., "Allogeneic Cardiospheres Safely Boost Cardiac Function and Attenuate Adverse Remodeling After Myocardial Infarction in Immunologically Mismatched Rat Strains", Journal of the American College of Cardiology, Mar. 12, 2013, vol. 61, No. 10, pp. 1108-1119.
Uemura et al., "Bone Marrow Stem Cells Prevent Left Ventricular Remodeling of Ischemic Heart Through Paracrine Signaling", Circulation Research, 2006, vol. 98, pp. 1414-1421.
Ueno et al., "Biphasic Role for Wnt/β-Catenin Signaling in Cardiac Specification in Zebrafish and Embryonic Stem Cells", Proceedings of the National Academy of Sciences of the United States of America (PNAS), Jun. 5, 2007, vol. 104, No. 23, pp. 9685-9690.
Ulloa-Montoya et al., "Culture Systems for Pluripotent Stem Cells", Journal of Bioscience and Bioengineering, 2005, vol. 100, No. 1, pp. 12-27.
Urbanek et al., "Cardiac Stem Cells Possess Growth Factor Receptor Systems That After Activation Regenerate the Infarcted Myocardium, Improving Ventricular Function and Long-term Survival", Circulation Research, 2005, vol. 97, pp. 663-673.
Urbanek et al., "Intense Myocyte Formation from Cardiac Stem Cells in Human Cardiac Hypertrophy", Proceedings of the National Academy of Sciences of the United States of America (PNAS), Sep. 2, 2003, vol. 100, No. 18, pp. 10440-10445.
Urbanek et al., Myocardial Regeneration by Activation of Multipotent Cardiac Stem Cells in Ischemic Heart Failure, Proceedings of the National Academy of Sciences of the United States of America (PNAS), Jun. 14, 2005, vol. 102, No. 24, pp. 8692-8697.
Van Der Geest et al., "Quantification in Cardiac MRI", Journal of Magnetic Resonance Imaging, 1999, vol. 10, pp. 602-608.
Van Gent et al., "Chromosomal Stability and the DNA Double-Stranded Break Connection", Nature, Mar. 2001, vol. 2, pp. 196-206.
Van Vliet et al., "Progenitor Cells Isolated from the Human Heart: a Potential Cell Source for Regenerative Therapy", Netherlands Heart Journal, May 2008, vol. 16, No. 5, pp. 163-169.
Van Winkle et al, "Cardiogel: A Biosynthetic Extracellular Matrix for Cardiomyocyte Culture", In Vitro Cellular & Developmental Biology—Animal, Sep. 1996, vol. 21, pp. 478-485.
Vela et al., "Quest for the Cardiovascular Holy Grail: Mammalian Myocardial Regeneration", Cardiovascular Pathology, 2008, vol. 17, No. 1-5.
Ventura et al., "Hyaluronan Mixed Esters of Butyric and Retinoic Acid Drive Cardiac and Endothelial Fate in Term Placenta Human Mesenchymal Stem Cells and Enhance Cardiac Repair in Infarcted Rat Hearts", The Journal of Biological Chemistry, May 11, 2007, vol. 282, No. 19, pp. 14243-14252.
Von Harsdorf, R "Can Cardiomyocytes Divide?" Heart, 2001, vol. 86, pp. 481-482.

Vrijsen et al., "Cardiomyocyte Progenitor Cell-Derived Exosomes Stimulate Migration of Endothelial Cells", Journal of Cellular and Molecular Medicine, 2010, vol. 14, No. 5, pp. 1064-1070.
Wagner, Richard, "The State of the Art in Antisense Research", Nature Medicine, Nov. 1995, vol. 1, No. 11, pp. 1116-1118.
Walder et al., "Up-Regulation of Neural Stem Cell Markers Suggests the Occurrence of Dedifferentiation in Regenerating Spinal Cord", Development Genes and Evolution, 2003, vol. 213, pp. 625-630.
Walravens et al., "Cardiosphere-Derived Cell and Mesenchymal Stem Cell Extracellular Vesicles Contain Distinct RNA Cargo", Scientific Program, ISEV2017, Dec. 2017, p. 173.
Wang et al. "The LIM Domain Homeobox Gene is/-1: Conversation of Human, Hamster, and Rat Complementary Deoxyribonucleic Acid Sequences and Expression in Cell Types of Non-neuroendocrine Lineage", Endocrinology, 1994, vol. 134, No. 3, pp. 1416-1422.
Wang et al., "Establishment of New Mouse Embryonic Stem Cell Lines is Improved by Physiological Glucose and Oxygen", Cloning and Stem Cells, 2006, vol. 8, No. 2, pp. 108-116.
Wernig el al., "c-Myc Is Dispensable for Direct Reprogramming of Mouse Fibroblasts", Cell Stem Cell, Jan. 2008, vol. 2, pp. 10-12.
White et al. "Intrinsic Cardiac Origin of Human Cardiosphere-Derived Cells", European Heart Journal, 2013, vol. 34, pp. 68-75.
Wilmut et al., "Viable Offspring Derived from Fetal and Adult Mammalian Cells", Nature, Feb. 27, 1997, vol. 385, pp. 810-813.
Wilson et al., "Bioluminescence Reporter Gene Imaging of Human Embryonic Stem Cell Survival, Proliferation, and Fate", Methods in Molecular Biology, 2009, vol. 574, pp. 87-103.
Wong et al., "Loss of the Y Chromosome: An Age-Related or Clonal Phenomenon in Acute Myelogenous Leukemia/Myelodysplastic Syndrome?" Archives of Pathology & Laboratory Medicine, Aug. 2008, vol. 132, pp. 1329-1332.
Wu et al., "Cellular Therapy and Myocardial Tissue Engineering: The Role of Adult Stem and Progenitor Cells", European Journal of Cardio-Thoracic Surgery, 2006, vol. 30, pp. 770-781.
Yamada et al., "Type V Collagen-Induced Oral Tolerance Plus Low-Dose Cyclosporine Prevents Rejection of MHC Class I and II Incompatible Lung Allografts", The Journal Immunology, Jul. 1, 2009, vol. 183, No. 1, pp. 237-245.
Yang et al., "Human Cardiovascular Progenitor Cells Develop from a $KDR^+$ Embryonic-Stem-Cell-Derived Population", Nature, May 22, 2008, vol. 453, pp. 524-528.
Yau MD et al., "Beneficial Effect of Autologous Cell Transplantation on Infarcted Heart Function: Comparison Between Bone Marrow Stromal Cells and Heart Cells", The Annals of Thoracic Surgery, 2003, vol. 75, No. 1, pp. 169.
Yee et al. "Allogeneic Cardiospheres Delivered via Percutaneous Transendocardial Injection Increase Viable Myocardium, Decrease Scar Size, and Attenuate Cardiac Dilation in Porcine Ischemic Cardiomyopathy", PLoS One, Dec. 2, 2014, pp. 1-29.
Yu et al., "Induced Pluripotent Stem Cell Lines Derived from Human Somatic cells," Science, Dec. 21, 2007, vol. 318, pp. 1917-1920.
Yu et al., "miR-221 and miR-222 Promote Schwann Cell Proliferation and Migration by Targeting LASS2 after Sciatic Nerve Injury", Journal of Cell Science, Jan. 25, 2012, vol. 125, No. 11, pp. 2675-2683.
Zammit et al., "The Skeletal Muscle Satellite Cell: Stem Cell or Son of Stem Cell?" Differentiation, 2001, vol. 68, pp. 193-204.
Zha et al., "Complementary Functions of ATM and H2AX in Development and Suppression of Genomic Instability", Proceedings of the National Academy of Sciences of the United States of America (PNAS), Jul. 8, 2008, vol. 105, No. 27, pp. 9302-9306.
Zhang et al., "Do Cardiac Stem Cells Arise from Cardiomyocyte Dedifferentiation?" Circulation Research, Nov. 2006, vol. 99, No. 11, p. 1278. Abstract only.
Zhao et al., "Targeting Human $CD34^+$ Hematopoietic Stem Cells With Anti-CD45 x Anti-Myosin Light-Chain Bispecific Antibody Preserves Cardiac Function in Myocardial Infarction", Journal of Applied Physiology, Feb. 21, 2008, pp. 1793-1800, vol. 104.

(56) References Cited

OTHER PUBLICATIONS

Zhou et al., "Down-Regulation of microRNA-26a Promotes Mouse Hepatocyte Proliferation During Liver Regeneration", PLoS One, Apr. 2012, vol. 7, No. 4, e33577, pp. 1-7.
Zhou et al., "Generation of Induced Pluripotent Stem Cells Using Recombinant Proteins", Cell Stem Cell, May 1, 2009, vol. 4, No. 5, pp. 381-384.
Zuo et al., Assessment of Myocardial Blood Perfusion Improved by CD151 in a Pig Myocardial Infarction Model, Acta Pharmacologica Sinica, Jan. 2009, vol. 30, No. 1, pp. 70-77.
Anastasiou-Nana et al., "Relative Efficiency and Risk of Endomyocardial Biopsy: Comparisons in Heart Transplant and Nontransplant Patients," Catheter Cardiovascular Diagnosis Journal, Sep. 1989, vol. 18, No. 1, pp. 7-11.
Barile et al., "Beneficial Effects of Exosomes Secreted by Cardiac-Derived Progenitor Cells and Other Cell Types in Myocardial Ischemia", Stem Cell Investigation, Nov. 18, 2017, pp. 93-99.
Carr et al., "Cardiosphere-Derived Cells Improve Function in the Infarcted Rat Heart for at Least 16 Weeks—an MRI Study", PLoS One, Oct. 2011, vol. 6, No. 10, pp. 1-10.
Catalano, Mariadelva, "Engineering Exosomes Toward Folate Receptor Expressing Cells", Dec. 7, 2017, pp. 3.
Chen et al., "Transformation of Cell-Derived Microparticles into Quantum-Dot-Labeled Nanovectors for Antitumor siRNA Delivery", Angewandte Chemie International Edition, vol. 54, No. 3, Nov. 20, 2014, pp. 1036-1040.
De Couto et al., "Exosomal MicroRNA Transfer into Macrophages Mediates Cellular Postconditioning", Circulation, American Heart Association, vol. 136, No. 2, Jul. 11, 2017, pp. 200-214 (47 pages total).
Declaration of Rachel Smith, PH.D., Curriculum Vitae, Exhibit A U.S. Appl. No. 13/412,051, 13 pages.
Girard et al., "A Germline-Specific Class of Small RNAs Binds Mammalian Piwi Proteins", Nature, Jul. 13, 2006, vol. 442, pp. 199-202.
Ibrahim et al., "Augmenting Canonical Wnt Signaling in Therapeutically Inert Cells Converts them into Therapeutically Potent Exosome Factories", Nature Biomedical Engineering, Sep. 2019, vol. 3, pp. 695-705.
Ibrahim et al., "Small Molecule Inhibitors and Culture Conditions Enhance Therapeutic Cell and EV Potency via Activation of Beta-Catenin and Suppression of THY1", Nanomedicine: Nanotechnology, Biology, and Medicine, Dec. 13, 2020, vol. 33, pp. 7.
Kasai-Brunswick et al., "Cardiosphere-Derived Cells do not Improve Cardiac Function in Rats with Cardiac Failure," Stem Cell Research & Therapy, 2017, vol. 8, No. 36, 9 pages.
Kim, PhD et al., "Engineering Macrophage-Derived Exosomes for Targeted Paclitaxel Delivery to Pulmonary Metastases:in Vitroandin Vivoevaluations", Nanomedicine, Nanotechnology, Biology, and Medicine, vol. 14, 2018, pp. 195-204.
Kim, PhD et al., "Exosome Mediated Delivery of Paclitaxel for the Treatment of Multi Drug Resistant Pulmonary Metastases", Dissertation, Chapel Hill, Dec. 31, 2016, pp. 112.
Li et al., "Skeletal Myoblast-Seeded Vascularized Tissue Scaffolds in the Treatment of a Large Volumetric Muscle Defect in the Rat Biceps Femoris Muscle", Termis, Tissue Engineering: Part A, vol. 23, No. 17 & 18, 2017, pp. 989-1000.
Magarotto et al., "Muscle Functional Recovery is Driven by Extracellular Vesicles Combined with Muscle Extracellular Matrix in a Volumetric Muscle Loss Murine Model", Biomaterials 269, 2021, pp. 1-15.
Mason, "Techniques for Right and Left Ventricular Endomyocardial Biopsy", American Journal of Cardiology, 1978, vol. 41, No. 5, pp. 887-892.
Pilia et al., "Transplantation and Perfusion of Microvascular Fragments in a Rodent Model of Volumetric Muscle Loss Injury", European Cells and Materials, vol. 28, 2014, pp. 11-24.
Shen et al., "The Early Cryptic Transmission and Evolution of SARS-CoV-2 in Human Hosts", Available at SSRN 3724275, Aug. 2019, https://www.oyeyeah.com/wp-content/uploads/2020/11/SSRN-is3724275.pdf, pp. 22.
Sicari et al., "An Acellular Biologic Scaffold Promotes Skeletal Muscle Formation in Mice and Humans with Volumetric Muscle Loss", Science Translational Medicine, Apr. 30, 2014, vol. 6, No. 234, pp. 1-10.
Smyth et al., "Surface Functionalization of Exosomes Using Click Chemistry", Bioconjugate Chemistry, vol. 25, No. 10, Sep. 30, 2014, pp. 1777-1784.
USPTO Patent Trial and Appeal Board., "Decision on Appeal", in U.S. Appl. No. 13/412,051, dated Jun. 8, 2020, 12 pages.
USPTO Patent Trial and Appeal Board., "Declaration of Rachel R. Smith, PhD," in U.S. Appl. No. 13/412,051, dated Oct. 13, 2017, 32 pages.
Vella et al., "PIWI-Interacting RNA (piRNA) Signatures in Human Cardiac Progenitor Cells", The International Journal of Biochemistry & Cell Biology, 2016, vol. 76, pp. 1-11.
Wan et al., "Aptamer-Conjugated Extracellular Nanovesicles for Targeted Drug Delivery", Cancer Research, vol. 78, No. 3, Dec. 7, 2017, pp. 798-808.
Wang et al., Challenges in the Development and Establishment of Exosome-Based Drug Delivery Systems, Journal of Controlled Release, 2021, vol. 329, pp. 894-906.
Wang et al., "The Use of RGD-Engineered Exosomes for Enhanced Targeting Ability and Synergistic Therapy Toward Angiogenesis", Nanoscale, vol. 9, No. 40, Jan. 1, 2017, pp. 15598-15605.
Zhang et al., "Magnetic and Folate Functionalization Enables Rapid Isolation and Enhanced Tumor-Targeting of Cell-Derived Microvesicles", ACS Nano, vol. 11, No. 1, Jan. 24, 2017, pp. 277-290.
Zhao et al., "Exosomes as Drug Carriers for Cancer Therapy and Challenges Regarding Exosome Uptake" Biomedicine & Pharmacotherapy, 2020, vol. 128, 9 pages.
Ausar et al., "Characterization of Casein Micelle Precipitation by Chitosans", Journal of Dairy Science, vol. 84, No. 2, Feb. 2001, pp. 2-4.
O'Brien et al., "Human hy4 Ro RNA (associated with erythrocyte Ro RNP's)", National Library of Medicine, <https://www.ncbi.nlm.nih.gov/nucleotide/x57566>, 1991, 1 page.
Ou et al., "The Nuclear Pore Complex Protein Tpr is a Common Autoantigen in Sera that Demonstrate Nuclear Envelope Staining by Indirect Immunofluorescence", Clinical and Experimental Immunology, May 2004, vol. 136, No. 2, pp. 379-387.
Shimomura et al., "Steroid Treatment for Duchenne Muscular Dystrophy", Brain and Development, 2011, vol. 43, pp. 24-29.
USPTO Patent Trial and Appeal Board., "Decision on Appeal", in U.S. Appl. No. 14/437,812, dated Jun. 19, 2020, 22 pages.
Warsito et al., "Antibacterial Efficacy of 2-Citronellyl Benzimidazole Nanoencapsulation with Chitosan-Tripolyphosphate and Casein Micellar Coatings", IOP Conf. Series: Earth and Environmental Science, vol. 299, 2019, pp. 1-7.

* cited by examiner

Figure 1.
Improved cardiac function
Fig. 1A
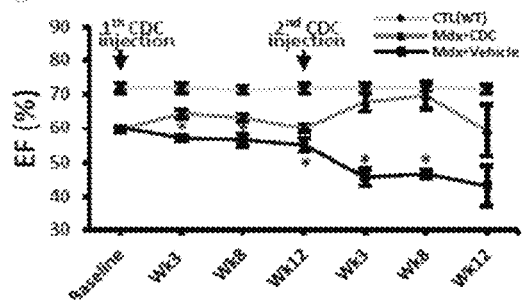
Increased exercise capacity
Fig. 1B
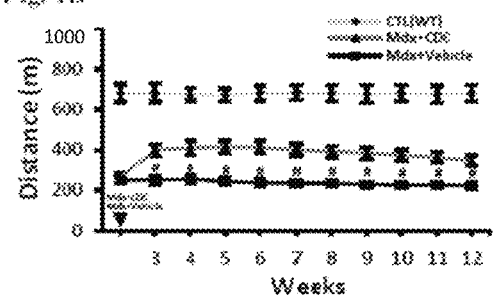
Increased survival rate
Fig. 1C
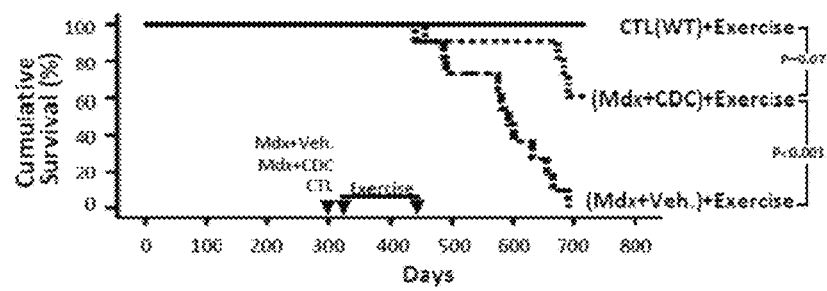

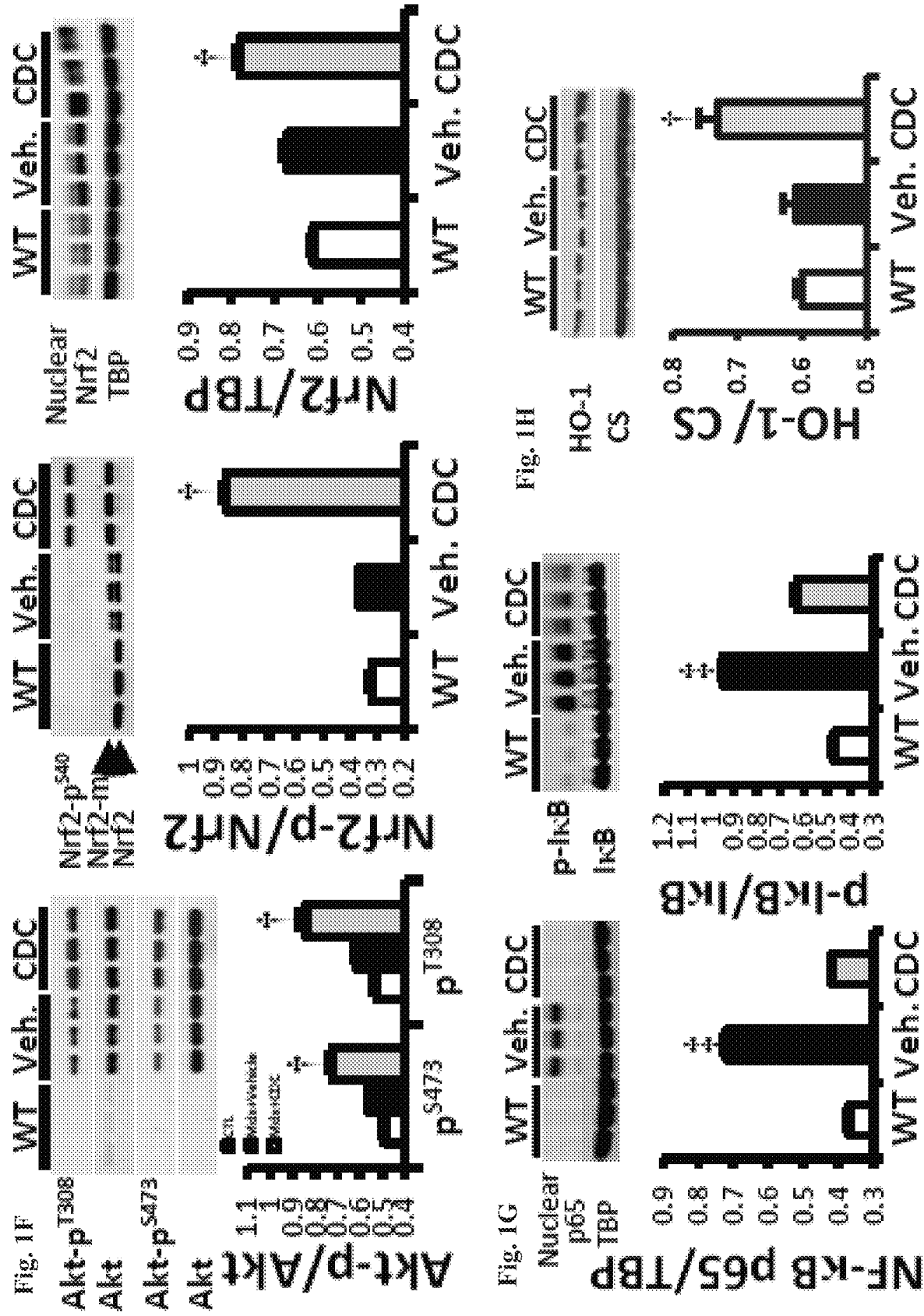

Figure 3.
Fig. 3B
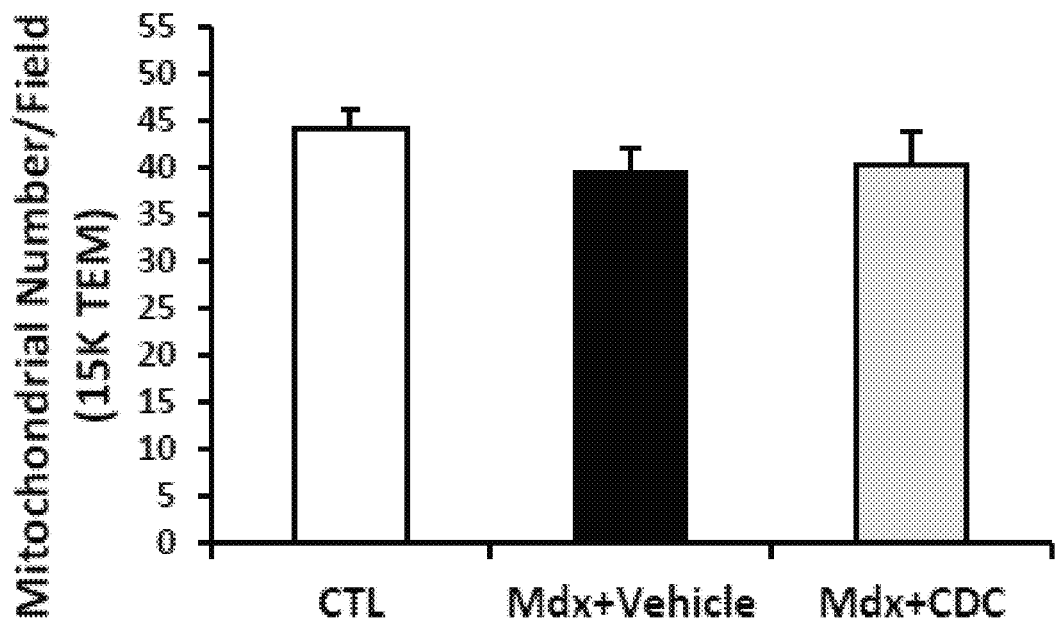
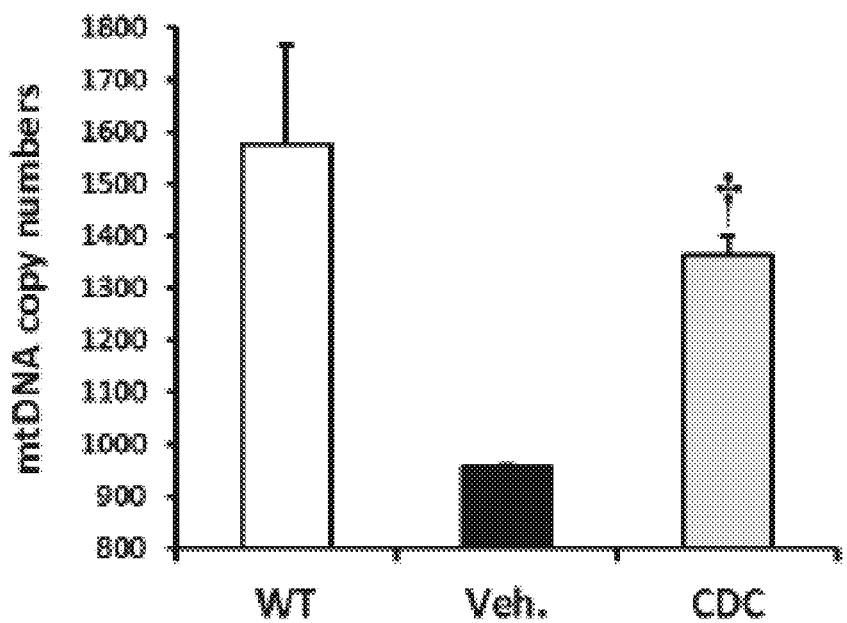

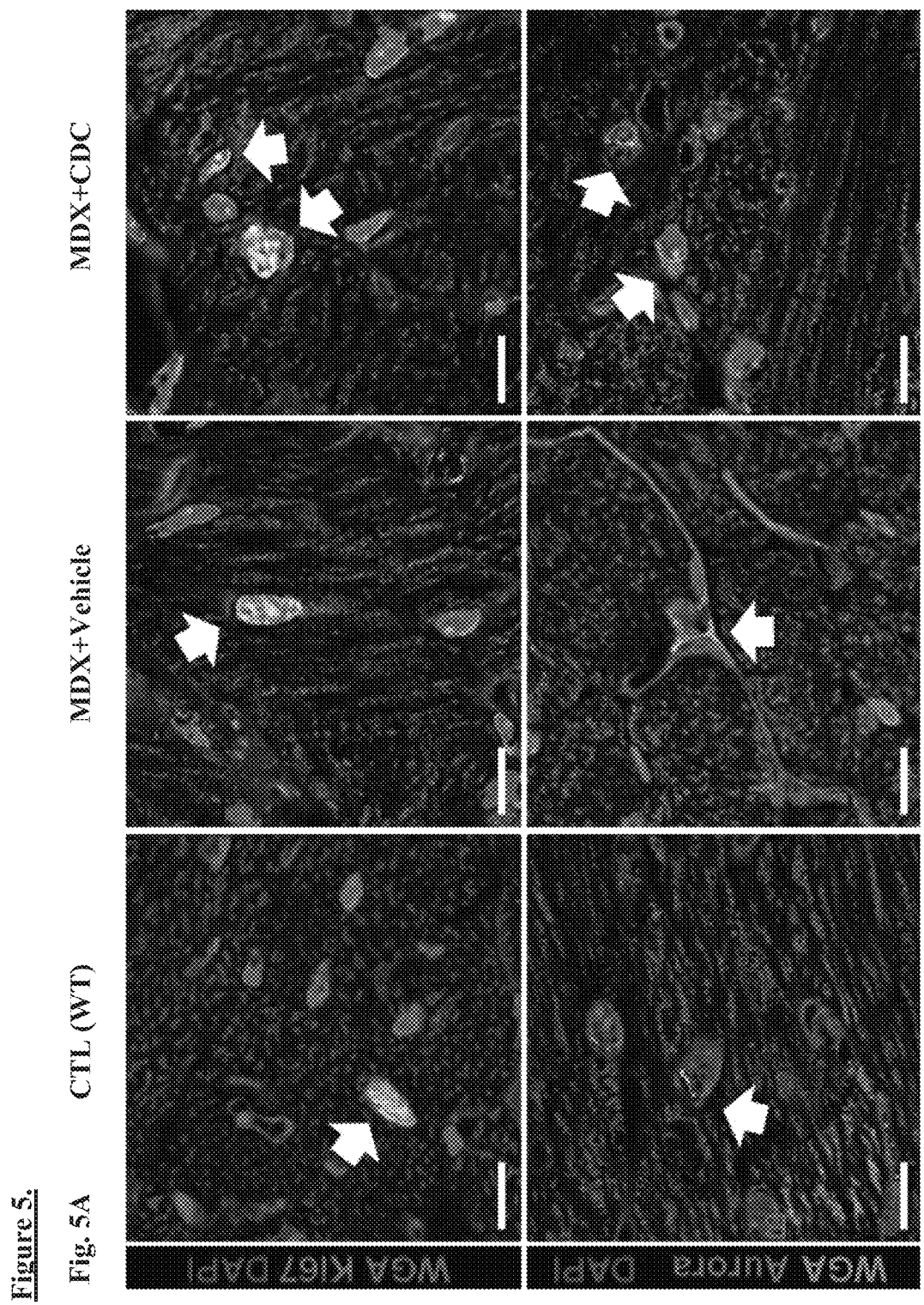

Figure 10.
Fig. 10A
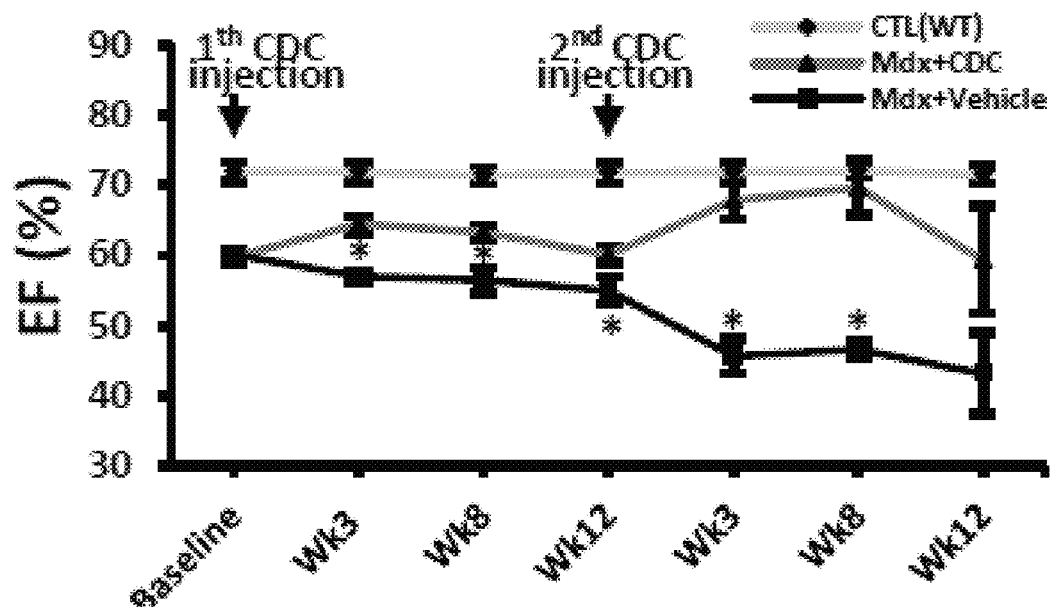
Fig. 10B
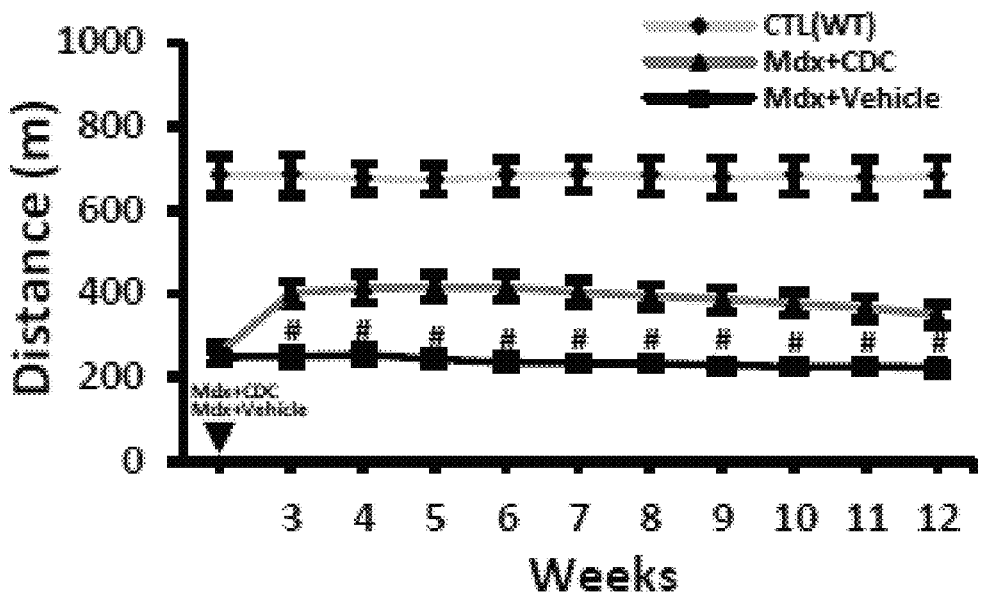

Figure 11.
Fig. 11B
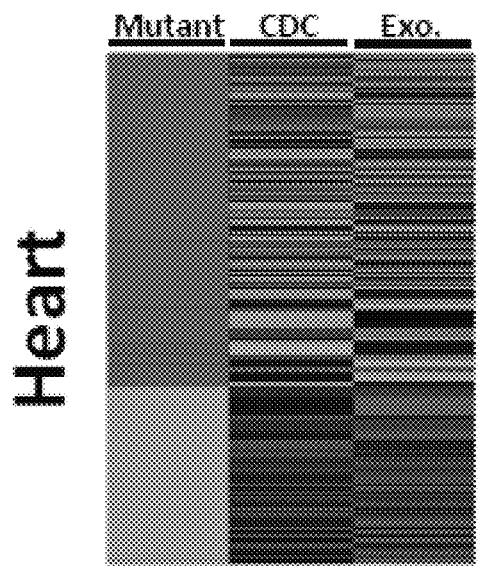
Fig. 11C
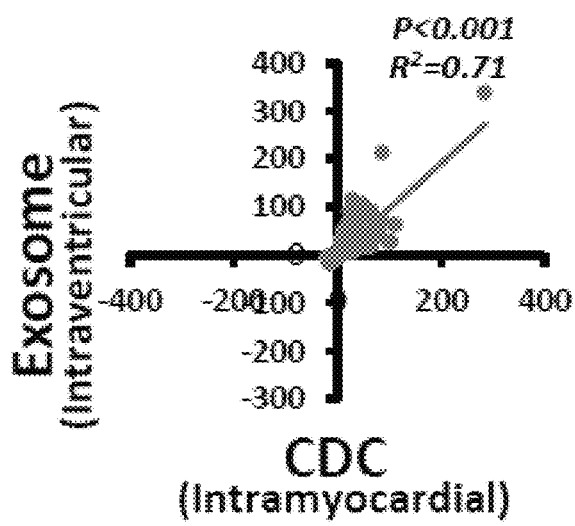
Fig. 11D
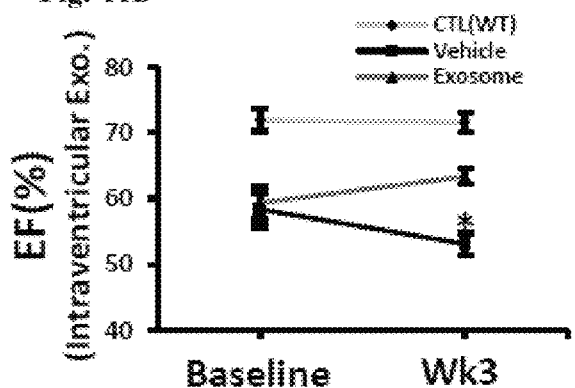
Fig. 11E
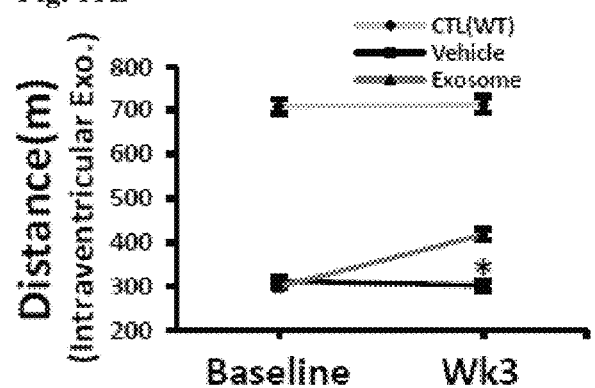

Figure 11.
Fig. 11F
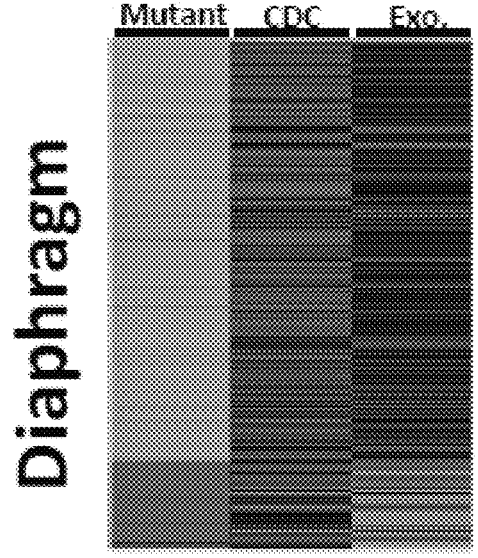
Fig. 11G
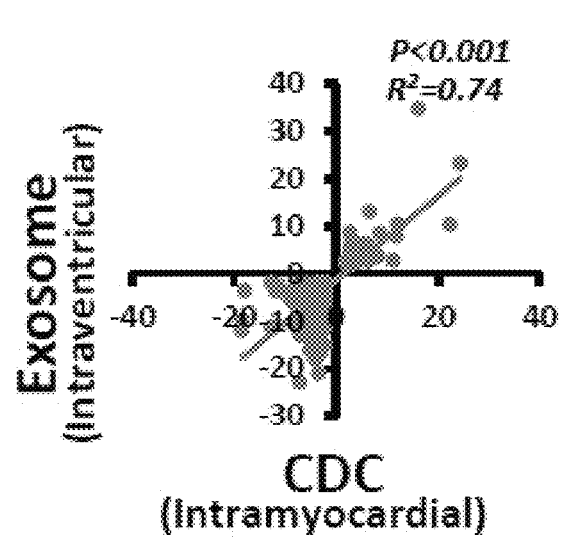
Fig. 11H
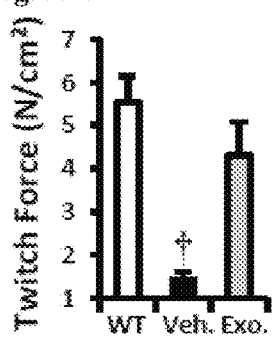 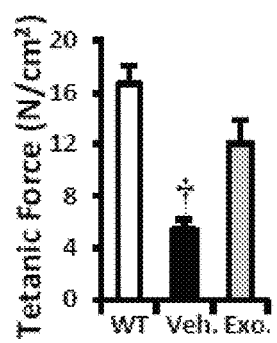 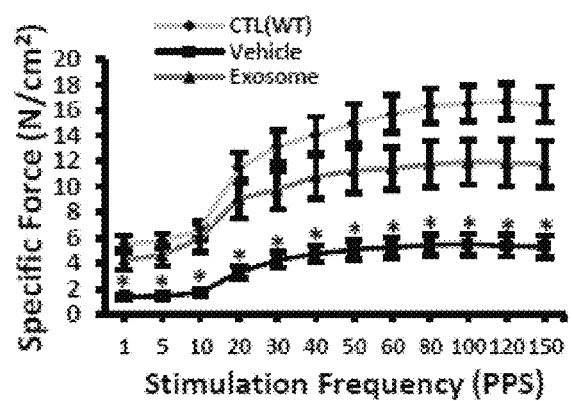

Figure 11.
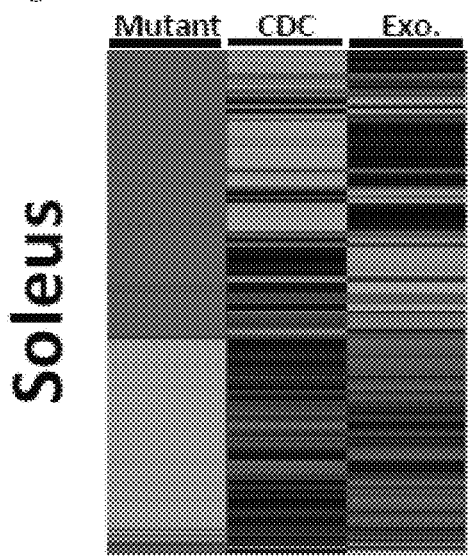
Fig. 11I
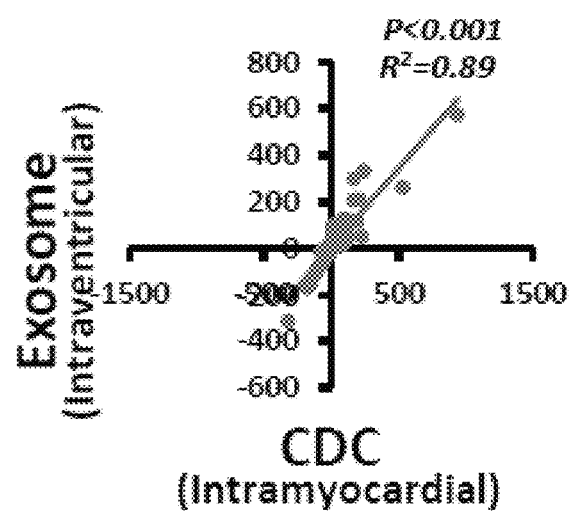
Fig. 11J
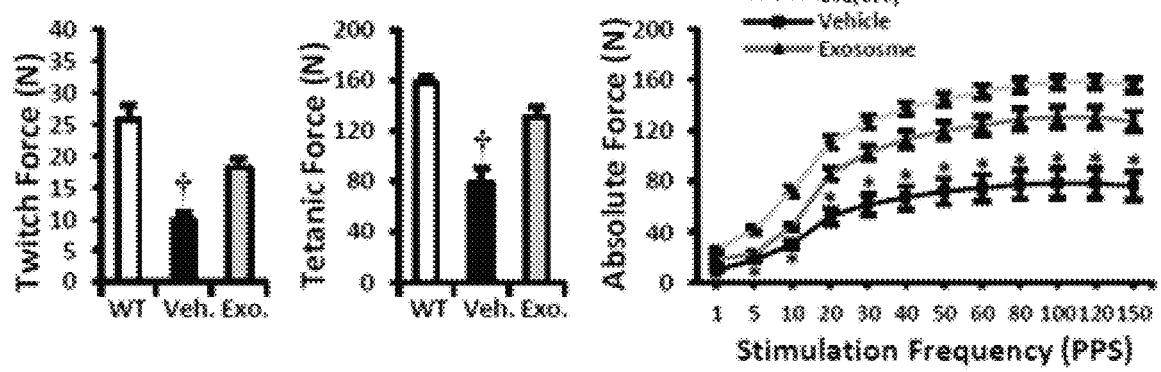
Fig. 11K

Figure 11.
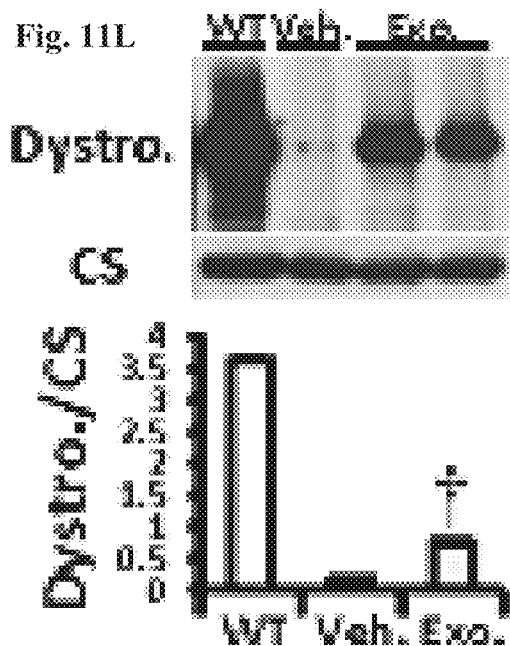
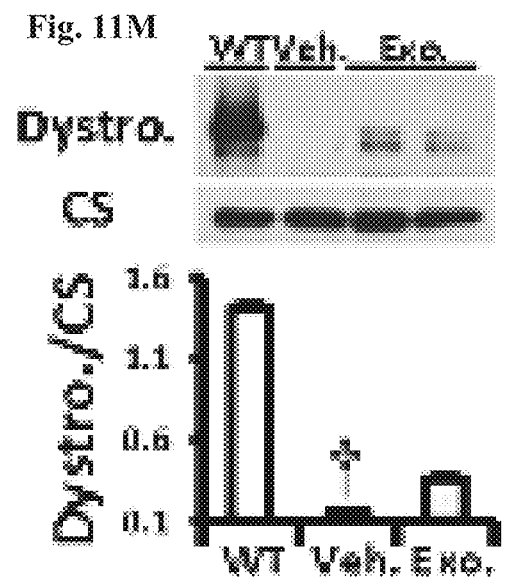
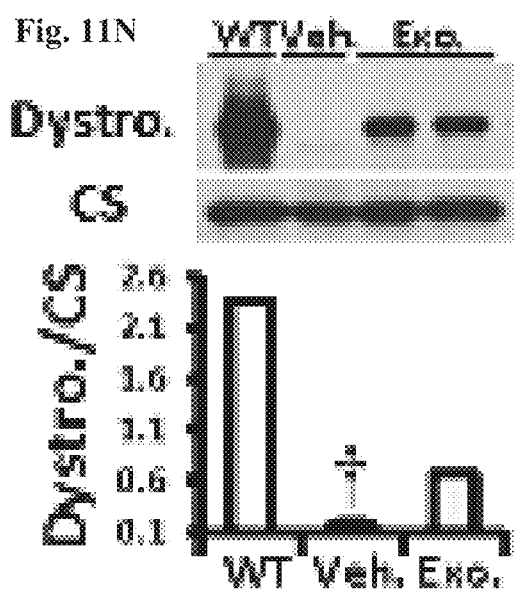

Figure 13.
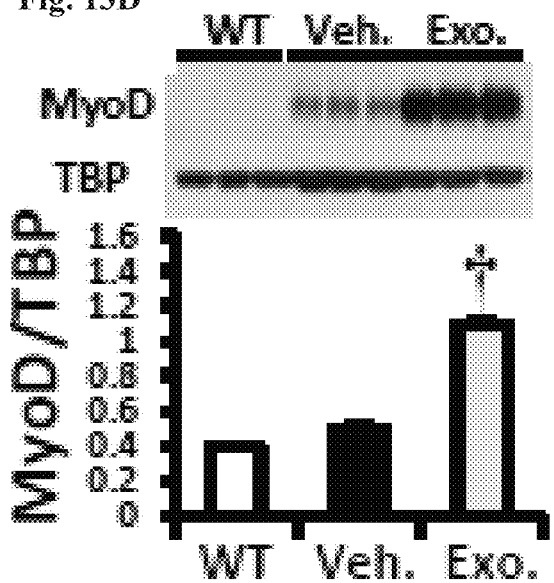
Fig. 13D
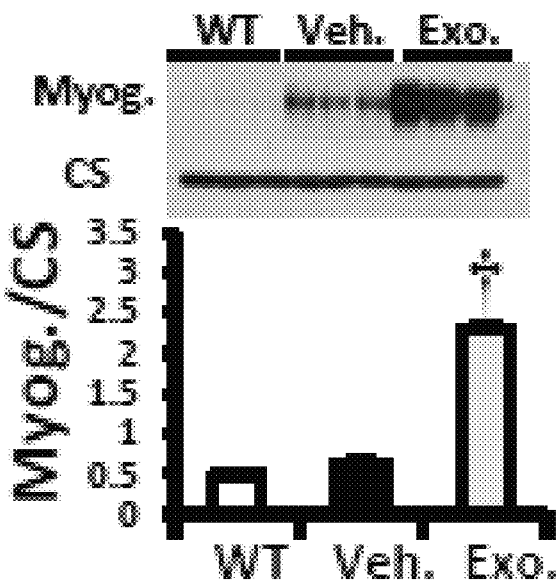
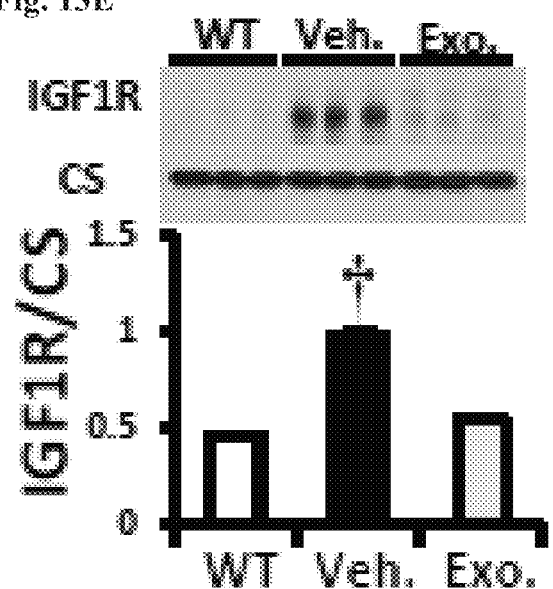
Fig. 13E
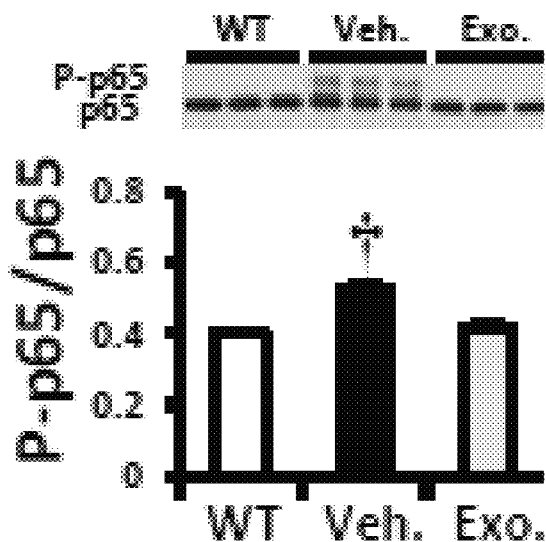
Fig. 13F Figure 13.
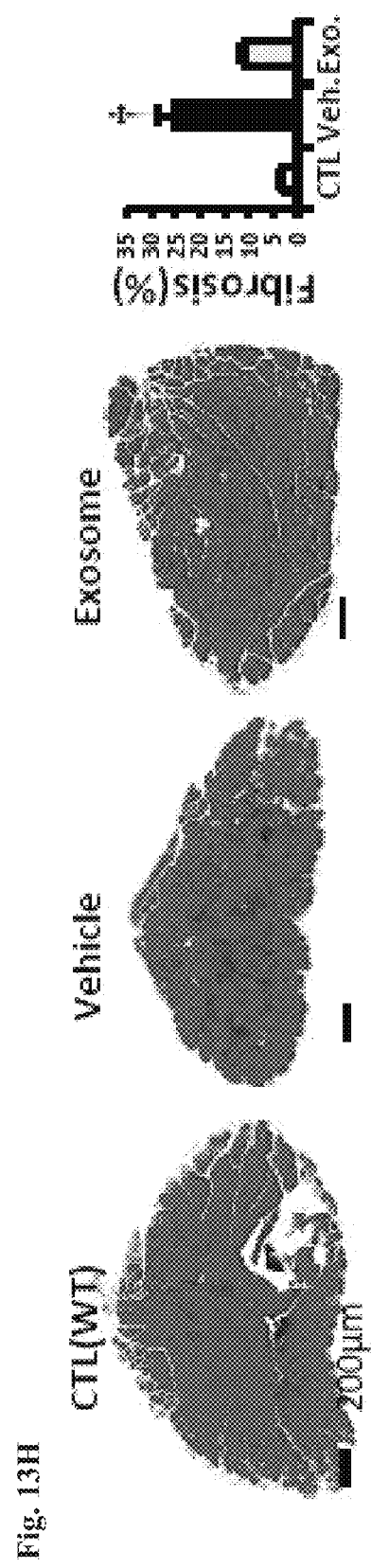
Fig. 13H
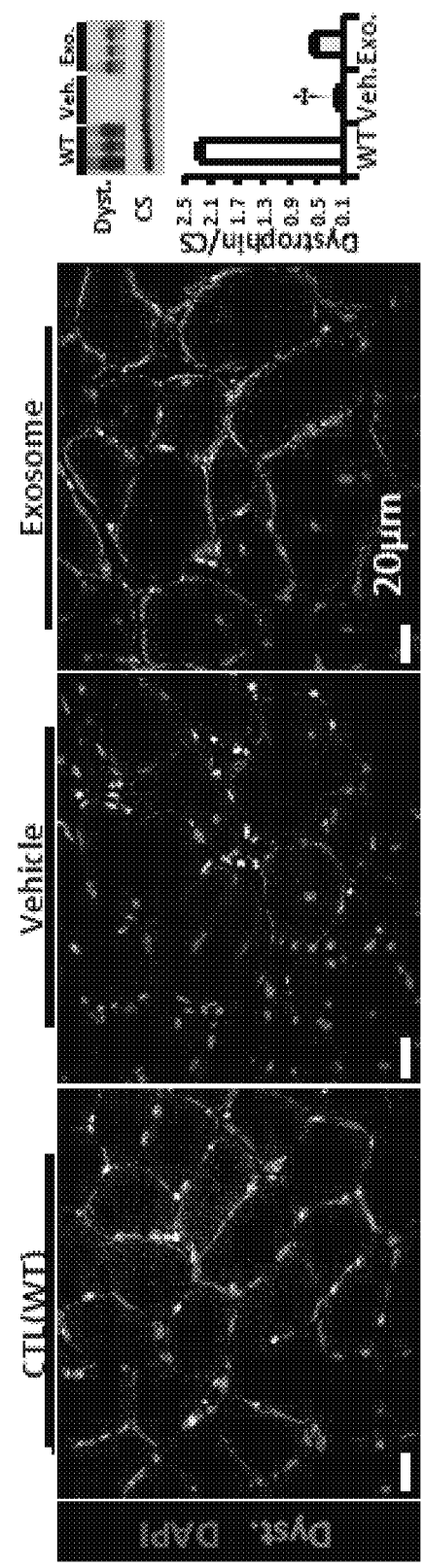
Fig. 13I

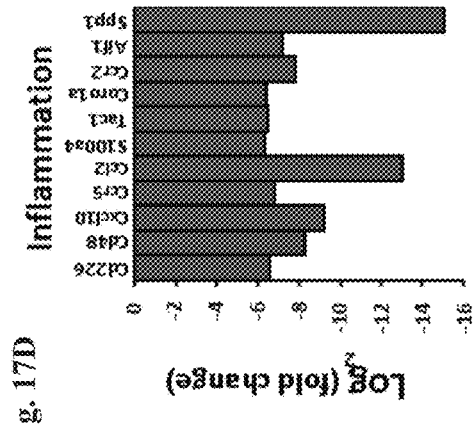
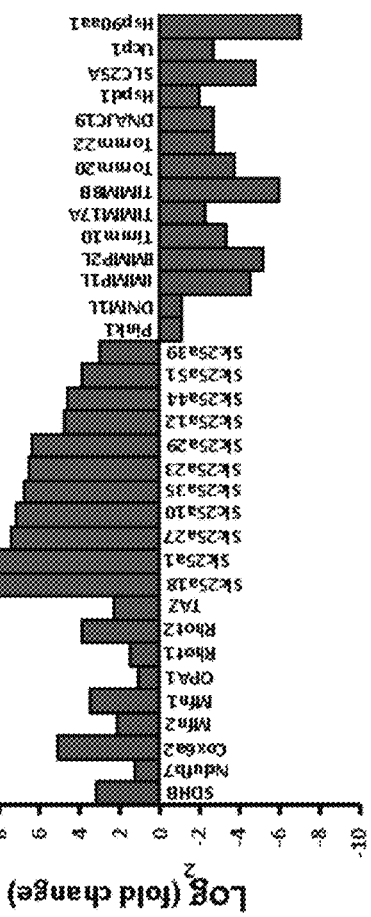
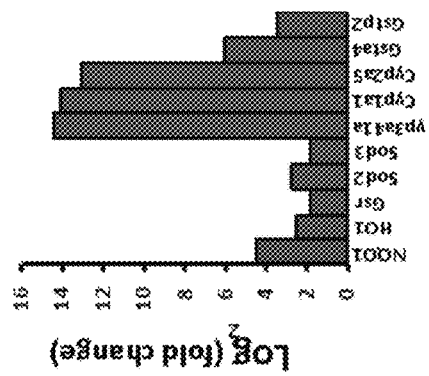
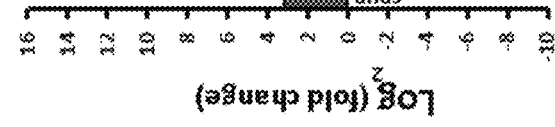
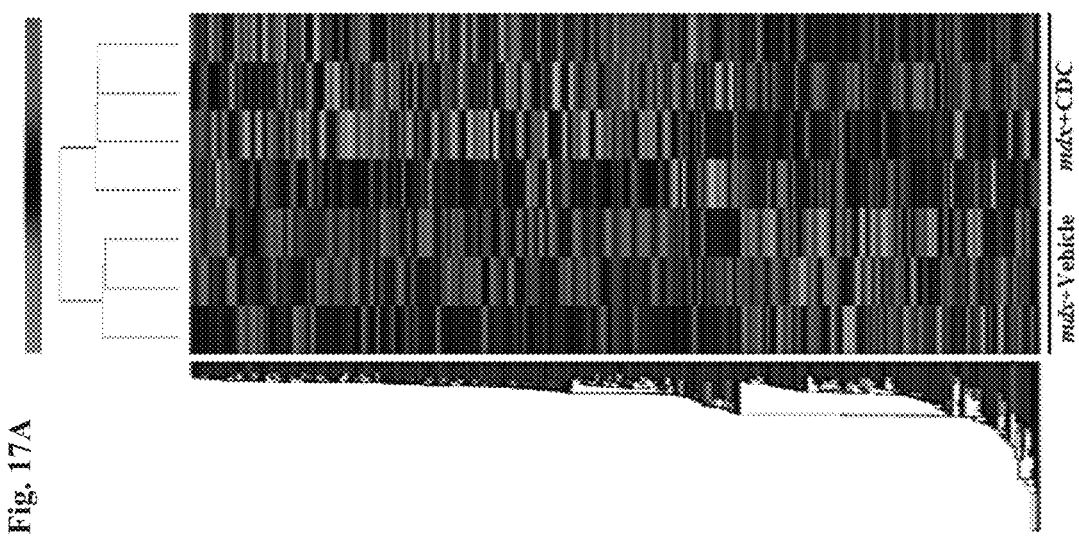
Figure 17.
Fig. 17A
Fig. 17B
Fig. 17C
Fig. 17D Figure 20.
Fig. 20A
Mdx+Vehicle
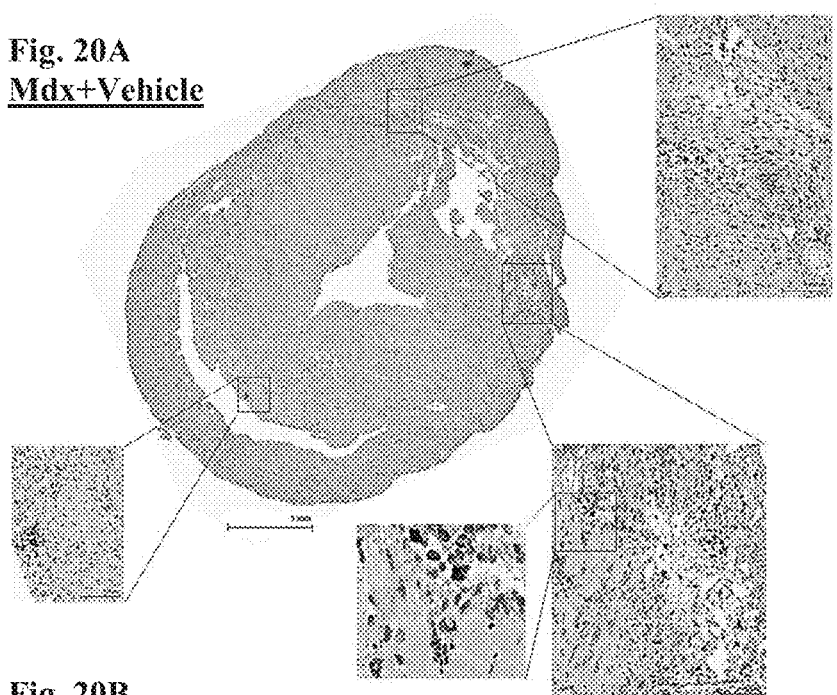
Fig. 20B
Mdx+CDC
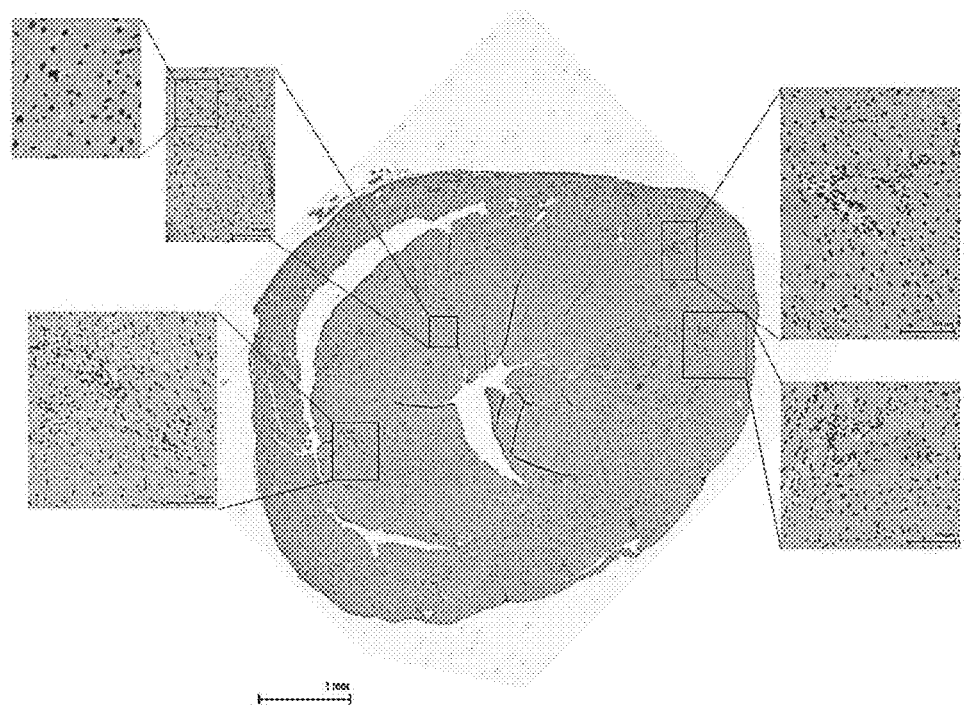

CTL(WT)

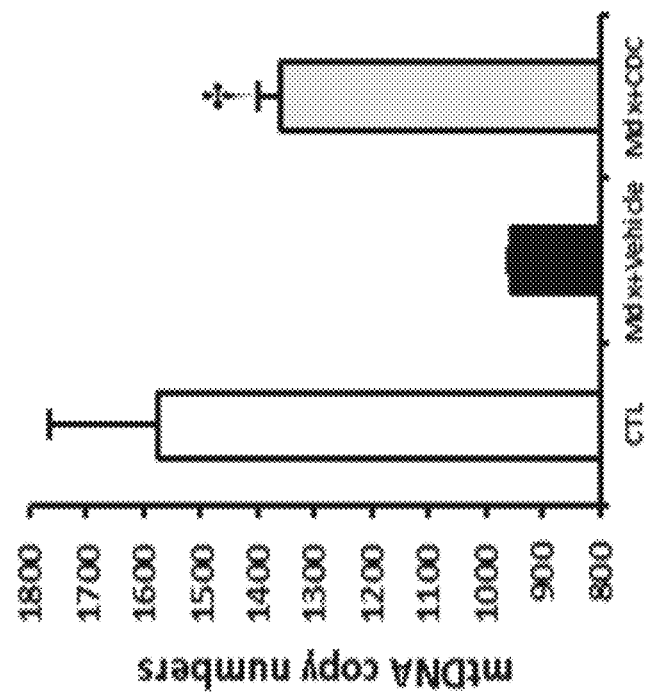
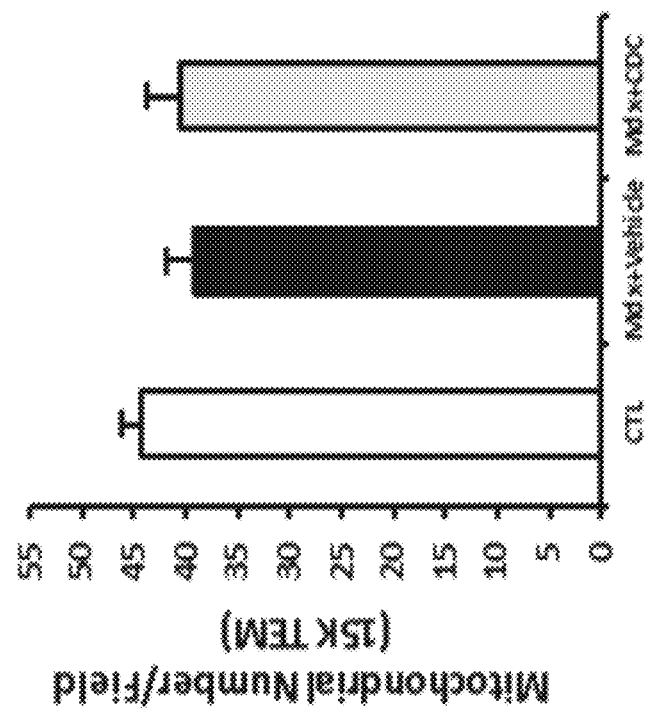
Figure 21.

Figure 22.
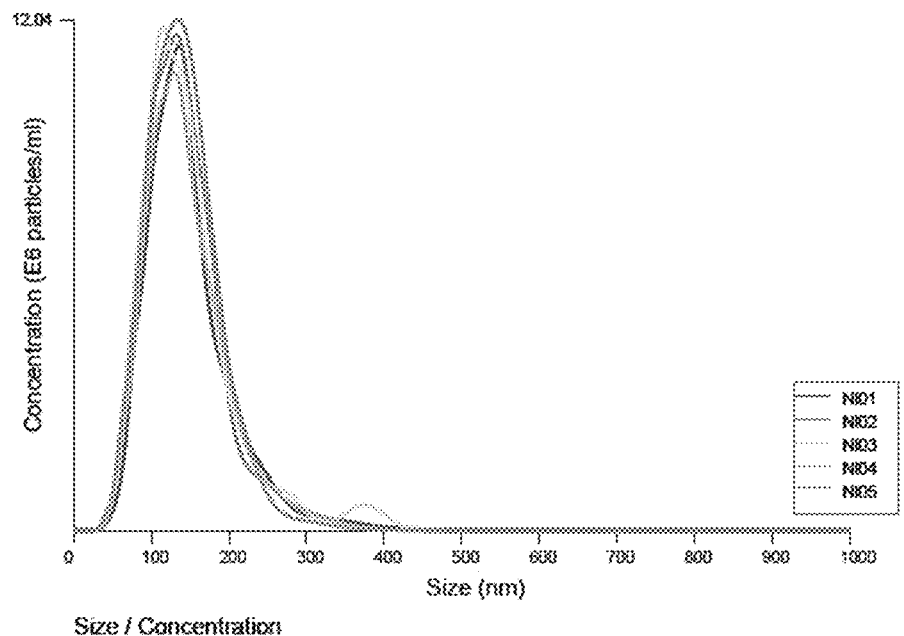
Size / Concentration
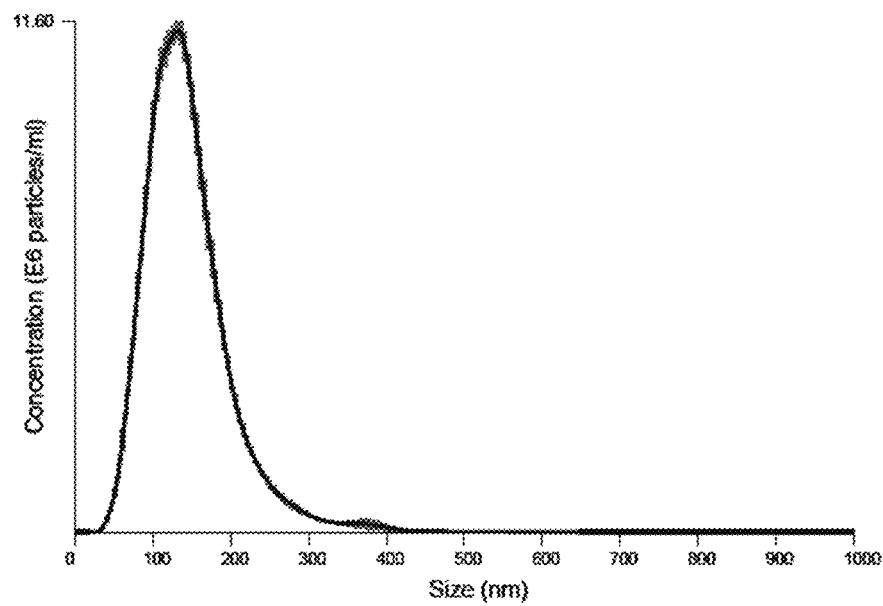
Averaged Size / Concentration
Red error bars indicate +/- 1 standard error of the mean

Figure 28.

Figure 31.
Fig. 31A
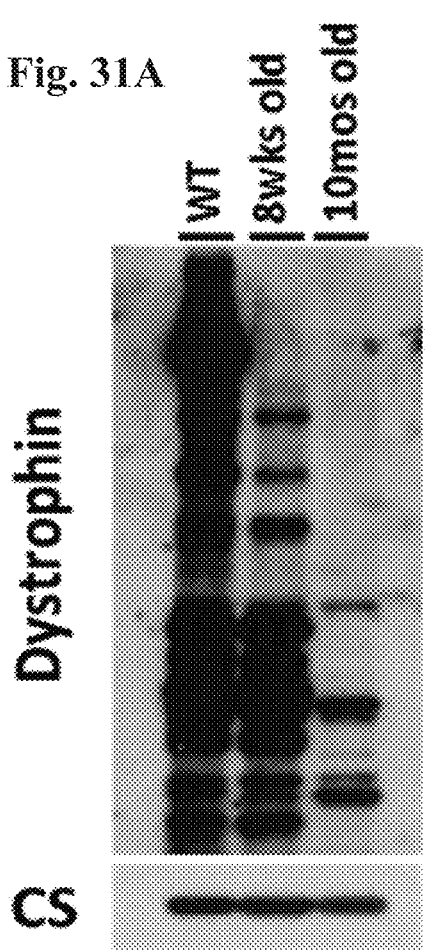
Fig. 31B
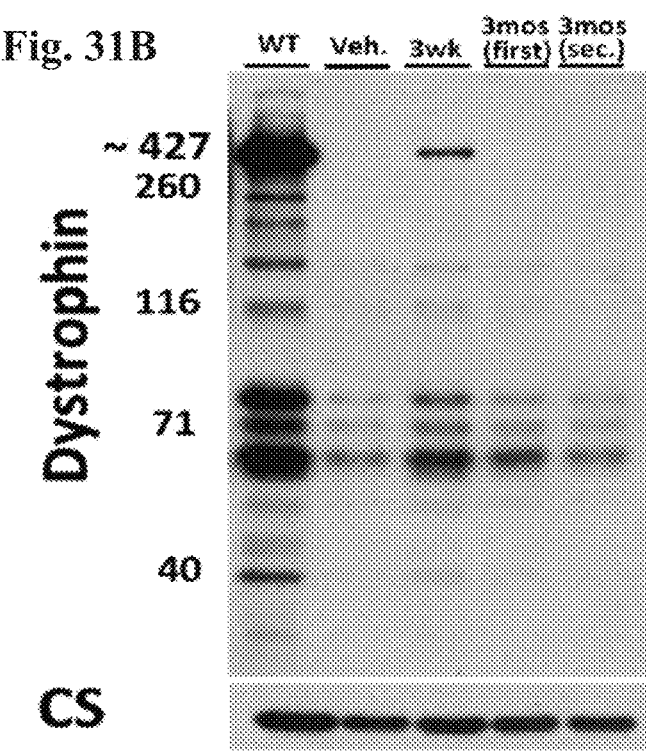

Figure 32.
Fig. 32A
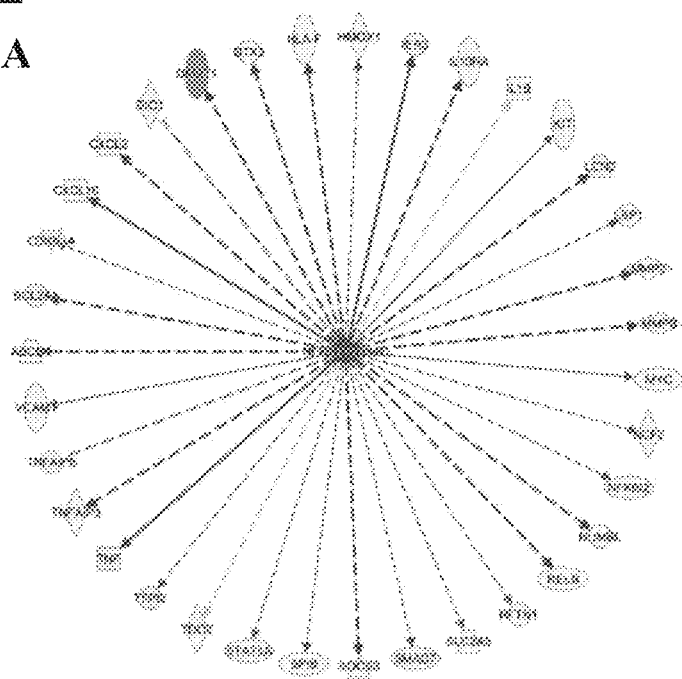
Fig. 32B
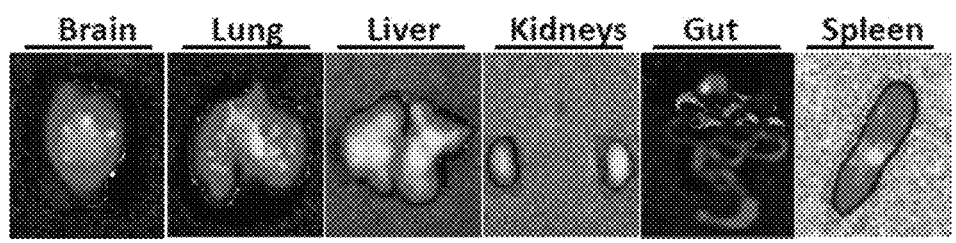
Fig. 32C
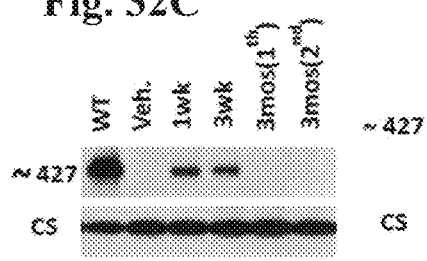
Fig. 32D
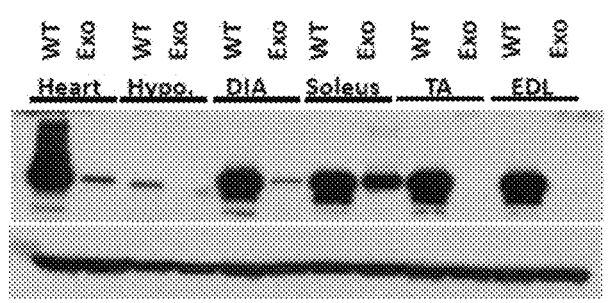

Figure 34.
Fig. 34A
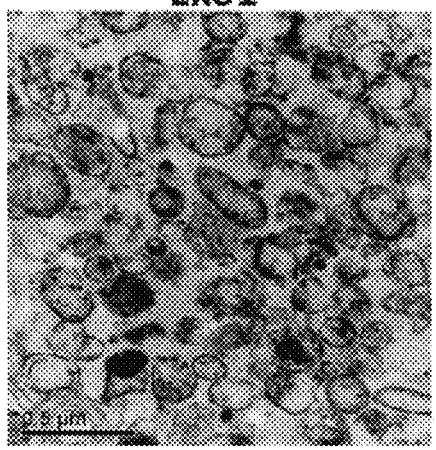
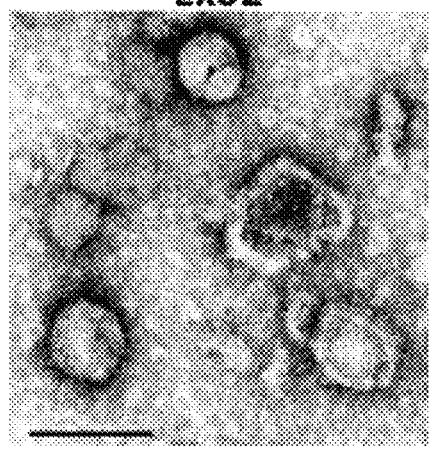
Fig. 34B
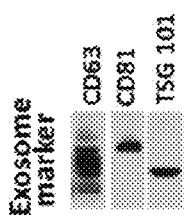
Fig. 34C
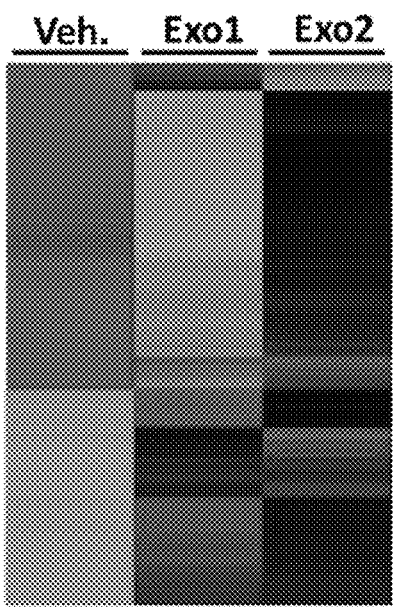
Fig. 34D
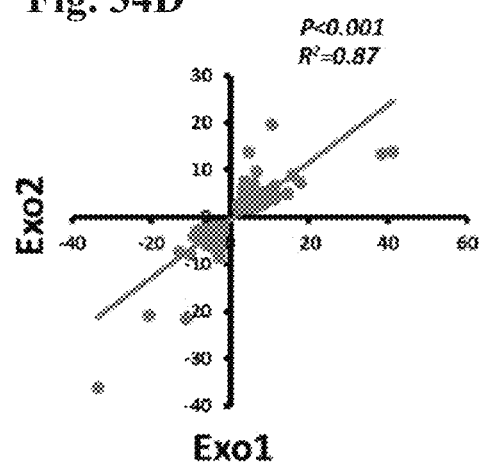

Figure 37.
Fig. 37A
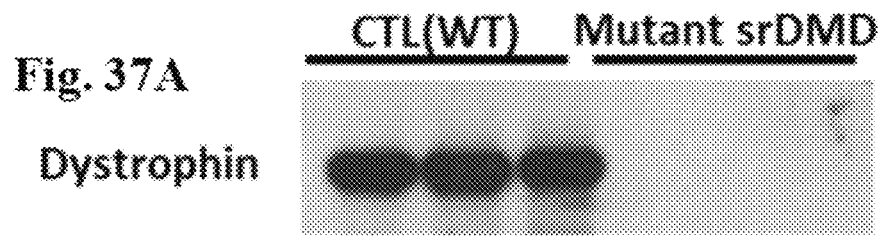
Fig. 37B
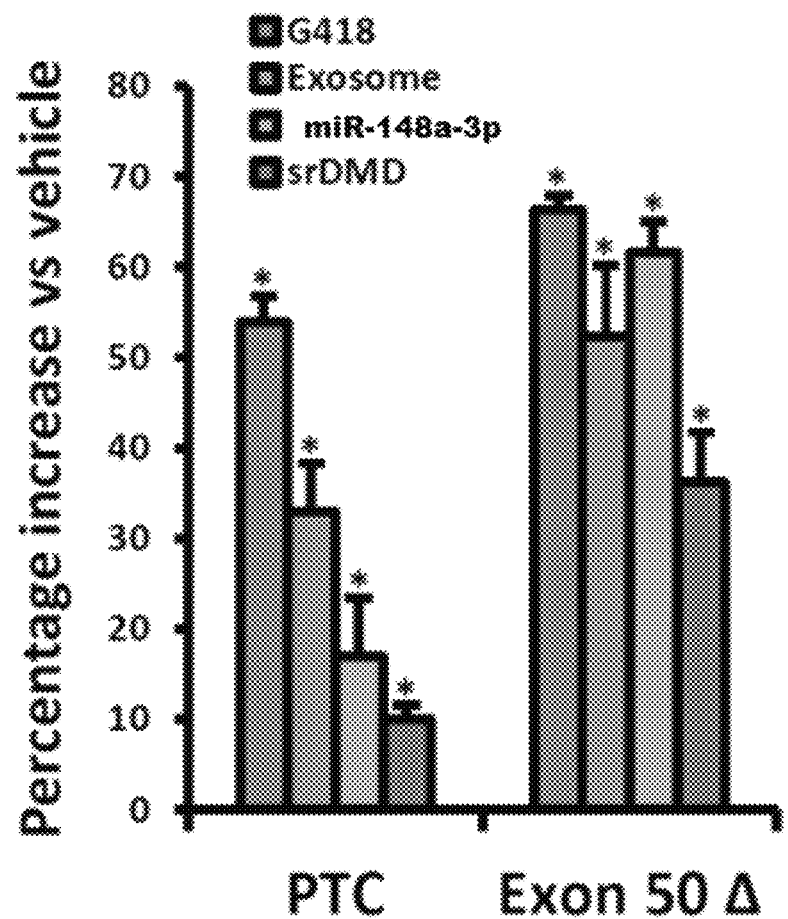

Figure 38.
Fig. 38A
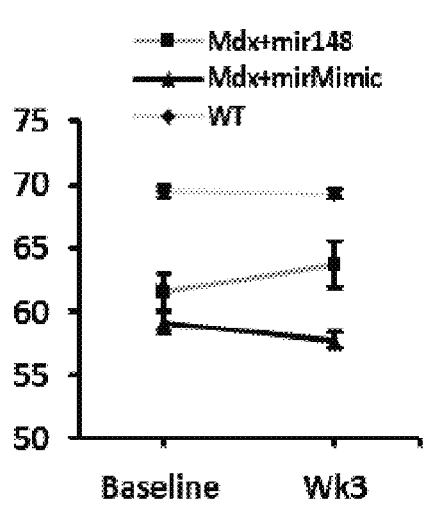
Fig. 38B
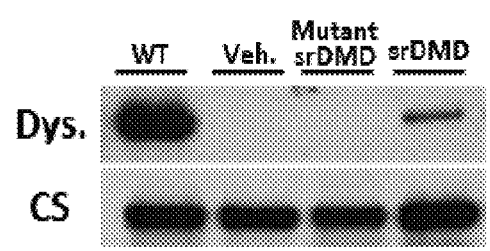

Figure 39.
Fig. 39A
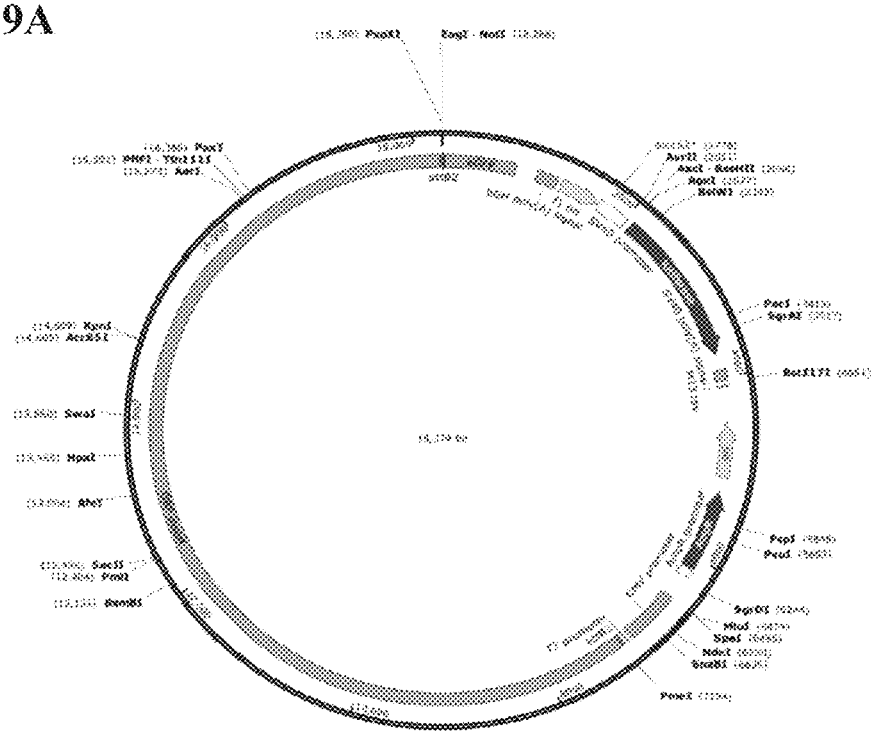
Fig. 39B
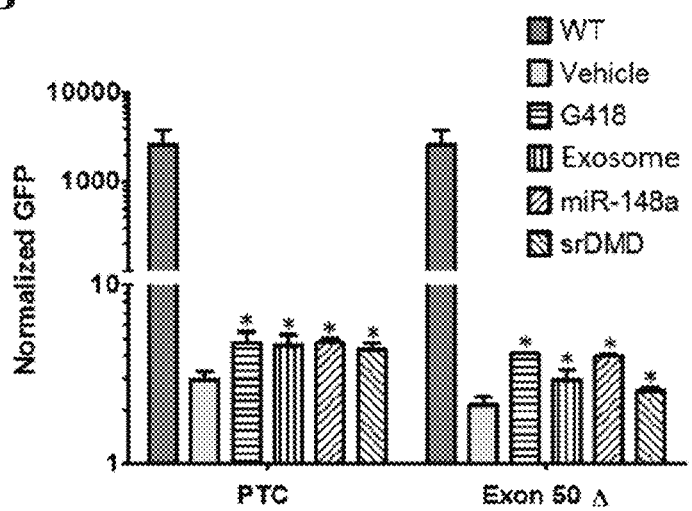

Figs. 40A-D
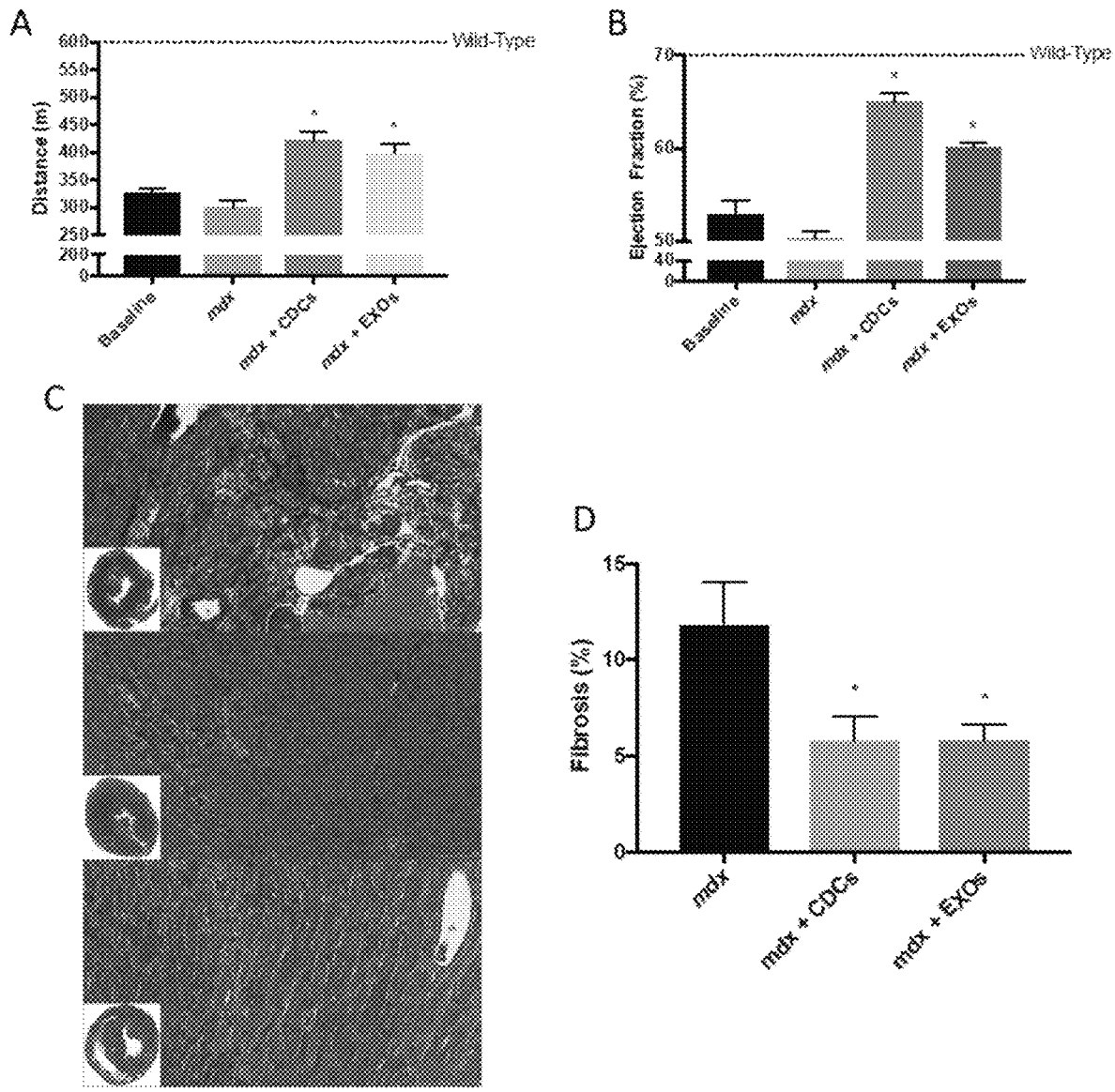

Figs. 41A-D
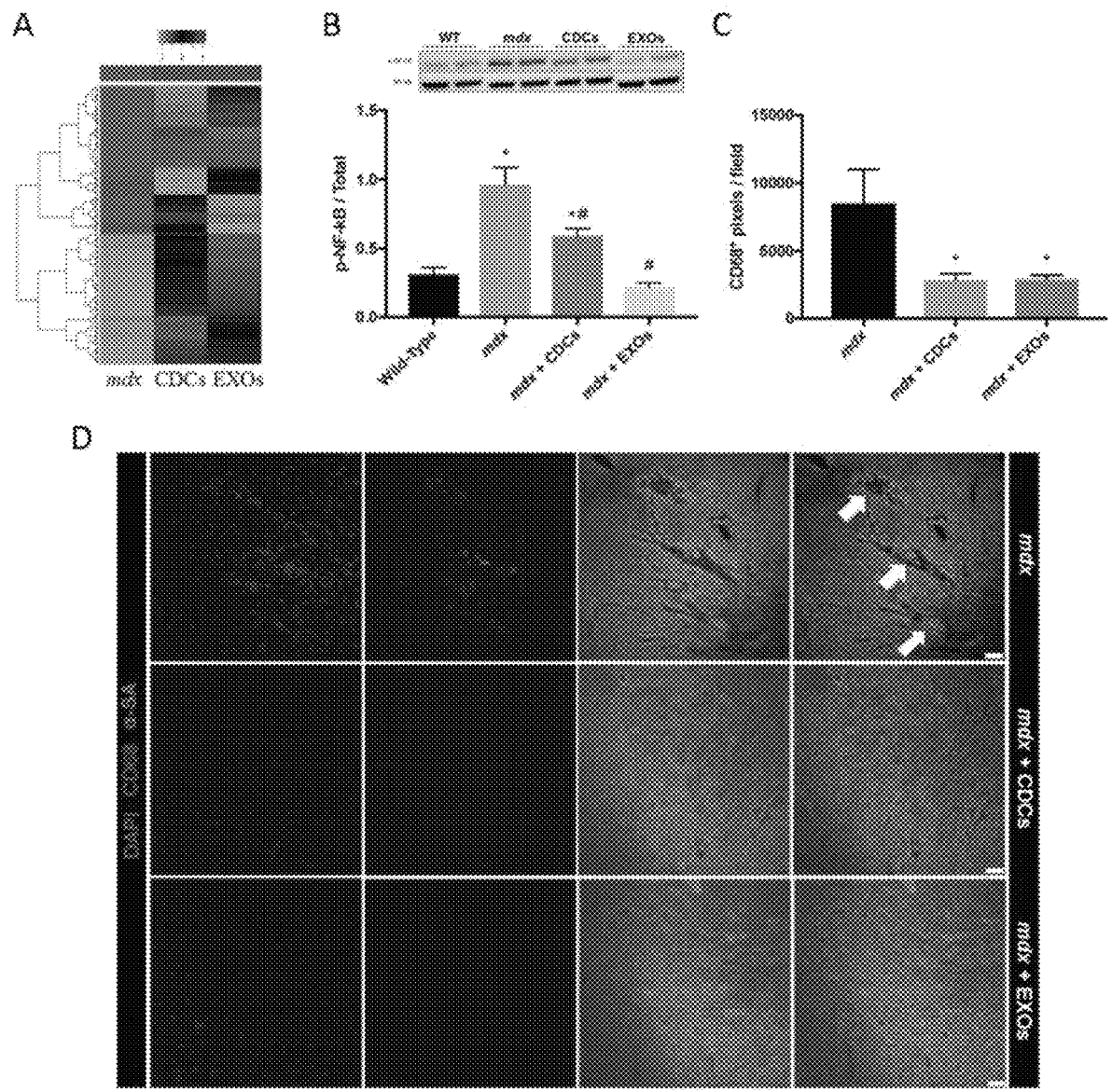

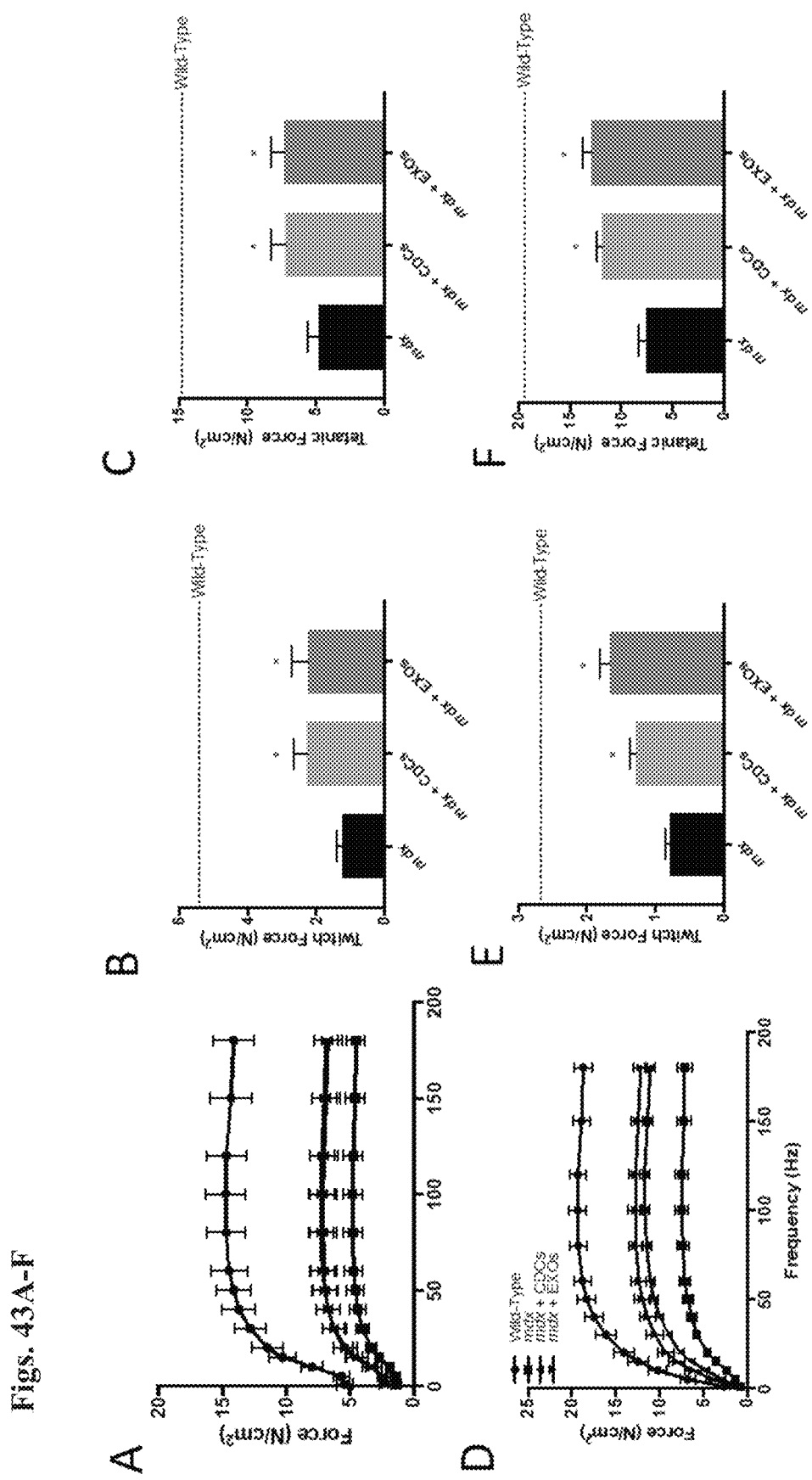

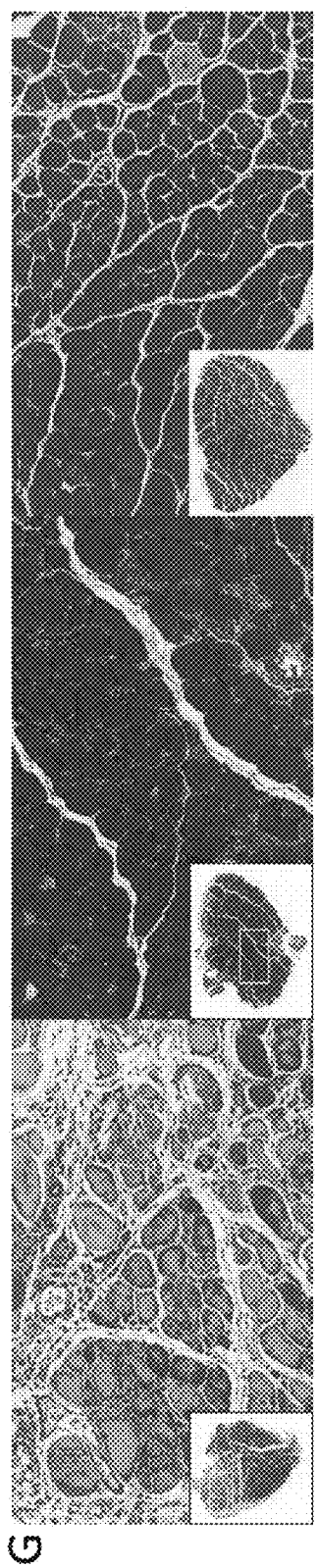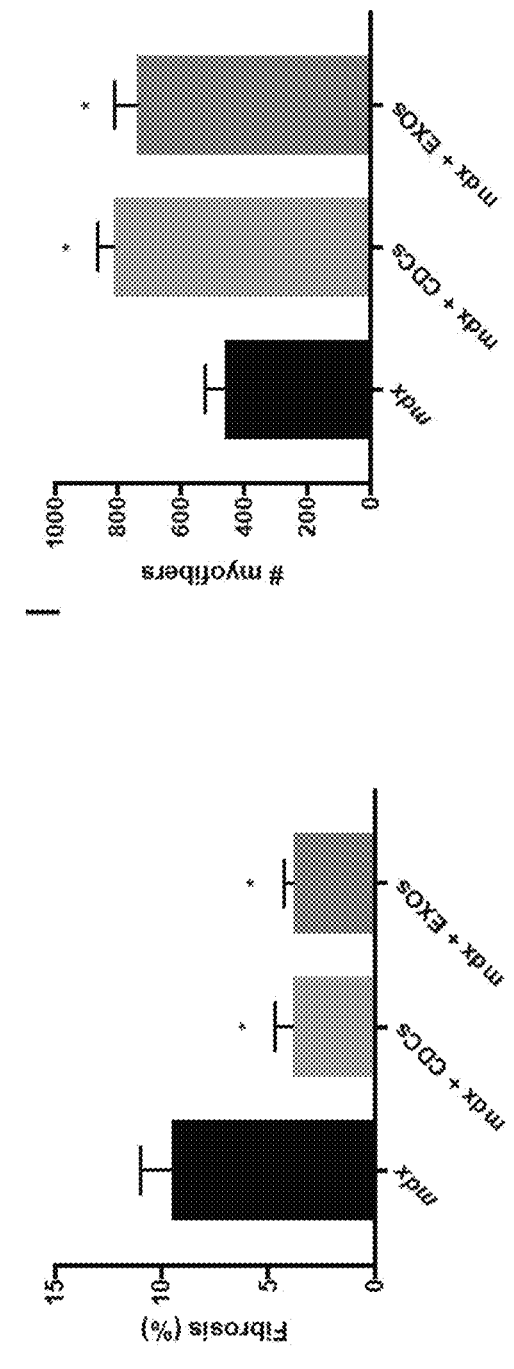
Figs. 43G-H

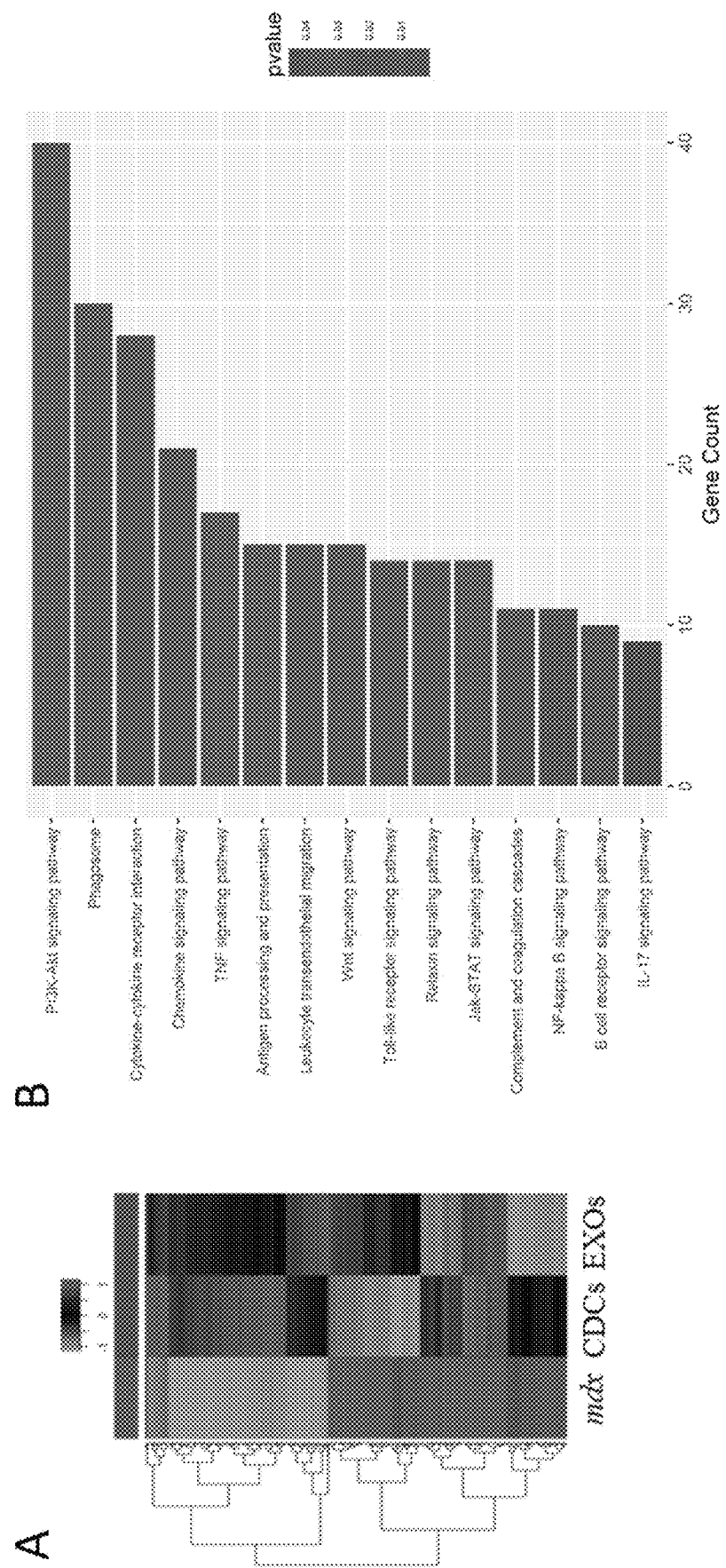
Figs. 44A-B

Figs. 45A-B
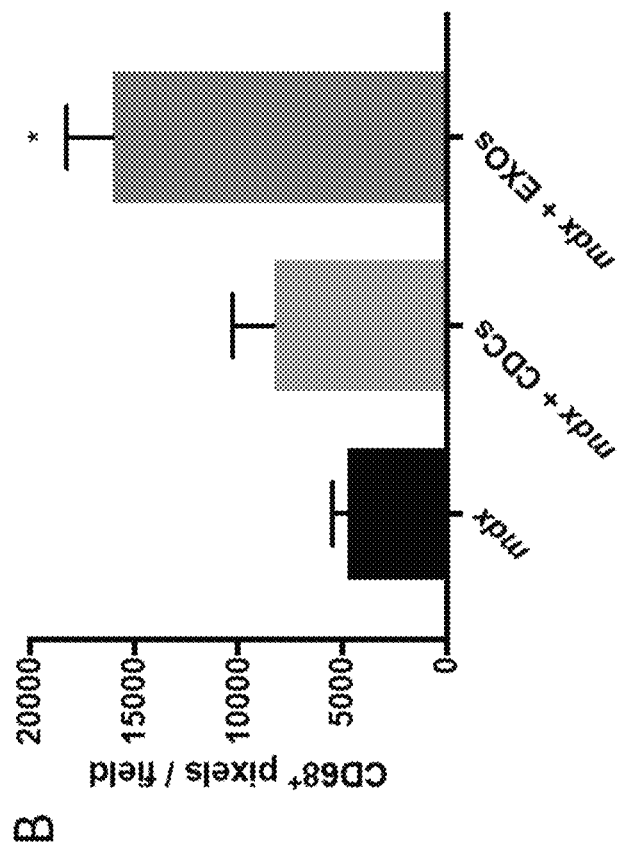
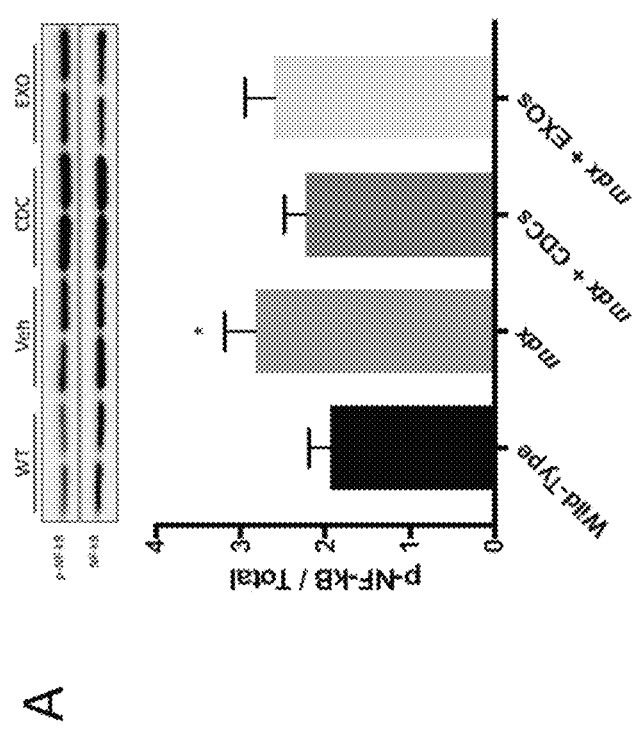

Figs. 46A-B
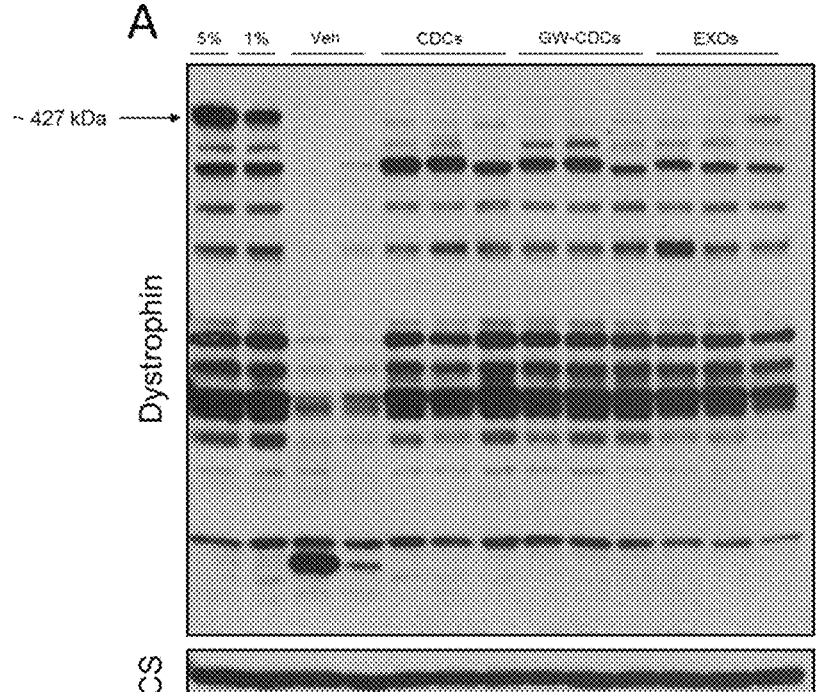
Soleus
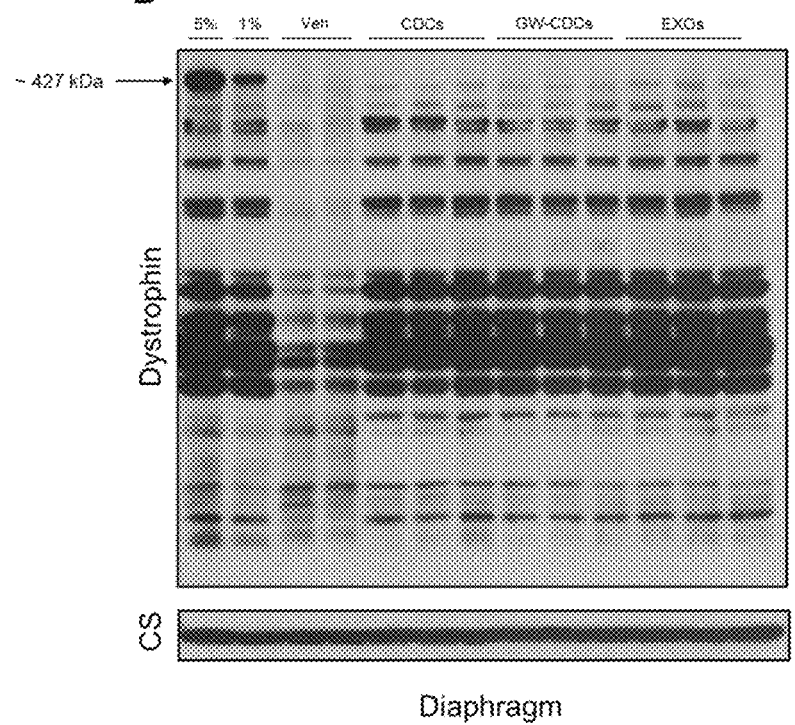
Diaphragm

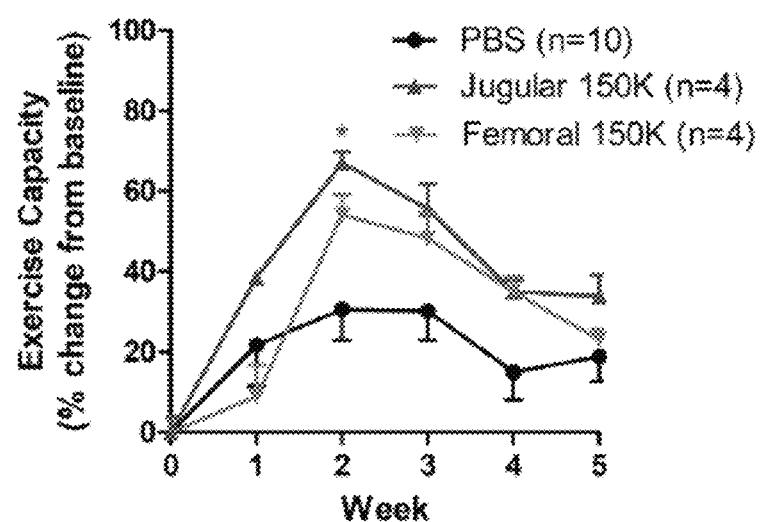

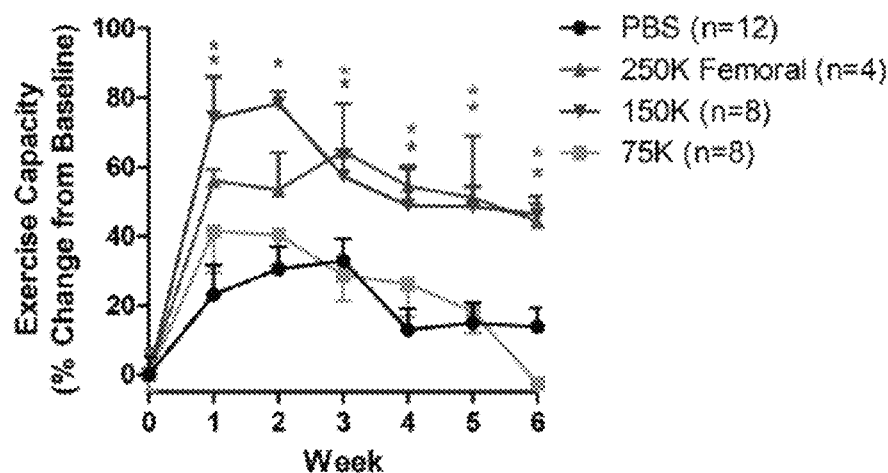

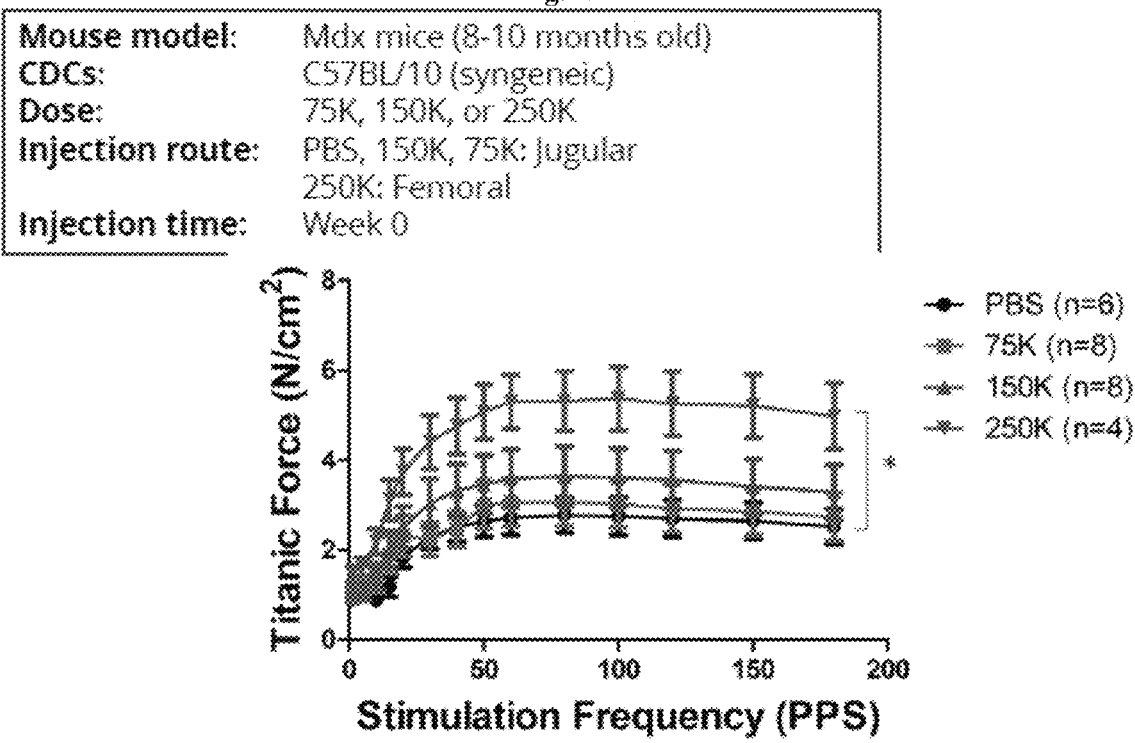

Fig. 51
Vehicle alone – Left ventricle area
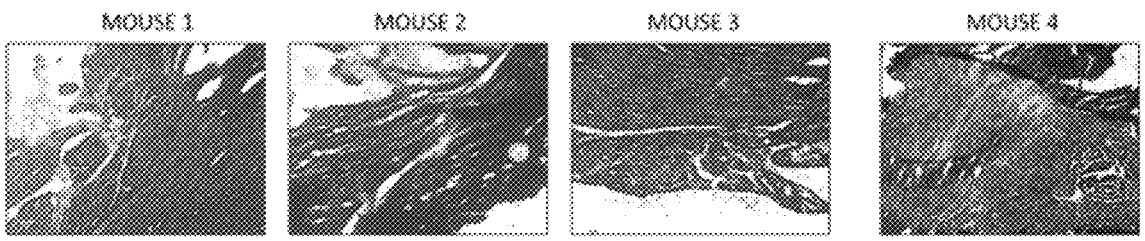
150K CDCs – Left ventricle area
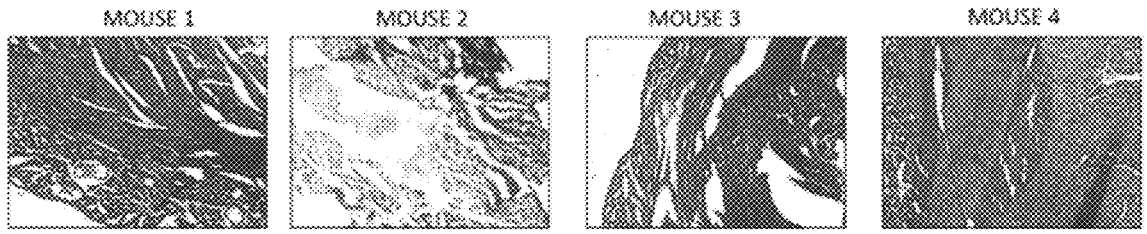

Masson's Trichrome Stain

Fig. 68
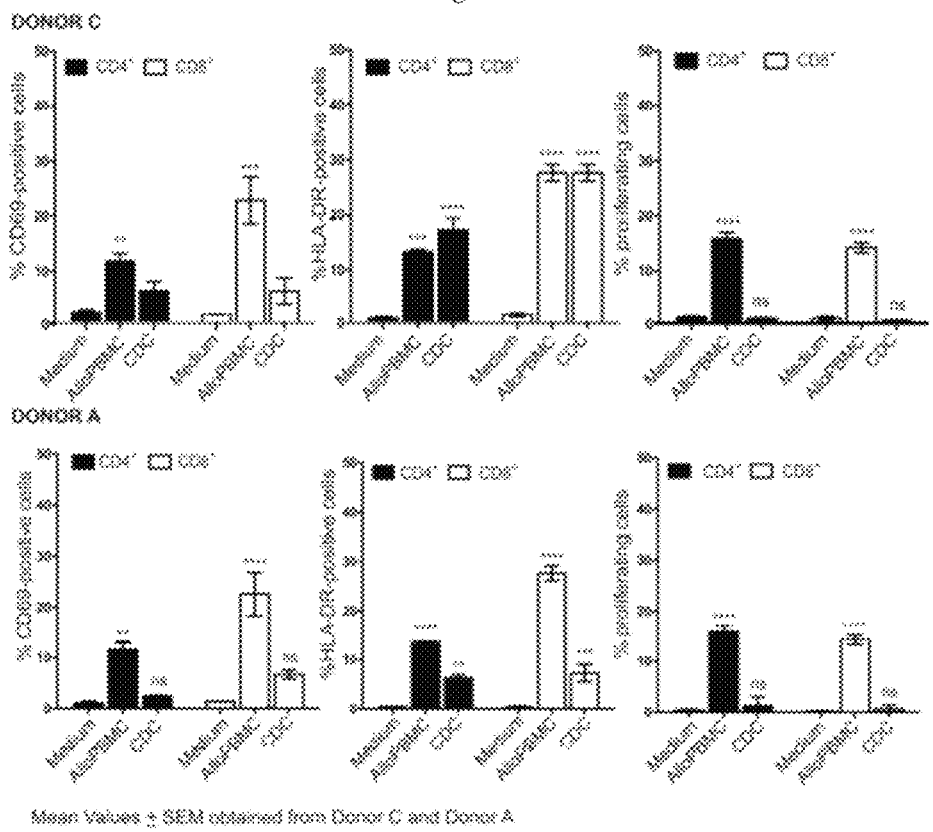
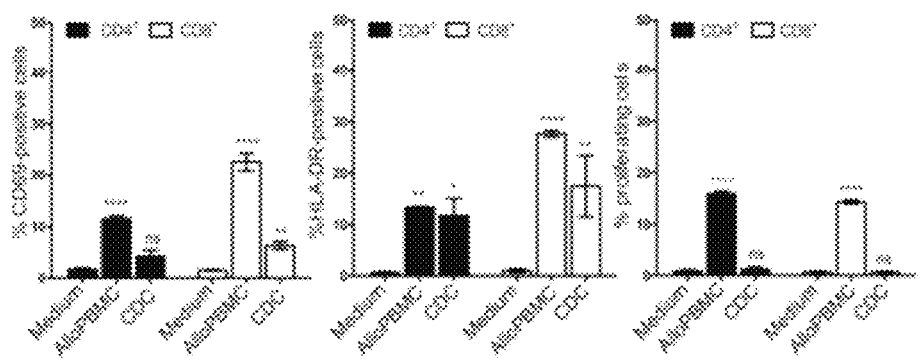

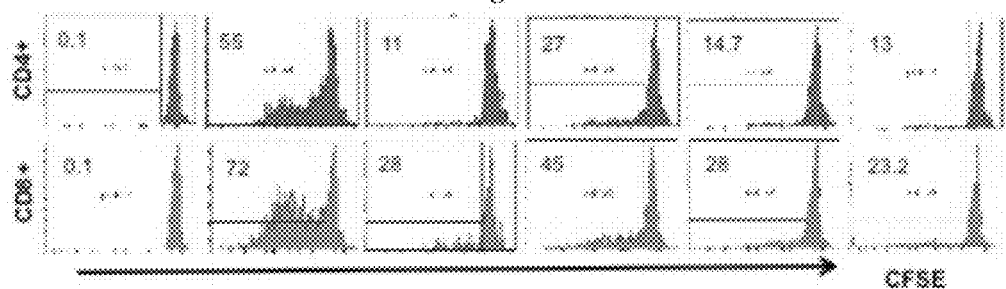
Fig. 82
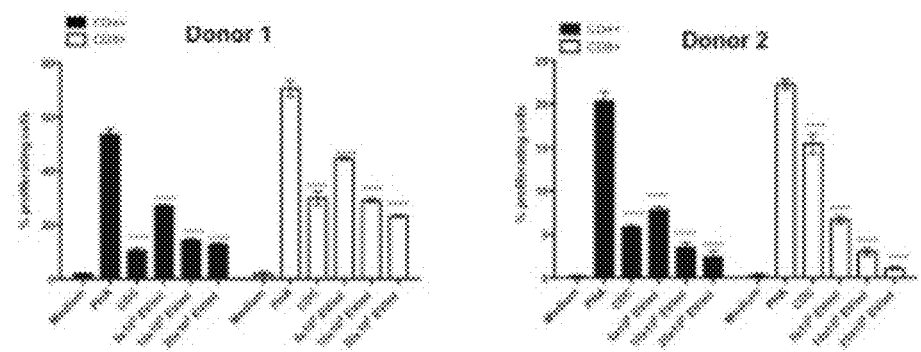
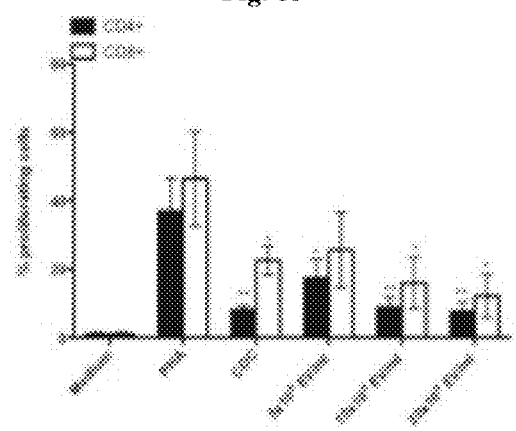
Fig. 83

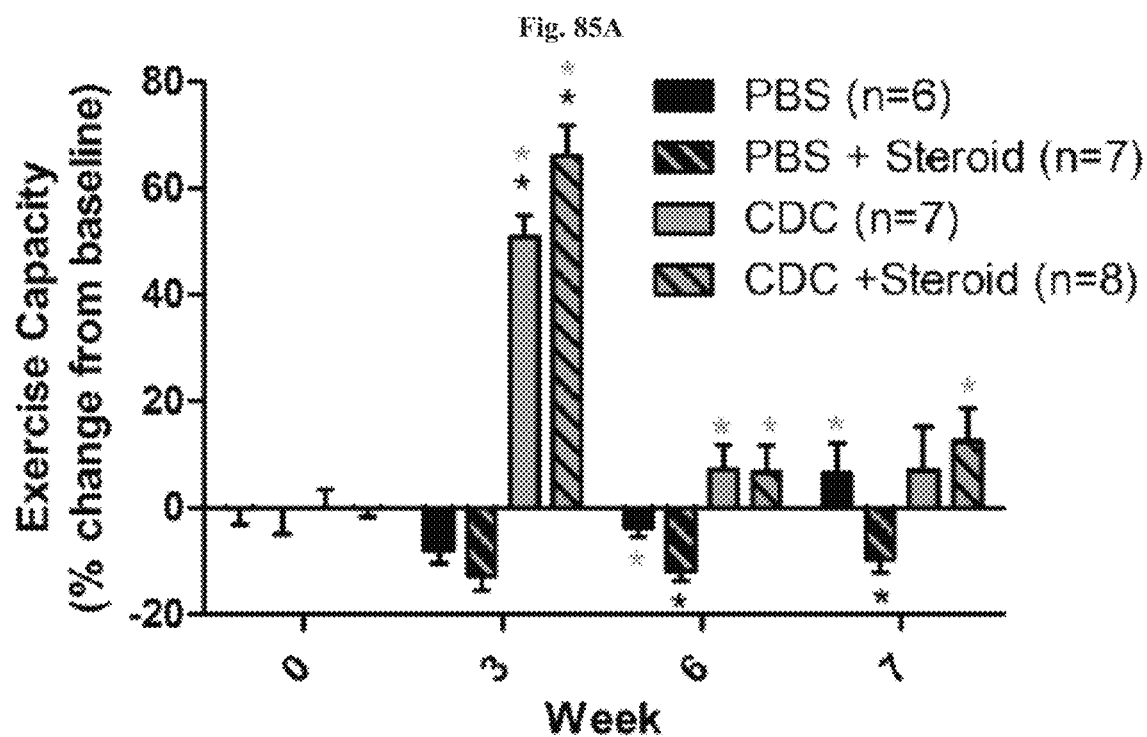

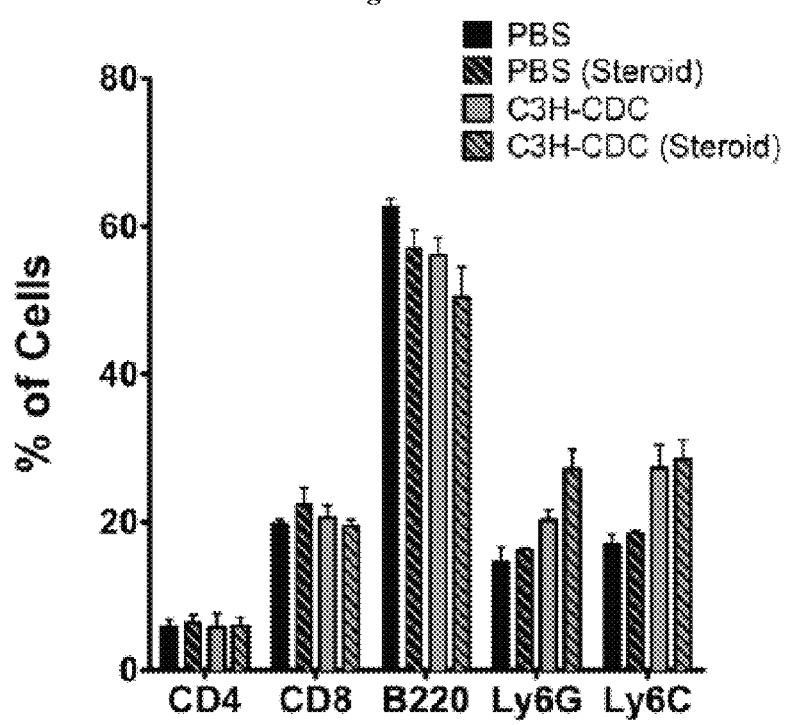

METHODS AND COMPOSITIONS FOR TREATING SKELETAL MUSCULAR DYSTROPHY

CROSS REFERENCE TO RELATED APPLICATIONS

This application is the U.S. National Phase of International Application No. PCT/US2018/028184, filed Apr. 18, 2018, which claims priority to U.S. Provisional Application No. 62/487,393, filed Apr. 19, 2017, U.S. Provisional Application No. 62/487,402, filed Apr. 19, 2017, and U.S. Provisional Application No. 62/487,408, filed Apr. 19, 2017, U.S. Provisional Application No. 62/535,672, filed Jul. 21, 2017, U.S. Provisional Application No. 62/569,440, filed Oct. 6, 2017 and U.S. Provisional Application No. 62/614,753, filed Jan. 8, 2018. All of the foregoing applications are hereby incorporated by reference in their entireties.

STATEMENT REGARDING FEDERALLY-SPONSORED RESEARCH

This invention was made with government support under Grant No. HL124074 awarded by the National Institutes of Health. The government has certain rights in the invention.

BACKGROUND

Field

Some embodiments relate to the use of cardiosphere-derived cells and extracellular vesicles derived therefrom (e.g., exosomes, etc.), as well as the isolated molecular cargo thereof (e.g., nucleic acids, short non-coding RNAs, microRNAs, and/or mutants and synthetic analogs thereof), for treating dystrophinopathy (muscular dystrophy, Duchenne muscular dystrophy and Becker muscular dystrophy), and symptoms or disease states associated therewith (including skeletal muscle myopathy associated with Duchenne muscular dystrophy).

Background

Duchenne muscular dystrophy (DMD) afflicts ~20,000 boys and young men in the USA. The central cause is a genetic abnormality in the dystrophin complex, with secondary damage to skeletal muscle and heart tissue, Dystrophin is a large, rod-shaped, sarcolemmal protein that provides a physical link between the intracellular cytoskeleton and the extracellular matrix. With dystrophin deficiency, the sarcolemma is destabilized and the muscle fibers are susceptible to physical damage with repeated contraction. This devastating K-linked muscle wasting disease has no specific treatment. Affecting 1 in 3500 male births, DMD accounts for 80% of all cases of muscular dystrophy. Dystrophic muscle undergoes myopathy (cell membrane damage in muscle fiber), leading to loss of ambulation at a very early age, with subsequent respiratory muscle weakness and cardiac failure. In pediatric subjects, skeletal muscle weakness starts 3-5 years from onset, progressive weakness occurs, with wheelchair dependency at approximately 13 years from onset. Importantly, cardiomyopathy is observed to take hold in ⅓ of patients from less than 13 years from onset, increasing to ½ of patients less than 18 years from onset, and in all patients after 18 years. Heart failure resulting from and/or secondary to DMD (HF-DMD), particularly at later stages, presents significant exclusionary comorbidities, wherein cell, tissue, heart or mechanical transplantation may not be an option for late stage heart failure with over symptomatic or advanced heart failure (HF). Patients may further suffer from smooth muscle myopathy including vascular dysfunction, further including gastrointestinal and urinary tract systems involvement. Common prognosis is death from respiratory insufficiency or cardiomyopathy.

Underlying these clinical features is a dystrophin gene mutation (deletion) wherein loss of dystrophin results in cellular membrane damage and leakage of extracellular $Ca^{2+}$ into the cell. Elevated intracellular calcium levels ultimately result in increased oxidative and/or nitrosative stress and inflammation, and activation of calpain. The combination of these effects results in muscle proteolysis and apoptosis, leading to the degradative features described above. Current treatment is limited to the use of corticosteroids, and cardioprotective medications to ease the effects of the disease, but does not treat or slow down the progression of the disease itself. Accordingly, there still exists a great need in the art for treatments, including pediatric subjects where early intervention would ward off emergence of late stage comorbidities.

SUMMARY

Described herein are methods of treating a dystrophinopathy and/or one or more disease states associated therewith, by administering a therapeutically effective amount of cardiosphere-derived cells (CDCs), exosomes derived from CDCs (CDC-XOs), and/or combinations thereof to a patient suffering from a dystrophinopathy and/or a disease state associated therewith. In some embodiments, the dystrophinopathy is one or more of Duchenne's muscular dystrophy (DMD) and/or Becker muscular dystrophy. In some embodiments, the disease state that is treated is a skeletal myopathy (e.g., skeletal DMD or skeletal Becker muscular dystrophy). In some embodiments, administration of CDCs and/or CDC-XOs delays the onset of muscular dysfunction (including in skeletal muscle dysfunction) and/or maintains, improves, and/or restores muscular function and integrity (including in skeletal muscles) in the subject having a dystrophinopathy. In some embodiments, dystrophic skeletal muscles of the patient that are treated include one or more of the diaphragm, the limb muscles (e.g., in the arms and/or legs), and/or torso muscles.

For brevity, several embodiments are disclosed with reference to CDC-XOs and CDCs specifically. It should be understood, however, that one or more of the treatments disclosed herein can be achieved with extracellular vesicles derived from CDCs (referred to herein as CDC-EVs, which may include CDC-derived microvesicles (CDC-MVs)), the isolated molecular cargo of CDC-XOs or CDC-EVs, and combinations thereof. Thus, in some embodiments, the methods of treatment described herein can be performed using one or more of CDC-MN, CDCs, CDC-EVs, isolated and/or purified molecular cargo of CDC-XOs, isolated and/or purified molecular cargo of CDC-EVs, and/or combinations thereof.

In some embodiments, the methods of treatment comprise administering to the subject (e.g., a patient suffering from dystrophinopathy or a disease state associated therewith) a therapeutically effective amount of CDCs, CDC-XOs, and/or CDC-EVs. In some embodiments, the CDCs, CDC-XOs, and/or CDC-EVs are autologous or allogeneic to the subject (e.g., derived from their own tissue, from another subject's tissue, and/or from the tissue of another animal species). In some embodiments, the methods of treatment comprise administering to the subject a therapeutically effective amount of molecular cargo from CDC-XOs and/or CDC-EVs (including CDC-derived microvesicles (CDC-MVs)). In some embodiments, molecular cargo of CDC-MN or CDC-EVs is isolated and/or synthesized and that molecular cargo particular molecules and/or combinations of different molecules, including RNA polynucleotides and/or short non-coding RNAs) is administered to the subject in need thereof (e.g., a subject having a dystrophinopathy and/or a disease state thereof). In some embodiments, the method of treatment comprises administering to the subject a therapeutically effective amount of an isolated RNA polynucleotide or a vector encoding (and/or containing) a RNA polynucleotide found in CDC-XOs and/or CDC-EVs.

In some embodiments, the CDCs, CDC-EVs, and/or CDC-XOs are delivered to the subject systemically. In some embodiments, the CDCs, CDC-EVs, and/or CDC-XOs are delivered to the subject systemically and locally. In some embodiments, the CDCs, CDC-EVs, and/or CDC-XOs are delivered to the subject systemically but not locally. In some embodiments, the CDCs, CDC-EVs, and/or CDC-XOs are delivered to the subject systemically locally. In some embodiments, the CDCs, CDC-EVs, and/or CDC-XOs are delivered to the subject locally but not systemically. In some embodiments, non-limiting examples of a methods to administer a therapeutically effective amount of CDCs, CDC-EVs, and/or CDC-XOs include systemic administration intravenous, intra-arterial, intraventricular, intra-aortic, and/or intraperitoneal injection and/or infusion). In some embodiments, the CDCs, CDC-EVs, and/or CDC-XOs are injected or infused intravenously. In some embodiments, a therapeutically effective amount of CDCs, CDC-EVs, and/or CDC-XOs is administered to a patient by intramuscular injection and/or infusion. In some embodiments, a therapeutically effective amount of CDCs, CDC-EVs, and/or CDC-XOs is administered to a patient by infusion directly at a local site (e.g., into or near a dystrophic skeletal muscle and/or a target site where treatment is desired). In some embodiments, an effective amount of CDCs, CDC-EVs, and/or CDC-XOs is delivered systemically via injection and/or infusion at an area of the body that is not in the heart. In some embodiments, the intravenous administration of CDCs, CDC-EVs, and/or CDC-XOs includes jugular and/or femoral vein injection and/or infusion.

In some embodiments, the administration of CDCs, CDC-EVs, and/or CDC-XOs to a subject in need thereof includes a single dose and/or multiple doses (e.g., 2, 4, 6, 8, 10, or more doses). In some embodiments, where multiple doses are used, the administration of CDCs, CDC-EVs, and/or CDC-XOs is performed daily, weekly, biweekly, every three weeks, monthly, every six months, or every year. In some embodiments, the dosing schedule is performed over a period of, for example, 2 weeks, 1 month, 2 months, 3 months, 5 months, 6 months, a year, 5 years, or ranges including and/or spanning the aforementioned, values. For illustration, in some embodiments, the interval includes the administration of 2-10 doses at intervals of 1-5 months. In some embodiments, the dosing schedule is 3 doses with about 3 months between each dose. In some embodiments, the dosing schedule is 5 doses with about 1 week separating each dose. In some embodiments, the dosing schedule is 3 administrations (e.g., 3 single doses at different times) at weeks 0, 6 and 9. In some embodiments, an interval schedule is used, where there are periods of dosing and periods of rest between dosing periods (e.g., weekly doses for a month followed by a rest period of 5 months, followed by weekly doses for a month and so on). In some embodiments, a single dose comprises a therapeutically effective amount of CDCs, CDC-XOs, and/or CDC-EVs. In some embodiments, the dosing periods and/or interval schedule is performed throughout the life of the patient. In some embodiments, multiple administrations of each single dose are provided to the subject. In various embodiments, as disclosed elsewhere herein, the administration can be in repeated doses, such as two, three, four, four or more sequentially-applied doses.

In some embodiments, a therapeutically effective amount of CDCs includes at least about $75 \times 10^6$ to $500 \times 10^6$ CDCs. In some embodiments, a therapeutically effective amount of CDCs includes greater than or equal to about: $75 \times 10^6$ CDCs, $150 \times 10^6$ CDCs, $300 \times 10^6$ CDCs, $400 \times 10^6$ CDCs, $500 \times 10^6$ CDCs, or ranges including and/or spanning the aforementioned values. In some embodiments, a therapeutically effective amount of CDCs includes less than or equal to about: $75 \times 10^6$ CDCs, $150 \times 10^6$ CDCs, $300 \times 10^6$ CDCs, $400 \times 10^6$ CDCs, $500 \times 10^6$ CDCs, or ranges including and/or spanning the aforementioned values.

In some embodiments, the number of CDC-EVs or CDC-XOs administered in each dose (where a single or multiple doses are used) and/or over the course of a treatment regimen is equal to or at least about: $1 \times 10^6$, $1 \times 10^7$, $1 \times 10^8$, $1 \times 10^9$, $1 \times 10^{10}$, $1 \times 10^{11}$, $1 \times 10^{12}$, or ranges including and/or spanning the aforementioned values. In some embodiments, the quantities of CDC-EVs or CDC-XOs administered in each dose (where a single or multiple doses are used) and/or over the course of a treatment regimen ranges from $1 \times 10^6$ to $1 \times 10^7$, $1 \times 10^7$ to $1 \times 10^8$, $1 \times 10^8$ to $1 \times 10^9$, $1 \times 10^9$ to $1 \times 10^{10}$, $1 \times 10^{10}$ to $1 \times 10^1$, $1 \times 10^1$ to $1 \times 10^{12}$, $1 \times 10^{12}$ or more.

In some embodiments, the number of CDC-XOs (or CDC-ESV) delivered to the subject in a dose (or dosing regimen) is determined based on the number of CDCs that would be used in a clinically effective dose in a cell-based therapy method. For example, in some embodiments, where $75-500 \times 10^6$ CDCs is an effective dose for therapeutic treatment of skeletal myopathy, using the equivalent amount of CDC-XOs or CDC-MVs that would be released by those CDCs in vivo would be administered to a patient in a "cell-free" method of treatment. In other words, CDC equivalent doses of CDC-XOs and/or CDC-MVs can be used. As an illustration, in some embodiments, 3 mL/$3 \times 10^8$ CDCs, is capable of providing therapeutic benefit. Therefore, a plurality of CDC-XOs as would be derived from that number of CDCs over the time course of those CDCs' residence in the body is used. In some embodiments, the amount of CDC-XOs or CDC-EVs delivered to the patient is the amount of CDC-XOs or CDC-EVs that would be released via an injection of equal to or at least about: $75 \times 10^6$ CDCs, $150 \times 10^6$ CDCs, $300 \times 10^6$ CDCs, $400 \times 10^6$ CDCs, $500 \times 10^6$ CDCs, or ranges including and/or spanning the aforementioned values. In some embodiments, the number of CDCs administered in any single dose is $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$ (or ranges including and/or spanning the aforementioned values). In some embodiments, the amount of CDC-XOs or CDC-EVs delivered to the patient is the amount of CDC-XOs or CDC-EVs that would be released via an injection of equal to or at least about: $1 \times 10^5$ CDCs. $1 \times 10^6$ CDCs, $1 \times 10^7$ CDCs, $1 \times 10^8$ CDCs, $1 \times 10^9$ CDCs, $1 \times 10^{10}$ CDCs, $1 \times 10^{11}$ CDCs, $1 \times 10^{12}$ CDCs, or ranges including and/or spanning the aforementioned values. In some embodiments, a dose of CDCs ranges between about 10 and 90 million CDCs, including about 10 to about 20 million, about 20 to about 30 million, about 30 to about 50 million, about 50 to about 60 million, about 60 to about 70 million, about 70 to about 75 million, about 75 million to about 80 million, about 80 million to about 90 million, and ranges including and/or spanning the aforementioned values. Some such does are particularly favorable for coronary delivery. In several embodiments, the dose of CDCs ranges from about 30 million to about 1.5 billion CDCs, including about 30 million to about 45 million, about 40 million to about 50 million, about 50 million to about 50 million, about 60 to about 75 million, about 75 to about 1 billion, about 90 million to about 1.1 billion, about 1 billion to 1.25 billion, about 1.25 billion to about 1.5 billion, and ranges including and/or spanning the aforementioned values. Without being bound to a particular theory, when injected, it is believed that CDCs are transient residents in the subject. Depending on the embodiment, the degree of CDC retention varies. For example, in several embodiments, the retention rate is between about 0.01% and 10%, including about 0.01% to about 0.05%, about 0.05% to about 0.1%, about 0.1% to about 0.5%, about 0.5% to about 1.0%, about 1.0% to about 2.5%, about 2.5% to about 5%, about 5% to about 10%, and ranges including and/or spanning the aforementioned values. Thus, in some embodiments, the equivalent amount of CDC-XOs or CDC-EVs delivered to the patient is calculated as the amount of CDC-XOs or CDC-EVs that would be released via an administration (e.g., injection or infusion) of the disclosed amounts CDCs over a given time of CDC residence in the body of about 1 week, about 2 weeks, about 3 weeks, or more. In certain instances, the dosage may be prorated to body weight (range 100,000-1M CDCs/kg body weight total CDC dose). In some embodiments, for injection into the heart, the number of administered CDCs includes 25 million CDCs per coronary artery (i.e., 75 million CDCs total) as another baseline for XO or EV dosage quantity.

In some embodiments, the CDC, CDC-XO, and/or CDC-EV quantity delivered to the patient (e.g., the dose) may be measured by weight (in mg) of CDCs, CDC-XOs, and/or CDC-EVs (e.g., where the solution and/or milieu surrounding the CDCs, CDC-XOs, and/or CDC-EVs has been removed or substantially removed). For instance, in some embodiments, a dose of CDCs, CDC-MN, and/or CDC-EVs may comprise equal to or at least about the following weights in mg: about 0.001 to about 0.005, about 0.005 to about 0.01, about 0.01 to about 0.05, about 0.05 to about 0.1, about 0.1 to about 0.5, about 0.5 to about 1, about 1 to about 10, about 10 to about 25, about 25 to about 50, about 50 to about 75, about 75 to about 100, or ranges including and; or spanning the aforementioned values. As discussed in additional detail herein, those masses are representative, of the number of CDCs, CDC-XOs or CDC-EVs that are dosed to a subject, depending on the embodiment. For example, in several embodiments, the number of CDCs in a dose can range from about $5 \times 10^4$ to about $2 \times 10^9$, including about $5 \times 10^4$ to about $1 \times 10^5$, about $1 \times 10^5$ to about $2.5 \times 10^5$, about $2.5 \times 10^5$ to about $1 \times 10^6$, about $1 \times 10^6$ to about $1 \times 10^7$, about $1 \times 10^7$ to about $1 \times 10^8$, about $1 \times 10^8$ to about $1 \times 10^9$, about $1 \times 10^9$ to about $2 \times 10^9$, about $2 \times 10^9$ to about $5 \times 10^9$, and ranges including and/or spanning the aforementioned values. Likewise, depending on the embodiment, the number of exosomes or particles (e.g., vesicles) dosed to a subject can range from about $1 \times 10^9$ to about $2 \times 10^{14}$, including about $1 \times 10^9$ to about $2 \times 10^9$, about $2 \times 10^9$ to about $4 \times 10^9$, about $4 \times 10^9$ to about $1 \times 10^{10}$, about $1 \times 10^{10}$ to about $1 \times 10^{11}$, about $1 \times 10^{11}$ to about $1 \times 10^{12}$, about $1 \times 10^{12}$ to about $2 \times 10^{12}$, about $2 \times 10^{12}$ to about $2 \times 10^{13}$, about $2 \times 10^{13}$ to about $1 \times 10^{14}$, about $1 \times 10^{14}$ to about $2 \times 10^{14}$, and ranges including and/or spanning the aforementioned values. In some embodiments, the CDC, CDC-XO, and/or CDC-EV quantity delivered to the patient may be measured by protein weight (in mg) and/or by total cell or vesicle weight (e.g., where water has been removed from the area outside the cells or vesicles). In some embodiments, the CDC, CDC-XO, and/or CDC-EV quantity delivered to the patient is equal to 1-10, 10-25, 25-50, 50-75, 75400, or 100 or more mg protein. In some embodiments, administering a therapeutically effective amount of a composition includes about 1 to about 100 mg XO and/or EV protein in a single dose.

In some embodiments, a formulation or a composition comprising CDCs, CDC-EVs, and/or CDC-XOs is provided. In some embodiments, the formulation and/or composition includes a pharmaceutically acceptable carrier. In some embodiments, the carrier is water at physiologic pH and/or isotonicity. In some embodiments, the formulation or composition is used in the treatment of dystrophinopathy (e.g., skeletal muscular dystrophy, dystrophic cardiomyopathy, etc.) according to the aforementioned methods. In some embodiments, the formulation or composition is used to effectively and/or safely treat dystrophinopathy in a subject in need thereof wherein a formulation and/or composition comprising a therapeutically effective amount of CDCs, CDC-EVs, and/or CDC-XOs is delivered to a targeted dystrophic skeletal muscle.

In some embodiments, as disclosed elsewhere herein, method of treatment is for a subject (e.g., patient) afflicted with myopathy. In some embodiments, the muscle myopathy includes one or more of cell membrane degradation, interstitial inflammation, fatty replacement, and fibrosis, one or more of which is treated and/or substantially alleviated during the treatment as disclosed herein.

In some embodiments, as disclosed elsewhere herein, method of treatment is for a subject (e.g., patient) afflicted with cardiomyopathy. In some embodiments, the subject is afflicted with cardiomyopathy, but not heart failure. In some embodiments, the subject is diagnosed with cardiomyopathy. In some embodiments, the subject is diagnosed with cardiomyopathy, but not heart failure. In some embodiments, the cardiomyopathy includes one or more of left ventricle posterobasal fibrosis, conduction abnormalities that are intra-atrial, including SVT with abnormal AV nodal conduction, one or more of which is treated and/or substantially alleviated by the treatment as disclosed herein. In various embodiments, cardiomyopathy includes advanced stages of ventricle enlargement, dyspnea, peripheral edema and liver enlargement, one or more of which is treated and/or substantially alleviated by the treatment as disclosed herein. In various embodiments, heart failure (HF) includes asymptomatic abnormalities in cardiac structure and function wherein heart function is depressed (stage B), overt symptomatic HF (stage C), to advanced HF (stage D), one or more of which is treated and/or substantially alleviated by the treatment as disclosed herein.

In various embodiments, subject is afflicted with skeletal muscle myopathy smooth muscle myopathy including vascular dysfunction, further including GI and urinary tract systems involvement. In some embodiments, one or more of these disease states is treated and/or substantially alleviated by the methods as disclosed elsewhere herein. In some embodiments, the myopathy includes one or more of cell membrane degradation, interstitial inflammation, fatty replacement, and fibrosis, one or more of which is treated and/or substantially alleviated by the treatment as disclosed herein.

In some embodiments, treatment of the subject further includes assessing functional improvement in the subject, including functional improvement in skeletal muscle tissue. In some embodiments, the methods disclose herein result in functional improvement of muscle tissue. In some embodiments, the methods disclose herein result in functional improvement in, for example, voluntary muscle contraction. In some embodiments, the functional improvement includes one or more of increased contractile strength, improved ability to walk, improved ability to stand from a seated position, improved ability to sit from a recumbent or supine position, and improved manual dexterity such as pointing and/or clicking a mouse. In some embodiments, treatment of the subject further includes assessing cognition in response to treatment of neural damage, blood-oxygen transfer in response to treatment of lung damage, and immune function in response to treatment of damaged immunological-related tissues.

In some embodiments, said subject in need of treatment for dystrophinopathy is a human subject. In some embodiments, the human subject is a pediatric subject at the age of less than or equal to about: 3, 8, 11, 12, 15, 18, or ranges including and/or spanning the aforementioned values. In some embodiments, the human subject is a pediatric subject at the age, for example, about 3 to about 11 years old, or about 12 to about 18 years old. In some embodiments, the subject is categorized by one or more of the above characteristics, such as one of the recited age groups, and/or is afflicted and/or diagnosed with one or more of the above disease states (e.g., myopathy, cardiomyopathy and/or heart failure). In some embodiments, the patient suffers from one or more of the disease states disclosed above, but not others. For example, a subject that is 3-11 years old, afflicted with and/or diagnosed with cardiomyopathy, but not heart failure. As another illustration, the subject may be 8-15 years old and afflicted with skeletal muscle myopathy but not cardiomyopathy or heart failure.

In some embodiments, as disclosed elsewhere herein, infusion can be intra-arterial or intravenous. The arteries and veins can include those in a limb, in the torso (e.g., at or around the lung), the neck, etc. In some embodiments, infusion delivers a therapeutically effective dose of CDC-XOs, CDC-EVs, and/or CDCs to one or more locations in the body locations at the infusion site or away from the infusion site). In some embodiments, infusion delivers a therapeutically effective dosage of exosomes to smooth or skeletal muscle tissue, in some embodiments, administering a therapeutically effective amount of a composition includes injection. In some embodiments, the injection includes injection into the heart, including intramyocardial injection, cavities and chambers of the heart, vessels associated thereof. In some, embodiments, injection into the heart, cavities and chambers of the heart, vessels associated thereof, is capable of delivering a therapeutically effective dosage of exosomes to smooth or skeletal muscle tissue. In some embodiments, injection results in and/or is performed to achieve systemic delivery. In some embodiments, injection delivers a therapeutically effective dose of CDC-XOs, CDC-EC's, and/or CDCs to one or more targeted locations in the body (e.g., locations that may be at the injection site or away from the injection site). In some embodiments, the injection includes skeletal muscle injection (into the skeletal muscle). In some embodiments, the injection includes intraperitoneal injection. In some embodiments, the injection includes percutaneous injection.

According to several embodiments, there are provided herein methods of treating muscular dystrophy (e.g., a dystrophinopathy) in a subject in need thereof, the method comprising administrating to the subject a therapeutically effective amount of cardiosphere-derived cells (CDCs). In several embodiments, there are also provided methods of treating cardiomyopathy in a subject in need thereof, the method comprising systemically administering to the subject a therapeutically effective amount of CDCs. In several embodiments, the cardiomyopathy is dystrophic cardiomyopathy, with some embodiments, wherein the dystrophic cardiomyopathy is heart failure secondary to a chronic muscular dystrophy. In several embodiments, the methods employ exosomes derived from CDCs, in place of, or in addition to CDCs themselves. In several embodiments, methods of treating a dystrophinopathy are provided, the methods, comprising administering a therapeutically effective amount of exosomes to a pediatric subject afflicted with a dystrophinopathy, thereby treating the subject. In several embodiments, the plurality of the exosomes is isolated from cardiosphere-derived cells (CDCs) grown in serum-free media. In several embodiments, there are provided methods of treating a dystrophic skeletal muscle, comprising administering cardiosphere-derived cells (CDCs) and/or CDC-derived exosomes (CDC-XOs) to a subject afflicted with a dystrophinopathy, thereby treating the dystrophic skeletal muscle, wherein the CDCs and/or CDC-XOs are administered to the subject at a site that is not the heart and wherein the dystrophic skeletal muscle is a targeted dystrophic skeletal muscle and wherein the targeted dystrophic skeletal muscle receives a therapeutically effective amount of CDCs and/or CDC-XOs. In one embodiment, there is provided a method of treating skeletal muscular dystrophy in a subject in need thereof, the method comprising administering to the subject a first dose of a composition comprising a therapeutically effective amount of cardiosphere-derived cells (CDCs), wherein the therapeutically effective amount of the first dose ranges from about $1\times10^7$ to about $1\times10^9$ CDCs, waiting a first period of time after administration of said first dose, wherein said first period of time is between about 1 and 6 months, administering to the subject a second dose of a composition comprising a therapeutically effective amount of CDCs, wherein the therapeutically effective amount of the second dose ranges from about $1\times10^7$ to about $1\times10^9$ CDCs, waiting a second period of time after administration of said second dose, wherein said second period of time is between about 1 and 6 months, administering to the subject at least one additional dose of a composition comprising a therapeutically effective amount of CDCs, wherein the therapeutically effective amount of the at least one additional dose ranges from about $1\times10^7$ to about $1\times10^9$ CDCs, waiting at least one additional period of time after administration of said at least one additional dose, wherein said second period of time is between about 1 and 6 months, wherein said administrations result in an improvement in exercise capacity or muscle function, wherein said CDCs are allogeneic with respect to said subject, wherein said administrations do not induce a significant immune response in the subject, and wherein said administrations comprise systemic administration. In several embodiments, the administration of CDCs (one or more times) alters expression of one or more markers of T cell activation or proliferation, the markers comprising CD69 and/or HLA-DR.

In several embodiments, the therapeutically effective amount of CDCs is sufficient to treat a dystrophic skeletal muscle of the subject, which according to some embodiments, is afflicted by Duchenne muscular dystrophy (DMD) or Becker muscular dystrophy, each involving dystrophinopathy of a skeletal muscle. Any skeletal muscle may be affected, however, according to several embodiments, the dystrophic skeletal muscle is a skeletal muscle of the diaphragm, the arm, or the leg.

Administration routes can vary, depending on the embodiment. For example, in several embodiments, the CDCs are administered to the subject via intramuscular injection at a dystrophic skeletal muscle a local administration). In several embodiments, the CDCs are administered to the subject systemically, of which several routes are optional. For example, in several embodiments, systemic administration is via intravenous injection or infusion. In several embodiments, systemic administration via injection into the right ventricle, whereas in additional embodiments, systemic administration is via injection into the left ventricle.

In some embodiments, administration of the CDCs is via a single dose, while in some embodiments, two or more doses are administered. In several embodiments, with multiple doses, the doses are given at intervals of about 3 weeks to about three months, for example, about 3-4 weeks, 4-5 weeks, 5-6 weeks, 6-8 weeks, 8-12 weeks, or any time there between, including endpoints. In several embodiments, the subsequent doses are given at 6 and 12 weeks after an initial CDC dose is administered. Depending on the embodiment, the number of CDCs and/or the location of administration can vary over the repeated doses. Alternatively, the dosing regimen can use constant CDC numbers and locations across a regimen.

By way of example, the methods disclosed herein can employ dose (e.g., a therapeutically effective amount of CDCs) of at least, about $75 \times 10^6$ CDCs. More specifically, in several embodiments, the dose is at least about $150 \times 10^6$ CDCs, at least about $300 \times 10^6$ CDCs, at least about $350 \times 10^6$ CDCs, at least about $400 \times 10^6$ CDCs, at least about $450 \times 10^6$ CDCs, at least about $500 \times 10^6$ CDCs, at least about $550 \times 10^6$ CDCs, at least about $600 \times 10^6$ CDCs, or any number there between. In those embodiments employing exosomes, some embodiments, comprise a dose of about 1 to about 100 mg exosome protein in a single dose.

In several embodiments the CDCs or exosomes are allogeneic with respect to the subject receiving the CDCs.

In several embodiments, the administration of CDCs or exosomes results in increased dystrophin expression (e.g., increased over 'normal' dystrophin expression, for example a control population or an earlier time point in a disease). In several embodiments, the increase in dystrophin is detectable in for example, the skeletal muscle and/or the diaphragm.

In several embodiments, the methods further comprise administering (e.g., separately or co-administering) a steroid with the CDCs.

In several embodiments, the methods, uses and compositions disclosed herein result in an improvement in muscle function, or a decrease in muscle fibrosis or tissue damage. In several embodiments, the improvements are with respect to skeletal muscle. In some embodiments, improvements are with respect to cardiac muscle.

Also provided herein is the use of a composition comprising CDCs and/or CDC-exosomes, wherein the composition is suitable for systemic administration to a subject having a muscular dystrophy, and wherein the administration of the composition treats said muscular dystrophy (e.g., skeletal muscle is treated).

Further provided, in several embodiments, is a composition comprising an isolated RNA polynucleotide derived from a CDC, a CDC-XO, or a CDC-derived extracellular vesicle (CDC-EV) or a vector encoding the RNA polynucleotide, wherein the RNA polynucleotide comprises a short non-coding RNA. In several embodiments, the RNA polynucleotide sequence comprises at least about 80%, 85%, 90%, 95%, 96%, 97%. 98%, or 99% percentage identity to short non-coding RNA from DMD (srDMD). In several embodiments, the short non-coding RNA comprises srDMD. In several embodiments, the short non-coding RNA comprises a microRNA. Depending on the embodiment, the microRNA may comprise GCG on the 5' end or 3' end. In several embodiments, the RNA polynucleotide comprises at least about 80%, 85%, 90%, 95%, 96%, 97%, 98%, 99% percentage identity to miR-148a. In one embodiment, the microRNA comprises miR-148a. In several embodiments, the vector is a virus (e.g., a parvovirus, a retrovirus, lentivirus, etc.). In one embodiment, the adenovirus or adeno-associated virus.

In some embodiments, the methods disclosed herein achieve one or more desired patient outcomes. In some embodiments, the treatment of a subject results in an increase in dystrophin expression. In some embodiments, increase in dystrophin expression occurs in skeletal muscle. In some embodiments, the increase in dystrophin expression in the skeletal muscles includes skeletal muscle in limbs (e.g., the arms or legs), such as a soleus muscle. In some embodiments, the increase in dystrophin expression occurs in the diaphragm. In some embodiments, treatment of the subject results in decreased fibrosis, decreased inflammation, and/or increased mitochondrial function. In some embodiments, decreased fibrosis includes a reduction in collagen accumulation. In some embodiments, collagen includes collagen I and/or collagen III. In some embodiments, decreased inflammation includes an increase in cytoplasmic nuclear factor (erythroid-derived 2)-like 2 (Nrf2), reduction in fatty acid peroxidation end products, reduced numbers of inflammatory cells, and/or upregulated expression of antioxidants. In some embodiments, upregulated antioxidants include one or more of hems, oxygenase-1 (HO-1), catalase, superoxide dismutase-2 (SOD-2), and glutamate-cystein ligase catalytic (GCLC) subunit. In some embodiments, down regulated inflammatory cells include CD68+ macrophages and CD3+ T-cells. In some embodiments, increased mitochondrial function includes increased mitochondrial ultrastructure and/or increased mitochondrial biogenesis. In some embodiments, increased mitochondrial function includes increased nuclear PPAR-γ co-activator-1 (PGC-1) expression.

In some embodiments, as disclosed elsewhere herein, therapeutic compositions comprising one or more isolated components of the molecular cargo of CDC-XOs are used in the methods disclosed herein. In some embodiments, the therapeutic compositions comprise CDC-XO RNAs. In some embodiments, the RNAs can be isolated from CDCs, CDC-XOs, and/or CDC-MVs and re-combined (e.g., mixed and matched) to provide therapeutic mixtures for use in methods of treatment as disclosed elsewhere herein. In some embodiments, a therapeutic mixture of RNA can include a single RNA or multiple RNAs (e.g., 2, 3, 4, 5, 6, 7, 8, 9, 10 or more RNAs), including non-coding RNAs. In some embodiments, the non-coding RNAs include tRNAs, Y RNAs, rTNAs, mirRNAs, lncRNAs, piRNAs, snRNAs, snoRNAs, further including fragments thereof, among others. In some embodiments, the therapeutic mixture includes one or more microRNAs selected from the group consisting of: microRNAs miR 146a, miR-148a, miR-22, miR-24, miR-210, miR-150, miR-140-3p, miR-19a, miR-27h, miR-19b, miR-27a, miR-376c, miR-128, miR-320a, miR-143, miR-21, miR-130a, miR-9, miR-185, miR-23a, miR-215, miR-33a, miR 204, miR-376c, miR4532, miR-4742, miR-582, miR-223, miR-3125, miR-3677, miR-376h, miR-4449, miR-4773, miR-4787, miR-491, miR-495, miR-500a, miR-548ah, miR-550, miR-548ah, miR-550a, miR-551n, miR- 5581, miR-616, or any other microRNAs depicted as enriched in FIG. 29, and/or a polynucleotide having at least about 80%, 85%, 90%, 95%, 96%, 97%, 98%, or 99% percentage identity to any of the foregoing. In some embodiments, the therapeutic mixture can include one or more of miR-148a, miR-148-5p, miR-148-39, srDMD, and/or a polynucleotide having at least about 80%, 85%, 90%, 95%, 96%, 97%, 98%, or 99% percentage identity to any of the foregoing. In some embodiments, the therapeutic mixture microRNA includes miR-148a-3p, and/or a polynucleotide having at least about 80%, 85%, 90%, 95%, 96%, 97%, 98%, or 99% percentage identity to any of the foregoing. In some embodiments, the microRNA includes miR-148a-3p, and/or a polynucleotide having at least about 80%, 85%, 90%, 95%, 96%, 97%, 98%, or 99% percentage identity to any of the foregoing. In various embodiments, the exosomes include a small non-coding RNA from DMD, srDMD, and/or a polynucleotide having at least about 80%, 85%, 90%, 95%, 96%, 97%, 98%, or 99% percentage identity to any of the foregoing.

In some embodiments, the methods as disclosed s w herein, can be accomplished using non-coding RNAs isolated from CDC-XOs. \ out being bound to a particular theory, it is believed that non-coding RNAs appear to be well-suited for regulatory roles that require highly specific nucleic acid recognition, including short non-coding RNA genes have been identified and designated as microRNAs. In some embodiments, the isolated RNA polynucleotide is selected from one or more of miR-148a, miR-148-5p, miR-148-39, srDMD, and/or a polynucleotide having at least about 80%. 85%, 90%, 95%, 96%, 97%, 98%, or 99% percentage identity to miR-148a, miR-148-5p, miR-148-39, or srDMD. In some embodiments, the nucleotide sequence of miR-148a is:

(SEQ ID NO: 1)
5'GAGGCAAAGUUCUGAGACACUCCGACUCUGAGUAUGAUAGAAGUCAGU

GCACUACAGAACUUUGUCUC3';

the nucleotide sequence of miR-148-5p is:

(SEQ ID NO: 2)
5'AAAGUUCUGAGACACUCCGACU3';

the nucleotide sequence of miR-148-3p is:
5'UCAGUGCACUACAGAACUUUGU3' (SEQ ID NO: and the nucleotide sequence of srDMD is:

(SEQ ID NO: 4)
5'UGUACACAGAGGCUGAUCGAUCGAUUCUCCCUGAACAGCCUAUUACGG

AGGCACUGCAGAUCAAGCCCGCCUGGAGAGGUGGAGUUUCAAGAGUCCCU

UCCUGGUUCACCGUCUCCUUU3'.

In some embodiments, the one or more isolated components of the molecular cargo of CDCs, CDC-XOs, and/or CDC-MV's are delivered to the cell using viral or non-viral vectors. In some embodiments, the vector is a virus. In various embodiments, the virus is adenovirus or adeno-associated virus.

In some embodiments, a formulation or a composition comprising miR-148a, miR-148-5p, miR-148-39, srDMD, and/or a polynucleotide having at least about 80%, 85%, 90%, 95%, 96%, 97%, 98%, or 99% percentage identity to miR-148a, miR-148-5p, miR-148-39, or srDMD, for use in the treatment of skeletal muscular dystrophy and/or dystrophic cardiomyopathy according to the aforementioned method of effectively and/or safely treating dystrophinopathy in a subject in need thereof. In some embodiments, a use of the aforementioned formulation and/or composition for treating skeletal muscular dystrophy and/or dystrophic cardiomyopathy according to the aforementioned methods of effectively and/or safely treating dystrophinopathy in a subject in need thereof are provided.

In some embodiments, the CDCs are generated from a biopsy sample cultured into an explant, further cultured into an explant derived cell, additionally cultured as cardiosphere forming cells, thereafter cultured as cardiospheres, and subsequently cultured as CDCs from which XOs and EVs are isolated. In some embodiments, the CDCs are human. In various embodiments, the CDCs are generated from a biopsy sample obtained the subject afflicted with dystrophinopathy. In some embodiments, the CDCs are cultured under hypoxic conditions (e.g., 2% 02) for a period of about 24 hours. In some embodiments, the CDCs are cultured under serum-free conditions.

BRIEF DESCRIPTION OF THE DRAWINGS

FIGS. 1A-J, CDC transplantation into mdx hearts. Function, survival, antioxidant pathways, inflammation, mitochondrial dysfunction and dystrophin expression improved by CDC transplantation into mdx mice. FIG. 1A: Ejection fraction (EF) in CDC-injected mdx mice (Mdx+CDC) and vehicle-injected mdx mice (Mdx+Vehicle) in response to injections at baseline (10 months of age) and 3 months later (CTL: n=7; Mdx+Vehicle & Mdx+CDC: n=12 each). FIG. 1B: Exercise capacity in mice subjected to weekly high-intensity treadmill exercise, starting 3 weeks after single-dose CDC or vehicle administration (CTL: n=7; Mdx+Vehicle & Mdx+CDC: n=11 each). Cardiac and treadmill experiments were performed separately on different groups of experimental mice. FIG. 1C: Kaplan-Meier analysis of survival in the same animals as FIG. 1C shows lower survival in vehicle-treated. Inch mice than in CDC-treated mix mice or wild-type controls ($p<0.001$, log rank test); the latter two groups, however, were statistically comparable. FIG. 1D: Immunohistochemical images of Nrf2 in mdx mouse hearts 3 weeks after administration of vehicle or CDCs. Age-matched wild-type mice (CTL) served as control. The hearts are stained for inflammatory cell markers CD68, CD20, and CD3. Black arrows point to $CD68^+$ (upper row), $CD20^+$ (middle row), and $CD3^+$ (lower row) cells. FIG. 1E: Malondialdehyde protein adducts in mdx mouse hearts 3 weeks after administration of vehicle or CDCs (WT, n=4; Mdx+vehicle, n=6; and Mdx+CDC, n=6). FIG. 1F: Western blots and pooled data for protein abundance of phospho-Akt ($Akt-p^{T308}$, $Akt-p^{S473}$), cytoplasmic phospho-Nrf2 ($Nrf2-p^{S40}$), and nuclear Nrf2. FIG. 1G; Western blots and pooled data for protein abundance of nuclear p65, p-IκB (NE-κB pathway) in mdx mouse hearts. FIG. 1H: Western blots and pooled data for protein abundance of Nrf2 downstream gene product, heme oxygenase-1 (HO-1). FIG. 1I: Western blots, pooled data, and bar graph representing protein abundance of MCP1 (monocyte chemoattractant protein1) and average number of indicated inflammatory cells and in mdx mouse hearts. FIG. 1J: Immunohistochemical images of Nrf2 in mdx mouse hearts 3 weeks after administration of vehicle or CDCs. Pooled data are means±SEM; CM: cardiomyocytes; *$p<0.05$; #$p<0.005$; †$p<0.05$; ‡$p<0.002$; scale bars: 10 μm.

FIG. 2A: Transmission electron microscopy (TEM) images from mdx mouse hearts 3 weeks after administration of vehicle or CDCs. Age-matched WT mice served as control. Scale bars: 5 µm. Mitochondrial structures displayed a clear restoration of organized structure. FIG. 2B: Western blots and pooled data for mitochondrial respiratory chain subunits in WT and vehicle/CDC mdx heart tissues and oxygen consumption rate (OCR) of mitochondria isolated from the hearts of WT and CDC- or vehicle-treated mdx mice 3 weeks after treatment (WT, n=3; Mdx+vehicle and Mdx+CDC, n=8 each). Substrates (pyruvate, malate, and ADP), a selective uncoupler (FCCP) and blockers (oligomycin; anti mycin and rotenone) of oxidative phosphorylation were applied when indicated, FIGS. 3A-B. Repopulation with stable competent mitochondria. FIG. 3B: Numbers of mitochondria from TEM images, wherein the same mitochondrial number between groups existed, and mitochondrial DNA copy numbers per nuclear genome in mdx heart tissue.

FIG. 4A: Diminished cardiac fibrosis. Representative Masson trichrome images of a wild-type heart, an mdx heart that had been vehicle-injected and an mdx heart that had been CDC-injected, and pooled data for morphometric analysis. FIG. 4B: Western blots and pooled data for myocardial cardiac collagen IA1 and IIIA 1, 3 weeks after CDC injection in mdx hearts. Data are means±SEM; †p<0.05; #p<0.05.

FIGS. 5A-B. Cardiomyogenesis. Enhanced cardiomyogenesis 3 weeks after CDC injection in mdx trace is evident from representative immunohistochemical images and pooled data. FIG. 5A: Immunohistochemical images (wild type, vehicle-treated and CDC-treated mdx mouse hearts stained for Ki67 and Aurora B; n=4-6 per group). Arrows point to Ki67$^+$ (upper row) and Aurora B$^+$ (lower row) cardiomyocytes. FIG. 5B: Pooled data for morphometric analysis of Aurora B$^+$ and ki67$^+$ staining. Data are means±SEM; †p<0.05; scale bars: 10 µm.

FIG. 7A: Immunohistochemical images, western blots, and pooled data for protein abundance of dystrophin isoforms: dp427, dp260, dp140, dp116, dp71, dp40 in mdx mouse hearts 3 weeks after administration of vehicle or CDCs. CDC injection in mdx hearts resulted in restoration of dystrophin expression across all measured isoforms. FIG. 7B: Additional representative depiction.

FIG. 9A: Western blots and pooled data for cardiac collagen IA and IIIA, WGA (wheat germ agglutinin) was applied for staining and delineation of cell membrane. FIG. 9B: Immunohistochemical, images and pooled data (wild type, n=4; vehicle-treated and CDC-XO-treated, n=6 each) from mdx mouse hearts stained for Ki67 and Aurora B. Arrows point to Ki67$^+$ (upper row) and Aurora B$^+$ (lower row) cardiomyocytes. FIG. 9C: Western blots and pooled data for protein abundance of dystrophin isoforms: dp427, dp260, dp140, dp116, dp71, dp40 in mdx mouse hearts 3 weeks after administration of vehicle, CDCs or CDC-XOs (n=4-6). FIG. 9D: Injection of CDC-XOs into mdx hearts retarded progressive decrease in ejection fraction (n=11). Data are means±SEM; *p<0.05; †p<0.02; ‡p<0.01. Scale bar: 10 µm.

FIGS. 10A-B, Disproportional increase in cardiac function and exercise capacity in CDC-treated mdx mice. This could be due to CDCs themselves, secreted mediators (exosomes, EVs, proteins, etc.) from engrafted CDCs, modulated cardiac secretome, and/or improved systemic hemodynamics. FIG. 10A: Disproportional increase in cardiac function and FIG. 10B: exercise capacity in CDC-treated mdx mice.

FIGS. 11A-N. Intraventricular injection of CDC-XOs, Administration of CDC-XOs demonstrated similar beneficial results, FIG. 11A: Systemic biodistribution of CDC-XOs after intraventricular injection in mdx mice. CDC-XOs were stained with fluorescent lipid dye and tracked 6 hours later using bioluminescence imaging. FIG. 11B: CDC-XOs modulated gene expression in a manner mirroring CDCs. FIG. 11C: Dimensional hierarchical clustering using genes from hearts of non-treated mdx mice and of mdx mice treated intramyocardially with CDCs or intraventricularly with CDC-XOs. Genes with at least 2-fold differences with corresponding transcripts in non-treated mdx mice were included. FIG. 11D: Ejection fraction improved with intraventricular injection of CDC-XOs. FIG. 11E: Exercise capacity improved with intraventricular injection of CDC-XOs. FIG. 11F: Correlation of fold changes in expression of the same genes in the diaphragm 3 weeks after intramyocardial CDC injection or intraventricular CDC-XO injection. FIG. 11G: 2-Dimensional hierarchical clustering using genes from the diaphragm of non-treated mice and of mdx mice treated intramyocardially with CDCs or intraventricularly with CDC-XOs. Genes with at least 2-fold differences with corresponding genes in nontreated mdx mice were included, FIG. 11H: Diaphragm contractile properties 3 weeks after intraventricular CDC-XO injection. Both twitch and specific force improved with intraventricular CDC-XO injection. FIG. 11I: These results were further observed in the soleus, as shown for gene expression results. FIG. 11J: Dimensional hierarchical clustering. FIG. 11K: Contractile properties from the soleus 3 weeks after intraventricular CDC-XO injection. Both twitch and specific force improved with intraventricular CDC-XO injection. Dystropin levels shown for FIG. 11L: heart, FIG. 11M: diaphragm, FIG. 11N: soleus. Data are means±SEM; *p<0.05; †P<0.05.

FIG. 12 shows distribution of CDC-XOs stained with fluorescent lipid dye in mdx mice.

FIGS. 13A-J. Intramuscular injection of CDC-XOs resulted in muscle growth and reversal of pathophysiological abnormalities of muscular dystrophy. FIG. 13A: H&E and immunohistochemical images of the soleus stained for MyoD (wild type, vehicle-treated and CDC-XO-treated mdx mouse soleus). Arrows in H&E images point to the linearly arranged nuclei (left column) and myofibers (right column). In the immunohistochemistry, linearly arranged nuclei were positive for MyoD (middle column), FIGS. 13B & 13C: Frequency distribution of myofiber sizes and number of myoblasts (MyoD$^+$) 3 weeks after vehicle and CDC-XO injection in mdx soleus (n=59). FIGS. 13D-13F: Western blots and pooled data for protein abundance of FIG. 13D: MyoD and myogenin, FIG. 13E: IGF1 receptor, and FIG. 13F: cytoplasmic p-p65 in mdx soleus 3 weeks after intrasoleus vehicle and CDC-XO injection (n=4-6), FIG. 13G: CDC-XO microRNA reads as a measure of myogenesis. FIG. 13H: Representative Masson trichrome images and morphometric analysis in mdx soleus 3 weeks after administration of vehicle and CDC-XOs into flax soleus (n=5-9). FIG. 13I: Immunohistochemical images of dystrophin in mdx mouse soleus 3 weeks after intrasoleus injection of vehicle and CDC-XOs (n=4-6). Age-matched wild-type mice served as control. Western blots and pooled data for protein abundance of dystrophin isoform dp427 in mdx mouse soleus 3 weeks after administration of vehicle and CDC-XOs (n=4-6). FIG. 13J: Ex vivo measurement of soleus contractile properties: twitch force and absolute force 3 weeks after vehicle and CDC-XO injection into mdx soleus. Pooled data are means±SEM; *p<0.05; †p<0.05; ‡<0.002; scale bars: 5 µm (FIG. 13A, right column). 10 µm (FIG. 13A, middle column), 50 µm (FIG. 13A, left column), 200 µm (FIG. 13H), 20 µm (FIG. 13I).

FIG. 14A: CDC-XO injection was capable of modulating transcriptome of diaphragm. FIG. 14B: Western blots and pooled data for protein abundance of dystrophin isoforms in human Duchenne cardiomyocytes (DMD CM) one week after priming with CDC-XOs. Calcium transients from normal and DMD CM measured during 1 Hz burst pacing. Duchenne cardiomyocytes were primed with vehicle or CDC-XOs 1 week before assessment. Bar graphs are of calcium transient alternans (variation in beat-to-beat calcium transient amplitude) and time to peak. Western blots and pooled data for protein abundance of dystrophin isoforms: dp427, dp260, dp140, dp116, dp71, dp40 in mdx mouse hearts after 3 weeks. FIG. 14C: Oxygen consumption rate (OCR) in DMD CM primed with CDC-XOs or EVs derived from normal human dermal fibroblasts (NHDF-XOs) 1 week before OCR measurement. Normal and non-treated amp CM were studied in parallel.

FIG. 17A: 2-Dimensional hierarchical clustering using 560 genes with at least 2-fold differences between vehicle-treated and CDC-treated nay hearts. Each column represents an mdx heart and each row a gene. Probe set signal values were normalized to the mean across MA hearts. The relative level of gene expression is depicted from the lowest (green) to the highest (red), according to the scale shown on the top. Examples of fold changes of transcripts for genes involved in the various pathways of interest are plotted here, including FIG. 17B: mitochondrial integrity, FIG. 17C: oxidative stress, and FIG. 17D: inflammation.

FIGS. 20A-C. Immunohistochemical images. Depicted are mdx hearts stained for inflammatory cell marker CD3 with blowups of the boxed areas, including FIG. 20A: vehicle-treated mdx heart, FIG. 20B: CDC-treated mdx heart, and FIG. 20C: wild type heart as control, FIGS. 21A-B. Mitochondria. FIG. 21A: Numbers of mitochondria from TEM images. FIG. 21B: Mitochondrial DNA copy numbers per nuclear genome in the heart tissue 3 weeks after treatment.

FIG. 22. XO analysis. Isolated XOs obtained by ultracentrifugation were analyzed by nanoparticle tracking, using the NanoSight NS300 system (NanoSight Ltd, UK), Videos were collected and analyzed using NTA-software (version 2.3), with the minimal expected particle size, minimum track length, and blur setting all set to automatic. Camera shutter speed was fixed at 30.01 ms and camera gain was set to 500. Camera sensitivity and detection threshold were set close to maximum (15 or 16) and minimum (3 or 4), respectively, to reveal small particles. Ambient temperature was recorded manually, ranging from 24° C. to 27° C. For each sample, five videos of 60 seconds duration were recorded, with a 10-second delay between recordings, generating five replicate histograms that were averaged. Representative five replicate histograms depicting size/concentration. Standard error of the mean concentration, calculated from 5 replicates, is shown in red.

FIG. 27. IPA analysis of differentially expressed genes. Depicted are genes involved in inflammation in the liver of mdx mice treated intramyocardially with CDC or vehicle, denoting inhibition of the NF-ΚB inflammatory pathway in mdx livers 3 weeks after intramyocardial CDC injection. The lines marked with a * represents inhibition of function/response and the genes inside the circle and rectangle represent up and downregulation, respectively.

FIG. 28. Fold change of mitochondrial-related microRNAs in XOs from hypoxically-cultured CDCs relative to XOs from CDCs grown under normoxia. Depicted is 2-dimensional hierarchical clustering using microRNAs with −6 to 6 times log 2 fold change (230 microRNAs). The relative log 2 fold change of microRNAs is represented from the lowest (red (bottom), −6) to the highest ((top), +6) in the hypoxic group, according to the scale shown at the top. Each column represents an XO preparation and each row a microRNA species. Among 389 detected microRNAs in hypoxic XOs, 248 were previously reported to be mitochondria-related microRNAs.

FIGS. 31A-B. Age-related changes in dystrophin expression in mdx hearts. FIG. 31A: Dystrophin expression in young (8 weeks) and old (10 months) mdx hearts, FIG. 31B: Western blot of dystrophin protein in wild-type control mouse heart and mdx mouse hearts 3 weeks and 3 months after first intramyocardial CDC injection and 3 months after second (repeat) CDC injection into myocardium. All hearts were from mice 10 months old at baseline. CS: citrate synthase.

FIGS. 32A-D. Non-cardiac manifestations CDC or CDC-XO injections. FIG. 32A: Ingenuity pathway analysis of differentially expressed genes involved in inflammation in the liver of mdx mice injected intramyocardially with CDCs or vehicle, showing inhibition of the NF-κB inflammatory pathway in mdx livers 3 weeks after intramyocardial CDC injection. The blue color represents inhibition of function/response and the red and green colors represent up and downregulation, respectively. FIG. 32B: Bioluminescence imaging of mdx mouse organs after systemic injection of dyed human CDC-XOs. 6 hours after injection of XOs systemically into the mdx mouse left ventricular cavity, the indicated organs were dissected and imaged using IVIS molecular imaging systems (Caliper Life Sciences, Hopkinton, Mass., USA). FIG. 32C: Western blot of dystrophin protein in wild type mouse heart and mdx mouse hearts 1 week, 3 weeks and 3 months after first intraventricular CDC-XO injection and 3 months after second (repeat) CDC-XO injection. FIG. 32D: Western blot showing protein content of dystrophin in wild type control and in mdx mouse heart, hypothalamus, diaphragm, soleus, tibialis anterior, and extensor digitorum longus, 3 weeks after systemic CDC-XO delivery by intraventricular injection. CS: citrate synthase loading control. Although no dystrophin expression is evident in the EDL, contractile force was increased in EDL after intramyocardial CDC injection, suggesting that dystrophin re-expression may not be the sole mechanism of benefit in skeletal muscle.

FIGS. 34A-D. Verification that the bioactivity of the XOs studied here are attributable to exosomes characterized. Exosomes were floated on a linear iodixanol density gradient, which demonstrated vesicles by transmission electron microscopy (TEM) and the presence of membrane proteins, and showed that the biological effect is vesicle associated. FIG. 34A: TEM images of sequentially-centrifuged exosomes with (Exo1, left) and without (Exo2, right) purification with linear iodixanol density gradient show vesicles in both conditions. The vesicles are variable in size and morphology, consistent with previous work. FIG. 34B: Western blot on lysed exosomes for key proteins characteristic of exosomes: CD63, CD81, and TSG. FIG. 34C, FIG. 34D: Biological activity of Exo1 and Exo2 were compared by injection into mdx soleus and evaluation of mdx soleus transcriptome 3 weeks after injection. FIG. 34C: Changes in mdx soleus transcriptome 3 weeks after Exo1 and Exo2 injection. 2-Dimensional hierarchical clustering using 332 genes with at least 2-fold differences between vehicle/Exo1 and vehicle/Exo2 in mdx soleus. FIG. 34D: Correlation of fold changes in expression of the same genes 3 weeks after Exon and Exo2 injection in mdx soleus. The similarity of the effects of Exo1 and Exo2 support the notion that the bioactivity of the vesicles isolated by the default protocol is genuinely due to exosomes, and not to other types of vesicles that might have been co-purified by ultracentrifugation. Scale bars: 50 μm (Exo1); 100 nm (Exo2).

FIG. 35A: Differential expression of miR-148a-3p and srDMD in CDC-XOs isolated from hypoxic conditioned media (2% $O_2$) compared to CDC-XOs isolated from normoxic conditioned media (n=2), along with depiction of apparent secondary structure of srDMD. FIG. 35B: Western blots and pooled data for protein abundance of dystrophin isoforms: dp427, dp260, dp140, dp116, dp71, dp40 in mdx mouse hearts 3 weeks after intramyocardial injection of vehicle, CDCs, CDC-XOs (n=4-6), miR-148a-3p, or srDMD. FIG. 35C: Western blots and pooled data for protein abundance of dystrophin isoforms: dp427, dp260, dp140, dp116, dp71, dp40 in mdx mouse hearts 3 weeks after intramyocardial injection of vehicle, CDCs, CDC-XOs (n=4-6), miR-148a-3p, and srDMD.

FIG. 36A: miR-148a results in decreases in both NFκB p65 and phospho-Akt levels. FIG. 36B: RT-PCR using primers that flank the exon 23 of dystrophin. It was used to assess exon 23 inclusion in expressed dystrophin in mdx hearts from vehicle, miR-148a-3p, and srDMD-treated mice (n=4-6). Sashimi plots of RNA-seq data for dystrophin from vehicle, miR-148a-3p, or srDMD-treated mdx hearts depict no junction read that span exon 23. All data are means±SEM; ‡p<0.03.

FIGS. 37A-B. Western blot detection of dystrophin. FIG. 37A: Western blot depicting protein content of dystrophin in wild type mouse hearts and srDMD-treated mdx mouse hearts 3 weeks after intramyocardial injection of srDMD. FIG. 37B: Percentage increase relative to vehicle (PBS) in dystrophin/eGFP expression after treatment with CDC-XOs, miR-148a-3p, or srDMD in transfected HEK293 NT cells with dual reporter constructs harboring a point mutation in exon 23 of dystrophin gene or deletion of exon 50 of dystrophin gene.

FIGS. 38A-B. Dystrophin expression and its consequences. FIG. 38A: Ejection fraction at baseline and 3 weeks after intramyocardial injection of miR-148a-3p or microRNA mimic control in mdx mice. Wild type EF values also shown for reference; n=5 per group. FIG. 38B: Western blot depicting protein content of dystrophin in wild type mouse hearts and in vehicle-, mutant srDMD, or srDMD-injected mdx mouse hearts 3 weeks after intramyocardial injection.

FIGS. 39A-B. FIG. 39A: Plasmid map of synthetic DNA constructs cloned into mammalian expression vectors. Full length human dystrophin was cloned into the ORF, either as wild-type or as one of two mutants: UAA premature termination codon in exon 23 (PTC), or exon 50 deletion (Exon 50 Δ). The construct creates a fusion protein of full-length dystrophin in frame with eGFP, such that green fluorescence can be taken as a reporter of dystrophin expression. Constitutive luciferase expression (driven independently by an SV40 promoter) was used to normalize for transfection efficiency. FIG. 39B: Dystrophin eGFP expression in HEK-293NT cells transfected with full-length (WT), PTC or Exon 50 Δ constructs. Fluorescence and luminescence of total cell lysates were quantified on a well-by-well basis in a 96-well spectrophotometer; fluorescence in each well was also quantified with nontransfected cells at an equivalent seeding density and lysis volume.

FIGS. 40A-D. Ten-to-twelve month old mdx mice were treated with the following: a single dose of vehicle (mdx), $2.5 \times 10^5$ syngeneic CDCs, or $2.0 \times 10^9$ human CDC-exosomes (CDC-XOs) via intravenous injection into the femoral vein. FIG. 40A Shows maximal exercise capacity (n=8-10 per group) and FIG. 40B in vivo cardiac ejection fraction (n=6-8 per group) before (baseline) and 3 weeks following treatment. FIG. 40C shows Masson's trichrome micrographs of hearts from vehicle-(top panel), CDC-(middle panel), or XO-(bottom panel) treated mdx mice. FIG. 40D shows pooled data analyzing area of blue staining (collagen) relative to red staining (cytoplasm) as a marker of cardiac fibrosis (n=5-6 per group). Data are represented as mean±SEM. * indicates statistically different from vehicle treatment. Statistical significance was set to P<0.05.

FIGS. 41A-D. Animals were treated as described in FIG. 40, FIG. 41A shows whole transcriptome analysis of hearts from RNA-sequencing data. Transcripts with a 2-fold or higher change with P<0.05 were considered differentially expressed and represented in the heatmap in panel A. The mdx column was compared to an age-matched wild-type mouse heart, while the CDCs and XOs columns were each compared to mdx mouse hearts. FIG. 41B shows representative Western blot and pooled data probing for phosphorylated NFκB protein levels (n=5-6 per group) in the hearts from wild-type (WT), vehicle (mdx), CDC, or XO treated mice. FIG. 41C shows pooled data from CD68 immunofluorescent images (n=3 per group) FIG. 41D from mdx, CDC, or XO treated hearts. Data are represented as mean±SEM. * indicates statistically different from vehicle treatment. Statistical significance was set to P<0.05.

FIG. 42A. Pooled data from Western blot analysis of mitochondrial electron transport chain complexes (n=6 per group) from WI, mdx, CDC, or XC) treated hearts. FIG. 42B. Protein-carbonyl adduct formation (n=8-10 per group) in WI, mdx, CDC, or XO treated hearts. FIG. 42C. Pooled data from Ki-67 immunofluorescent images (n=3 per group). FIG. 42D from mdx, CDC, or XO treated hearts. Data are represented as mean±SEM. * indicates statistically different from vehicle treatment. Statistical significance was set to P<0.05.

FIGS. 43A-F. Animals were treated as described in FIG. 40. FIG. 43A. Force-frequency relationship of solei (n=5-8 per group) from WI (circle), mdx (square), CDCs (upward triangle), or XOs (downward triangle). FIG. 43B Twitch and FIG. 43C tetanic force developed by solei from WT, mdx, CDCs, or XO treated mice. FIG. 43D Force-frequency relationship of diaphragms (n=5-6 per group) from WI (circle), mdx (square), CDCs (upward triangle), or CDC-XOs (downward triangle). FIG. 43E Twitch and FIG. 43F tetanic force developed by diaphragms from WT, mdx, CDCs, or CDC-XO treated mice. FIG. 43G Masson's trichrome micrographs from mdx (left panel), CDC-(middle panel), or CDC-XO-(right panel) treated mice. FIG. 43H Pooled data analyzing area of blue staining (collagen) relative to red staining (cytoplasm) as a marker of skeletal muscle fibrosis in the soleus (n=5-6 per group). FIG. 43I Quantification of the number of myofibers per whole muscle section of the soleus (n=5-6 per group). Data are represented as mean±SEM. * indicates statistically different from vehicle treatment. Statistical significance was set to P<0.05.

FIGS. 44A-D. Animals were treated as described in FIG. 40. FIG. 44A. Whole transcriptome analysis of hearts from RNA-sequencing data. Transcripts with a 2-fold or higher change with P<0.05 were considered differentially expressed and represented in the heatmap in panel A. The mdx column was compared to an age-matched wild-type mouse soleus, while the CDCs and CDC-XOs columns were each compared to mdx mouse solei. FIG. 44B. Kyoto Encyclopedia of Genes and Genomes analysis of a CDC-XO treated soleus. Pathways listed are considered upregulated relative to mdx soleus many are involved in inflammation. Fold change in genes known to be involved in FIG. 44C TNF and FIG. 44D NFκB signaling altered in the soleus by CDC and CDC-XO treatment.

FIGS. 45A-C. Animals were treated as described in FIG. 40. FIG. 45A Representative Western blot and pooled data probing for phosphorylated NFκB protein levels (n=3 per group) in the soleus from wild-type (WT), vehicle (mdx), CDC, or CDC-XO treated mice. FIG. 45B Pooled data from CD68 immunofluorescent images (n=3 per group). FIG. 45C from mdx, CDC, or CDC-XO treated hearts. Data are represented as mean±SEM. * indicates statistically different from vehicle treatment. Statistical significance was set to P<0.05.

FIGS. 46A-B. Animals were treated as described in FIG. 40. Western blot probing for full-length (427 kDa) dystrophin in the soleus FIG. 46A and diaphragm FIG. 46B from vehicle (mdx), CDC, GW4869 treated CDCs, and CDC-XO treated mice. The left 2 columns represent a relative level of WT dystrophin (e.g., 5% and 1%).

FIGS. 48A-48B graphically show effects of intravenous (IV) administration of CDCs on the exercise capacity of mdx mice injected with 75,000, 150,000, or 250,000 (referred to as "75K," "150K," and "250K," in the figure) CDCs versus phosphate buffered saline (PBS) control.

FIG. 49 graphically shows the effects of jugular IV administration of CDCs on the diaphragm muscle function of mice injected with 75K-250K CDCs versus PBS control.

FIG. 51 shows that CDCs administered in accordance with several embodiments disclosed herein reduce fibrosis in the hearts of mdx mice (shown is collagen staining, an indicator of fibrosis).

FIG. 67A shows the representative dot plots (from Donor A); FIG. 67B shows the proliferation of T cells from three different PBMC donors; FIG. 67C shows the proliferation of T cells from 3 different donors. For FIG. 67B, results are mean values±SD from triplicates. For FIG. 67C, results are mean values±SD obtained from three different donors each in triplicates.

FIG. 68 graphically shows the purified T cells activation and proliferation in response to CDCs. Results are mean values±SD obtained from responses (duplicates) for each donor (upper and middle panels) and as mean values±SEM obtained from both donors each in duplicate (lower panel).

FIG. 73A shows the representative images of tailored-MLR cultures; FIG. 73B shows the expression of CD69 and HLADR by CD4+ and CD8+ T cells.

FIG. 74A shows the representative dot plots; FIG. 74B shows the proliferation of T cells from 3 different donors presented as mean values±SD from triplicates.

FIG. 82 graphically shows that CDCs and CDC-EVs down regulate PHA-induced T cells proliferation. Results are mean values±SD obtained from triplicates.

FIG. 83 graphically shows that Immune modulation of PHA-induced $CD4^+$ and $CD8^+$ T cells proliferation by CDC and CDC-EVs. Results are mean percentage values±SEM from 2 different donors each done in triplicates.

FIG. 85A is a graphical depiction of changes from baseline in exercise capacity with two administrations of allogeneic CDCs (from C3H mice), a steroid, and/or PBS vehicle. FIG. 85B is a graph of the percent of cells positive for various genetic markers.

DETAILED DESCRIPTION

Figures 1, 1D:
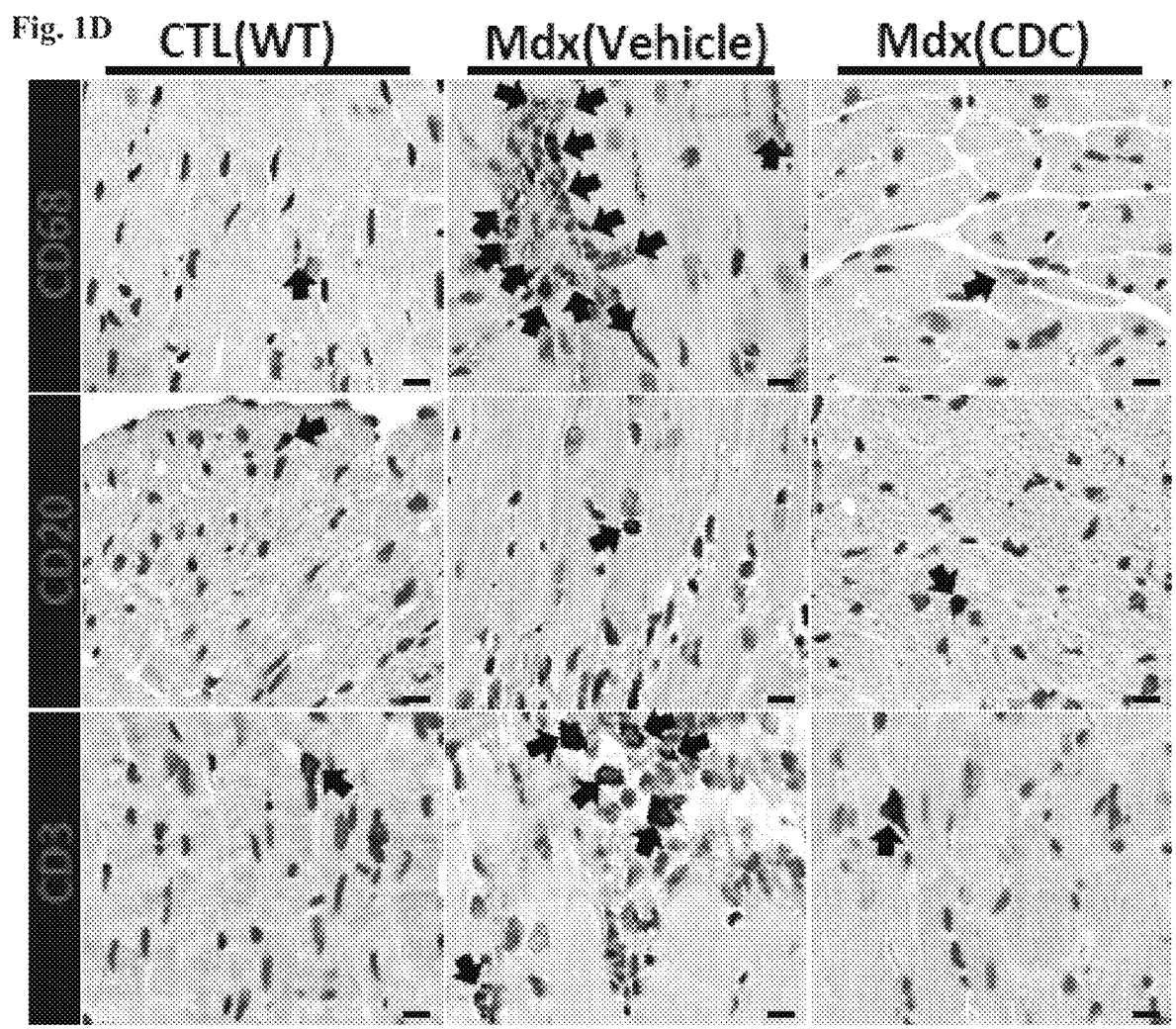

Some embodiments disclosed herein pertain to methods of treating disease, disease states, and/or symptoms of disease using CDCs, CDC-XOs, CDC-EVs, the isolated molecular cargo of CDCs (e.g., individual molecules or combinations of molecules derived from CDCs, CDC-XOs, and/or CDC-EVs), and/or combinations of the forgoing. In some embodiments, the disease is a dystrophinopathy. In some embodiments, the disease state is a dystrophic disorder. In some embodiments, the dystrophinopathy includes one or more of Duchenne muscular dystrophy (DMD) and/or Becker muscular dystrophy. In some embodiments, the disease state is a myopathy. In some embodiments, the myopathy is a skeletal muscle myopathy. In some embodiments, the method includes administering a therapeutically effective amount of CDCs, CDC-XOs, CDC-EVs, the molecular cargo of CDC-XOs or CDC-EVs, and/or combinations of the forgoing to a subject (e.g., a patient) suffering from the disease, thereby treating the disease and/or its symptoms. Some embodiments of the methods and compositions provided herein are based on the surprising discovery that, inter alia, despite the finding that intravenous administration of CDCs to mdx mice resulted in accumulation of the at least a portion of administered CDCs in their lungs, functional improvements at dystrophic skeletal muscles were achieved as demonstrated by the various data presented herein, thereby enabling an effective treatment of a human subject suffering from skeletal muscular dystrophy, e.g., Duchenne muscular dystrophy (DMD), by administering a therapeutically effective amount of CDCs to a human subject suffering from skeletal muscular dystrophy.

As used herein, "and/or" refers to and encompasses any and all possible combinations of one or more of the associated listed items, as well as the lack of combinations when interpreted in the alternative ("or").

"Treat" or "treating" or "treatment" refers to any type of action that imparts a modulating effect, which, for example, can be a beneficial effect, to a subject afflicted with a disorder, disease or illness, including preventing the manifestation of disease states associated with the condition, improvement in the condition of the subject (e.g., in one or more symptoms or in the disease), delay or reduction in the progression of the condition, and/or change in clinical parameters, disease or illness, curing the illness, etc.

The term "therapeutically effective amount," as used herein, refers to an amount of the therapeutic (e.g., CDC-XOs, CDC-EVs, CDCs, molecular cargo of XOs and EVs, or combinations thereof) that imparts a modulating effect, which, for example, can be a beneficial effect, to a subject afflicted with a disorder, disease or illness, including improvement in the condition of the subject (e.g., modulating one or more symptoms), delay or reduction in the progression of the condition, prevention or delay of the onset of the disorder, and/or change in clinical parameters, disease or illness, etc. For example, in some embodiments, an effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Actual dosage levels of active ingredients and agents in an active composition of the disclosed subject matter can be varied so as to administer an amount of the active agent(s) that is effective to achieve the desired response for a particular subject and/or application. The selected dosage level will depend upon a variety of factors including, but not limited to, the activity of the composition, formulation, route of administration, combination with other drugs or treatments, severity of the condition being treated, and the physical condition and prior medical history of the subject being treated. Determination and adjustment of an effective dose, as well as evaluation of when and how to make such adjustments, are contemplated herein. The term "a therapeutically effective amount" can mean an amount of CDC-XOs, CDC-EVs, CDCs, and/or molecular cargo XOs and EVs sufficient to reverse dystrophinopathy through dystrophin re-expression and/or to durably (e.g., substantially irreversibly) restore skeletal muscle function at a targeted dystrophic skeletal muscle.

The term "a targeted dystrophic skeletal muscle" as used herein is the delivery of an amount of CDC-XOs, CDC-EVs, CDCs, a molecular cargo CDC-XOs and CDC-EVs, and/or combinations thereof at the site of a dystrophic skeletal muscle. In some embodiments, targeted delivery does not include incidental, accidental, or inadvertent delivery CDC-XOs, CDC-EVs, CDCs, and/or molecular cargo CDC-XOs and CDC-EVs to a target site. In some embodiments, targeted delivery does not include systemic delivery. In some embodiments, targeted, delivery does not include incidental, accidental, or inadvertent delivery CDC-XOs CDC-EVs CDCs, and/or molecular cargo of CDC-XOs and CDC-EVs in an amount that would be insufficient to treat dystrophinopathy at the site of a dystrophic skeletal muscle.

The term "dystrophic" as used herein is a lack of or deficiency of dystrophin (e.g., in skeletal and/or heart muscles).

Cells release into the extracellular environment diverse types of extracellular vesicles (EVs) of endosomal and plasma membrane origin called exosomes (XOs) and microvesicles (MVO. EVs represent an important mode of intercellular communication and serve as vehicles for the transfer of molecular cargo (e.g., one or more of cytosolic proteins, lipids, and RNA) between cells and through cell membranes. XOs, secreted lipid vesicles containing a rich milieu of biological factors, provide powerful paracrine signals by which stem cells potentiate their biological effects to neighboring cells, including diseased or injured cells. Through the encapsulation and transfer of proteins, bioactive lipid and nucleic acid cargo, these natural delivery devices can induce significant phenotypic and functional changes in recipient cells that lead to activation of regenerative programs. Administration of XOs has been demonstrated to treat heart failure in mdx mice in WO2016/05491, which is herein incorporated by reference in its entirety.

Some embodiments disclosed herein pertain to the use of CDCs and CDC-XOs in methods of therapeutic use. In some embodiments, described herein are methods of treating a dystrophic disorder, including a step of administering a therapeutically effective amount of CDCs and/or CDC-XOs to a subject afflicted or having dystrophinopathy, thereby treating the subject. In some embodiments, the subject is a pediatric subject afflicted with a dystrophinopathy. In some embodiments, the XOs are isolated from CDCs. In some embodiments, the CDCs are grown in serum-free media. In some embodiments, the dystrophinopathy is Duchenne muscular dystrophy. In other embodiments, the dystrophinopathy is Becker muscular dystrophy. In some embodiments, CDC-XOs, CDC-EVs, molecular cargo of CDC-XOs or CDC-EVs, CDCs producing XOs and EVs, and/or combinations of the forgoing are used in a method for achieving dystrophin re-expression. In some embodiments, the CDC-XOs, CDC-EVs, molecular cargo of CDC-XOs or CDC-EVs, CDCs producing XOs and EVs, and/or combinations upon systemic intraventricular injection of CDC-EVs, as well as upon direct intramuscular injection of CDC-EVs into skeletal muscles of mdx mice, whereby the present inventors conceived of the novel treatment method as described for the first time herein, e.g., a method of treating skeletal DMD by administering a therapeutically effective amount of CDCs and/or CDC-EVS in a single or multiple systemic administrations. In some embodiments, the disease is muscular dystrophy.

The data and experiments disclosed herein demonstrate an unexpected advantage of CDCs, CDC-XOs, and/or CDC-EVs in inducing dystrophin expression. As shown elsewhere herein, injection of CDCs into the hearts of mdx mice boosts full-length dystrophin protein levels in both heart and skeletal muscle, dramatically and durably improving cardiac function, ambulatory capacity and survival. Similar results are demonstrated with human Duchenne cardiomyocytes. Positive factors appear to exist in cellular XO's produced by CDCs, which are the lipid bilayer nanovesicles secreted by cells when multivesicular endosomes fuse with the plasma membrane.

In some embodiments, XOs and EVs) secreted by human CDCs are demonstrated to reproduce the benefits of CDCs in mdx mice and in human Duchenne cardiomyocytes. In some embodiments, the delivery of noncoding RNA species found in CDC-XOs (e.g., miR-148a) mimics the ability of CDCs, CDC-XOs, and/or CDC-EVs to increase dystrophin protein levels, without affecting transcript length or exon/intron junctions. In some embodiments, CDC-XO mediated transfer of noncoding RNAs ameliorates DMD by restoring dystrophin in heart and skeletal muscle.

In some embodiments, the results described herein demonstrate CDCs and their XOs (and/or EVs) as a therapeutic option for dystrophinopathy. CDCs and their secreted XOs (and/or EVs) robustly increase dystrophin levels in heart and skeletal muscle. In some embodiments, the increasing dystrophin levels in the heart and skeletal muscle leads to major durable systemic benefits after injection of CDCs, CDC-XOs, and/or CDC-EVs into the body (e.g., systemically or locally, including locally into the skeletal muscle). In some embodiments, as disclosed herein, CDCs, CDC-XOs, and/or CDC-EVs are not only regenerative, but also anti-inflammatory and anti-fibrotic. CDCs secrete diffusible factors that promote angiogenesis, recruit endogenous progenitor cells, and coax surviving heart cells to proliferate; transplanted CDCs also suppress maladaptive remodeling, and apoptosis. In some embodiments, CDCs operate through indirect pathways (via CDC-XOs and/or CDC-EVs); they work indirectly via the secretion of CDC-XOs and/or CDC-EVs laden with noncoding RNA including microRNAs (constituents of the molecular cargo). In some embodiments, while allogeneic CDCs are cleared completely within several weeks, but their functional and structural benefits persist at least 6 months. These diverse mechanisms are mediated via the secretion of CDC-MN and/or CDC-EVs laden with noncoding RNA including microRNAs.

Without being bound to a particular theory, the above mechanisms afford CDCs, CDC-EVs, or CDC-XOs the capacity to treat DMD, with application to similar muscular dystrophies such as Becker muscular dystrophy. In some embodiments, CDCs, CDC-XOs, and/or CDC-EVs replace dystrophin, and offset the pathophysiological consequences of dystrophin deletion, by recruiting regenerating cells, reversing fibrosis and targeting inflammation. In some embodiments, reversing the central deficits of DMD in pediatric patients, the methods herein are capable of forestalling or preventing progression of the disease, allowing those patients to avoid comorbidities which may otherwise significantly limit options for therapeutic intervention.

While the disclosed methods herein include those involving the delivery of CDCs to a patient, in some embodiments, using CDC-EVs CDC-XOs) secreted by CDCs, and not cells, may provide advantages when compared to transplant and delivery of cells themselves, in some embodiments, CDC-EVs and CDC-XOs, including those produced by CDCs, can provide a potent and rich source for developing "cell-free" therapies. CDC-XO-based, "cell-free" therapies, in contrast to cell therapy, provide one or more of the following advantages in regenerative medicine. In some embodiments, as non-viable entities, with reduced or non-existent immunogenic or tumorigenic potential, these features significantly obviate certain safety issues. In some embodiments, stem cell-derived exosomes (and/or CDC-XOs) can be less immunogenic than parental cells, as a result of a lower content of membrane-bound proteins, including MHC complex molecules. In some embodiments, CDC-XO encapsulation of bioactive components in lipid vesicles allows protection of contents from degradation in vivo, thereby potentially negating obstacles often associated with delivery of soluble molecules such as cytokines, growth factors, transcription factors and RNAs. In some embodiments, the ease of administration (and/or storage) for CDC-XOs and/or CDC-EVs can ultimately allow for repeated and sustained delivery to patients, thereby maximizing the potential for regeneration and repair of diseased and/or dysfunctional tissue.

In some embodiments, CDCs and/or CDC-XOs can be used to stimulate numerous cellular, tissue and physiological processes, including immune modulating processes, angiogenesis, and migration of endothelial cells. As disclosed herein, based on the pathophysiology of DMD patients, including an environment of increased oxidative and/or nitrosative stress, elevated inflammation, pro-apoptotic and remodeling states, therapeutic approaches involving CDCs and/or CDC-XOs secreted by cells, provide significant benefits in reversing the course of the disease (and one or more of the aforementioned disease states and/or manifestations). In some embodiments, CDCs, CDC-XOs, and/or CDC-EVs promote anti-oxidative, anti-inflammatory, anti-apoptotic, anti-remodeling effects. In some embodiments, CDCs, CDC-XOs, and/or CDC-EVs enhance regenerative capacity of diseased cells and tissues. In some embodiments, CDC, CDC-XO, and/or CDC-EV administration is beneficial in retarding and/or reversing DMD, and exosome populations derived from CDCs allow for these benefits to be delivered. Early therapeutic intervention in pediatric subjects provides durable and systemic benefits that will prevent or ward off comorbidities in late stage disease, such as heart failure. In some embodiments, durable benefits are those lasting equal to or at least about: 3 months, 6 months, 12 months, or ranges including and/or spanning the aforementioned values.

Some Embodiments of Exosomes. XOs are lipid bilayer vesicles that are enriched in a variety of biological factors, including cytokines, growth factors, transcription factors, lipids, and coding and non-coding nucleic acids. XOs are found in blood, urine, amniotic fluid, interstitial and extracellular spaces. These exocytosed vesicles of endosomal origin can range in size between 30-200 nm, including sizes of 40-100 nm, and possess a cup-shaped morphology, as revealed by electron microscopy. Their initial formation begins with inward budding of the cell membrane to form endosomes, which is followed by invagination of the limiting membrane of late endosomes to form multivesicular bodies (MVB). Fusion of the MVB with the plasma membrane results in the release of the internal vesicles to the extracellular space, through the formation of vesicles thereafter known as exosomes. In some embodiments, XOs as described herein are those extracellular vesicles that are exocytosed and/or are of endosomal origin. In some embodiments, XO as described herein can have diameters of less than or equal to about: 30 nm, 50 nm, 100 nm, 150 nm, 200 nm, or ranges including and/or spanning the aforementioned values.

As described herein, the "cargo" contents of XOs reflect their parental cellular origin, as containing distinct subsets of biological factors in connection with their parent cellular origin, including the cell regulatory state of the parental cells when formed. The rich biological milieu of different proteins, including cytokines and growth factors, lipids, coding and noncoding RNA molecules, within exosomes are all necessarily derived from their parental cells. In addition to containing a rich array of cytosolic derivatives, exosomes further express the extracellular domain of membrane-bound receptors at the surface of the membrane.

In some embodiments, the described encapsulation and formation processes create heterogeneity in XO compositions based on parental cellular origin and regulatory state at time of formation. Nevertheless, in some embodiments, generic budding formation and release mechanisms establish a common set of features as a consequence of their origin, such as endosome-associated proteins (e.g., Rab GTPase, SNARES, Annexins, and flotillin), proteins that are known to cluster into microdomains at the plasma membrane or at endosomes (four transmembrane domain tetraspanins, e.g., CD63, CD81, CD82, CD53, and CD37), lipid raft associated proteins (e.g., glycosylphosphatidylinositol-anchored proteins and flotillin), cholesterol, sphingomyelin, and hexosylceramides.

In some embodiments, in addition to components reflecting their vesicle origin, XOs contain both mRNA and microRNA associated with signaling processes, with both cargo mRNA being capable of translation in recipient cells, or microRNA functionally degrading target mRNA in recipient cells. In some embodiments, other noncoding RNAs, capable for influencing gene expression, may also be present in XOs. While the processes governing the selective incorporation of mRNA or microRNA populations into XOs is not entirely understood and without being bound to any particular theory, it is believed that RNA molecules are selectively, not randomly incorporated into XOs, as demonstrated by the enrichment of XOs cargo RNAs when compared to the RNA profiles of other exosomes and their originating cells. In some embodiments, in view of RNA molecules potential a role in disease pathogenesis and regenerative processes, without being bound by a theory, the presence of RNA molecules in XOs and apparent potency in affecting target recipient cells allow XOs and their molecular cargo therapeutically effective as disclosed elsewhere herein.

In some embodiments, the natural bilayer membrane encapsulation of exosomes also provides a protected and controlled, internal microenvironment that allows cargo contents to persist or migrate in the bloodstream or within tissues without degradation. In some embodiments, the later release of this cargo into the extracellular environment allows for interaction with recipient cells via adhesion to the cell surface mediated by lipid-ligand receptor interactions, internalization via endocytic uptake, or by direct fusion of the vesicles and cell membrane. These processes lead to the release of exosome cargo content into the target cell.

In some embodiments, XO-cell interactions can modulate genetic pathways in the target recipient cell, as induced through any of several different mechanisms including antigen presentation, the transfer of transcription factors, cytokines, growth factors, nucleic acid such as mRNA and microRNAs.

Isolation and Preparation of Exosomes. In some embodiments, XO isolation can be accomplished using their generic biochemical and biophysical features for separation and analysis, in some embodiments, differential ultracentrifugation can be used as a technique wherein secreted XOs are isolated from the supernatants of cultured cells. In some embodiments, this approach allows for separation of XOs from nonmembranous particles, by exploiting their relatively low buoyant density. In some embodiments, size exclusion allows for their separation from biochemically similar, but biophysically different MVs, which possess larger diameters of up to 1,000 nm. In some embodiments, MVs are also included in therapeutic mixtures with XOs (where EVs encompass both XOs and MVs) and/or MVs are not removed from XOs. In other embodiments, XOs can be isolated from MVs so that the XOs are enriched and/or substantially free of MVs. In some embodiments, differences in flotation velocity further allows for separation of differentially sized exosomes. In some embodiments, XOs sizes will possess a diameter ranging from 30-200 nm, including sizes of 40-100 nm. In some embodiments, the disclosed MVs and EVs have sizes (in nm) of greater than or equal to about: 1000, 750, 500, 400, 300, 250, 200, or ranges including and/or spanning the aforementioned values.

In some embodiments, further purification of XOs may be performed based on specific properties of the particular exosomes of interest. This includes, for example, use of immunoadsorption with a protein of interest to select specific vesicles with exoplasmic or outward orientations.

In some embodiments, while any one of differential centrifugation, discontinuous density gradients, immunoaffinity, ultrafiltration and high performance liquid chromatography (HPLC) may be used to isolate XOs (and/or MVO, differential ultracentrifugation is used. In some embodiments, this technique utilizes increasing centrifugal force from 2000×g to 10,000×g to separate the medium- and larger-sized particles and cell debris from the exosome pellet at 100,000×g. While centrifugation alone allows for significant separation/collection of XOs from a conditioned medium, in some embodiments, ultracentrifugation may also remove various protein aggregates, genetic materials, particulates from media and cell debris that are common contaminants. In some embodiments, enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/ml) or application of a discrete sugar cushion in preparation.

In some embodiments, ultrafiltration can be used to purify exosomes without compromising their biological activity. In some embodiments, membranes with different pore sizes—such as molecular weight cut-off (MWCO) less than or equal to about: 200 kDa, 100 kDa, 75 kDa, 50 kDa, or ranges including and/or spanning the aforementioned values. In some embodiments, gel filtration can alternatively or also be used to eliminate smaller particles. In some embodiments, membrane (e.g., dialysis, ultrafiltration, etc.) and/or gel filtration is performed using a substantially physiological pH and/or at substantially physiological salt concentrations (e.g., avoiding the use of a nonneutral pH or non-physiological salt concentration). In some embodiments, tangential flow filtration (TEE) systems used. In some embodiments, TFF systems are scalable (to >10,0000, allowing one to not only purify, but concentrate the XO fractions. In some embodiments, such approaches are advantageously less time consuming than differential centrifugation. In some embodiments, HPLC is used to purify the XOs. In some embodiments, HPLC can also be used to purify exosomes to homogeneously sized particles and preserve their biological activity as the preparation is maintained at a physiological pH and salt concentration.

In some embodiments, chemical methods are used to isolate XOs. In some embodiments, these chemical methods include separation by differential solubility in precipitation techniques. In sortie embodiments, a precipitation reagent is added to a solution of XOs to purify the XOs. In some embodiments, these chemical methods include separation by addition to volume-excluding polymers (e.g., polyethylene glycols (PEGs), etc.). In some embodiments, these chemical methods can be combined with additional rounds of centrifugation or filtration, etc. In some embodiments, for example, a precipitation reagent, ExoQuick®, is added to a conditioned cell media to quickly and rapidly precipitate a population of exosomes. In some embodiments, flow field-flow fractionation (FIFFF) is an elution-based technique that is used to separate and characterize macromolecules (e.g., proteins) and nano- to micro-sized particles (e.g., organelles and cells) and which is successfully applied to fractionate exosomes from culture media.

In some embodiments, beyond the techniques disclosed elsewhere herein, relying on biochemical and biophysical features of the XOs, focused techniques may be applied to isolated specific exosomes of interest. In some embodiments, antibody immunoaffinity is used to recognize XO-associated antigens. In some embodiments, XOs express the extracellular domain of membrane-bound receptors at the surface of the membrane of the parent cells. In some embodiments, this expression allows isolating and segregating XOs in connections with their parental cellular origin, based on a shared antigenic profile. In some embodiments, conjugation to magnetic beads, chromatography matrices, plates or microfluidic devices, and/or combinations of such techniques with other techniques disclosed herein allows isolating of specific XO or MV populations of interest (e.g., as may be related to their production from a parent cell of interest or associated cellular regulatory state). Other affinity-capture methods use lectins which bind to specific saccharide residues on the XO surface.

Exosome-Based Therapies. In some embodiments, as disclosed elsewhere herein, XO-based therapy advantageously allows potential "cell-free" therapies (e.g., where CDCs etc. are separated from CDC-XOs, etc.). The use of a "cell-free" therapy holds potential benefits of cellular therapeutics with reduced risks and/or can be used in scenarios in which cell therapy would be unavailable (and/or impossible). In some embodiments, as described elsewhere herein, the therapeutic benefits of cell-based therapies such as CDCs may occur through indirect mechanisms involving regenerated tissue arising from endogenous origin. In some embodiments, cellular XOs produced by CDCs may allow for production and delivery of growth factors, transcription factors, cytokines and nucleic acids for new therapeutic approaches in a manner that not only ameliorates progression of the disease, but repairs and regenerates disease and/or dysfunctional tissue. In this regard, CDC-derived exosomes can effectively address a major unmet medical need, by recruiting synergistic mechanisms to attract endogenous stem cells to sites of myocardial injury, promote cellular differentiation, reversing chronic disease pathophysiology such as Duchenne muscular dystrophy. In some embodiments, CDCs can be used as XO (and/or EV) factories, advantageously providing a lasting source of XOs throughout the time of residence of the CDC in the patient.

In some embodiments, particularly for chronic conditions, such as DMD, repeated and sustained delivery to patients of CDC-XOs or CDCs that produce XOs may enhance the potential for regeneration and repair of diseased and/or dysfunctional tissue, in a manner that would be easier and potentially safer than when using a cell-based therapy. Dosing regimens and schedules are disclosed in additional detail elsewhere herein.

In some embodiments, as disclosed elsewhere herein, the administration methods and amounts of XOs and/or CDCs provided to a patient can be provided in a variety of ways to deliver a therapeutic dose. In some embodiments, for example, administering a composition and/or solution for administration of XOs includes about 1 to about 100 mg CDC-XO protein in a single dose. In some embodiments, a dose of CDC-EVs (e.g., CDC-XOs) may comprise a weight of EVs or XOs (in mg) of equal to or at least about 1, 10, 25, 50, 75, 100, 200, or ranges including and/or spanning the aforementioned values. In some embodiments, the administration method includes multiple administrations of each single dose to the subject. In some embodiments, administering a composition (e.g., a composition including CDC-XOs, CDC-EVs, CDCs, or combinations thereof) includes injection. In some embodiments, injection includes skeletal muscle injection. In some embodiments, injection includes intraperitoneal injection. In some embodiments, administering a composition includes intra-arterial or intravenous infusion. In some embodiments, treatment of the subject (e.g., by delivery of a dose or doses of CDC-XOs and/or CDCs that release CDC-XOs) results in increased dystrophin expression. In some embodiments, increased dystrophin expression occurs in skeletal muscle in a limb (e.g., one or more of an arm or leg). In some embodiments, increased dystrophin expression occurs in the diaphragm. In some embodiments, patient undergoing therapy as disclosed elsewhere herein is a pediatric subject afflicted with cardiomyopathy. In some embodiments, the pediatric subject is diagnosed with cardiomyopathy. In some embodiments, the pediatric subject is afflicted with cardiomyopathy, but not heart failure. In some embodiments, the pediatric subject is 3-11 years old. In other embodiments, the pediatric subject is 12-18 years old. In some embodiments, the human subject is a pediatric subject at the age of less than or equal to about: 3, 6, 11, 12, 15, 18, or ranges including and/or spanning the aforementioned values.

In some embodiments, as disclosed elsewhere herein, administering a composition (e.g., one including CDCs, CDC-XOs, or CDC-EC's) includes injection. In some embodiments, the injection includes skeletal muscle injection. In some embodiments, the injection includes intraperitoneal injection. In some embodiments, administering a composition includes intra-arterial or intravenous infusion. In some embodiments, treatment of the subject results in increased dystrophin expression. In some embodiments, increased dystrophin expression occurs in skeletal muscle in a limb. In other embodiments, the increased dystrophin expression occurs in the diaphragm. In other embodiments, the subject is afflicted with cardiomyopathy. In other embodiments, the subject is diagnosed with cardiomyopathy. In other embodiments, the subject is afflicted with cardiomyopathy, but not heart failure. In other embodiments, the subject is 3-11 years old. In other embodiments, the subject is 12-18 years old.

Described herein are compositions and methods providing significant benefits in the repair or regeneration of damaged or diseased tissues via CDCs and CDC-XOs. Certain supporting techniques are described in, for example, U.S. app. Ser. Nos. 11/666,685, 12/622,143, 12/622,106, 14/421,355, PCT App. No. PCT/US20137054732, PCT/US2015705385, PCT/US2015/054301 and PCT/2US2016/035561, which are fully incorporated by reference herein.

In some embodiments, described herein is a method of treating a skeletal myopathy disease including administering a therapeutically effective amount of CDCs and/or CDC-XOs to a subject, thereby treating the subject. Further described herein is a method of treating a skeletal myopathy disease including administering a therapeutically effective amount of a composition including CDCs and/or CDC-XOs to a subject, thereby treating the subject. In other embodiments, the composition includes a pharmaceutically acceptable carrier. Further described herein is a method of treating a chronic muscular disease including administering a therapeutically effective amount of a composition including a plurality of CDCs and/or CDC-XOs to a subject, thereby treating the subject. In various embodiments, the plurality of the CDCs and/or CDC-XOs are isolated from CDCs grown in serum-free media. In various embodiments, the exosomes have a diameter of about 90 nm to about 200 nm and are CD81+, CD63+, or both. In other embodiments, the chronic muscular disease includes a dystrophinopathy. In various embodiments, the dystrophinopathy includes Duchenne muscular dystrophy. In various embodiments, the dystrophinopathy includes Becker muscular dystrophy. In various embodiments, the subject is a pediatric patient of less than 18 years old, in various embodiments, the subject is a prepubescent patient of less than 13 years old. In various embodiments, the subject is a prepubescent patient of less than 12 years old. In various embodiments, the subject is a prepubescent patient of less than 11 years old. In various embodiments, the subject is a prepubescent patient of less than 10 years old. In various embodiments, the subject is 3-11 years old in various embodiments, the subject is 12-18 years old.

In some embodiments herein is a method of treating a skeletal myopathy disease including administering a therapeutically effective amount of CDC-XOs, CDC-EVs, and/or XO-releasing CDCs to a subject, thereby treating the subject. Some embodiments, pertain to a method of treating a skeletal myopathy disease including administering a therapeutically effective amount of a composition including CDC-XOs, CDC-EVs, and/or XO-releasing CDCs to a subject, thereby treating the subject. In some embodiments, the composition includes a pharmaceutically acceptable carrier. Further described herein is a method of treating a chronic muscular disease including administering a therapeutically effective amount of a composition including CDC-XOs, CDC-EVs, and/or XO-releasing CDCs to a subject, thereby treating the subject. In some embodiments, the chronic muscular disease includes a dystrophinopathy. In other embodiments, the dystrophinopathy is Duchenne muscular dystrophy. In some embodiments, the dystrophinopathy includes Becker muscular dystrophy. In various embodiments, the subject is a pediatric patient of less than 18 years old. In various embodiments, the subject is a prepubescent patient of less than 13 years old. In various embodiments, the subject is a prepubescent patient of less than 12 years old. In various embodiments, the subject is a prepubescent patient of less than 11 years old. In various embodiments, the subject is a prepubescent patient of less than 10 years old. In various embodiments, the subject is 3-11 years old. In various embodiments, the subject is 12-18 years old.

In various embodiments, the subject is afflicted with cardiomyopathy. In various embodiments, the subject is afflicted with cardiomyopathy, but not heart failure. In various embodiments, the subject is diagnosed with cardiomyopathy. In various embodiments, the subject is diagnosed with cardiomyopathy, but not heart failure.

In various embodiments, the cardiomyopathy includes one or more of cell membrane degradation, interstitial inflammation, fatty replacement and fibrosis. In various embodiments, cardiomyopathy includes left ventricle posterobasal fibrosis; conduction abnormalities that are intra-atrial, including SVT with abnormal AV nodal conduction. In various embodiments, cardiomyopathy includes advanced stages of ventricle enlargement, dyspnea, peripheral edema and liver enlargement. In various embodiments, heart failure (HF) includes asymptomatic abnormalities in cardiac structure and function wherein heart function is depressed (stage B), overt symptomatic HF (stage C), to advanced HF (stage D). In various embodiments, subject is afflicted with smooth muscle myopathy including vascular dysfunction, further including GI and urinary tract systems involvement.

In some embodiments, the subject is one or more of the above, such as one of the recited age groups, afflicted and/or diagnosed with cardiomyopathy and/or heart failure. This includes for example, a subject that is 3-11 years old, afflicted with and/or diagnosed with cardiomyopathy, but not heart failure.

In other embodiments, administering a therapeutically effective amount of a composition includes about $1\times10^5$ to about $1\times10^8$ or more CDCs in a single dose. In another example, the number of administered CDCs includes 25 million CDCs per coronary artery (i.e., 75 million CDCs total) as another baseline for exosome dosage quantity. In various embodiments, the numbers of CDCs includes $1\times10^5$, $1\times10^6$, $1\times10^7$, $1\times10^8$, $1\times10^9$ CDCs in a single dose as another baseline for exosome dosage quantity. In certain instances, this may be prorated to body weight (range 100,000-1M CDCs/kg body weight total CDC dose). In various embodiments, the administration can be in repeated doses, such as two, three, four, four or more sequentially-applied doses.

In other embodiments administering a therapeutically effective amount of a composition includes infusion, including intra-arterial and intravenous infusion. In other embodiments, infusion results in systemic delivery. In other embodiments, infusion is capable of delivering therapeutically effective dosages of exosomes to one or more locations in the body. In other embodiments, infusion is capable of delivering a therapeutically effective dosage of exosomes to smooth or skeletal muscle tissue. In other embodiments, administering a therapeutically effective amount of a composition includes injection. In other embodiments, the injection includes injection into the heart, including intramyocardial injection, cavities and chambers of the heart, and vessels associated thereof. In other embodiments, injection into the heart, cavities and chambers of the heart, vessels associated thereof, is capable of delivering a therapeutically effective dosage of exosomes to smooth or skeletal muscle tissue. In other embodiments, the injection includes skeletal muscle injection. In other embodiments, the injection includes intraperitoneal injection. In other embodiments, the injection includes percutaneous injection.

In other embodiments, treatment of the subject results in an increase in dystrophin expression. In other embodiments, increase in dystrophin expression occurs in skeletal muscle. This includes skeletal muscle in limbs, such as a soleus muscle. In other embodiments, increase in dystrophin expression occurs in the diaphragm. In other embodiments, treatment of the subject results in decreased fibrosis, decreased inflammation, and/or increased mitochondrial function. In other embodiments, decreased fibrosis includes a reduction in collagen accumulation. In other embodiments, collagen includes collagen I and/or collagen III. In other embodiments, decreased inflammation includes an increase in cytoplasmic nuclear factor (erythroid-derived like 2 (Nrf2), reduction in fatty acid peroxidation end products, reduced numbers of inflammatory cells, and/or upregulated expression of antioxidants. In other embodiments, antioxidants include heme oxygenase-1 (HO-1), catalase, superoxide dismutase-2 (SOD-2), and glutamate-cystein ligase catalytic (GCLC) subunit. In other embodiments, inflammatory cells include CD68+ macrophages and CD3+ T-cells. In other embodiments, increased mitochondrial function includes increased mitochondrial ultrastructure and/or increased mitochondrial biogenesis. In other embodiments, increased mitochondrial function includes increased nuclear PPAR-γ co-activator-1 (PGC-1) expression.

In various embodiments, the CDCs are generated from a biopsy sample cultured into an explant, further cultured into an explant derived cell, additionally cultured as cardiosphere forming cells, thereafter cultured as cardiospheres, and subsequently cultured as. In other embodiments, the CDCs are human. In various embodiments, the CDCs are generated from a biopsy sample obtained the subject afflicted with a dystrophinopathy.

In other embodiments, treatment of the subject further includes assessing functional improvement in the subject, including functional improvement in skeletal muscle tissue. In various embodiments, functional improvement includes one or more of increased contractile strength, improved ability to walk, improved ability to stand from a seated position, improved ability to sit from a recumbent or supine position, and improved manual dexterity such as pointing and/or clicking a mouse. In other embodiments, treatment of the subject further includes assessing cognition in response to treatment of neural damage, blood-oxygen transfer in response to treatment of lung damage, and immune function in response to treatment of damaged immunological-related tissues.

In some embodiments, described herein is a method including isolating a biopsy specimen from a subject, culturing the biopsy specimen as an explant, generating explant derived cells (EDCs), culturing the EDCs into cardiospheres, and inducing formation of cardiosphere-derived cells (CDCs). In other embodiments, the method includes administering CDCs to a subject. In other embodiments, the method includes isolating exosomes from the CDCs and administering CDC-derived exosomes to a subject. In various embodiments, culturing the biopsy specimen as an explant includes mincing the biopsy specimen and culturing on a fibronectin coated vessel. In various embodiments, generating EDCs includes isolating cells from the explant. In various embodiments, isolated cells from the explant include loosely adherent cells and/or stromal-like cells. In various embodiments, culturing the EDCs into cardiospheres includes culturing of EDCs on poly-D-lysine dishes. In various embodiments, formation of CDCs includes culturing detached cardiospheres on a fibronectin coated vessel. Further examples and embodiments for CDC generation are described in U.S. Pat. Pub. No. 2008/0267921, which is fully incorporated by reference herein. In various embodiments, isolating CDC-derived exosomes includes use of any of the techniques described herein. In various embodiments, administering CDCs to a subject includes use of any of the techniques described herein. In various embodiments, administering CDCs or CDC-derived exosomes to a subject includes use of any of the techniques described herein. In various embodiments, the biopsy specimen is isolated from the same subject that is administered the CDCs or CDC-derived exosomes. In various embodiments, biopsy specimen is isolated from a different subject that the subject that is administered the CDC-derived exosomes. In various embodiments, the subject is afflicted with a chronic muscular disease. In other embodiments, the chronic muscular disease includes dystrophinopathy. In other embodiments, the dystrophinopathy is Duchenne muscular dystrophy. In other embodiments, the dystrophinopathy includes Becker muscular dystrophy. In various embodiments, the subject afflicted with a chronic muscular disease is a pediatric subject less than 18 years old. In various embodiments, the subject is a prepubescent subject less than 12 years old.

In some embodiments, delivery of noncoding RNA species found in CDC-derived exosomes (e.g., miR-148a-3p, or srDMD, a small 115-nucleotide RNA of previously unknown function) mimics the ability of CDCs and CDC-derived exosomes to increase dystrophin protein levels, without affecting transcript length or exon/intron junctions. In some embodiments, these noncoding RNAs ameliorate Duchenne muscular dystrophy by restoring dystrophin in heart and skeletal muscle. In some embodiments, disclosed herein are factors capable of replacing dystrophin, and offsetting the pathophysiological consequences of dystrophin deletion. In some embodiments, the factors include one or more of miR-148a-3p and srDMD that, transferred into recipient cells to influence dystrophin expression, establishing for the first time, nucleic acids as a therapeutic option for DMD.

In some embodiments, a RNA polynucleotide is whose sequence is at least 80%, 85%. 90%, 95%, 96%, 97%. 98%, 99% or 100% identical to any of the microRNAs or short non-coding RNAs mentioned elsewhere herein are used. As used herein, the term "identical" (i.e., "sequence identity") means that two polynucleotide sequences are the same (i.e., on a nucleotide-by-nucleotide basis) over a window of comparison. When referring a percentage of sequence identity, (i.e., sequences that are "X % identical", "percent identity"), the percentage of "identical" is calculated by comparing two aligned sequences, including optimally aligned sequences, over a window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. In some embodiments, a comparison window of at least 15 nucleotide positions, frequently over a window of at least 15-50, 50-100, or 100 or more nucleotides, wherein the percentage of sequence identity is calculated by comparing a reference sequence to a polynucleotide sequence of interest. In some embodiments, one or more comparison windows between reference and polynucleotide sequence of interest, including discontiguous segments in the polynucleotide sequence of interest, may be added together to calculate percentage of sequence identity to account for translocations. In some embodiments, the polynucleotide sequence of interest may include deletions or additions which total 20 percent or less of the reference sequence over the window of comparison. In some embodiments, microRNA of the invention may include additional nucleotides at the 5', 3', or both 5' and 3' ends of at least, at most or about 1, 2, 3, 4, 5, 6, 7, 8, 9, 10 or more nucleotides. This includes, for example, addition of GCG-modified miR-148a with GCG added on the 5' end or on the 3' end.

In some embodiments, the one or more polynucleotides is encoded in one or more vectors as disclosed elsewhere herein. In some embodiments, the one or more vectors is introduced into the cell via a gene delivery vehicle. In some embodiments, the delivery vehicle includes a viral vector such as an adenoviral vector and (e.g., an adeno-associated virus vector). In some embodiments, the delivery vehicle includes expression vectors and delivery vehicles. In some embodiments, polynucleotides are capable of acting on release factors or on the ribosome itself. In some embodiments, the one or more polynucleotides is capable of enhancing read-through of dystrophin transcript.

While in some embodiments, the therapeutic compositions can include CDCs, CDC-XOs, and/or CDC-EVs, in other embodiments, a therapeutic composition can lack CDCs and/or vesicles and instead includes a composition with an effective amount of RNA polynucleotide or vector encoding RNA polynucleotide. In some embodiments, an effective amount of an RNA therapeutic ranges between 0.1 and 20 mg/kg, 0.5 and 10 mg/kg. In some embodiments, the therapeutically effective amount is a single unit dose. In some embodiments, an effective amount includes concentration at a range between 0.1 nM and 10M. In some embodiments, the concentration ranges between 0.3 to 400 nM, and/or between 1 to 200 nM, in some embodiments, an effective amount includes an amount capable of increasing dystrophin expression in one or more tissues, including for example, cardiac and skeletal muscle tissue. In some embodiments, the short non-coding RNA and microRNA include length of an RNA polynucleotide that is at least, at most, or about 6, 7, 8, 9, 10, 11, 12, 13, 14, 15, 16, 17, 18, 19, 20, 21, 22, 23, 24, 25, 50, 100, 150 or 200 nucleotides, including all integers or ranges derivable there between, and ranges including and/or spanning the aforementioned values. In some embodiments, as with any administration disclosed herein, administration of the therapeutically effective amount in a dosage regime depends on the subject to be treated and can be extrapolated based on patient size (increased for larger patients, decreased for smaller patients, extrapolated from mouse models (such as multiplying a mouse dose by a factor of equal to or at least about: 1500, 2000 2500, 3000, and/or ranges including and/or spanning the aforementioned values, etc.). In some embodiments, administration in a dosage regime may be a single dose, or multiple administrations of dosages over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 23, 24 or more hours, and/or 1, 2, 3, 4, 5, 6, 7, days or more. In some embodiments, administration may be through a time release or sustained release mechanism, implemented by formulation and; or mode of administration.

In some embodiments, the one or more RNA polynucleotides possess biological activity. In some embodiments, biological activity can include enhanced translation readthrough of a peptide or protein of interest. This includes for example, assessment of biological activity using peptide or protein expression in a heterologous expression system. In some embodiments, using a heterologous expression fusion protein system, such as dystrophin-eGFP, wild-type or mutant protein can be transfected into cells as a measure of enhanced translation readthrough to assess biological activity. In some embodiments, biological activity can be assessed as a percentage of fluorescence normalized against vehicle only, when compared to wild-type or mutant proteins. In some embodiments, G418 can serve as a positive control. In some embodiments, percentage of fluorescence to assess biological activity includes an increase of about 10-25%, 25-50%, 50-75%, 75-100% or 100% more increase in fluorescence signal compare to a mutant. In some embodiments, percentage of fluorescence to assess biological activity includes a 0-25%, 25-50%, 50-75%, 75-100% or 100% of fluorescence of wild-type peptide or protein expression, or G418 positive control.

In some embodiments, administering an RNA polynucleotide composition includes infusion, including intra-arterial, intravenous, and myocardial infusion. In some embodiments, administering a composition includes injection. In some embodiments, the injection includes injection into the heart, including intramyocardial injection, cavities and chambers of the heart, vessels associated thereof. In some embodiments, the injection includes skeletal muscle injection. In some embodiments, the injection includes intraperitoneal injection. In some embodiments, the injection includes percutaneous injection. In some embodiments, administering a composition includes inhalation.

In some embodiments, treatment of the subject with an RNA polynucleotide composition results in an increase in dystrophin expression. In some embodiments, the increase in dystrophin expression occurs in skeletal muscle. In some embodiments, this includes skeletal muscle in limbs, such as a soleus muscle. In some embodiments, the increase in dystrophin expression occurs in the diaphragm. In some embodiments, treatment of the subject results in decreased fibrosis, decreased inflammation, and/or increased mitochondrial function. In some embodiments, decreased fibrosis includes a reduction in collagen accumulation. In some embodiments, collagen includes collagen I and/or collagen III. In some embodiments, decreased inflammation includes an increase, in cytoplasmic nuclear factor (erythroid-derived 2)-like 2 (Nrf2), reduction in fatty acid peroxidation end products, reduced numbers of inflammatory and/or upregulated expression of antioxidants. In some embodiments, antioxidants include heme oxygenase-1 (HO-1), catalase, superoxide dismutase-2 (SOD-2), and glutamate-cysteine ligase catalytic (GCLC) subunit. In some embodiments, inflammatory cells include CD68+ macrophages and CD3+ T-cells. In some embodiments, increased mitochondrial function includes increased mitochondrial ultrastructure and/or increased mitochondrial biogenesis. In some embodiments, increased mitochondrial function includes increased nuclear PPAR-γ co-activator-1 (PGC-1) expression.

In some embodiments, treatment of the subject with an RNA polynucleotide further includes functional improvement in the subject, including functional improvement in skeletal muscle tissue. In some embodiments, functional improvement includes one or more of increased contractile strength, improved ability to walk, improved ability to stand from a seated position, improved ability to sit from a recumbent or supine position, and improved manual dexterity such as pointing and/or clicking a mouse. In some embodiments, treatment of the subject further includes improved cognition in response to treatment of neural damage, blood-oxygen transfer in response to treatment of lung damage, and immune function in response to treatment of damaged immunological-related tissues.

In some embodiments, as disclosed elsewhere herein, described herein is an RNA polynucleotide composition including one or more RNA polynucleotides, such as 2, 3, 4, 5, 6, 7, 8, 9, 10 or more RNA polynucleotides. In some embodiments, the composition includes one or more RNA polynucleotides such as 2, 3, 4, 5, 6, 7, 8, 9, 10 or more RNA polynucleotides. In some embodiments, the RNAs include non-coding RNAs. In some embodiments, the non-coding RNAs include tRNAs, yRNAs, rTNAs, mirRNAs, lncRNAs, piRNAs, snRNAs, snoRNAs, further including fragments thereof, among others. In some embodiments, the one or more RNA polynucleotides are microRNAs. In some embodiments, the microRNAs are selected from the group consisting of miR-148a, miR-215, miR-33a, miR 204, miR-376c, miR4532, miR-4742, miR-582, miR-629, miR-223, miR-3125, miR-3677, miR-376b, miR-4449, miR-4773, miR-4787, miR-491, miR-495, miR-500a, miR-548ah, miR-550, miR-548ah, miR-551n, miR-5581, miR-616, or any other microRNAs depicted as enriched in FIG. 29. In some embodiments, the microRNAs are selected from the group consisting of: microRNAs miR-146a, miR148a, miR-22, miR-24, miR-210, miR-150, miR-140-3p, miR-19a, miR-27b, miR-19b, miR-27a, miR-376c, miR-128, miR-320a, miR-143, miR-21, miR-130a, miR-9, miR-185, and miR-23a. In smile embodiments, the microRNA includes miR-148a-3p. In some embodiments, the exosomes include a small non-coding RNA from DMD, srDMD. In some embodiments, the one or more polynucleotides are capable of increasing dystrophin expression in a subject. In some embodiments, the one or more polynucleotides or a vector including one or more polynucleotides can be incorporated into a pharmaceutically active mixture or composition by adding a pharmaceutically acceptable carrier. In some embodiments, the pharmaceutical composition includes one or more polynucleotides and/or a viral-based vector encoding the one or more polynucleotides and a pharmaceutically acceptable carrier. In some embodiments, the pharmaceutical composition including the one or more polynucleotides and/or a vector encoding the one or more polynucleotides, and a pharmaceutical acceptable carrier or excipient, includes excipients capable of forming complexes, vesicles and/or liposomes that deliver the one or more polynucleotides, and/or an oligonucleotide complexed or trapped in a vesicle or liposome through a cell membrane. In some embodiments, excipients can include one or more of polyethyleneimine, and derivatives, or similar cationic polymers, including polypropyleneimine or polyethyleneimine copolymers (PECs) and derivatives, synthetic amphiphiles, Lipofectin™, DOTAP and/or viral capsid proteins that are capable of self-assembly into particles that can deliver such one or more polynucleotides.

In some embodiments, concentration of the one or more polynucleotides ranges between 0.1 nM and 10M. In various embodiments, the concentration ranges between 0.3 to 400 nM, even more and/or between 1 to 200 nM. In some embodiments, the one or more polynucleotides may be used at a dose which is ranged between 0.1 and 20 mg/kg, and/or 0.5 and 10 mg/kg. In some embodiments, the one or more polynucleotides include concentrations that refer to the total concentration of polynucleotides or the concentration of each polynucleotides added.

In some embodiments, as described elsewhere herein, the RNA polynucleotide is a microRNA (and/or combination of microRNAs). In some embodiments, the microRNA includes miR-148a. In some embodiments, the miR-148a microRNA has the following sequence 5' GAGGCAAAGUUCUGAGACACUCCGACUCUG-AGUAUGAUAGAAGUCAGUGCACU ACAGAAC-UUUGUCUC3' [_SEQ ID NO: 1]. In some embodiments, a microRNA can be designated by a suffix "5P" or "3P", with "5P" indicating that the mature microRNA derives from the 5' end of the precursor and a corresponding "3P" indicates that it derives from the 3' end of the precursor. In some embodiments, the microRNA comprises miR-148-5p, whose sequence is 5'AAAGUUCUGAGACACUCCGACU3' [SEQ ID NO: 2]. In some embodiments, the microRNA comprises miR-148a-3p, whose sequence 5'UCAGUGCA-CUACAGAACUUUGU3' [SEQ ID NO: 3]. In various embodiments, the microRNA includes an RNA polynucleotide whose sequence is at least 80%, 85%, 90%, 95%, 96%, 97%, 98%, 99% or 100% identical to miR-148a, miR-148-5p, and/or miR-148a-3p and/or fragments of any of the foregoing. In some embodiments, for example, a comparison window of at least 15 nucleotide positions, frequently over a window of at least 15-50, 50-100, or 100 or more nucleotides, wherein the percentage of sequence identity is calculated by comparing a reference sequence to a polynucleotide sequence of interest. In some embodiments, one or more comparison windows between reference and polynucleotide sequence of interest, including discontiguous segments in the polynucleotide sequence of interest, may be added together to calculate percentage of sequence identity to account for translocations. In some embodiments, the polynucleotide sequence of interest may include deletions or additions which total 20 percent or less of the reference sequence over the window of comparison. In some embodiments, microRNA of the invention may include additional nucleotides at the 5', 3', or both 5' and 3' ends of at least, at most or about 1, 2, 3, 4, 5, 6, 7, 8, 9, 10 or more nucleotides. This includes, for example, addition of GCG-modified miR-148a with GCG added on the 5' end or on the 3' end.

In some embodiments, the RNA polynucleotide is a short non-coding RNA from Duchenne muscular dystrophy (DMD), srDMD, whose sequence is 5'UGUA-CACAGAGGCUGAUCGAUUCUCCCUGAACAGCC-UAUUACGGAGGCACUGC AGAUCAAGCCCGCCUG-GAGAGGUGGAGUUUCAAGAGUCCCUUCCUGGU-UCACCGU CUCCUUU3' [SEQ ID NO: 4]. In some embodiments, the short non-coding RNA includes an RNA polynucleotide whose sequence is at least 80%, 85%, 90%, 95%, 96% 97%, 98%, 99% or 100% identical to srDMD and/or fragments thereof. This includes, for example, a 113-nucleotide length variant of srDMD (srDMD variant) whose sequence is 5' UGUACACGGUGGAGUUU-CAAGAGUCCCUUCCUGGUUCACCGUCUCCUUUA-GAG GCUGAUCGAUUCUCCCUGAACAGCC-UAUUACGGAGGCACUGCAGAUC AAGCCCGC CUGGA3' [SEQ ID NO: 5]. Another example includes a srDMD mutant whose sequence is

[SEQ ID NO: 6]
5'UCCCCACAGAGGCUGAUCGAUUCUCCCUGAACAGCCUCCUCCGGAGGC

ACUGCAGAUCAAGCCCGCCUGGAGAGGUGGAGUUUCAAGAGUCCCUUCCU

GGUUCACCGUCUCCUUU3;.

In some embodiments, the short non-coding RNA, including microRNAs, include lengths that are, are at least, or are at most 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 140, 145, 150, 160, 170, 180, 190, 200 or more residues in length, including any integer or any range there between. In some embodiments, short non-coding RNAs, including microRNAs refers to a length of an RNA polynucleotide that is at least, at most, or about 6, 7, 8, 9, 10, 11, 12, 13, 14, 15, 16, 17, 18, 19, 20, 21, 22, 23, 24, 25, 50, 100, 150 or 200 nucleotides, including all integers or ranges derivable there between.

In some embodiments, the RNA polynucleotide possesses biological activity. In some embodiments, biological activity can include enhanced translation readthrough of a peptide or protein of interest. This includes for example, assessment of biological activity using peptide or protein expression in a heterologous expression system. For example, using a heterologous expression fusion protein system, such as dystrophin-eGFP, wild-type or mutant protein can be transfected into cells as a measure of enhanced translation readthrough to assess biological activity. In various embodiments, biological activity can be assessed as a percentage of fluorescence normalized against vehicle only, when compared to wild-type or mutant proteins. In various embodiments, G418 can serve as a positive control. In various embodiments, percentage of fluorescence to assess biological activity includes an increase of about 10-25%, 25-50%, 50-75%, 75-100% or 100% more increase in fluorescence signal compare to a mutant. In various embodiments, percentage of fluorescence to assess biological activity includes a 0-25%, 25-50%, 50-75%, 75-100% or 100% of fluorescence of wild-type peptide or protein expression, or G418 positive control.

In some embodiments, the RNA polynucleotide is synthetic. For example, nucleic acids can be synthesized by phosphotriester, phosphite, or phosphoramidite chemistry and solid phase techniques. In various embodiments, the RNA polynucleotide is produced in a recombinant method. For example, this includes the use of vectors (viral and non-viral), plasmids, cosmids, and other vehicles for delivering a nucleic acid to a cell, such as a host cell (to produce large quantities of the desired RNA molecule).

In some embodiments, the vector encoding an RNA polynucleotide is a viral vector such as an adenoviral vector (e.g., an adeno-associated virus vector). In various embodiments, the vector is a non-viral expression vector.

In some embodiments, an effective amount of RNA ranges between 0.1 and 20 mg/kg, and/or 0.5 and 10 mg/kg. In some embodiments, the therapeutically effective amount is a single unit dose. In some embodiments, an effective amount of RNA includes concentration at a range between 0.1 nM and 10M. In some embodiments, the concentration of RNA ranges between 0.3 to 400 nM, or between 1 to 200 nM. In some embodiments, the RNA polynucleotide or vector includes concentrations that refer to the total concentration of RNA polynucleotide or vector added. In some embodiments, an amount of a RNA polynucleotide or vector is provided to a cell or organism is an effective amount for a particular result, which refers to an amount needed to achieve a desired goal, such as inducing a particular cellular characteristic(s). In various embodiments, an effective amount of RNA polynucleotide includes an amount capable of increasing dystrophin expression in one or more tissues, including for example, cardiac and skeletal muscle tissue.

In some embodiments, the RNA polynucleotide or a vector encoding the RNA polynucleotide are incorporated into a pharmaceutically active mixture or composition by adding a pharmaceutically acceptable carrier or excipients. In some embodiments, the pharmaceutical composition includes the RNA polynucleotide and/or a viral-based vector encoding the RNA polynucleotides and a pharmaceutically acceptable carrier or excipient. In some embodiments, the pharmaceutical composition including the RNA polynucleotide and/or a vector encoding the RNA polynucleotide, and a pharmaceutical acceptable carrier or excipient, includes excipients capable of forming complexes, vesicles and/or liposomes that deliver the RNA polynucleotide, and/or an oligonucleotide complexed or trapped in a vesicle or liposome through a cell membrane. Many of these excipients are known to one of skill in the art, including polyethylenimine and derivatives, or similar cationic polymers, including polypropyleneimine or polyethyleneimine copolymers (PECs) and derivatives, synthetic amphiphils, Lipofectin™, DOTAP and/or viral capsid proteins that are capable of self-assembly into particles that can deliver such RNA polynucleotide. In other embodiments, the RNA polynucleotide is contained within an exosome. In some embodiments, the RNA polynucleotide contained within an exosome is enriched compared to the RNA polynucleotide within an exosome derived from a cell. In some embodiments, enrichment can include 10-100%, 100-200%, 200-400, 400-4000% greater levels of the RNA polynucleotide when compared to that RNA polynucleotide within an exosome derived from a cell.

In some embodiments, a method of treating a chronic muscular disease including administering an RNA polynucleotide or vector encoding a RNA polynucleotide is provided. In some embodiments, the administration of the composition treats a chronic muscular disease in the subject. In some embodiments, the chronic muscular disease is a dystrophinopathy. In some embodiments, the dystrophinopathy is Duchenne muscular dystrophy. In some embodiments, the dystrophinopathy is Becker muscular dystrophy. In some embodiments, the RNA polynucleotide is a microRNA. In various embodiments, the microRNA includes miR-148a [SEQ ID NO: 1]. In some embodiments, the microRNA includes miR-148-5p [SEQ. ID NO: 2], and/or miR-148a-3p [SEQ ID NO:3]. In some embodiments, the microRNA includes an RNA polynucleotide whose sequence is at least 80%, 85%, 90%, 95%, 96%, 97%, 98%, 99% or 100% identical (i.e., percentage identity) to miR-148a [SEQ ID NO:1] and/or fragments thereof (e.g., [SEQ ID NO:2], [SEQ ID NO:3]. In some embodiments, microRNA may include additional nucleotides at the 5', 3', or both 5' and 3' ends of at least, at most or about 1, 2, 3, 4, 5, 6, 7, 8, 9, 10 or more nucleotides. This includes, for example, addition of GCG-modified trig-148a with GCG added on the 5' end or 3' end. In some embodiments, the RNA polynucleotide is a short non-coding RNA from Duchenne muscular dystrophy (DMD), srDMD. In some embodiments, the short non-coding RNA includes an RNA polynucleotide whose sequence is at least 80%, 85%, 90%, 95%, 96%, 97%, 98%, 99% or 100% identical to srDMD [SEQ ID NO: 4] and/or fragments thereof. In some embodiments, the short non-coding RNA includes srDMD variant [SEQ ID NO:5] and/or srDMD mutant [SEQ ID NO:6].

In some embodiments, administering the composition includes a composition with an effective amount of RNA polynucleotide or vector encoding RNA polynucleotide. In some embodiments, an effective amount of RNA polynucleotide or vector encoding RNA polynucleotide ranges between 0.1 and 20 mg/kg, and/or 0.5 and 10 mg/kg. In some embodiments, the therapeutically effective amount is a single unit dose, in some embodiments, an effective amount includes concentration at a range between 0.1 nM and 10M. In some embodiments, the concentration ranges between 0.3 to 400 nM, and/or between 1 to 200 nM. In some embodiments, an effective amount includes an amount capable of increasing dystrophin expression in one or more tissues, including for example, cardiac and skeletal muscle tissue. In some embodiments, the short non-coding RNA and microRNA include length of an RNA polynucleotide that is at least, at most, or about 6, 7, 8, 9, 10, 11, 12, 13, 14, 15, 16, 17, 18, 19, 20, 21, 22, 23, 24, 25, 50, 100, 150 or 200 nucleotides, including all integers or ranges derivable there between.

In some embodiments, administration of the therapeutically effective amount in a dosage regime depends on the subject to be treated. In some embodiments, administration in a dosage regime may be a single dose, or multiple administrations of dosages over a period of time spanning 10, 20, 30, 40, 50, 60 minutes, and/or 1, 2, 3, 4, 5, 6, 7, 8, 9, 10, 11, 12, 13, 14, 15, 16, 17, 18, 19, 20, 21, 22, 23, 24 or more hours, and/or 1, 2, 3, 4, 5, 6, 7, days or more. Moreover, administration may be through a time release or sustained release mechanism, implemented by formulation and/or mode of administration.

In some embodiments, administering a composition includes infusion, including intra-arterial, intravenous, and myocardial infusion. In some embodiments, administering a composition includes injection. In some embodiments, the injection includes injection into the heart, including intramyocardial injection, cavities and chambers of the heart, vessels associated thereof. In some embodiments, the injection includes skeletal muscle injection. In some embodiments, the injection includes intraperitoneal injection. In some embodiments, the injection includes percutaneous injection. In some embodiments, administering a composition includes inhalation.

In some embodiments, treatment of the subject results in an increase in dystrophin expression. In some embodiments, increase in dystrophin expression occurs skeletal muscle. In some embodiments, this includes skeletal muscle in limbs, such as a soleus muscle. In other embodiments, increase in dystrophin expression occurs in the diaphragm. In some embodiments, treatment of the subject results in enhanced readthrough translation of a protein, including for example, dystrophin. In some embodiments, treatment of the subject further includes assessing functional improvement in the subject, including functional improvement in skeletal muscle tissue. In some embodiments, functional improvement includes one or more of increased contractile strength, improved ability to walk, improved ability to stand from a seated position, improved ability to sit from a recumbent or supine position, and improved manual dexterity such as pointing and/or clicking a mouse. In some embodiments, treatment of the subject further includes assessing cognition in response to treatment of neural damage, blood-oxygen transfer in response to treatment of lung damage, and immune function in response to treatment of damaged immunological-related tissues.

EXAMPLES

Embodiments herein demonstrate that CDCs and CDC-derived XOs can be used to reverse key pathophysiological hallmarks of Duchenne muscular dystrophy in mdx mice. Exosomes secreted by human CDCs reproduce the benefits of CDCs in mdx mice, and reverse abnormalities of calcium cycling and mitochondrial respiration in human Duchenne cardiomyocytes. Both CDCs and their exosomes improve heart function in mdx mice; a single injection of CDCs suffices to increase maximal exercise capacity and improve survival. Delivery of noncoding RNA species found in CDC-derived exosomes (e.g. miR-148a) mimics the ability of CDCs and CDC-derived exosomes to increase dystrophin protein levels, without affecting transcript length or exon/intron junctions. Thus, CDCs and CDC-derived exosomes ameliorate features of Duchenne muscular dystrophy via exosome-mediated transfer of singing molecules.

Example 1

Animal Study

The Inventors studied mdx mouse model of DMD (C57BL/10ScSn-Dmdmdx/J) and wild-type strain matched mouse (C57BL/10ScSnJ wild type mouse heart) (Jackson Laboratory, USA) from 10 months of age. To optimize the process of CDC transplantation, preliminary dose-response experiments were performed, which identified $1\times10^5$ cells in first injection and $1\times10^4$ cells in second injection (3 months after first injection) as effective doses, consistent with prior dose ranging experiments in ischemic and non-ischemic mouse models. A total of $1\times10^5$ cells/40 µL phosphate-buffered saline (PBS; first injection) or $1\times10^4$ cells/40 µL PBS (second injection) or PBS alone were injected into left ventricular (LV) myocardium divided equally among 4 sites as described. The LV was visually divided into three zones: basal, middle, and apical, with one injection in the basal, two in the middle and one in the apical zone. Ten-month old CDC/mdx and vehicle/mdx mice were injected with CDCs (Mdx+CDC, n=12) or vehicle [placebo: Mdx+Vehicle (PBS), n=12] twice (3 months interval), respectively. Injections were during open-chest thoracotomy via a 28½ gauge-needle. All surgical procedures were carried out while the animals were under general anesthesia (Dexmedetomidine (0.5 mg/kg)/Ketamine (75 mg/kg); IP; once before surgery). Similar protocols were used for injection of CDC-derived exosomes, NHDF-derived exosomes (as control), miR-148a-3p (Sigma-Aldrich Catalog No. HMI0237), microRNA mimic control (Sigma-Aldrich Catalog No. HMC0002), srDMD, and mutant srDMD. Intraventricular single injection of CDC-derived exosomes [$(10.32\pm3.28)\times10^9$/150 µL PBS] or PBS alone into LV cavity were performed during open-chest thoracotomy via a 28½ gauge-needle. Intraaortic injections of CDCs ($1\times10^4$ cells/40 µL PBS) or PBS were conducted using PE-10 catheter (ALZET; Cupertino, Calif.) via neck carotid artery. Intramuscular injection of exosomes into soleus (SOL) muscles were performed at a single site at the lower ⅓ of the muscle using a 25 µl Hamilton syringe (with 0.5 µl marks) with a 31 gauge needle. The needle was advanced up to the upper ⅓ of the muscle and then slowly retracted through the belly as exosomes [$(20.64\pm2.12)\times10^7$/3 µL] were injected.

Example 2

CDC, CDC-Derived Exosome, NHDF-Derived Exosome, miR-148a-3p, miR Mimic Control, srDMD and Mutant srDMD Mouse CDCs were expanded from wild-type strain-matched mouse hearts (C57BL/10ScSnJ wild type mouse heart) as described. Briefly, ventricular tissues were minced into ~1 mm explants, partially digested enzymatically and plated on adherent (fibronectin coated) culture dishes. These explants spontaneously yield outgrowth cells (explant-derived cells) which were harvested once confluent and plated in suspension culture ($10^5$ cells/mL on poly-D-lysine-coated dishes) to enable self-assembly of three-dimensional cardiospheres. Subsequent replating of cardiospheres on adherent culture dishes yielded CDCs which were used in all experiments at passage one, CDC-derived exosome: Exosomes were isolated from serum-free media conditioned overnight (24 hr) by cultured human CDCs. (CDC-derived exosome) [or normal human dermal fibroblasts (NHDF) as a control] in hypoxia (2% $O_2$; default condition) or normoxia (20% $O_2$, solely for studies comparing RNA content of exosomes). Ultracentrifugation (100,000 g for 1 hr) was used to isolate exosomes from conditioned media after sequential centrifugations at 300 g (10 min) and 10,000 g (30 min) and filtration with 0.22 micron filters. Isolated exosomes were re-suspended in PBS (for in vivo and in vitro experiments) and the ratio of exosome to protein was measured using Nanosight particle counter and Micro BCA Protein Assay Kit (Life technologies, Grand Island, N.Y.), respectively, Preliminary dose-response studies identified [$(2.24\pm1.34)\times10^7$] and [$6.19\pm3.68\times10^8$] exosomes from hypoxic CDCs as effective doses for in vitro and in vivo (intramyocardial CDC-derived exosome injection) experiments, respect.

A miR-148a-3p mimic and miR mimic control (hsa-miR-148a-3p & miRNA negative control 1; 2 µg each; Sigma-Aldrich, St. Louis, Mo.), short non-coding RNA, srDMD, or srDMD mutant (12 µg each; GE Dharmacon, Lafayette, Colo.) mixed with RNAiMAX transfection reagent (life technologies, Grand Island, N.Y.) for 30 min at room temperature at a total volume of 40 µl were injected into 4 points per heart as described above.

The nucleotide sequence of srDMD mutant is (SEQ ID NO: 6)
5'UCCCCACAGAGGCUGAUCGAUUCUCCCUGAACAGCCUCCUCCGGAGGC

ACUGCAGAUCAAGCCCGCCUGGAGAGGUGGAGUUUCAAGAGUCCCUUCCU

GGUUCACCGUCUCCUUU3;.

Example 3

Echocardiography

Echocardiographic studies were performed two days before (Baseline) and 3 weeks, 2 and 3 months after first CDC/CDC-derived exosome or vehicle injection and 3 weeks, 2 and 3 months after second CDC/CDC-derived exosome or vehicle injection (when applicable) using the Vevo 770 Imaging System (VisualSonics, Toronto, Canada). The same imaging system was used to perform echocardiographic studies at baseline (2 days before) and 3 weeks after selected RNA (or control) injection. After induction of light general anesthesia, the heart was imaged at the level of the greatest LV diameter. LV ejection fraction (LVEF) was measured with VisualSonics version 1.3.8 software from 2-dimensional long-axis views.

Changes in left ventricular (LV) end diastolic and systolic volumes after CDC injection. First and second CDC transplantation resulted in a sustained improvement of LV end-diastolic (LV EDV) and end-systolic (LV ESV) volumes in mdx mice, relative to placebo, for at least 6 months.

Example 4

Treadmill Exercise Testing and Survival Analysis

Exercise capacity was assessed weekly with Exer-3/6 open treadmill (Columbus Instruments, Columbus, Ohio), beginning 1 week pre-operatively and 3 weeks after CDC/vehicle injection (exercise capacity measured in a subset of mdx mice 1 week pre-operatively was equivalent to that measured 3 weeks post-operatively in the Mdx+Vehicle group). After an acclimation period (10 m/min for 20 min), stepwise increases in average speed (1 m/min) were applied every two minutes during treadmill exercise until the mouse became exhausted (spending >10 seconds on shocker; continuous nudging was used during treadmill to help mice stay on the track). Subsequently, the mouse was returned to the cage and the total distance recorded. The treadmill protocol conformed to guidelines from the American Physiological Society. After 3 months of weekly exercise, CDC/vehicle mdx mice along with wild-type age-matched mice were followed for assessment of mortality (FIG. 1C).

Example 5

In Vitro Isometric Contractile Properties of Skeletal Muscle

Mice were deeply anesthetized with Ketamine/Xylazine (80 mg/kg and 10 mg/kg body weight IP), the soleus (SOL) and/or extensor digitorum longus (EDL) and/or diaphragm (DIA) muscles were rapidly excised, and the animal was euthanized. Briefly, following a lateral midline skin incision of the lower leg the SOL and/or EDL muscle was dissected and isolated and its tendons of origin and insertion were tightened with silk suture (3-0) and rapidly excised. The SOL or EDL muscle was vertically mounted in a tissue bath containing a mammalian Ringer's solution of the following composition: (in mM) 137 NaCl, 5 KCl, 2 $CaCl_2$, 1 $MgSO_4$, 1 $NaH_2PO_4$, 24 $NaHCO_3$, 11 glucose. The solution was constantly aerated with 95% $O_2$ and 5% $CO_2$ with pH maintained at 7.35 and temperature kept at 24° C. For studies of the diaphragm, following a left costal margin skin and muscle incision, a section of the midcostal hemidiaphragm was transferred to a preparatory Sylgar-lined dish containing cold Ringer's and a narrow 3-4 mm wide strip of diaphragm was isolated maintaining fiber attachments to the rib and central tendon intact which were tighten with silk suture and mounted vertically in the tissue bath. One end of the SOL, EDL or DIA was secured to a clamp at the bottom of the dish and one end was attached to a calibrated force transducer (Cambridge Technology Model 30013, Watertown, Mass.). A micromanipulator linked to the system was used to adjust muscle length. Platinum plate electrodes placed on each side of the muscle were used for direct muscle stimulation (Grass Model S88 stimulator; Quincy, Mass.) using 0.2 msec duration monophasic rectangular pulses of constant current delivered at supramaximal intensity. Muscle length was adjusted until maximum isometric twitch force responses were obtained. Isometric contractile properties were determined at optimal length (Lo). Peak twitch force (Pt) was determined from a series of single pulses. Force/frequency relationships were measured at stimulus frequencies ranging from 5-150 pulses per second (pps). The stimuli were presented in trains of 1 sec duration with an interval of at least 1 min intervening between each stimulus train. Muscle forces generated, including Pt and maximum tetanic force (Po), were normalized for the estimated physiological cross-sectional areas (CSA) of the muscle segment (CSA=muscle weight/1.056×Lo; where 1.056 g/cm$^3$ represents the density of muscle) and expressed in Newtons (N)/cm$^2$, For the SOL and EDL muscle Lo was also normalized for muscle fiber length (0.71 and 0.44 of Lo, respectively) in estimating muscle specific force. Absolute muscle forces generated by the SOL and EDL are also reported (mN).

Example 6 iPSC Derived Cardiomyocytes

Urine-derived cells were seeded onto Matrigel (BD, San Jose, Calif.) coated 12 well plates at 50,000 cells/well and allowed to attach overnight (day 0). On day two, cells were transduced with high-titer OSKM viral supernatants in the presence of 8 µg/ml polybrene for three hours. Viral supernatants were replaced with fresh USC medium and after three days, replaced with mTeSR1 medium (StemCell Technology, Vancouver, BC) and changed daily. As iPSC-like colonies appeared over time, they were picked using glass Pasteur pipettes under a stereo dissection microscope (Leica M205C, Buffalo Grove, Ill.) and transferred to new Matrigel-coated plates for further expansion. Urine-derived iPSCs were differentiated to cardiomyocytes following an established protocol with modifications. Briefly, iPSC colonies were detached by 10 minute incubation with Versene (Life technologies, Carlsbad, Calif.), triturated to a single-cell suspension and seeded onto Matrigel-coated plastic dishes at a density of 250,000 cells/cm$^2$ in mTeSR1 medium and cultured for 4 more days. Differentiation was then initiated by switching the medium to RPMI-1640 medium supplemented with 2% insulin reduced B27 (Life Technologies) and fresh L-glutamine.

Example 7

Histology

Mice were sacrificed 3 weeks (CM: n=4; Mdx+Vehicle: n=6; Mdx+CDC/Mdx+CDC-derived exosome: n=6 each) or 3 months (CTL: n=4; Mdx+Vehicle: n=6; Mdx+CDC/Mdx+CDC-derived exosome: n=6) after first CDC/CDC-derived exosome injections and 3 weeks after miR-148 injection (n=6). Paraffin-embedded sections from apical, middle and basal parts of each heart were used for histology, Masson's trichrome staining (HT15 Trichrome Stain [Masson] Kit; Sigma-Aldrich, St. Louis, Mo.) was performed for evaluation of fibrosis, T cells. B cells and macrophages were assessed by immunostaining with antibodies against mouse CD3, CD20 and CD68, respectively, and the average number of cells was calculated by counting cells in 10 fields from each of 10 sections selected randomly from the apical (3 sections; 50 µm interval), middle (4 sections; 50 µm interval) and basal (3 sections; 50 µm interval) regions of each heart. The data were presented as number of cells/mm$^2$ field. Actively-cycling (Ki67$^+$) and proliferating (Aurora B$^+$) cardiomyocytes and the cardiomyocytes positive for dystrophin were counted in the same manner, and the cycling and proliferating fractions and the dystrophin positive cardiomyocytes were expressed as the number of Ki67$^+$, Aurora B$^+$ and dystrophin$^+$ cardiomyocytes divided by the total number of cardiomyocytes per high-power field (HPF) respectively, as described. Measurements were averaged for each heart.

Immunofluorescence staining: Heat-induced epitope retrieval in low or high pH buffer (DAKO, Carpinteria, Calif.) was followed by 2 hours permeabilization/blocking with Protein Block Solution (DAKO, Carpinteria, Calif.) containing 1% saponin (Sigma, St. Louis, Mo.; Protein Block Solution contained 3% saponin was applied for immunofluorescence staining of Ki67). Subsequently, primary antibodies in Protein Block Solution were applied overnight in 4 C.° for immunofluorescence staining of 5-µm sections from apical, middle and basal parts of each heart. After 3× wash with PBS, each 10 minutes, Alexa Fluor secondary antibodies (Life Technologies, Grand Island, N.Y.) were used for detection. Images were taken by a Leica TCS SP5× confocal microscopy system. Immunofluorescence staining was conducted using antibodies against mouse dystrophin (1 µg/ml; Thermo Fisher Scientific, Fremont, Calif.), Ki-67 (SP6; 1:50; Thermo Fisher Scientific, Fremont, Calif.), WGA (Wheat germ agglutinin; 1:200; Life Technologies, Grand Island, N.Y.), Nrf2 (C20; 1:50; Santa Cruz Biotechnology, Santa Cruz, Calif.), aurora B (1:250; BD Biosciences, San Jose, Calif.).

Immunoperoxidase staining: immunohistochemical detection of CD3, CD20 and CD68 was performed on 5-μm sections using prediluted rabbit monoclonal antibodies from Ventana Medical System (Tuscola, Ariz.; CD68) and Cell Marque (Rocklin, Calif.; CD3, CD20). Staining was conducted on the Leica Bond-Max Ventana automated slide stainer (Chicago, Ill.) using onboard heat-induced epitope retrieval method in high pH ER2 buffer (Leica Biosystems, Buffalo Grove, Ill.). Staining was visualized using the Dako Envision$^+$ rabbit detection System and Dako DAB (Carpinteria, Calif.). The slides were subsequently counterstained with Mayer's hematoxylin for 1 minute and coverslipped.

Electron microscopy: Apical (1 cube), middle (3 cubes from right, middle and left subparts) and basal (3 cubes from right, middle and left subparts) parts of posterior wall from each heart (CTL: n=3; Mdx+Vehicle: n=3; Mdx+CDC: n=3) were fixed by immersion of 1 mm$^3$ cubes in 2% glutaraldehyde, postfixed in osmium, and embedded in epon. Sections were cut at silver thickness, stained with uranyl acetate and lead citrate, and viewed with JEOL 1010 equipped with AMT digital camera system.

Example 8

Western Blots

Western blot analysis was performed to compare myocardial abundance of dystrophin and target proteins contributing to Nrf2 signaling [Nrf2, phospho-Nrf2 (Nrf2-p$^{s40}$) and Nrf2 downstream gene products: hence oxygenase-1 (HO-1), catalase, superoxide dismutase-2 (SOD-2), and catalytic subunit of glutamate-cysteine ligase (GCLC)], Nrf2 phosphorylation [phosphoAkt(Akt-p$^{308}$)], oxidative phosphorylation [CI (NDUFB8 subunit), CII (SDHB subunit), CIV (MTCO1 subunit), CIII (UQCRC2 subunit) and CV (ATPSA subunit)], mitochondrial biogenesis (PGC-1), mitophagy (PINK1), inflammation (NF-κB and MCP-1) and fibrosis (Collagen IA1 and collagen IIIA1). Myocardial density of malondialdehyde protein adducts, a marker of oxidative stress, was also measured by Western blotting (WB). Samples from apical, middle and basal parts of each heart (each 1 mm-thick transverse section) were mixed and homogenized, and nuclear and cytoplasmic fractions were extracted per manufacturer's instructions (CelLytic NUCLEAR Extraction Kit, Sigma-Aldrich, St. Louis, Mo.). Mitochondria were extracted from fresh whole hearts (CTL: n=3; Mdx+Vehicle: n=8; Mdx+CDC: n=8) as described in respirometry section. Cytoplasmic, nuclear and mitochondrial extracts for WB analysis were stored at −80C°. The protein concentrations in extracts were determined by the Micro BCA Protein Assay Kit (Life technologies, Grand Island, N.Y.). Target proteins in the cytoplasmic, nuclear and mitochondrial fractions were measured by Western blot analysis using the following antibodies: antibodies against mouse Nrf2, HO-1, catalase, SOD-2, GC LC collagen IA1, and collagen IIIA1, and PGC-1 were purchased from Santa Cruz Biotechnology (Santa Cruz, Calif.), phospho-Nrf2 (Nrf2-p$^{s40}$; Biorbyt, San Francisco, Calif.), respiratory chain subunits (Total OXPHOS Rodent WB Antibody Cocktail antibody), malondialdehyde, citrate synthase and TBP (Abcam, Cambridge, Mass.), Akt and Akt-p$^{308}$, IκB-α, p-IκB-α, (Cell Signaling Technology, Denver, Colo.), PINK1, MCP-1 and NF-κB p65 (Sigma-Aldrich, St. Louis, Mo.) antibodies were purchased from the cited sources. Antibodies to TBP (TATA binding protein) and citrate synthase were used for measurements of the housekeeping proteins for nuclear (TBP), cytosolic and mitochondrial (citrate synthase) target proteins.

Western blot methods: Briefly, aliquots containing 20 μg proteins were fractionated on 8, 10 and 4-12% Bis-Tris Tel (Life technologies, Grand Island, N.Y.) at 120 V for 2 h and transferred to a PVDF membrane (Life technologies, Grand island, N.Y.). The membrane was incubated for 1 h in blocking buffer (1×TBS, 0.05% Tween-20 and 5% nonfat milk) and then overnight in the same buffer containing the given antibodies at optimal dilutions. The membrane was washed 3 times for 5 min in 1×TBS, 0.05% Tween-20 before a 2-h incubation in a buffer (1× TBS, 0.05% Tween-20 and 3% nonfat milk) containing horseradish peroxidase-linked anti-rabbit IgG, anti-mouse IgG (Cell Signaling Technology, Denver, Colo.) and anti-goat IgG (Sigma-Aldrich, St. Louis, Mo.) at 1:1000-3000 dilution. The membrane was washed 3 times for 5 min in 1× TBS, 0.05% Tween20 and developed by autoluminography using the ECL chemiluminescent agents (Super Signal West Pico Chemiluminescent Substrate; Life Technologies, Grand Island, N.Y.). Citrate synthase and TBP were used as housekeeping proteins against which expressions of the proteins of interest were normalized. Phosphorylated Akt, Nrf2 and IκB-α were normalized to total Akt, Nrf2 and IκB-α. Western blot analyses of collagen I and collagen III were conducted under nonreducing, non-denaturing conditions.

Example 9

Statistical Analysis

All pooled data are presented as mean±SEM, except results for alternate data which are presented as mean±SD Normality and equality of variances of data sets were first tested using Kolmogorov-Smirnov and Levene's tests, respectively. If both were confirmed, t-test or analysis of variance followed by Bonferroni's post hoc test were used for determination of statistical significance; if either normality or equality of variances was not assured, nonparametric tests (Wilcoxon test or Kruskal-Wallis test followed by Dunn's post-test) were applied (SPSS II, SPSS Inc., Chicago, Ill.). No preliminary data were available for a power analysis. Results from a pilot project allowed us to power subsequent studies. The study followed preclinical reporting standards, as described. Age-matched mice were randomly allocated to experimental groups using computer generated randomization schedules. Conduct of experiments and analysis of results and outcomes were performed in a blinded manner (allocation concealment and blinded assessment of outcome). There was no post-hoc exclusion of mice or data after e analysis before unblinding.

Ejection Fraction Data: Preliminary data were collected from a pilot study of 5 animals per group measuring ejection fraction at baseline, and again 3 weeks after treatment with cells or vehicle control in inch and corresponding wild-type mice (C57BL/10ScSnJ). The measured treatment effect was approximately 4 units, with a time effect of approximately 1 unit, with group standard deviations of 3.5 units. The Inventors anticipated larger differences between groups over later time points with possible increase in measured variance. Therefore, with 12 animals per treatment group in the each of the mdx groups, and 7 wild-type control animals, the study had at least 80% power to detect a difference of 4.5 units or greater in treatment effect and 1.4 units or greater in time effect in a study design with 6 measurements per animal over time assuming a compound symmetry covariance structure, a correlation of 0.7 between measurements within animals over time, and a two-sided alpha of 0.05. (Power computed via PASS v. 11.0.)

Treadmill Data: Preliminary data were collected from a pilot study of 5 animals per group measuring treadmill distance (i.e., the distance ambulated before exhaustion, as described below) at baseline, and again 3 weeks after treatment with cells or vehicle control in mdx animals and corresponding wild-type animals. The measured treatment effect was approximately 150 meters, with limited differences observed over time in untreated groups. Group standard deviations were approximately 75 meters, with more variation observed after treatment. The Inventors anticipated larger differences between groups over later time points with possible increase in measured variance. Therefore, with 11 animals per treatment group in the each of the transgenic groups, and 7 wild-type control animals, the study had at least 80% power to detect a difference of 100 meters or greater in treatment effect and changes of at least 30 meters over time in a study design with 12 measurements per animal over time assuming a compound symmetry covariance structure, a correlation of 0.7 between measurements within animals over time, and a two-sided alpha of 0.05. (Power computed via PASS v. 11.0.).

Example 10

Assessment of CDC Engraftment by Real-Time Polymerase Chain Reaction

Quantitative polymerase chain reaction (PCR) was performed 1, 2 and 3 weeks after CDC injection to assess cell engraftment. Male CDCs were injected into female mdx mice to enable detection of the SKY gene located on the Y chromosome as a marker of engraftment using the TaqMan assay (Applied Biosystems, Foster City, Calif.). The whole mouse heart was harvested, weighed, and homogenized. A standard curve was generated with multiple dilutions of genomic DNA isolated from the injected CDCs. All samples were spiked with equal amounts of genomic DNA from non-injected mouse hearts as a control. For each reaction, 50 ng of genomic DNA was used. Real-time PCR was performed in triplicate.

Engraftment was quantified from the standard curve. Percentage engraftment of CDCs at 1 week was ~8% and <1% at 2 weeks. By 3 weeks, no surviving CDCs could be detected.

Example 11

Respirometry

Mice were sacrificed via cervical dislocation after isofluorane anesthesia. Hearts were immediately excised, rinsed in PBS and homogenized via polytron in 1 mL ice cold HES buffer (250 mM sucrose, 1 mM EDTA, 10 mM HEPES, pH 7.4). Lysates were spun down at 1000 g for 5 min at 4° C. to remove unbroken cells and large debris. Supernatant was then spun down at 7000 g for 10 min at 4° C. to separate mitochondria-enriched fraction from crude cytosol. Pellet was resuspended in 1 mL HES buffer (A subportion in lysis buffer for WB). Protein quantification was performed and adjustment with HES buffer to obtain sample containing 10 µg protein in 50 µL buffer which was loaded into a 24-well Seahorse cell culture plate, which was spun down at 2000 g for 20 min at 4° C. to allow mitochondria to adhere to the plate surface. 450 µL MAS buffer (70 mM sucrose, 220 mM mannitol, 5 mM KH2PO4, 5 mM MgCl2, 1 mM EGTA, 0.2% fatty acid-free BSA, pH 7.4) was then added prior to Seahorse XF24 mitochondria stress test. 5 mM/5 mM pyruvate/malate and 0.25 mM ADP was used to stimulate mitochondrial oxidative phosphorylation followed by 1 µM oligomycin, 1 µM FCCP, and a mixture of 1 µM antimycin, 500 nM rotenone. Citrate synthase activity was measured in sample lysates to normalize for actual amount of mitochondria loaded for test. Seahorse respirometry on normal and Duchenne iPSC cell-derived cardiomyocytes was performed using Seahorse™ XF96 Extracellular Flux analyzer as described.

Example 12

Bioluminescence Imaging of mdx Arouse Organs After Systemic Injection of Fluorescently-Labeled CDC-Derived Exosomes 6 hours after injection of fluorescently-labeled CDC-derived exosomes systemically into the mix mouse left ventricular cavity, the mice sacrificed and the organs dissected and imaged using IVIS molecular imaging systems (Caliper Life Sciences, Hopkinton, Mass., USA).

Intracellular $Ca^{2+}$ recordings: iPSC-derived cardiomyocytes were loaded for 30 min with 5 µM of the fluorogenic calcium-sensitive dye, Cal-520 (AAT Bioquest, Sunnyvale, CA) and paced via field stimulation at a frequency of 1 Hz using an Ion-Optix Myopacer (IonOptix Corp) delivering 0.2 ms square voltage pulses with an amplitude of 20 V via two platinum wires placed on each side of the chamber base (~1 cm separation). The Inventors used the xyt mode (2D) of a Leica TCS-SP5-II (Leica Microsystems Inc.; Wetzlar, Germany) to image intracellular $Ca^{2+}$. Cal 520 was excited with a 488 nm laser and its emission (>505 nm) was collected with a 10× objective (Leica: N PLAN 10×/0.25) at scan speeds ranging from 36 to 7 ms per frame depending on the field size. The fluorescence intensity (F) proportional to $Ca^{2+}$ concentration was normalized to baseline fluorescence, F0 (F/F0). Time to peak and $Ca^{2+}$ transient amplitude (F/F0) were analyzed with the software Clampfit (ver. 10.2, Molecular Devices, Inc.). Beat-to-beat alternans in each group calculated over the 5-10 sec interval of pacing at 1 Hz. The amplitude of each transient from each cell (n=10 cells in each group) was measured during pacing and mean and standard deviation were calculated and compared among groups.

RNA sequencing and 2-Dimensional hierarchical clustering: Nugen Ovation RNA-Seq System V2 kit was used to generate the double-stranded cDNA using a mixture of random and poly (T) priming Kapa LTP library kit (Kapa Biosystems, Wilmington Mass.) was used to make the sequencing library. The workflow consists of fragmentation of double stranded cDNA, end repair to generate blunt ends, A-tailing, adaptor ligation and PCR amplification. Different adaptors were used for multiplexing samples in one lane. Sequencing was performed on Illumina HiSeq 2500 for a pair read 100 run. Data quality check was done on Illumina SAV. Demultiplexing was performed with Illumines CASAVA 1.8.2. The reads were first mapped to the latest UCSC transcript set using Bowtie2 version 2.1.0 and the gene expression level was estimated using RSEM v1.2.15. TMM (trimmed mean of M-values) was used to normalize the gene expression. Differentially expressed genes were identified using the edgeR program. Genes showing altered expression with p<0.05 and more than 2 fold changes were considered differentially expressed. The pathway and network analyses were performed using Ingenuity (IPA). IPA computes a score for each network according to the fit of the set of supplied focus genes. These scores indicate the likelihood of focus genes to belong to a network versus those obtained by chance. A score >2 indicates 99% confidence that a focus gene network was not generated by chance alone. The canonical pathways generated by IPA are the most significant for the uploaded data set. Fischer's exact test with FDR option was used to calculate the significance of the canonical pathway. 2Dimensional hierarchical clustering used genes with at least 2 times fold change difference ($\log_2$) between vehicle/CDC or vehicle/CDC-derived exosome (intraventricular injection) mdx hearts, diaphragms, soleus and EDL muscles. Each column represents an mdx analyzed tissue and each row a gene. Probe set signal values were normalized to the mean across mdx analyzed tissues. The relative level of gene expression is depicted from the lowest (green) to the highest (red), according to the scale shown; examples of fold changes of transcripts for genes involved in the various pathways of interest are plotted.

Cardiac mitochondria after intramyocardial CDC injection: TEM images of sections from apical, middle and basal parts of each heart were used for calculating the average numbers of mitochondria in CTL (wild type) and CDC/vehicle mdx mouse hearts. Extracted DNAs (QIAamp DNA Mini Kit, QIAGEN, Germantown, Md.) from whole heart tissue were used to measure mitochondrial to nuclear DNA ratio using PCR format per manufacturer's instructions (NovaQUANT™ Mouse Mitochondria to Nuclear Ratio kit, EMD Millipore, Billerica, Mass.).

Example 13

CDC Transplantation mdx Hearts

Figures 1, 1E:
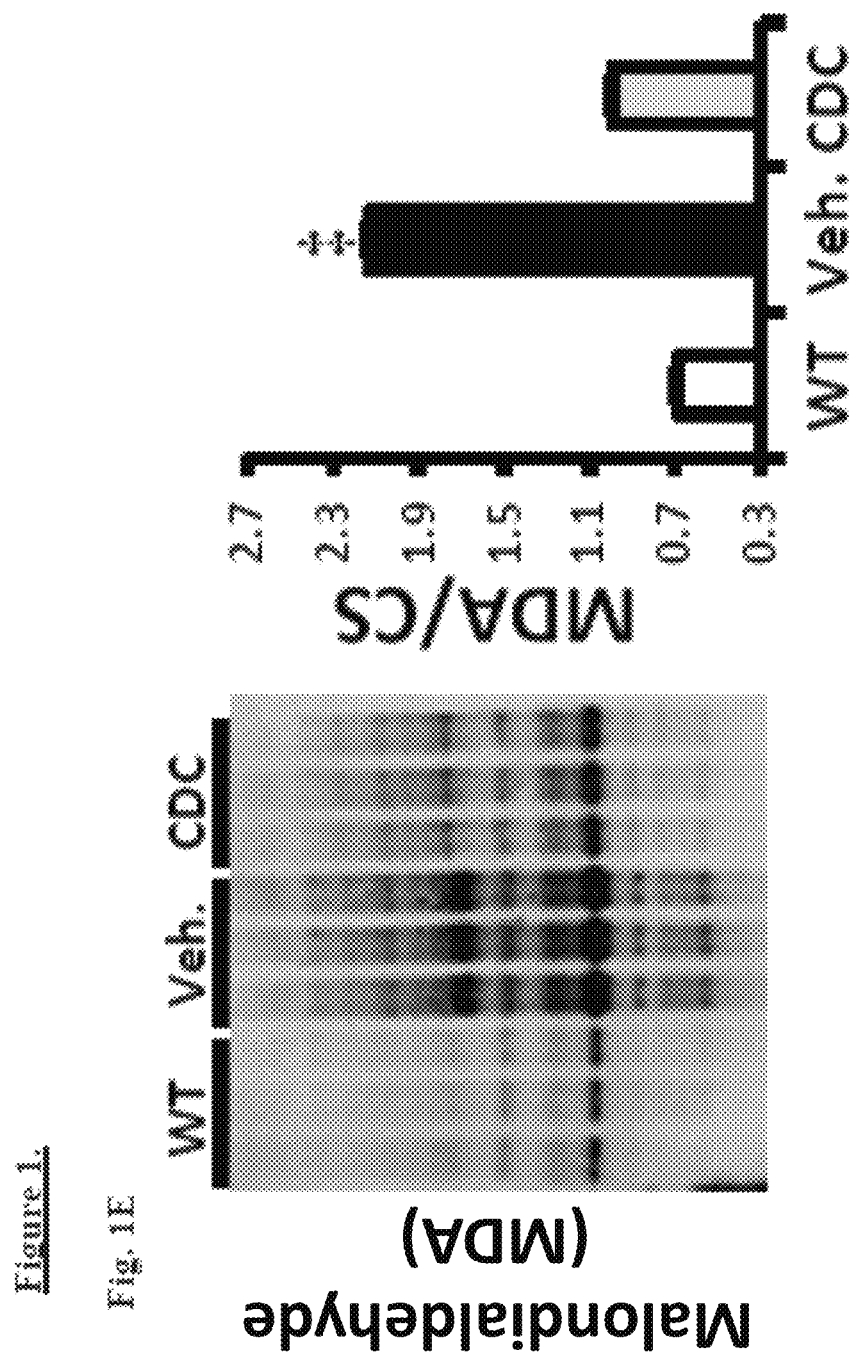
Figures 1, 1I:
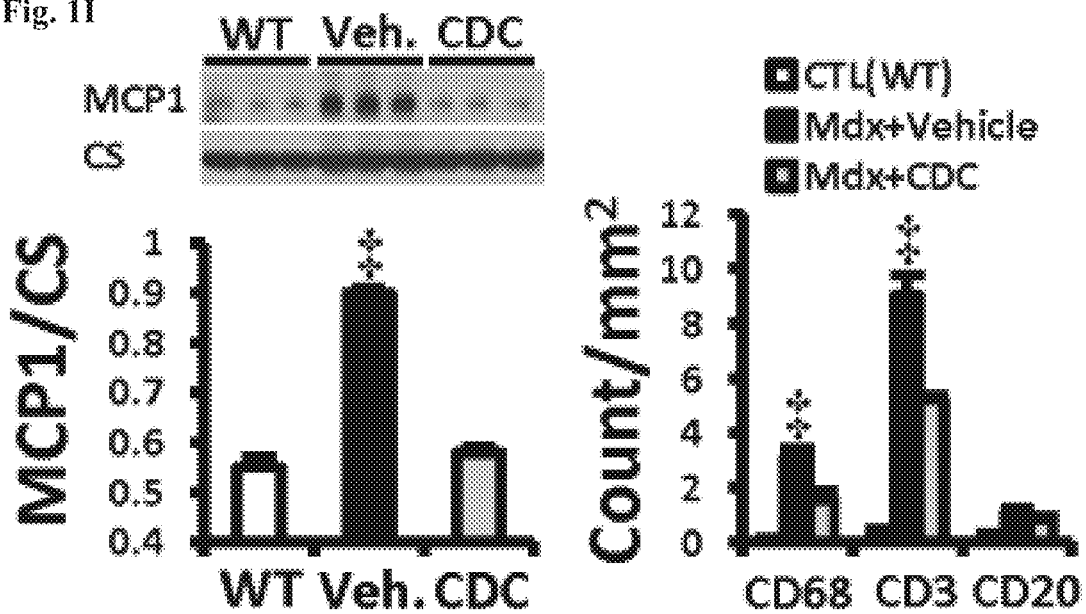
Figures 1, 1J:
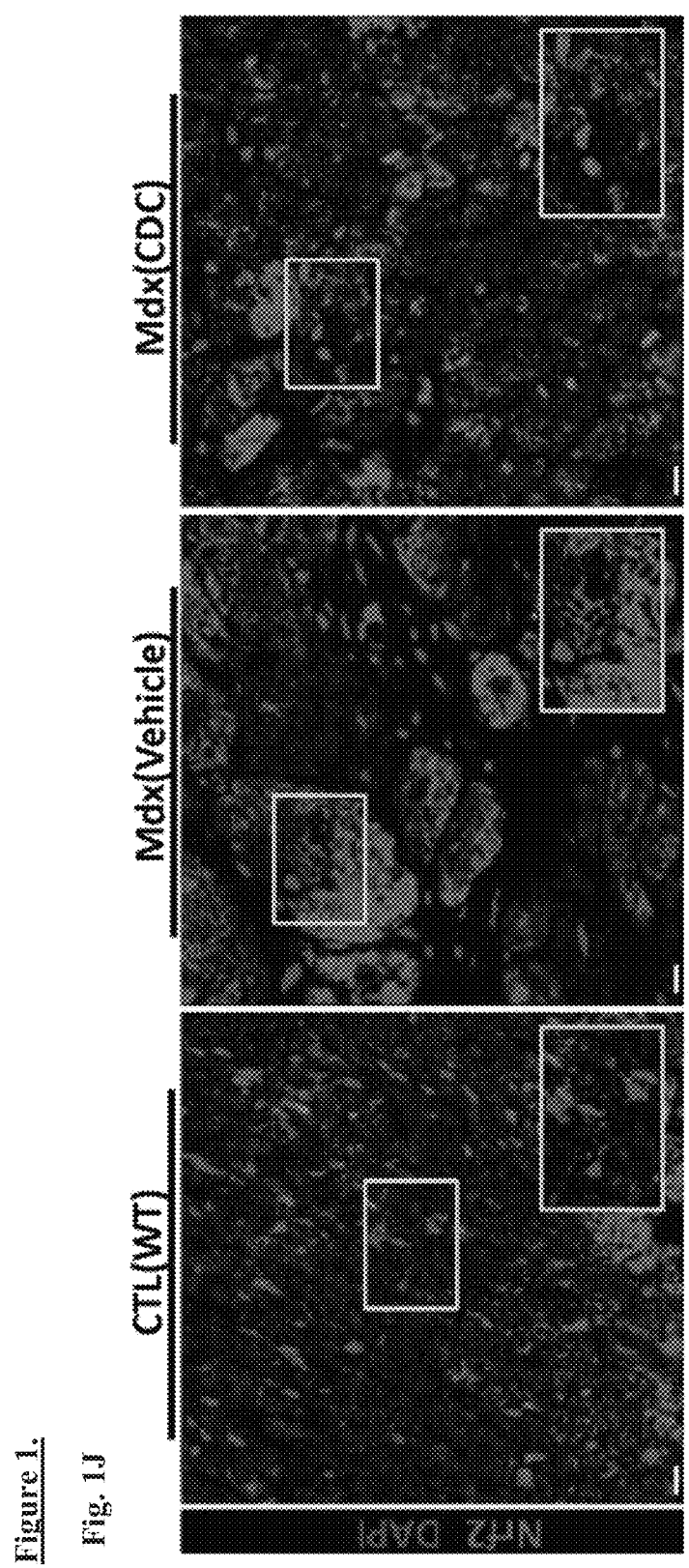

Following intramyocardial injections of CDCs, improvements were observed in cardiac function as shown in FIG. 1A, increased exercise capacity, as shown in FIG. 1B, and increased survival rate as shown in FIG. 1C. Oxidative stress & inflammation were also confirmed as major players in DMD. CDC administration resulted in decreased inflammatory cell infiltration, as shown in FIG. 1D, and reduction in oxidative stress as shown in FIG. 1E, FIG. 1F, and FIG. 1G.

Figures 2, 2A:
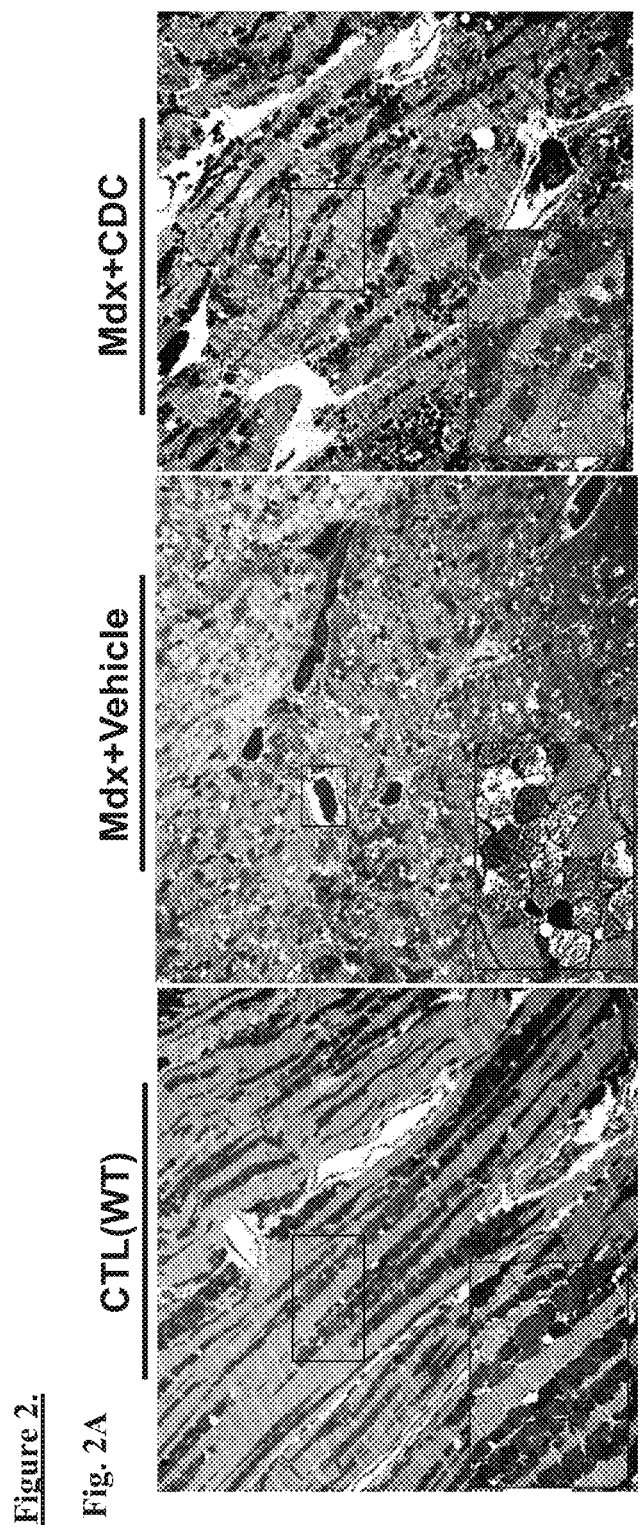
FIGS. 2A-B. Restoration of mitochondrial integrity.
Figures 2, 2B:
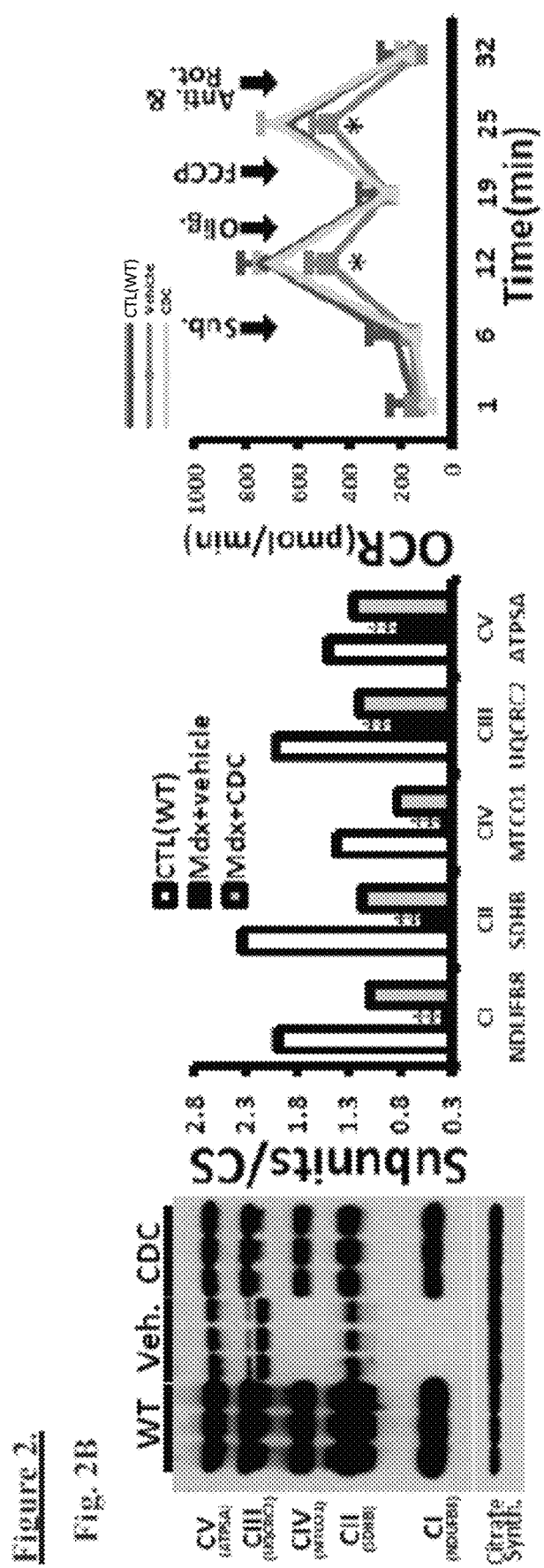
Figures 3, 3A:
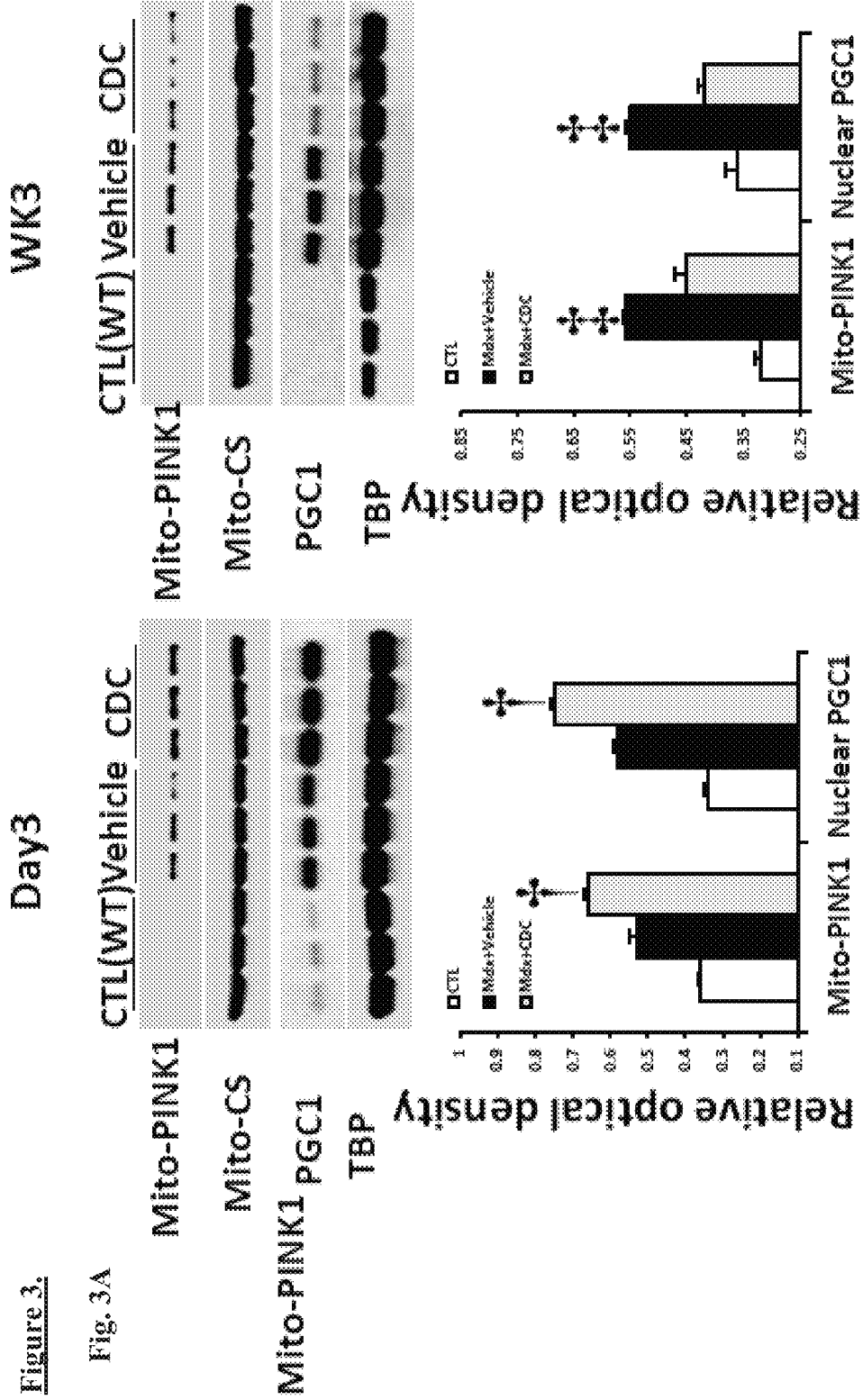
FIG. 3A: Initial turnover of damaged mitochondria was followed by repopulation with healthy mitochondria.

These results further included restoration of mitochondrial integrity. Mitochondrial structures displayed a clear restoration of organized structure as shown in FIG. 2A and confirmed by subunit measurements as shown in FIG. 2B. Repopulation with stable competent mitochondria was further observed. Initial turnover of damaged mitochondria was followed by repopulation with healthy mitochondria, as shown in FIG. 3A. The same mitochondrial number between groups existed as shown in FIG. 3B.

Figures 4, 4A:
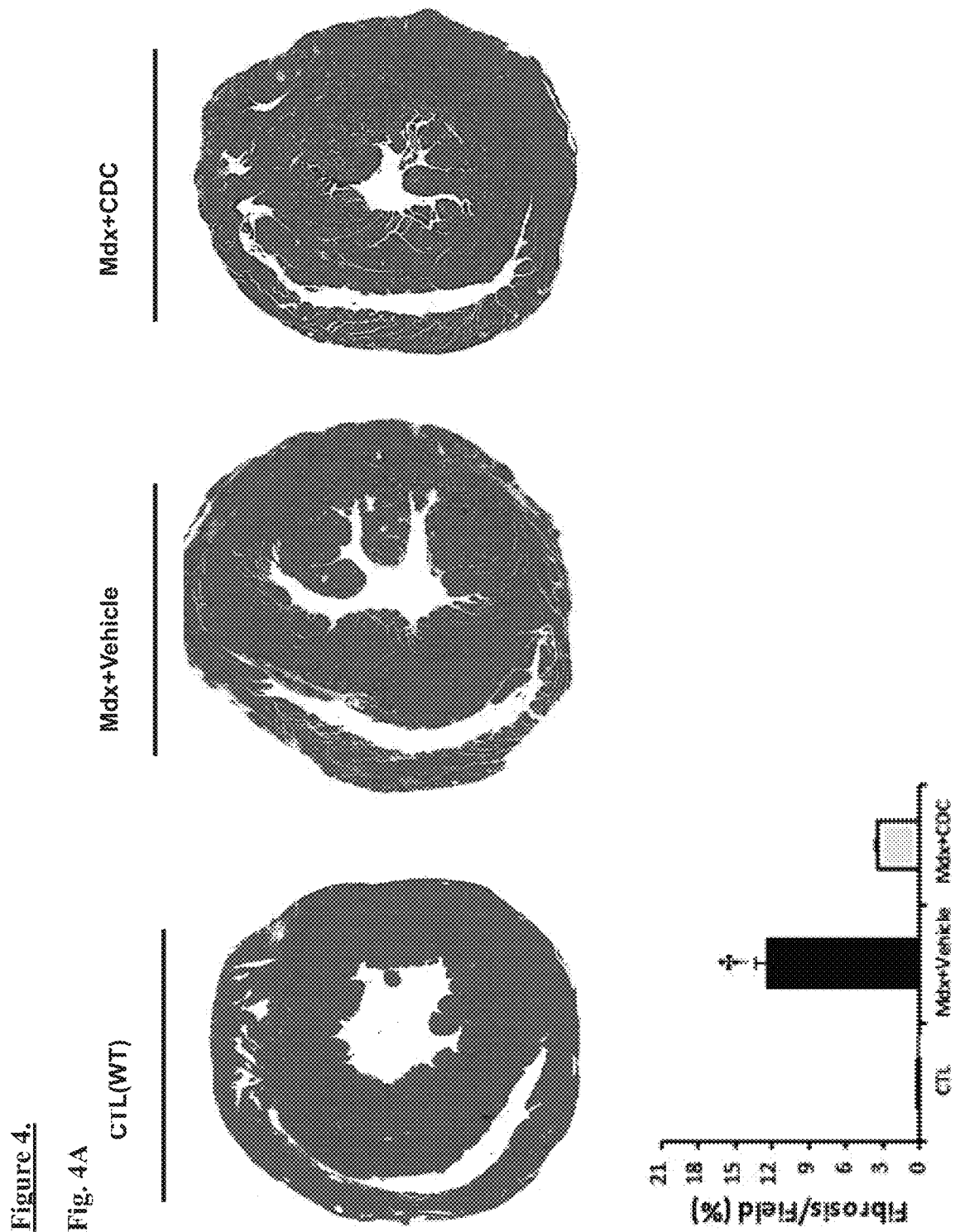
FIGS. 4A-B. Reduced cardiac collagen content and fibrosis.
Figures 4, 4B:
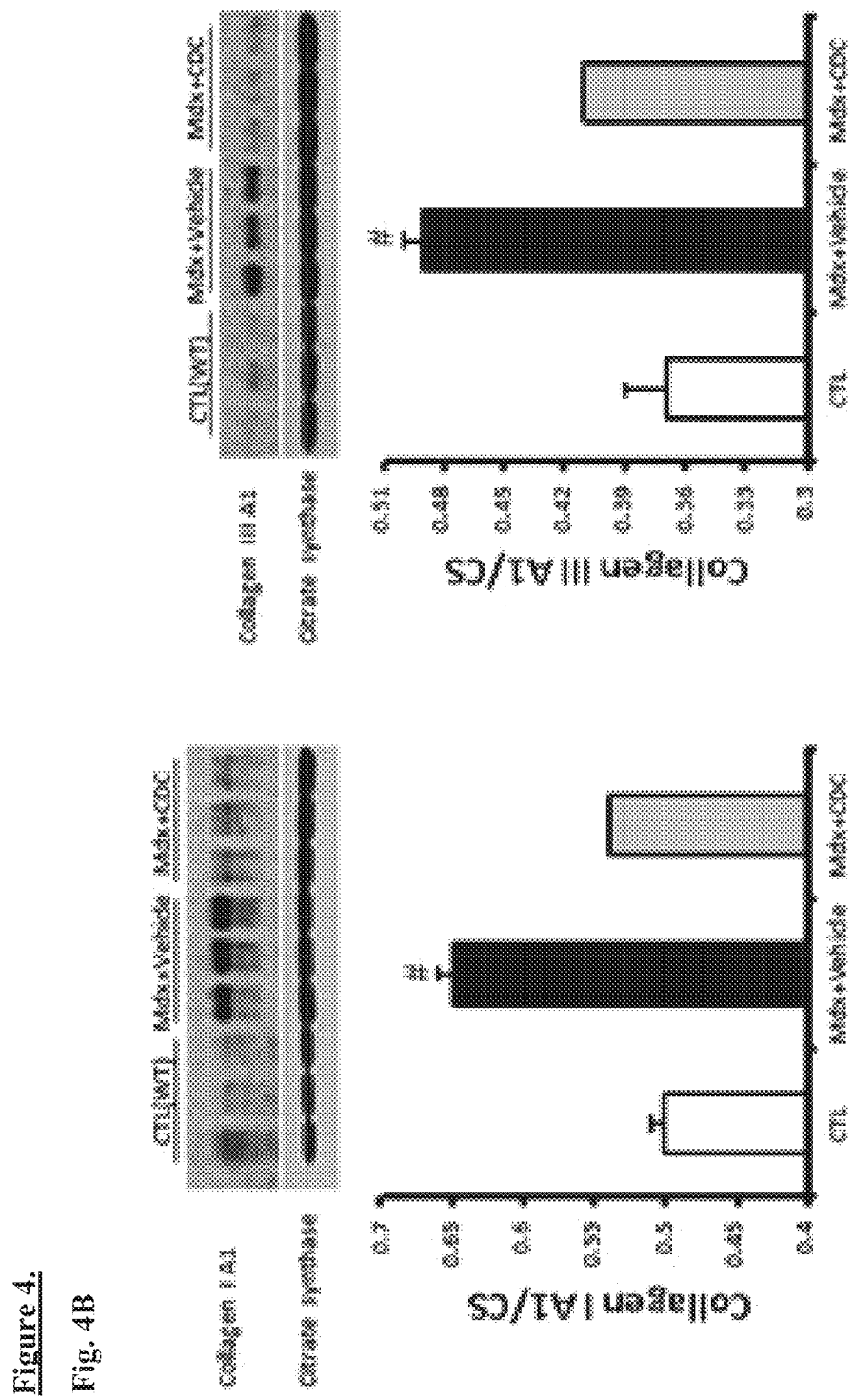
Figures 5, 5B:
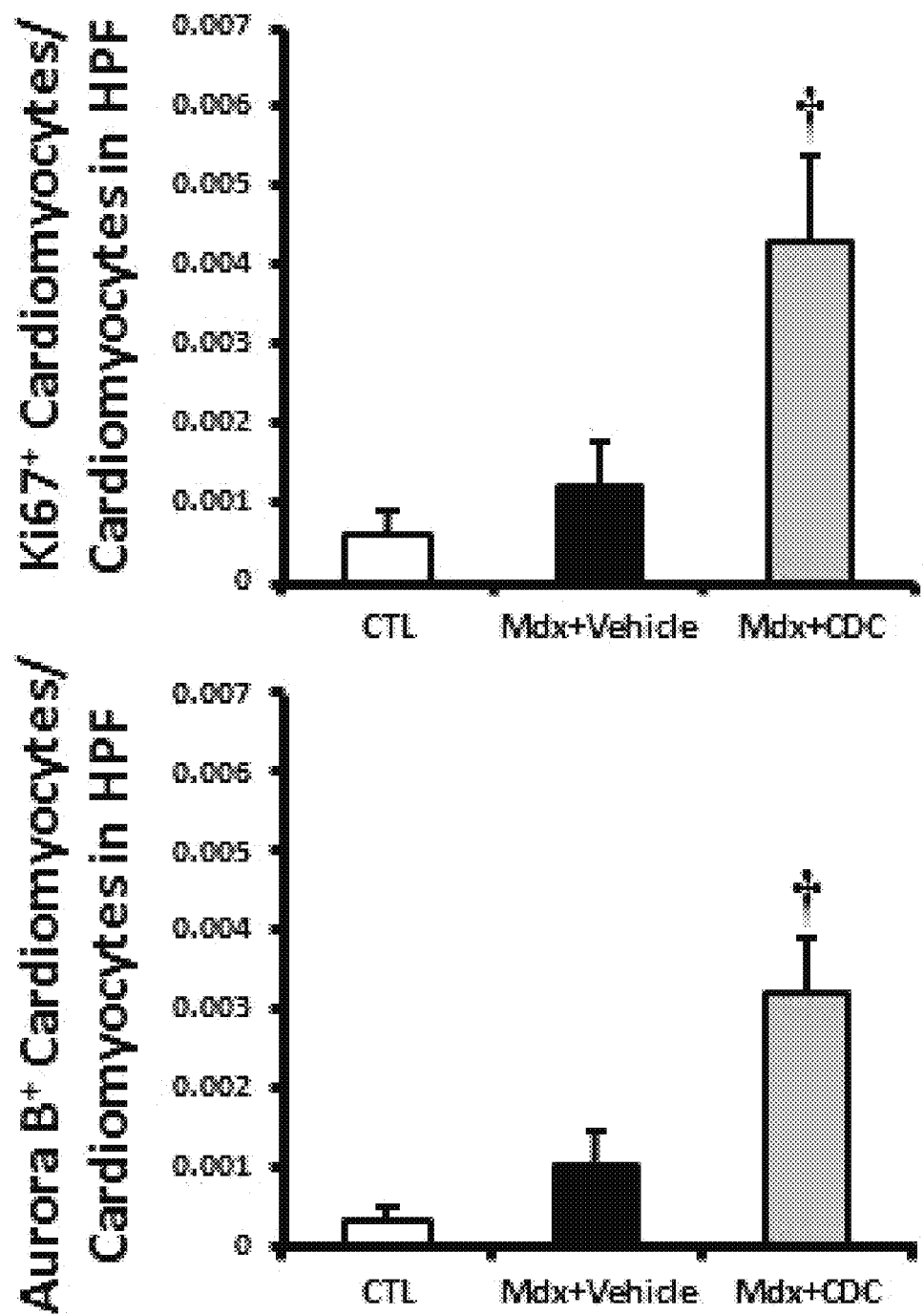
Figure 6:
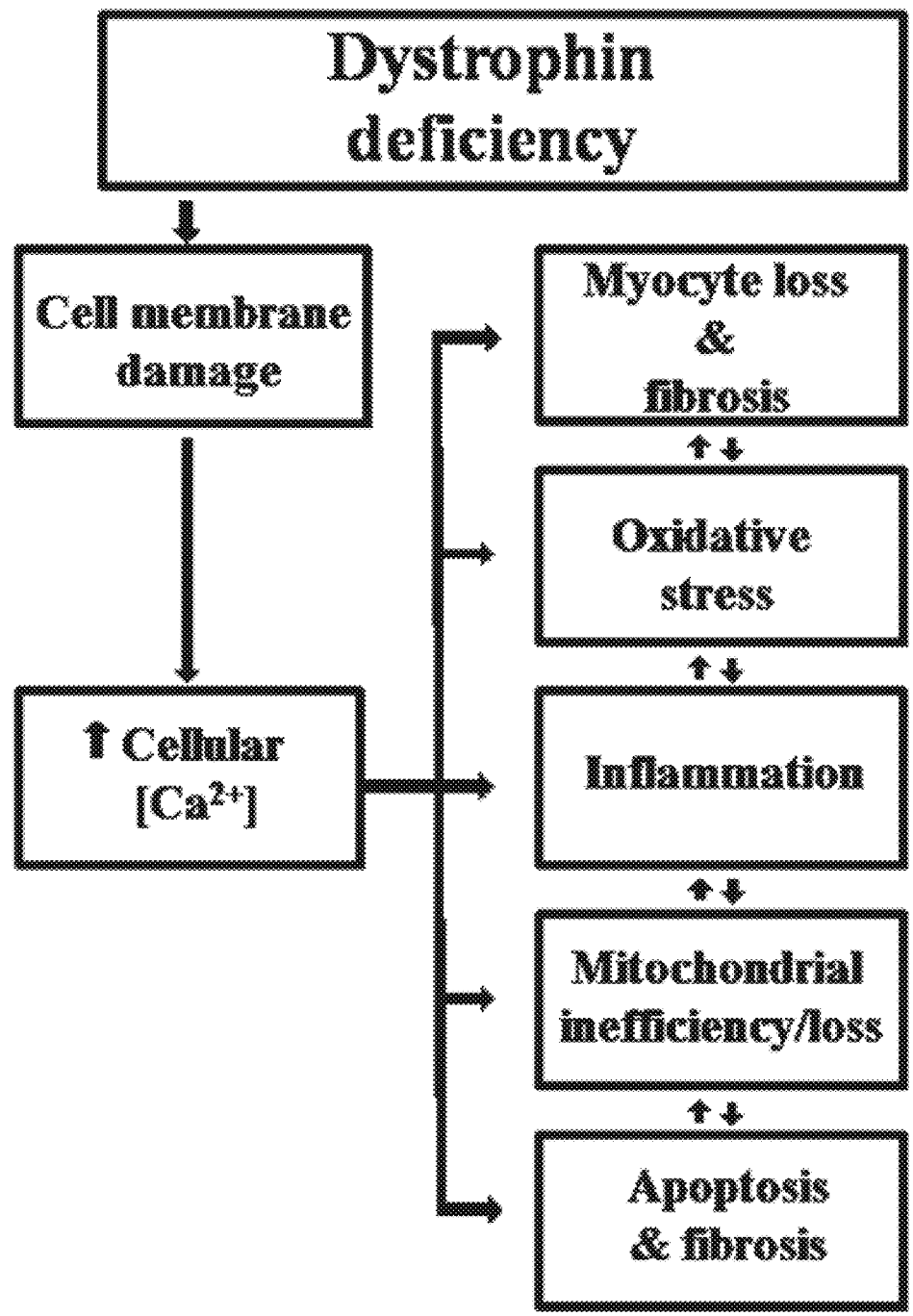
FIG. 6. Depiction of the various mechanisms unpinning muscular dystrophy pathogenesis involving myocyte loss, fibrosis, oxidative stress, inflammation, mitochondrial inefficiency/loss, apoptosis, fibrosis, etc.

In addition, reductions in cardiac collagen content and fibrosis was observed as shown in microscopic imaging as shown in FIG. 4A, and confirmed in collagen protein detection as shown in FIG. 4B. Further improvements in cardiomyogenesis were observed, as shown in FIG. 5A and via AuroraB+ and ki67+ staining in FIG. 5B.

In this aspect, CDCs are shown as effective in improving key features of DMD, including skeletal myopathy, cardiomyopathy resulting in myocyte loss, fibrosis, oxidative stress, inflammation, mitochondrial inefficiency/loss, apoptosis and fibrosis.

More specifically, intramyocardial injection of first and second (lower) doses of CDCs into the hearts of mdx mice improved left ventricular function (as manifested by ejection fraction [EF]) and volumes, relative to placebo, for at least 6 months. The CDC-induced improvement in EF persisted beyond the point at which no surviving CDCs were detectable in mdx hearts (3 weeks after CDC delivery). In addition to improving EF, CDC injection enhanced ambulatory function. Ten-month-old wild-type mice (CTL) and mdx mice (distinct from the mdx mice studied in other experiments) were subjected to weekly high-intensity treadmill exercise, starting 3 weeks after single-dose CDC or vehicle administration. CDC-treated mdx mice showed a substantial increase in maximal exercise capacity, relative to vehicle-treated mdx mice, over the 3 mos that exercise capacity was measured; survival also differed in the two groups. By 23 mos of age, all vehicle-treated mdx mice had died, whereas >50% of CDC-treated mdx mice remained alive. In investigating mechanism, the Inventors first studied the anti-oxidative, anti-inflammatory, anti-fibrotic, and cardiomyogenic effects of CDCs. Injection of CDCs led to major changes in the expression of genes related to oxidative stress, inflammation and mitochondrial integrity. The Nrf2 anti-oxidant pathway was activated in CDC-treated mdx heart. Nrf2 is normally repressed by Keap1, but oxidative stress (as well as Nrf2 phosphorylation by protein kinases such as Akt) causes dissociation of the Nrf2-Keap1 complex, culminating in nuclear translocation of Nrf2 and transcriptional activation of antioxidant enzymes. In mdx hearts, levels of phosphorylated Akt, total Nrf2 and nuclear Nrf2 were high (as expected in response to oxidative stress); CDC treatment further increased their protein levels and those of downstream gene products (heme, oxygenase-1 [HO-1], catalase, superoxide dismutase-2 [SOD-2], and the catalytic subunit of glutamate-cysteine Ligase [GCLC]). Concomitantly, oxidative stress was attenuated, as evidenced by a profound reduction of malondialdehyde adducts. Histological analysis revealed extensive fibrosis in vehicle-treated mdx hearts, but much less in CDC-treated mdx hearts (comparable to an age-matched wild-type [WT] control. Likewise, CDC treatment largely reversed the accumulation of collagens I and III in mdx heart tissue 3 weeks after treatment, CDCs inhibited the inflammation and mitochondrial dysfunction characteristic of mdx cardiomyopathy. NFκB, the master regulator of pro-inflammatory cytokines and chemokines, was activated in vehicle mdx hearts. Increases in phosphorylated IκB and nuclear p65 were accompanied by upregulation of MCP1 (monocyte chemoattractant protein1) and accumulation of CD68+ macrophages and CD3+ T cells. CDC treatment reversed activation of NFκB and decreased the number of inflammatory cells in mdx hearts 3 weeks after CDC injection. Mitochondrial structure and function are abnormal in muscular dystrophy-associated heart failure. Whole-transcriptome analysis revealed major changes in the expression of genes related to mitochondrial integrity in mdx hearts. Consistent with this finding, CDCs restored mitochondrial ultrastructure, increased mitochondrial DNA copy numbers (but not mitochondrial number), augmented levels of respiratory chain subunits and normalized the deficient respiratory capacity of isolated mdx mitochondria. Of note, the improved mitochondrial integrity and decreased mitochondrial turnover observed 3 weeks after CDC treatment in mdx mouse hearts were associated with upregulation of antioxidant enzymes and reductions of oxidative stress and inflammation. The Inventors also probed the effects of CDCs on cardiomyogenesis, Vehicle-treated mdx hearts exhibited a modest increase in the numbers of cycling (Ki67+) and proliferating (aurora B+) cardiomyocytes, presumably as a compensation for ongoing cardiomyocyte loss. CDCs are known to increase endogenous cardiomyogenesis in ischemic and non-ischemic models, Similar effects were seen in the mdx heart: CDC treatment promoted cardiomyocyte cycling and proliferation, as evidenced by a marked increase in Ki67+ and aurora B+ cardiomyocytes.

Figures 7, 7A:
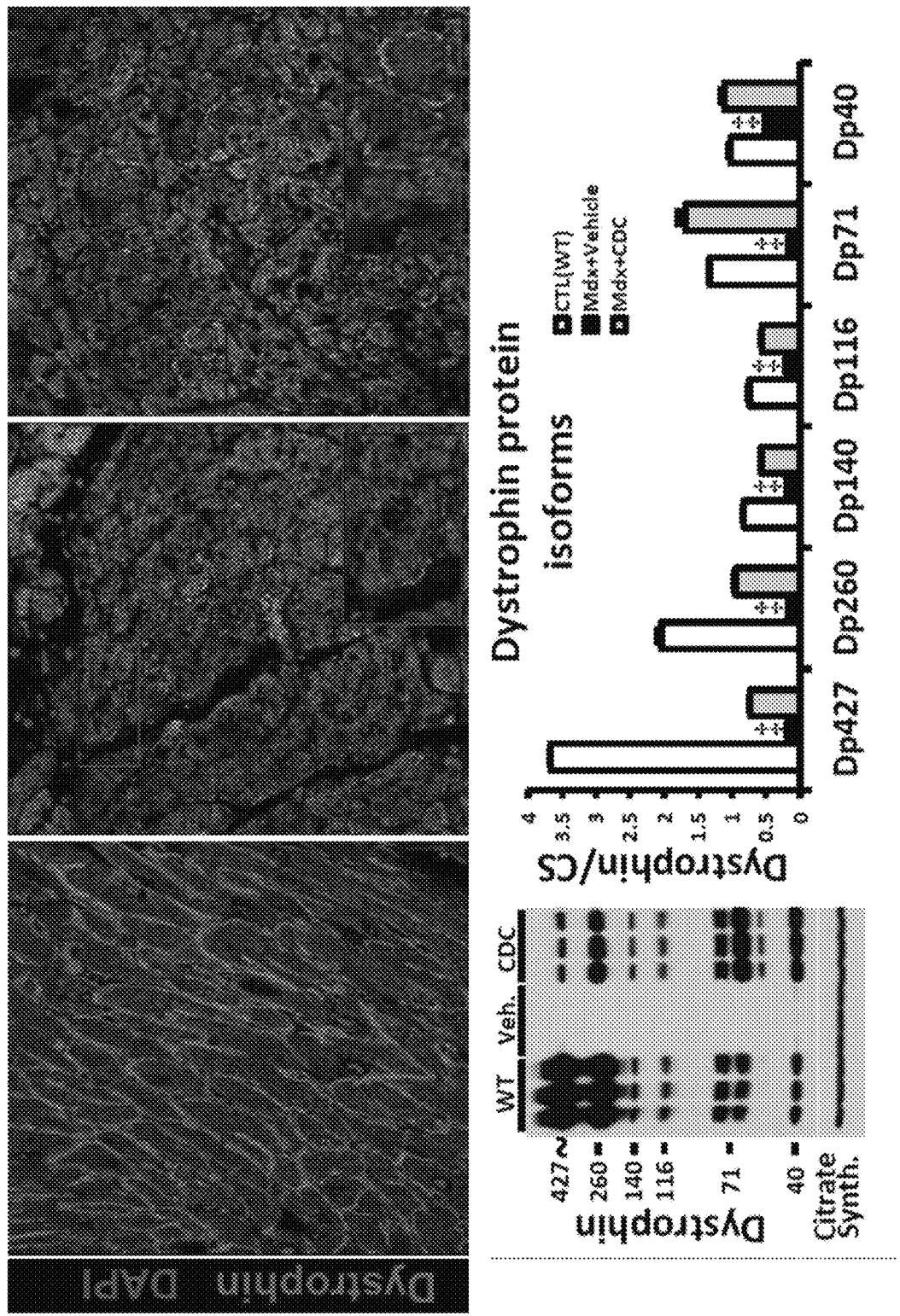
FIGS. 7A-B. Restoration of dystrophin expression.
Figures 7, 7B:
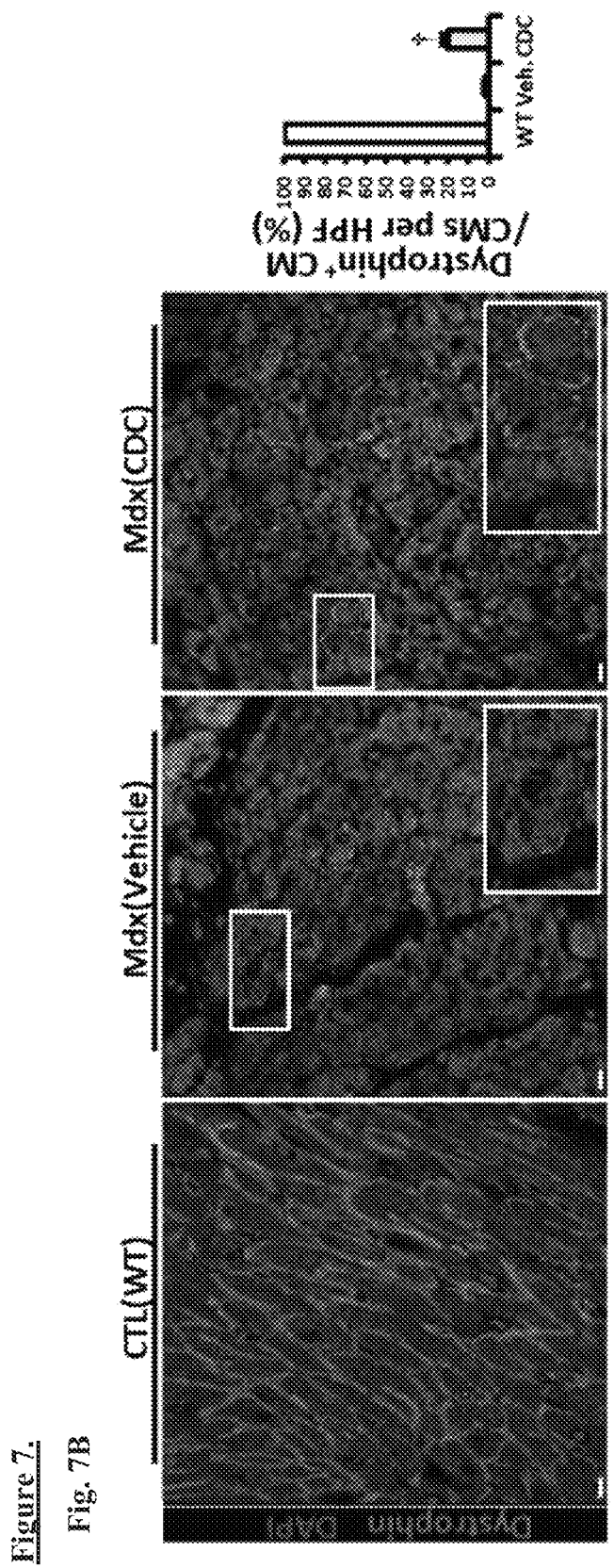

Interestingly, the Inventors found, appreciable dystrophin staining by immunohistochemistry (IHC) in CDC-treated inch hearts (19.8±2.7% dystrophin positive cardiomyocytes). Western blotting (using an antibody against the C-terminal of dystrophin) further revealed a virtual absence of dystrophin in vehicle-treated mdx hearts, but much higher levels after CDC injection. All of the naturally-occurring isoforms of dystrophin were augmented by CDCs; the physiologically-relevant full-length isoform was restored, on average, to 20.1±0.8% of control levels by western blot densitometry. The values for dystrophin restoration, measured either by IHC or the more quantitatively reliable immunoblots, are notable, as CRISPR/Cas 9-mediated restoration of dystrophin expression in this range and even lower suffices to produce substantial functional benefit. Intramyocardial CDC injection (LV 4 injection sites), resulted in an increase in expression of dystrophin as shown in FIG. 7A, including across all measured isoforms as shown in FIG. 7B.

Example 14

CDC-Derived Exosome Transplantation in mdx Hearts

Figure 8:
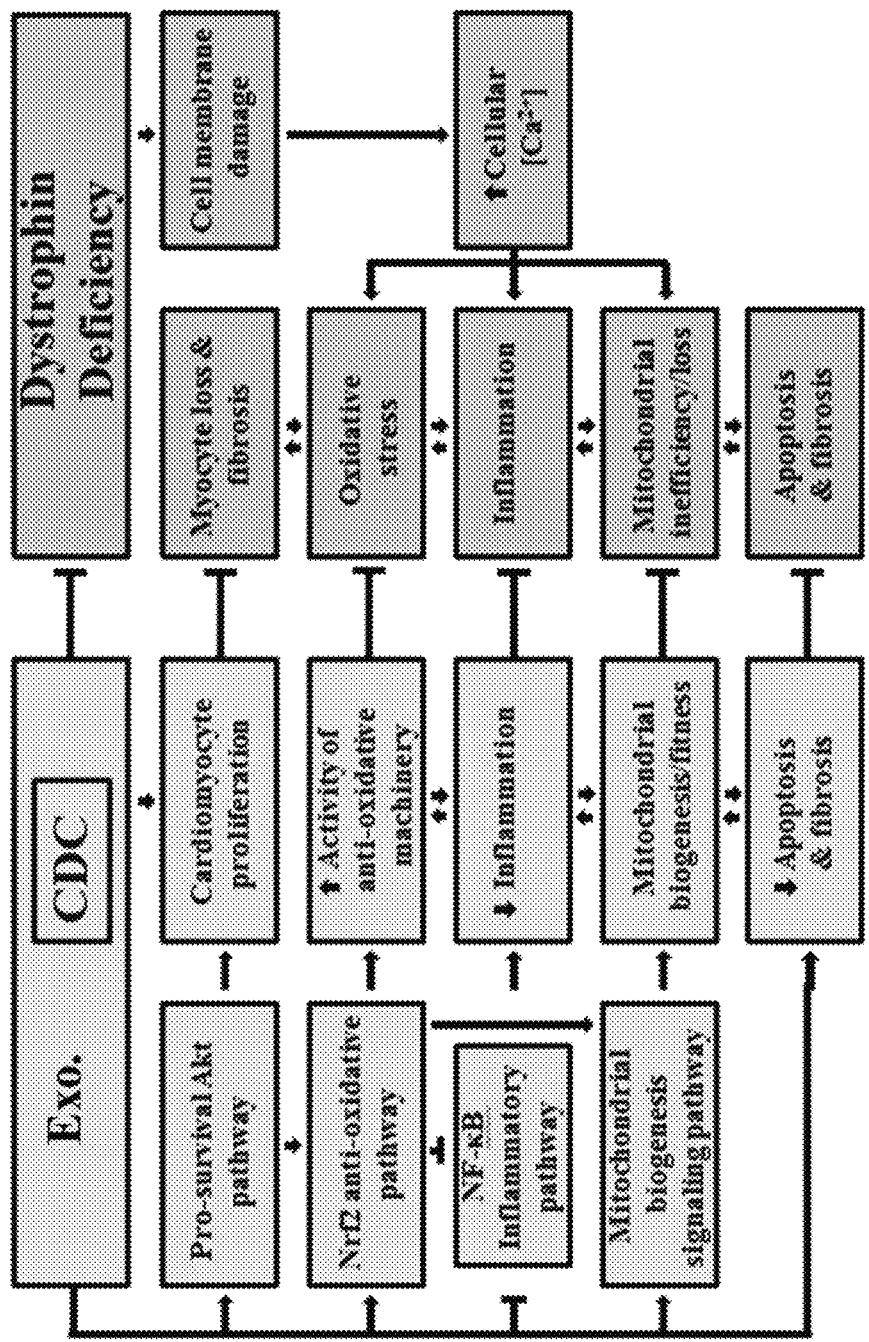
FIG. 8. Schematic of pathophysiological mechanisms operative in muscular dystrophy and the cellular mechanisms recruited by CDCs and CDC-XOs involving myocyte loss, fibrosis, oxidative stress, inflammation, mitochondrial inefficiency/loss, apoptosis, fibrosis, etc.
Figures 9, 9A:
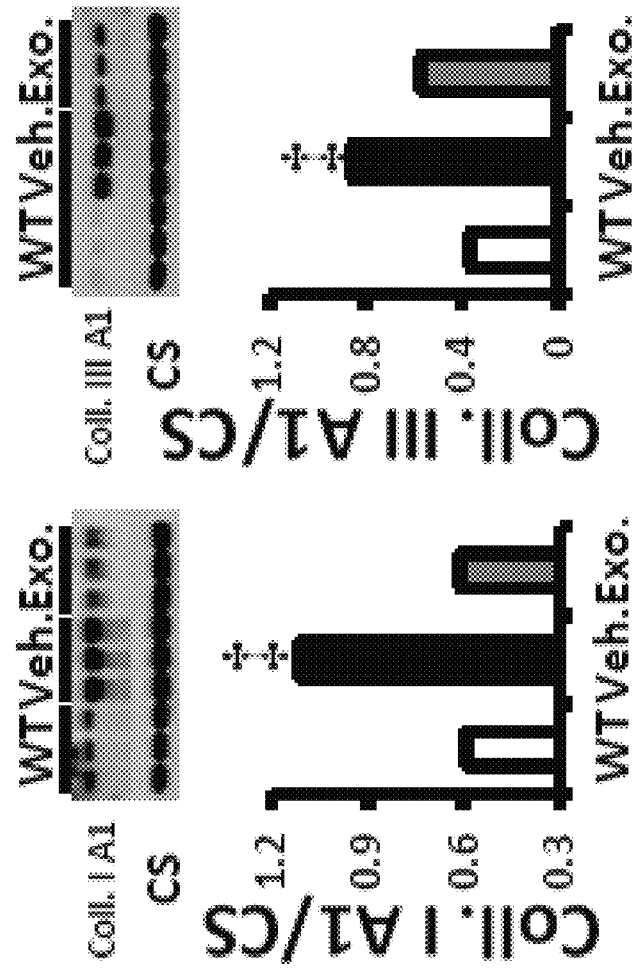
FIGS. 9A-D. CDC-XOs recap effects of CDCs. Intramyocardial injection of CDC-XOs reduces collagen to nearly the same levels as wild-type.
Figures 9, 9B:
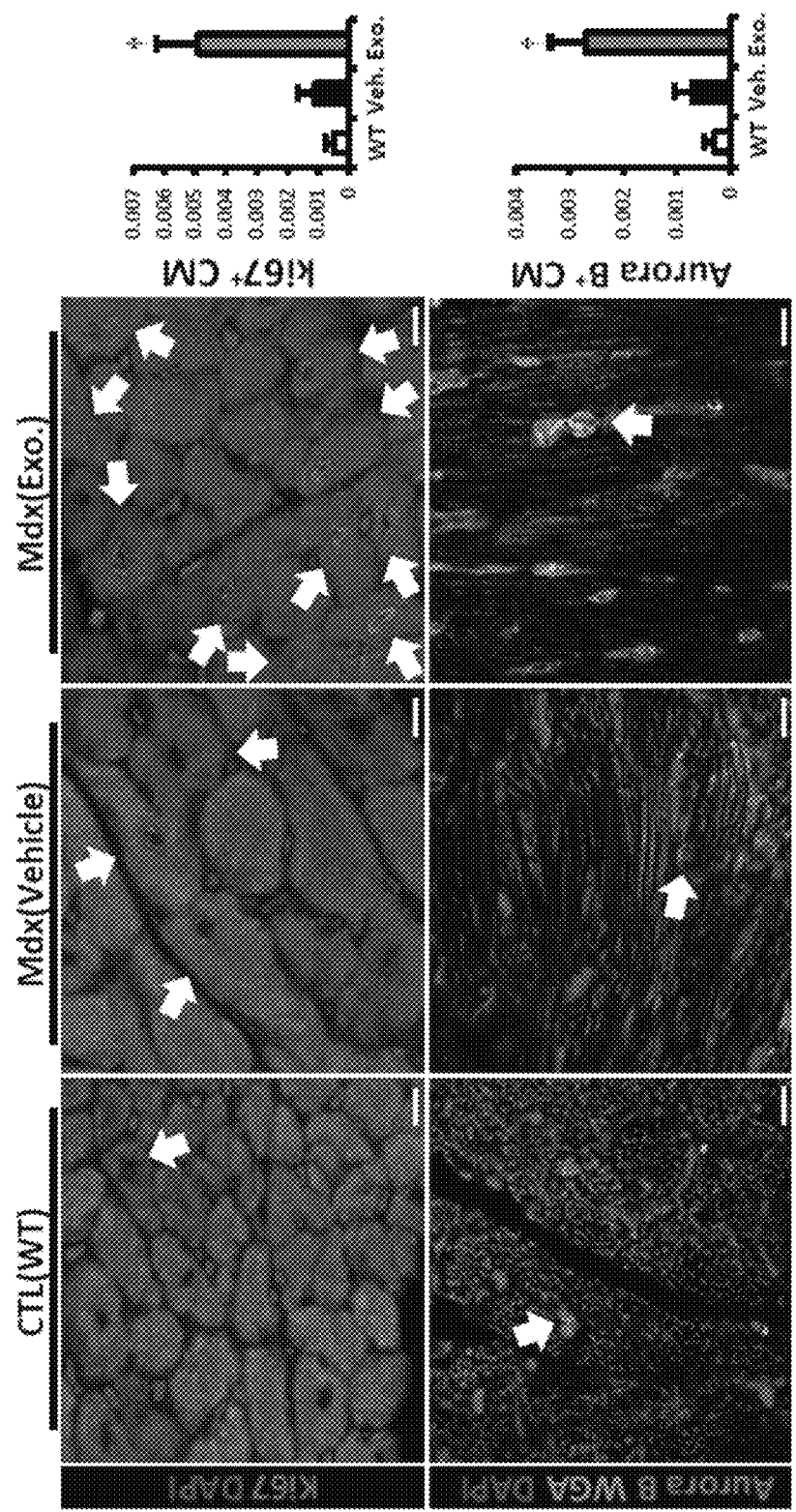
Figures 9, 9C:
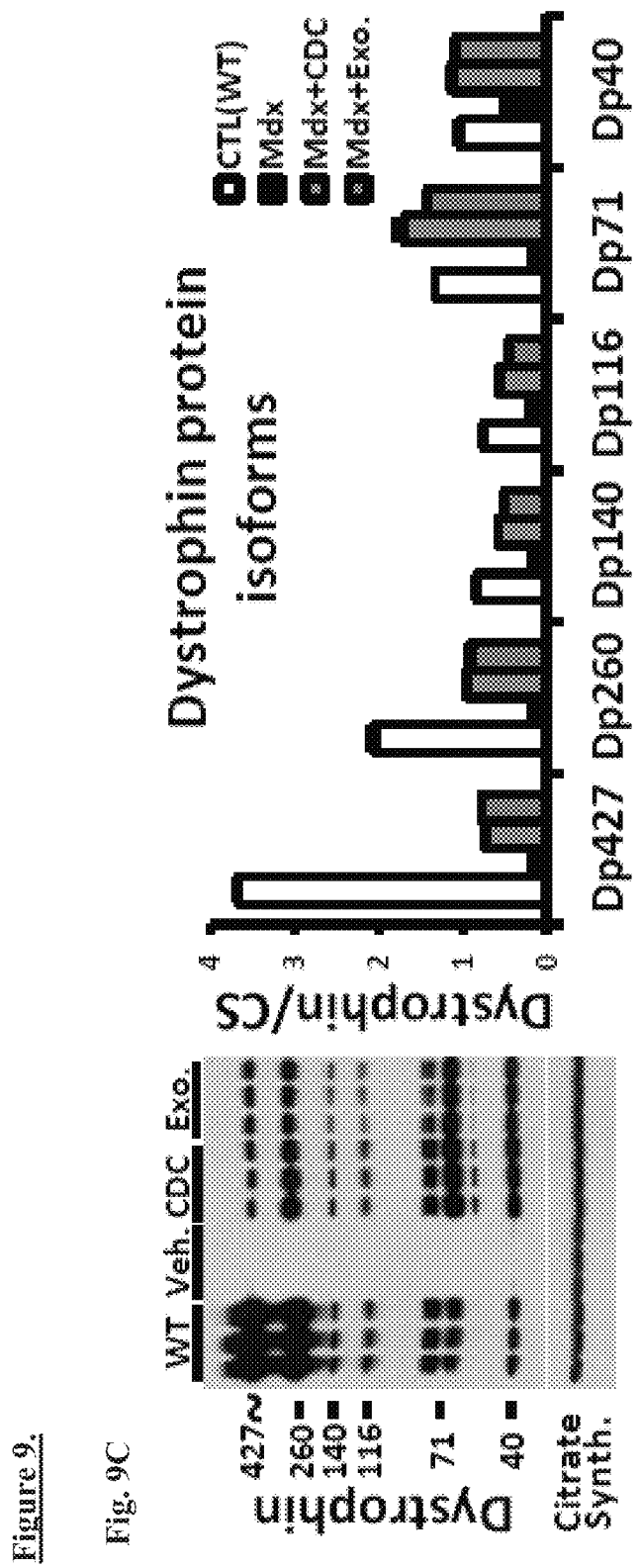
Figures 9, 9D:
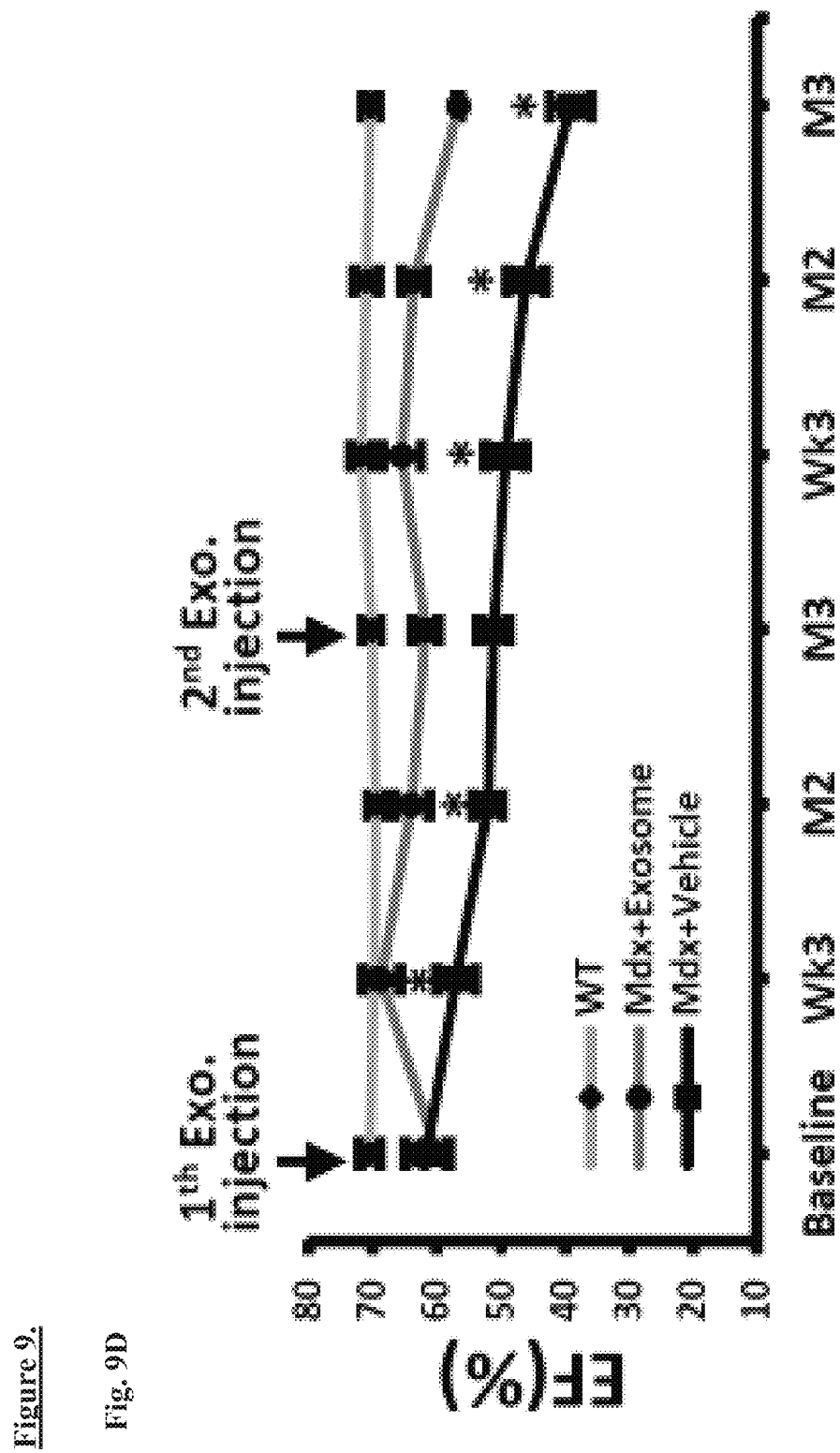

Consistent with reports related to CDC mediating their therapeutic effects via secreted vesicle exosomes, a depiction of role of CDCs and CDC-derived exosomes in retarding or reversing Duchenne muscular dystrophy is shown in FIG. 8. CDCs prevent myocyte loss, reduce apoptosis, fibrosis, and inflammation as mediated via. CDC-derived exosomes. Interestingly, intramyocardial exosomes recap effects of CDCs. Intramyocardial CDC-derived exosome injection reduces collagen, to nearly the same levels as wild-type as shown in FIG. 9A. Moreover, intramyocardial exosomes recap effects of CDCs as shown in FIG. 9B and FIG. 9C. Injection of exosomes was able to retard progressive decrease in ejection fraction as shown in FIG. 9D.

A disproportional increase in cardiac function and exercise capacity in CDC-treated mdx mice. This could be due to CDCs themselves, secreted mediators (exosomes, ECV, proteins, etc.) from engrafted CDCs, modulated cardiac secretome, and/or improved systemic hemodynamics. Disproportional increase in cardiac function as shown in FIG. 10A and exercise capacity as shown in FIG. 10B in CDC-treated mdx mice.

Exosomes secreted by CDCs (i.e., CDC-derived exosomes) mimic the functional and structural benefits of CDCs in a murine model of myocardial infarction. In mdx mice, likewise, the benefits of CDCs were reproduced by exosomes isolated from media conditioned by hypoxic CDCs (~30-200 nm in diameter), Two repeat doses of human CDC-derived exosomes (separated by 3 months) led to sustained improvement in EF, relative to vehicle injection, with a minimal but detectable Immoral response in the non-immunosuppressed mdx mice. Collagen I and III levels decreased while the numbers of cycling (Ki67$^+$) and proliferating (aurora B$^+$) cardiomyocytes increased in CDC-derived exosome-injected mdx hearts. The effects of CDC-derived exosomes were mediated at least in part via clathrin-mediated endocytosis by the surrounding myocardium. As with the parent CDCs, intramyocardial CDC-derived exosome injection increased dystrophin expression in mdx hearts. The extent of dystrophin protein upregulation was comparable after treatment with CDCs or CDC-derived exosomes.

Example 15

Systemic CDC-Derived Exosome Injection

To further evaluate the potential of exosomes to mediate systemic benefits, the Inventors injected CDC-derived exosomes into the left ventricular cavity of mdx hearts.

Figures 11, 11A:
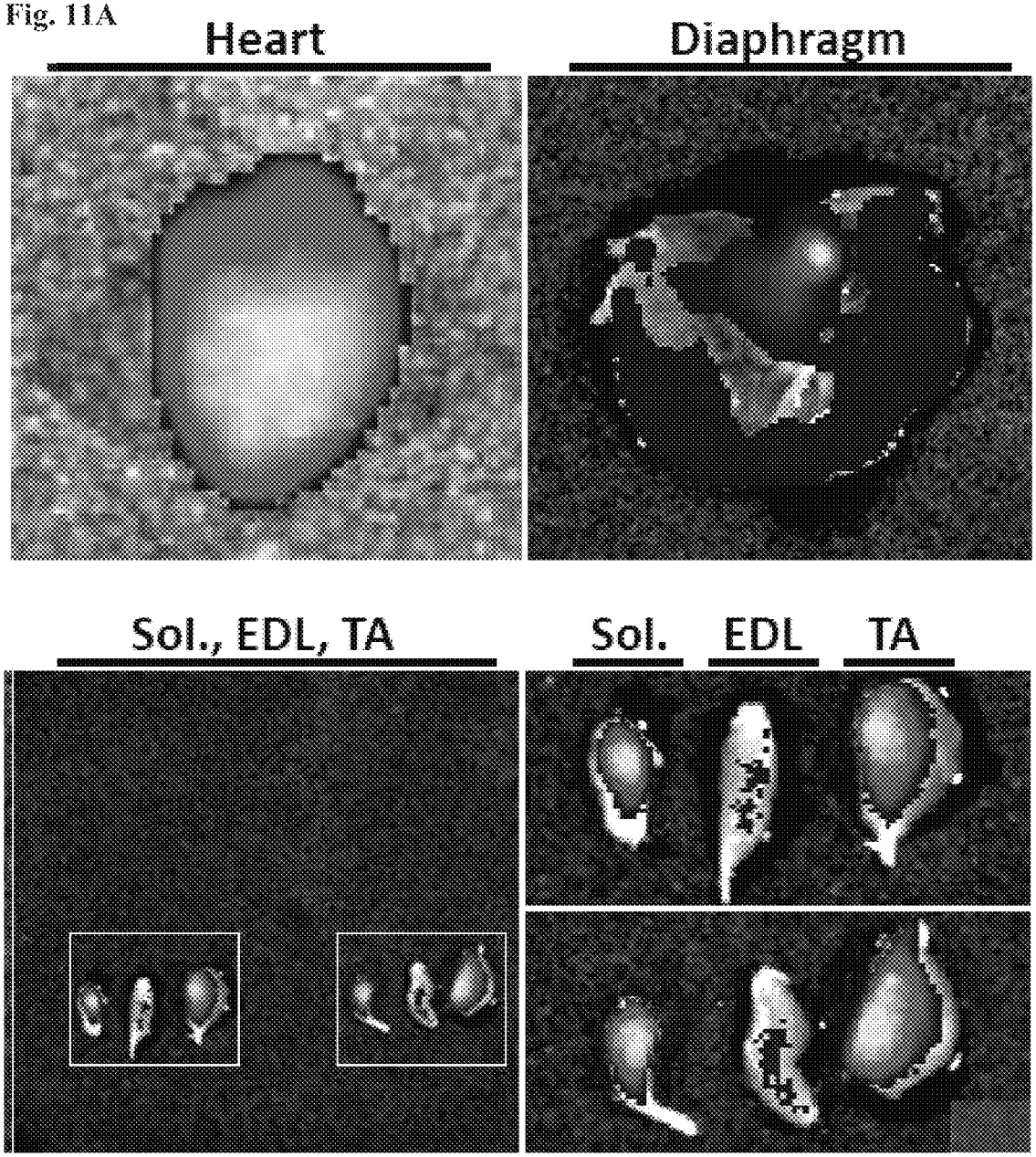
Figure 12:
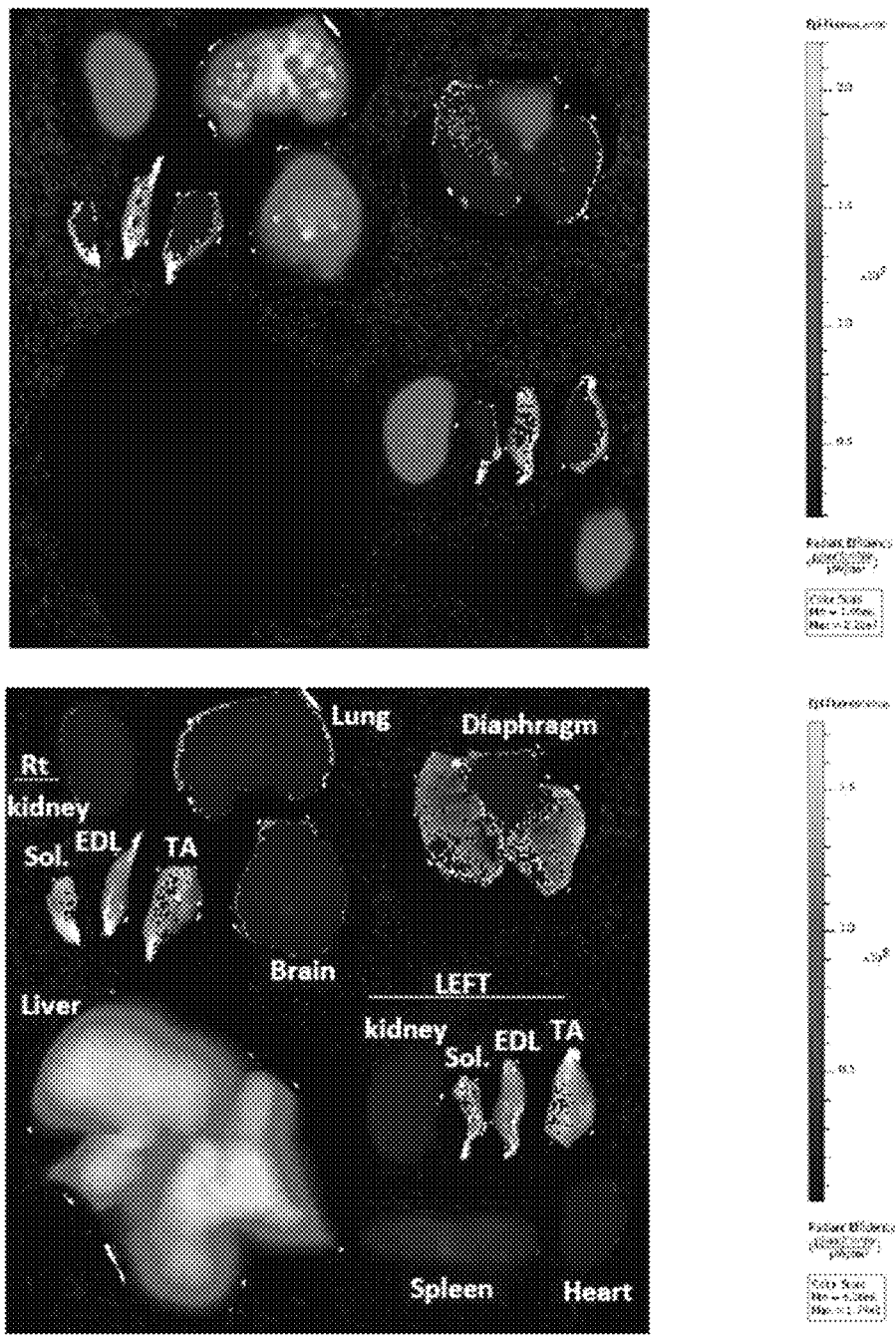
FIG. 12. Biodistribution after intraventricular CDC-XO injection.

Intraventricular injection of CDC-derived exosomes demonstrated similar beneficial results in the heart as shown in FIG. 11A. CDC-derived exosomes were capable of modulating gene expression in a manner mirroring CDCs themselves as shown in FIG. 11B, and with a high degree of correlation as shown in FIG. 11C. Moreover, both ejection fraction and distance improved with CDC-derived exosome injection, as shown in FIG. 11D and FIG. 11E, respectively. These results were further observed in diaphragm, as shown for gene expression results in FIG. 11F and FIG. 11G. Both twitch and specific force improved with CDC-derived exosome injection as shown in FIG. 11H. These results were further observed in soleus as shown for gene expression results in FIG. 11I and FIG. 11J. Both twitch and specific force improved with CDC-derived exosome injection as shown in FIG. 11K. Biodistribution after intraventricular CDC-derived exosome injection showed wide distribution across many tissue types.

Six hours post-injection, fluorescently-labeled CDC-derived exosomes were evident not only in the heart and skeletal muscle, but also in brain, liver, lung, spleen, gut and kidneys. Changes in mdx heart, diaphragm and soleus 3 weeks after intraventricular CDC-derived exosome injection mimicked the modifications seen in these organs after intramyocardial CDC injection. In the mdx heart 3 weeks after injection of CDC-derived exosomes, the inventors found major transcriptomic changes which mirrored the changes seen after intramyocardial CDC injection. Meanwhile, cardiac dystrophin levels increased, EF improved and exercise capacity was augmented, diaphragm similarly showed extensive transcriptomic changes which correlated well with those seen in mdx diaphragm after intramyocardial CDC injection, as well as increased dystrophin levels. The function of diaphragm was virtually normalized 3 weeks after intraventricular CDC-derived exosome injection. Likewise, the soleus exhibited characteristic changes in gene expression, robust restoration of dystrophin, and enhanced muscle function. The results collectively implicate CDC-derived exosomes as mediators of intramyocardial CDC injection.

Example 16

CDC-Derived Exosome Injection Into mdx Skeletal Muscle

Figures 13, 13A:
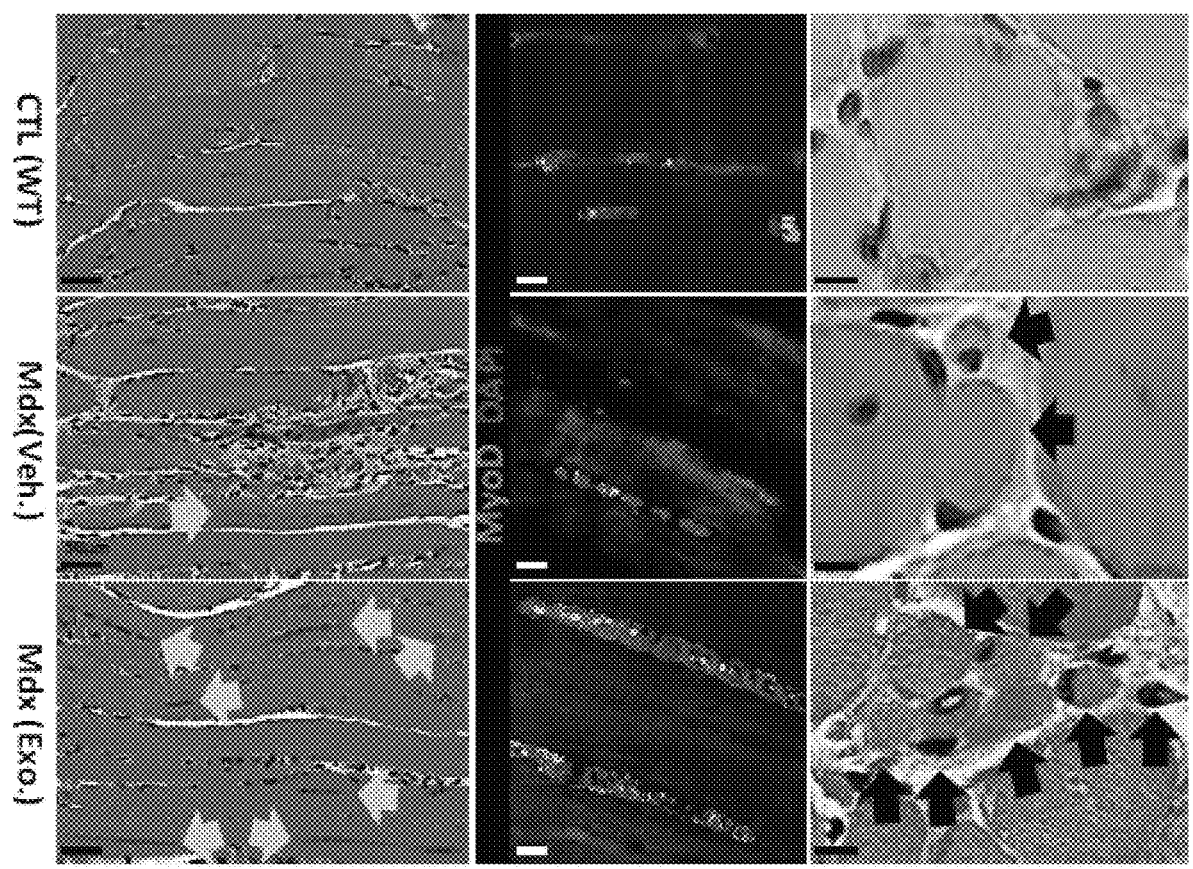
Figures 13, 13B, 13C:
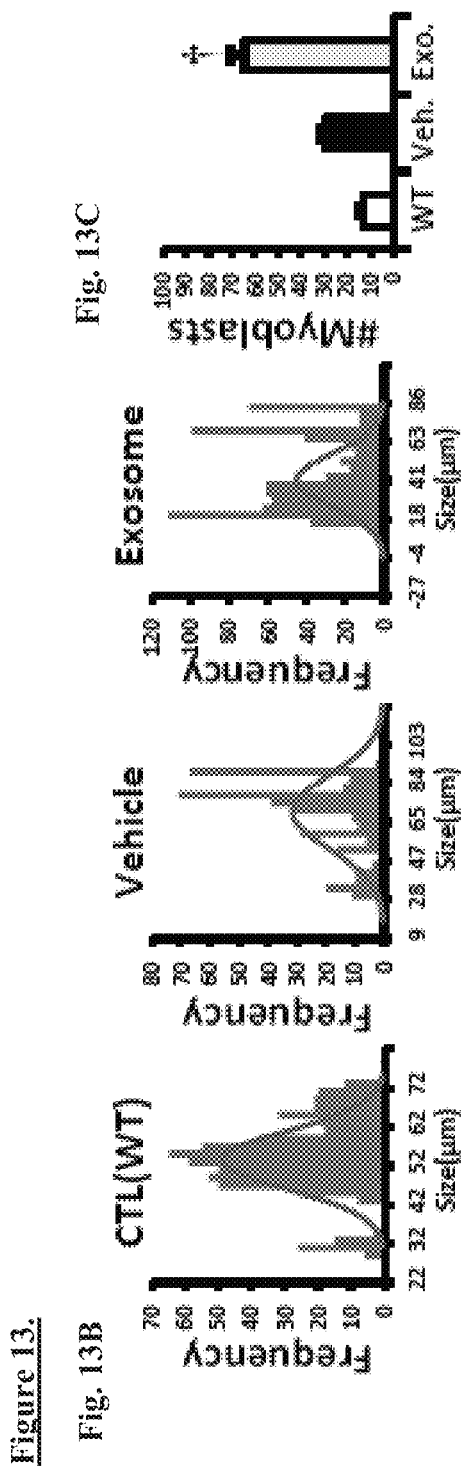
Figures 13, 13G:
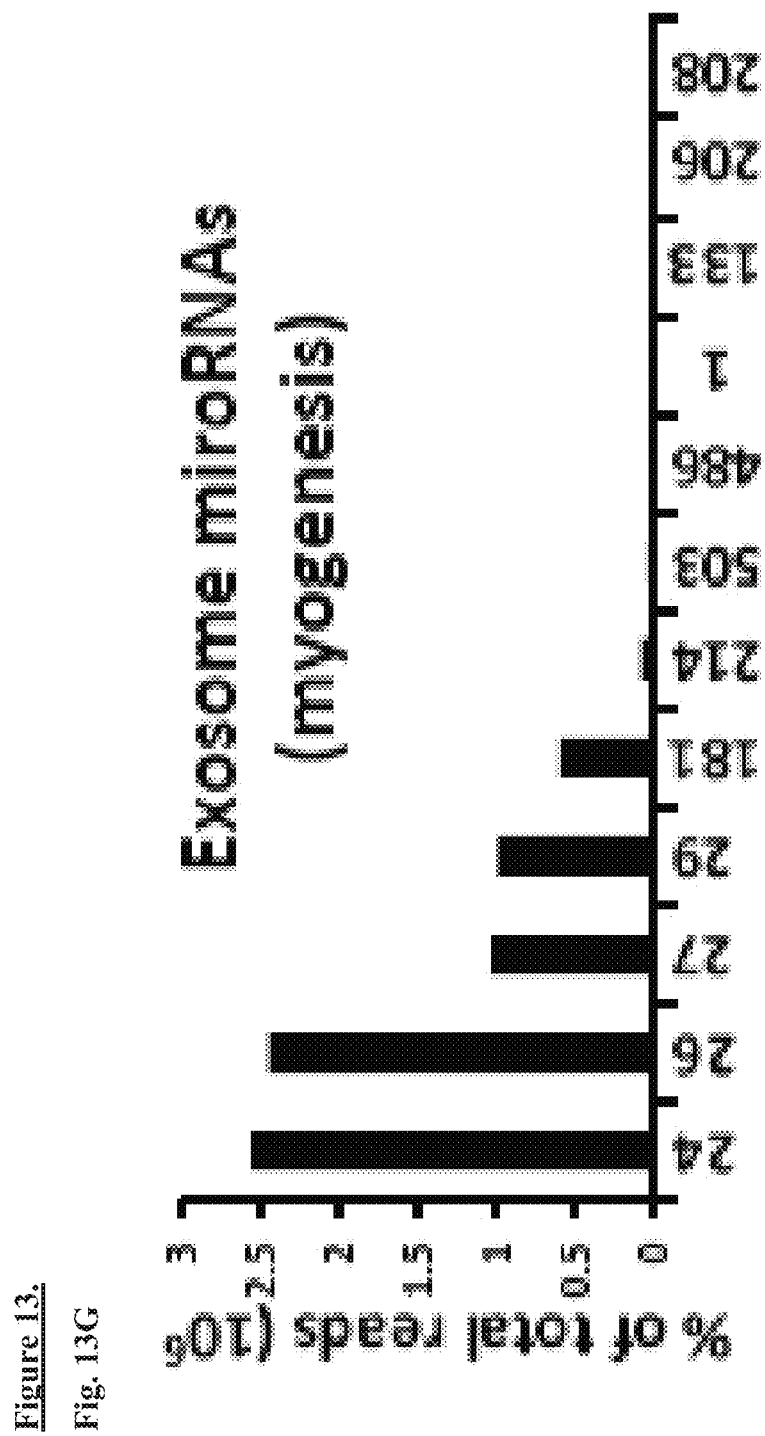
Figures 13, 13J:
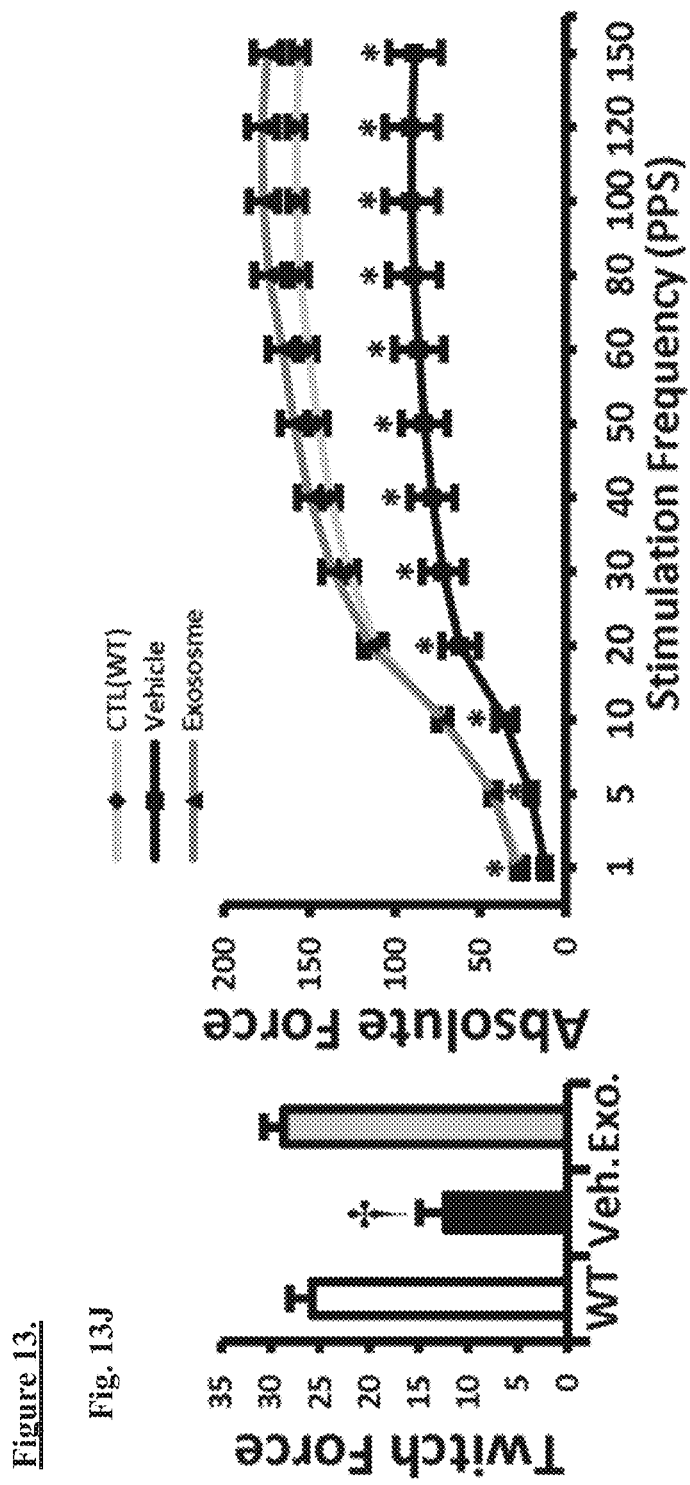

To investigate primary effects on skeletal muscle, the Inventors injected CDC-derived exosomes directly into the soleus in Inch mice. The above results indicated that the observed effects in skeletal tissue effect is mediated at least in part via CDC-derived exosomes. Results of Direct CDC-derived exosome injection into soleus is shown in FIG. 13A, FIG. 13B, and FIG. 13C. Further improvements in MyoD and Myogenin levels are shown in FIG. 13D. Levels of IGF1R and p-p65 reaching nearly the same as wild-type levels in FIG. 13F and FIG. 13G. Visible improvements were observed in soleus mass as shown in FIG. 13H, and dystrophin expression and distribution as shown in FIG. 13I. These improvements were further measured in improvements in twitch and absolute force as shown in FIG. 13J.

Figures 14, 14A:
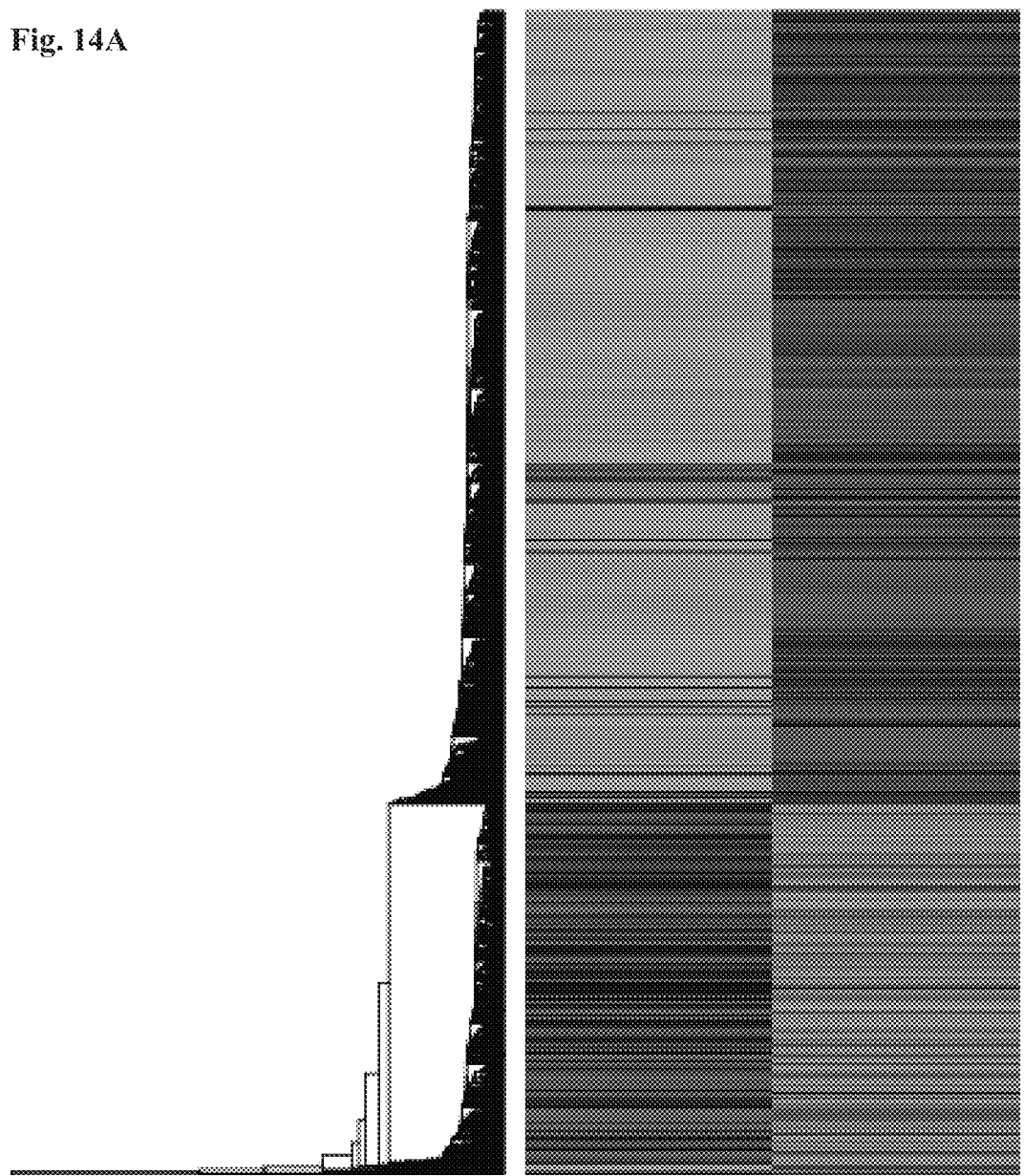
FIGS. 14A-C.
Figures 14, 14B:
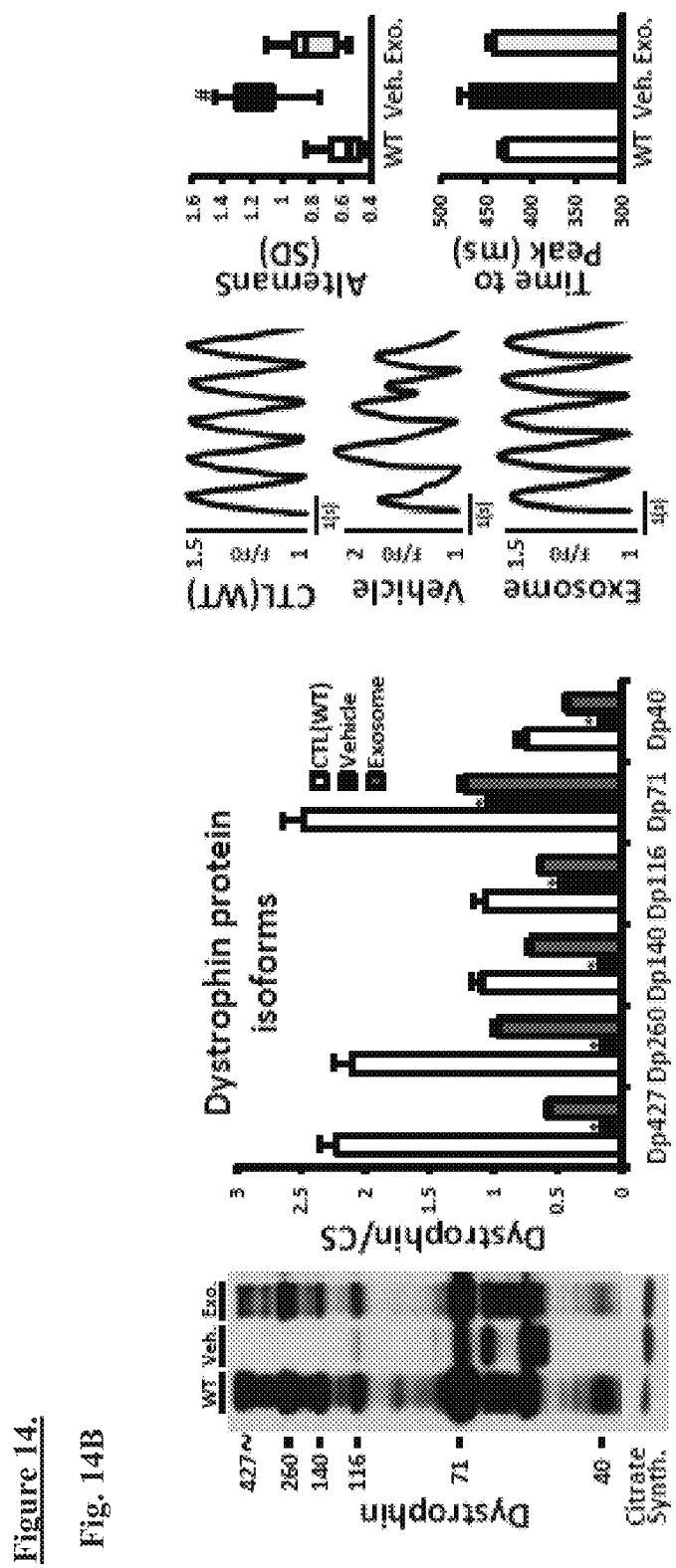
Figures 14, 14C:
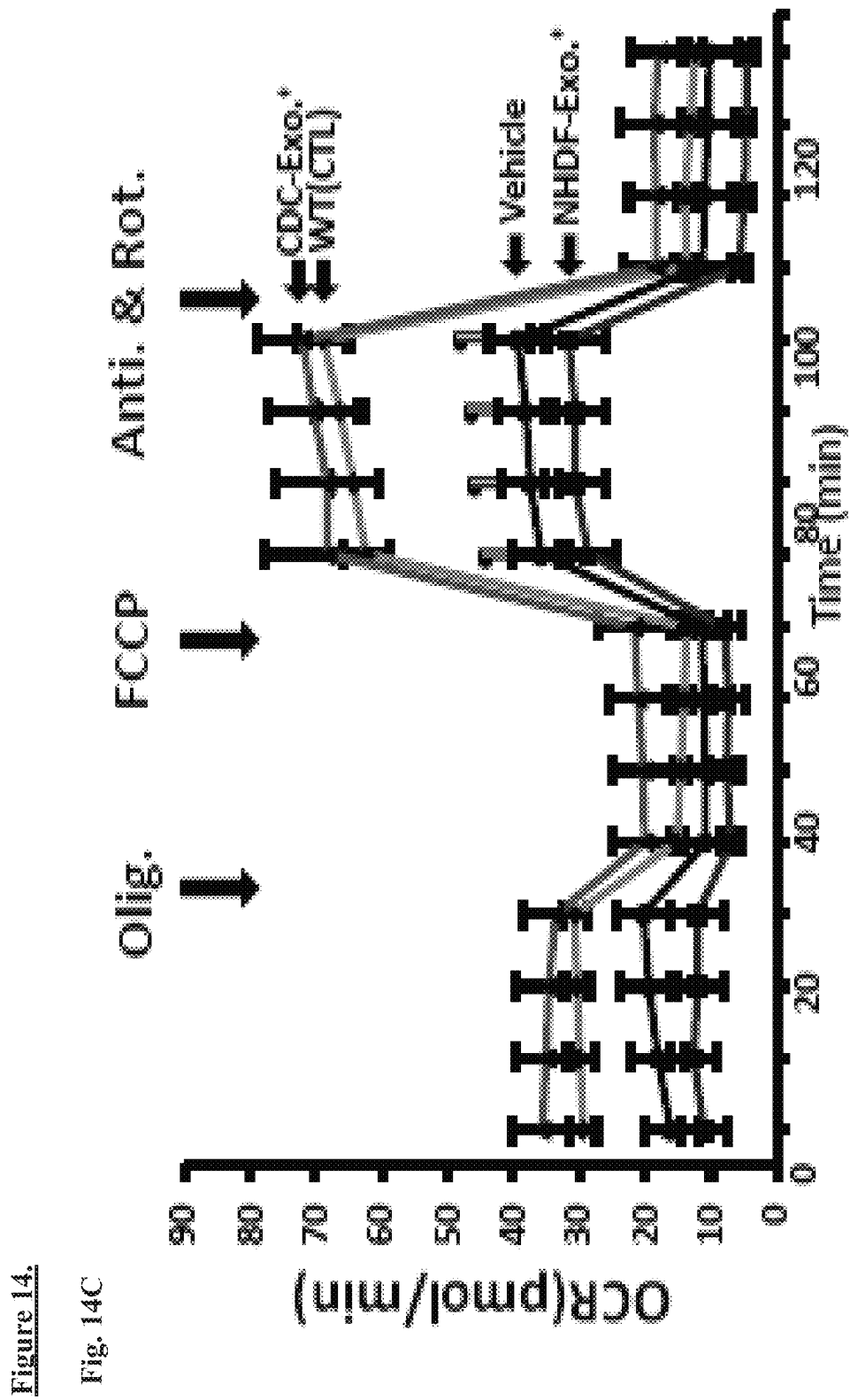
Figure 15:
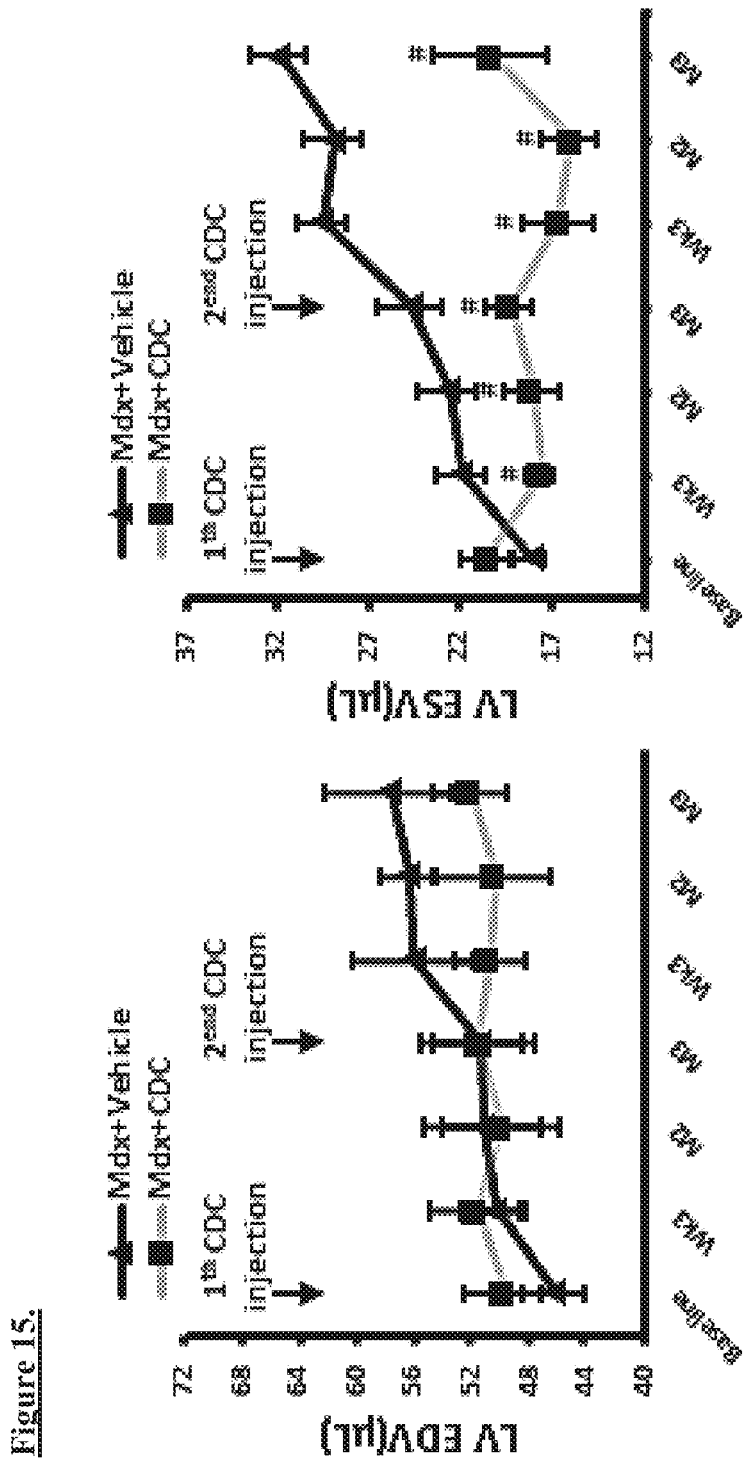
FIG. 15. Left ventricular end-diastolic (LV EDV) and end-systolic (LV ESV) volumes after CDC administration, CDC transplantations resulted in a sustained improvement of LV EDV and LV ESV for 3 months after both first and second (3 months interval) injections in mdx mice, relative to placebo. Data are means±SEM; n=1.2 in each group; #p<0.05.
Figure 16:
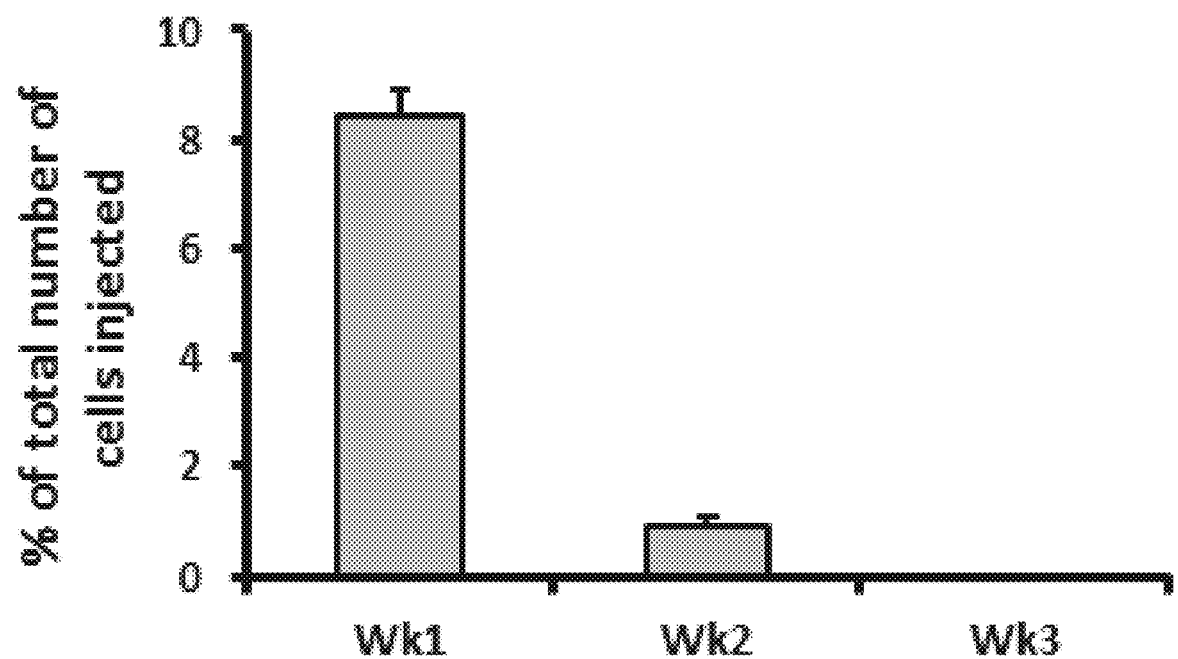
FIG. 16. Percentage engraftment of CDCs in the heart 1, 2 and 3 weeks after transplantation. Percentage engraftment of CDCs at 1 week was ~8% and <1% at 2 weeks. By 3 weeks, no surviving CDCs could be detected. n=3 at each time point.
Figure 18:
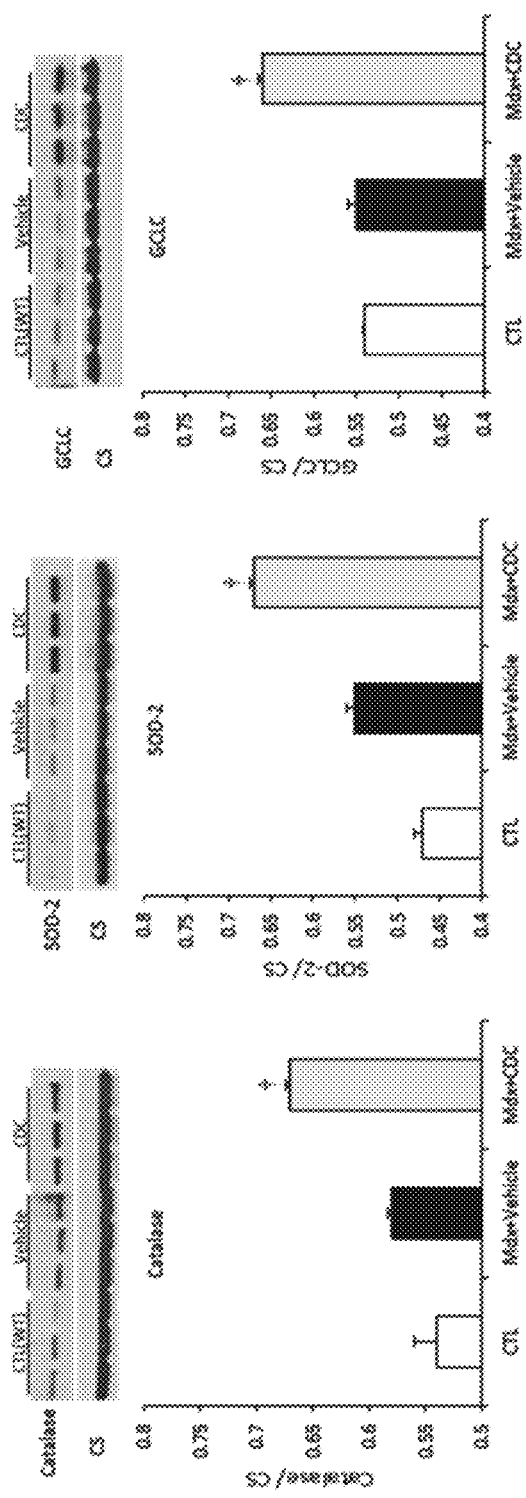
FIG. 18. Western blots and pooled data for protein abundance. Measurements including catalase, superoxide dismutase-2 (SOD-2), and catalytic subunit of glutamate-cysteine ligase (GCLC) in mdx mouse hearts 3 weeks after administration of vehicle or CDCs.
Figure 19:
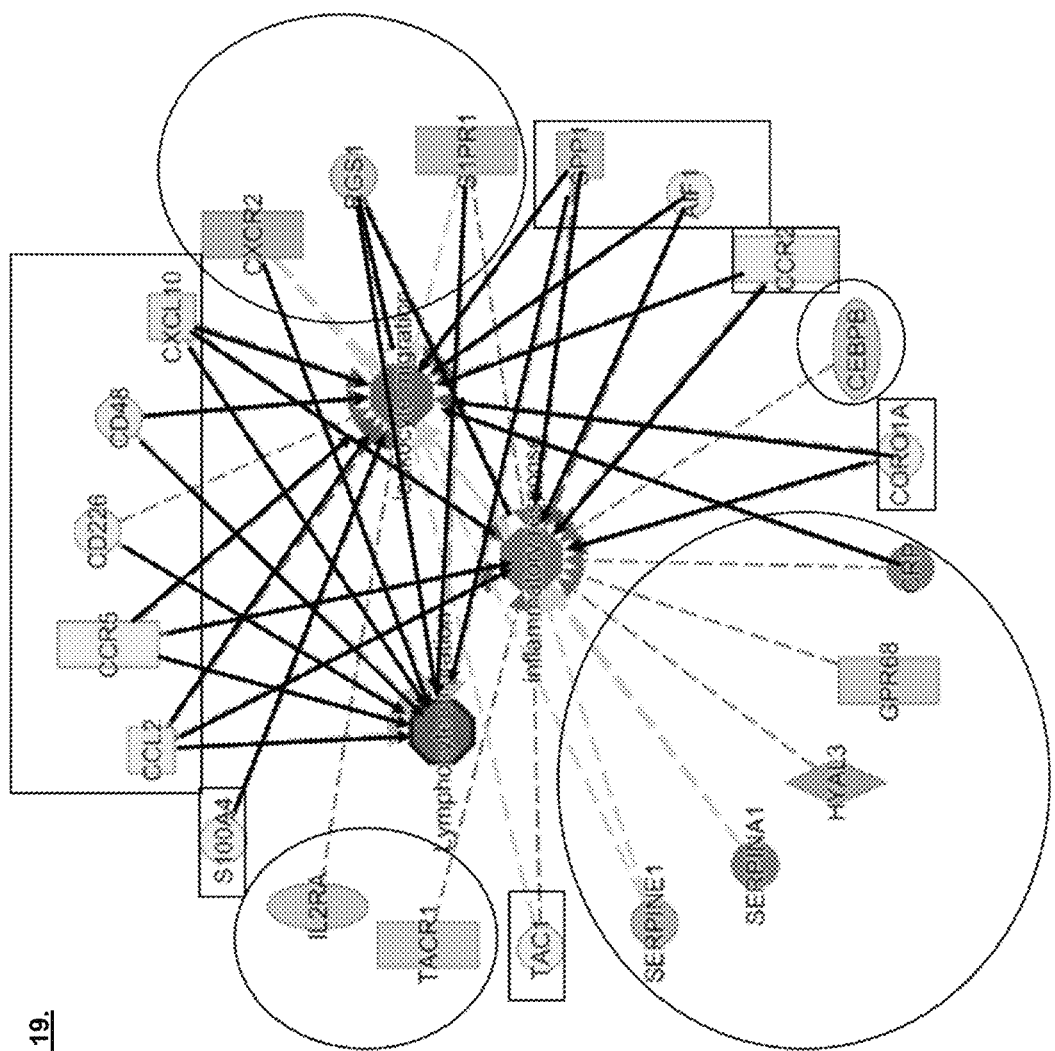
FIG. 19. IPA analysis of differentially expressed genes. Depicted are genes involved in inflammation in CDC-treated and vehicle-treated mdx hearts, denoting inhibition of inflammatory response concomitantly with reduced migration of inflammatory cells in mdx hearts 3 weeks after CDC treatment. The solid lines represents inhibition of function/response and the genes inside the circle and rectangle represent up and downregulation, respectively.
Figures 20, 20C:
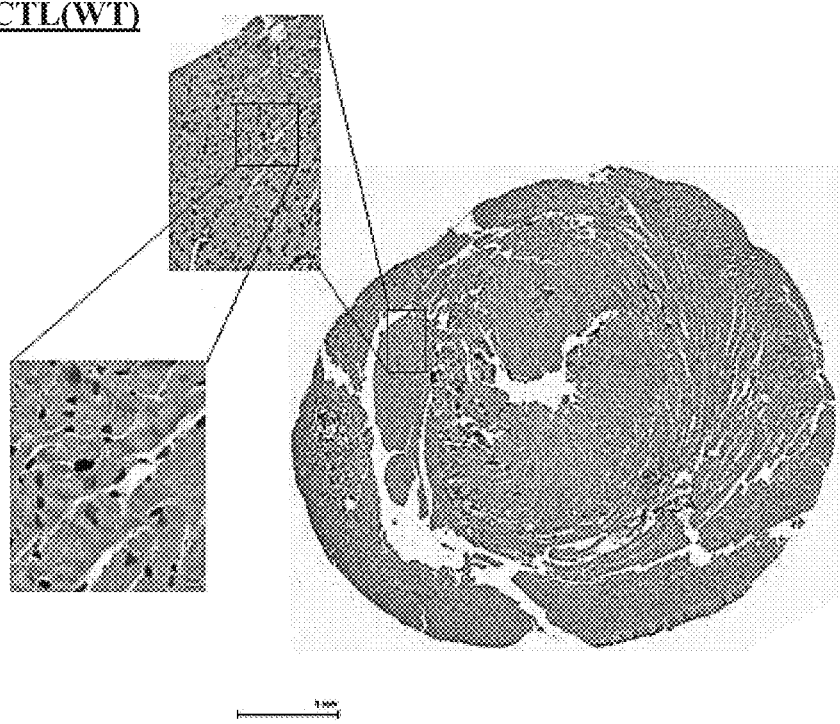
Figure 23:
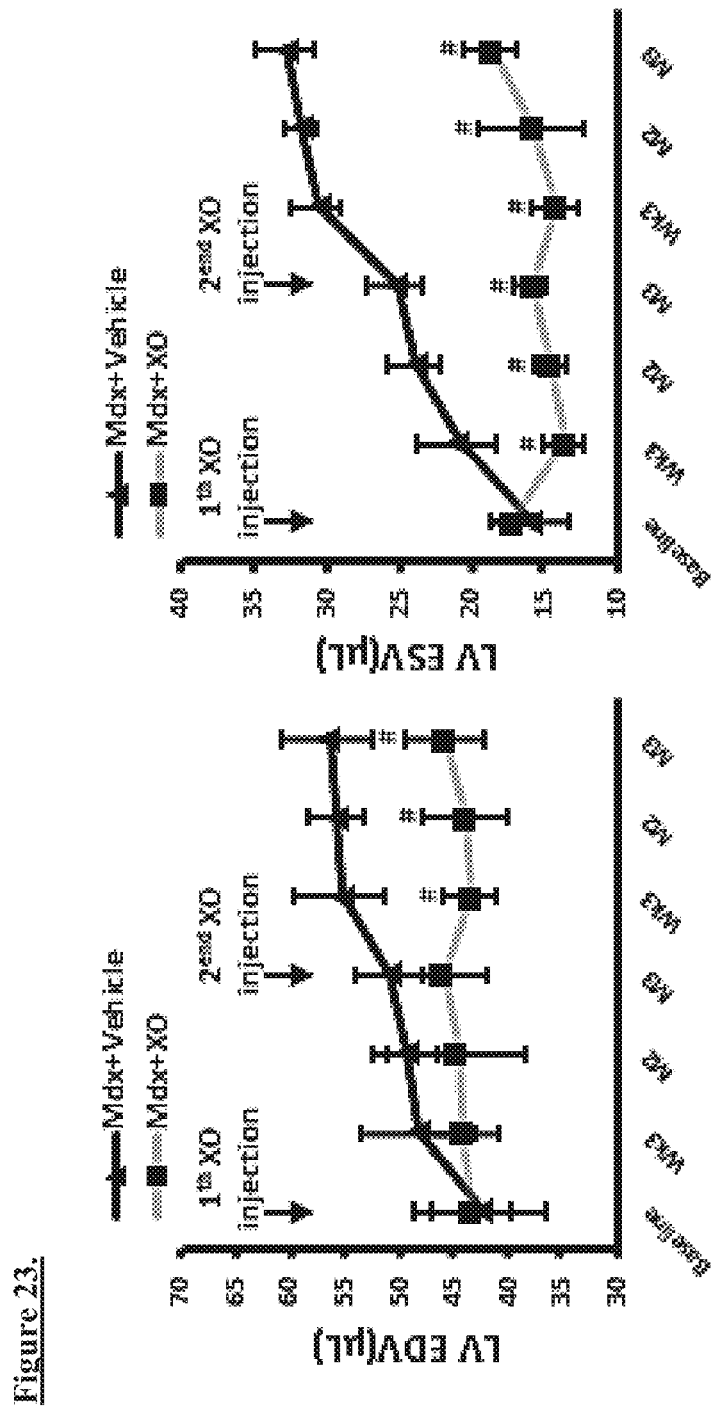
FIG. 23. LV end-diastolic (LV EDV) and end-systolic (LV ESV) volumes after CDC-XO administration. CDC-XO transplantation resulted in a sustained improvement of LV EDV and LV ESV for 3 months after both first and second (3 months interval) injections in mdx mice, relative to placebo. Data are means±SEM; n=11 in each group; #p<0.05.
Figure 24:
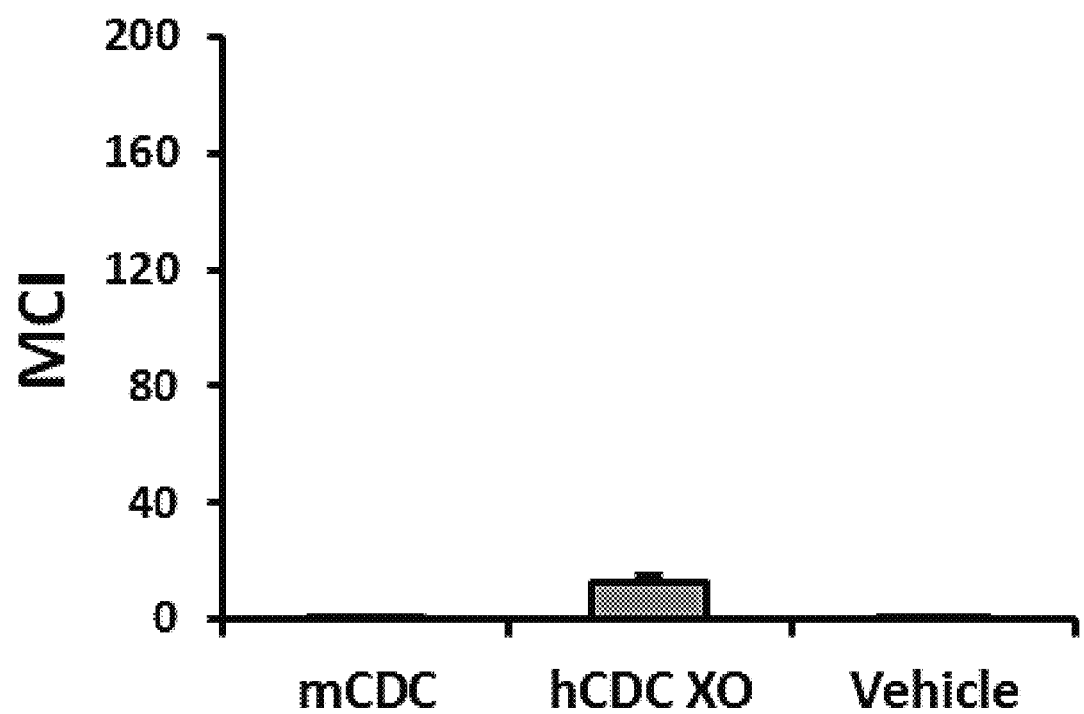
FIG. 24. Immunoglobin serum level. IgG serum levels 6 months after the first injection and 3 months after repeat injection of mouse CDCs, human CDC-XOs, and vehicle in mdx mice. Circulating anti-donor IgG antibodies were screened by flow cytometry.
Figure 25:
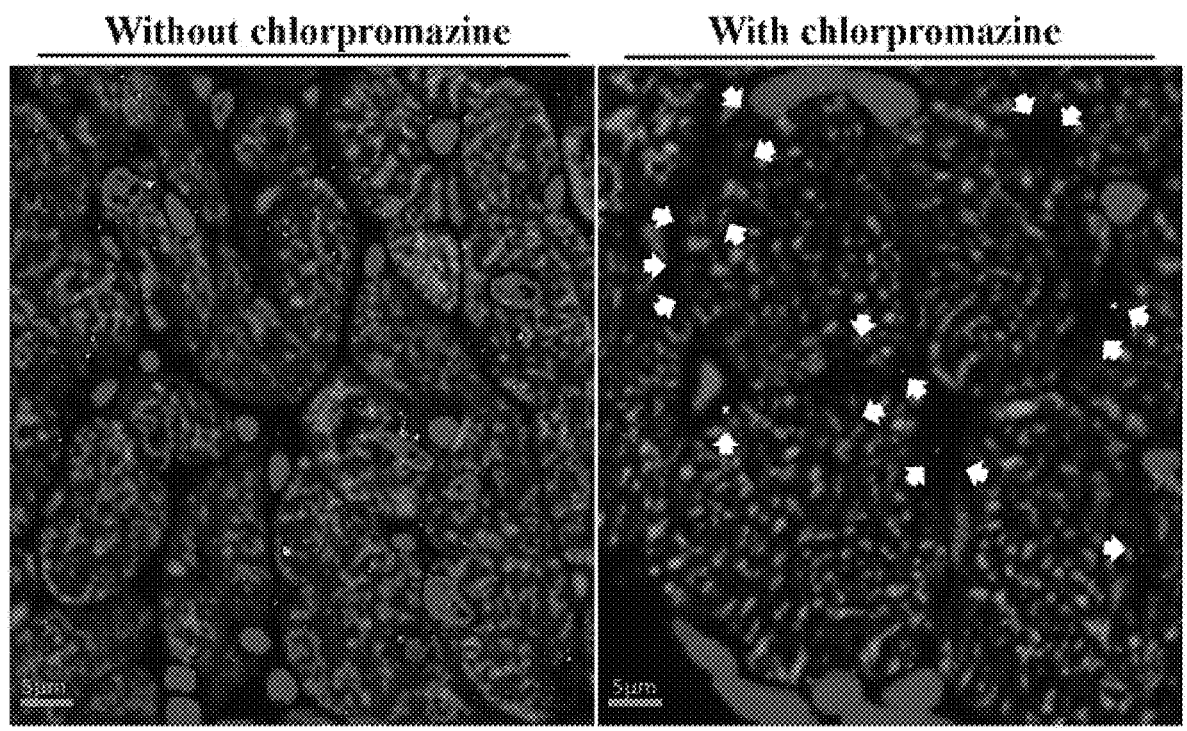
FIG. 25. Clathrin-dependent myocardial uptake of XOs. Distribution of intramyocardially injected CDC-XOs in the mdx mouse heart with and without chlorpromazine (CPZ) pretreatment. CPZ is an inhibitor of clathrin-dependent endocytosis. Fluorescent-labeled XOs (XenoLight DiR, 5 µM, overnight incubation; Caliper Life Sciences, Hopkinton, Mass.) were injected intramyocardially into the apex of inch mouse hearts; 6 hours later, the hearts were harvested, fixed and sectioned for evaluation of XO distribution. The average number of labelled XOs in the interior of cardiomyocytes (verified by co-staining for sarcomeric α-actin [green] and DAPI [blue]) was calculated by counting intracardiomyocyte XOs in 10 fields from each of 10 sections selected randomly from the apical (3 sections; 50 µm interval), middle (4 sections; 50 µm interval) and basal (3 sections; 50 µm interval) regions of each heart. The presence of fluorescently labeled XOs in the interior of the cardiomyocytes is a measure of endocytic uptake; pretreatment with CPZ (50 µg/g, i.p., single dose, 1 hour before XO injection), resulted in marked reduction in intracellular presence of XOs, indicating participation of clathrin-mediated uptake in internalization of CDC-XOs in mdx cardiomyocytes, among others. Bar graph depicts the number of labeled XOs (purple) in the interior of cardiomyocytes with and without CPZ administration, expressed as the number of intracardiomyocyte labelled XOs divided by the total number of cardiomyocytes per high-power field (HPF). Arrows point to fluorescent-labeled exosomes. Pooled data are means±SEM; †p<0.001.
Figure 26:
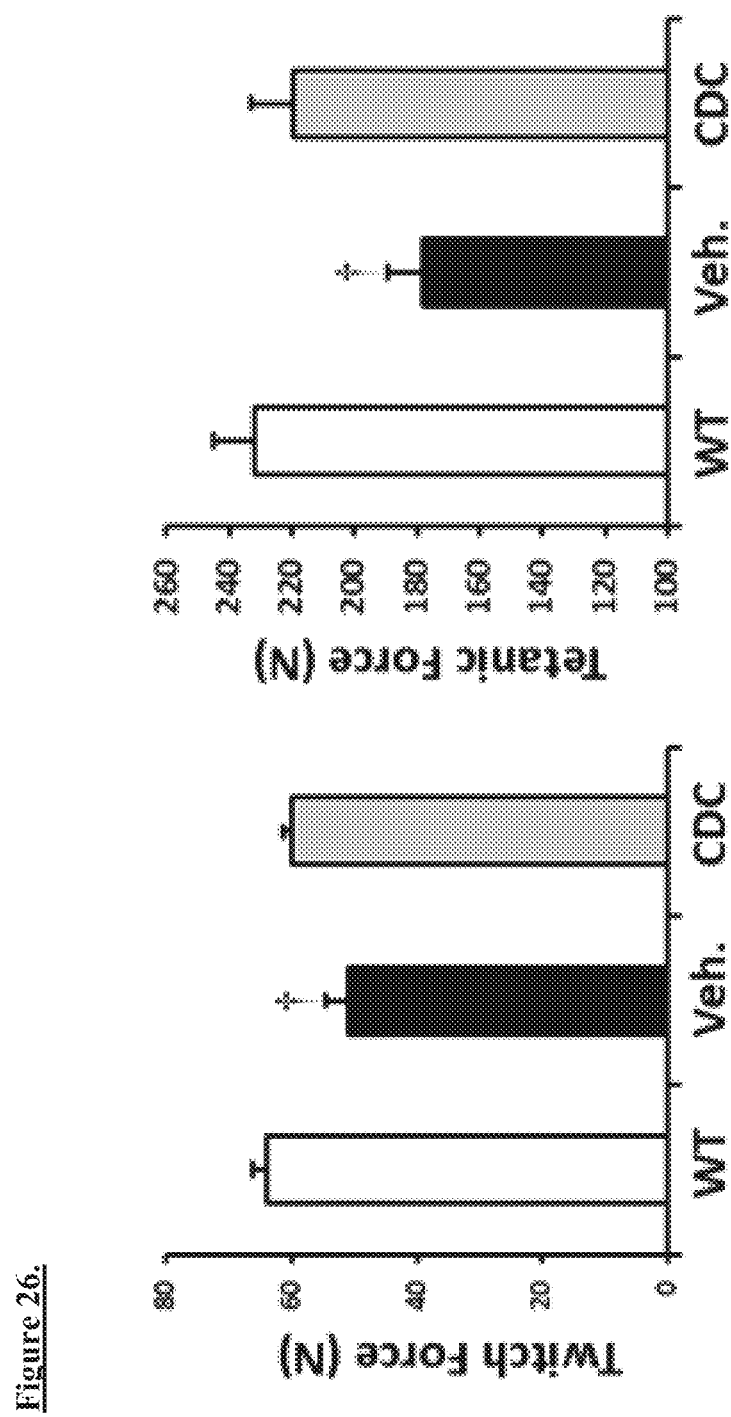
FIG. 26. Contractile properties. Depicted are extensor digitorum longus (EDL) contractile properties after intramyocardial CDC injection: In situ measurement of EDl, contractile properties, absolute twitch and maximum tetanic force, 3 weeks after CDC/vehicle treatment of mdx hearts.
Figure 17:
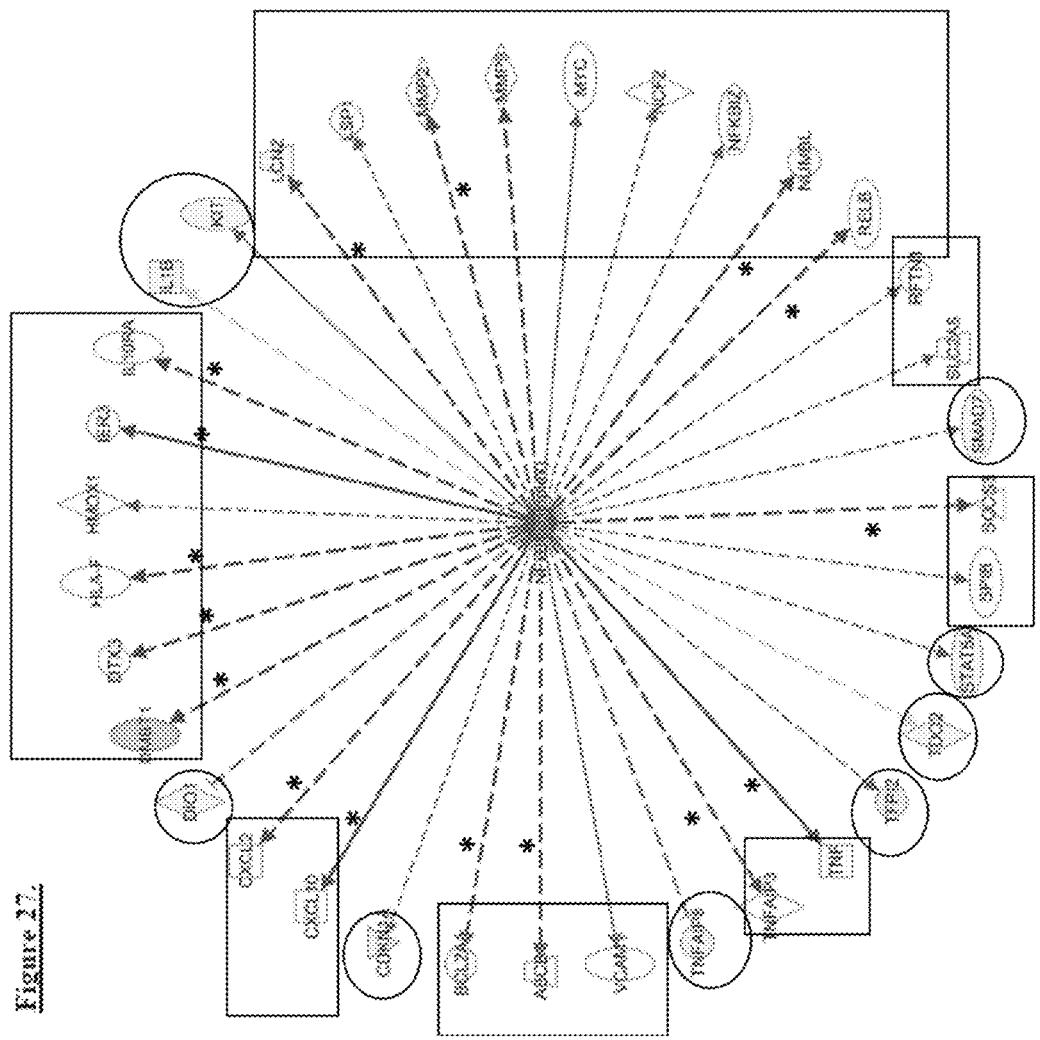
FIGS. 17A-D. Changes in mdx heart transcriptome 3 weeks after CDC treatment.

In an intra-aortic arch injection of CDCs in mdx mice. CDC-derived exosome injection was capable of modulating transcriptome of diaphragm as shown in FIG. 14A. When evaluating Human Duchenne cardiomyocytes derived from iPSC cells, similar improvements in dystrophin protein expression was observed, as shown in FIG. 14B and FIG. 14C.

Histological analysis revealed a paucity of surviving myofibers in vehicle injected mdx soleus relative to wild-type controls, and those that remained were hypertrophic. CDC-derived exosomes markedly increased the total number of myofibers and shifted the size distribution to smaller diameters, indicative of myofiber proliferation 3 weeks after injection. Consistent with this interpretation, the number of MyoD$^+$ cells was augmented after CDC-derived exosome injection, with increased tissue levels of MyoD and myogenin, the major transcription factors orchestrating myoblast and myofiber differentiation. In physiological muscle growth, IGF-1 is commonly implicated as an upstream signal, but the effects of CDC-derived exosomes on mdx soleus muscle were independent of IGF-1 receptors. Along with enhanced muscle regeneration, intrasoleus CDC-derived exosome injection decreased inflammation and fibrosis while increasing expression of dystrophin protein in mdx soleus muscle (evident by both immunohistochemistry and western blotting). The net effect was complete restoration of contractile force in the soleus muscles that had been injected with CDC-derived exosomes.

Example 17

CDC-Derived Exosomes in Human Duchenne Cardiomyocytes Derived From iPSC Cells

Demonstration of efficacy in multiple models of DMD would bolster the notion that CDC-derived exosomes may be viable therapeutic candidates. Duchenne human induced pluripotent stem cell (iPSC)-derived cardiomyocytes (DMD CMs) exhibit a number of phenotypic deficits characteristic of amp, including decreased oxygen consumption rate (OCR) reminiscent of that observed in mdx heart mitochondria, and abnormal calcium cycling. Priming DMD CMs with CDC-derived exosomes one week earlier increased dystrophin expression (here to 27.2±1.1% of control levels, even greater than in mdx hearts), suppressed beat-to-beat calcium transient alternans during 1 Hz burst pacing (a measure of arrhythmogenicity) and normalized OCR. The congruence of experimental findings in the two DMD models is noteworthy: the mdx mouse has a missense mutation in exon 23 of the murine dystrophin gene, while the DMD patient whose iPSC cells were studied here has a fundamentally different genetic lesion in the dystrophin gene (exon 50 deletion with frame shift). Thus, the active principle of CDC-derived exosomes is not specific for a single dystrophin mutation or for a single class of dystrophin imitations.

Example 18

CDC-Derived Exosomes Prepared Under Serum Free Hypoxic Conditions

Figure 28:
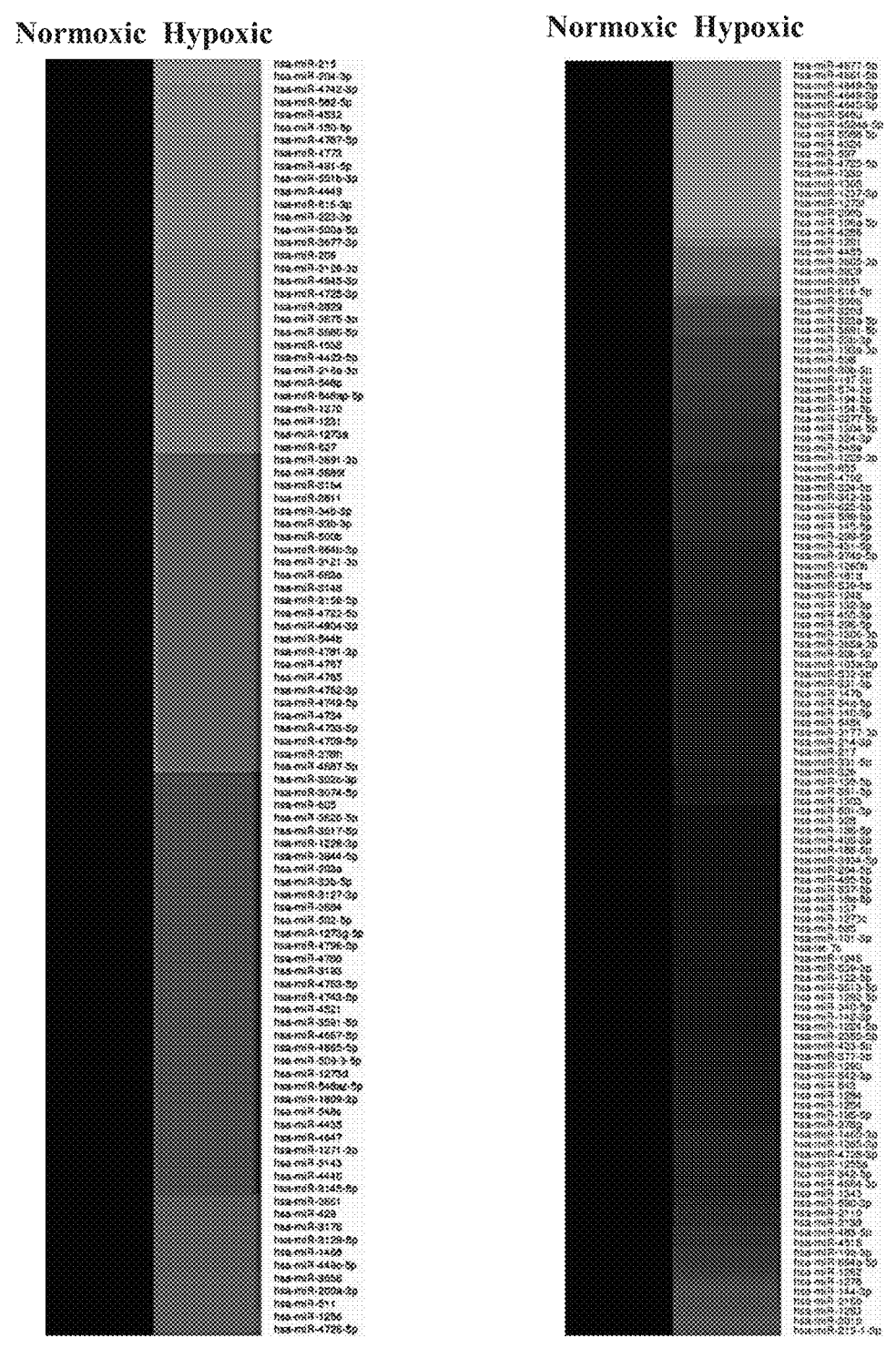
Figure 29:
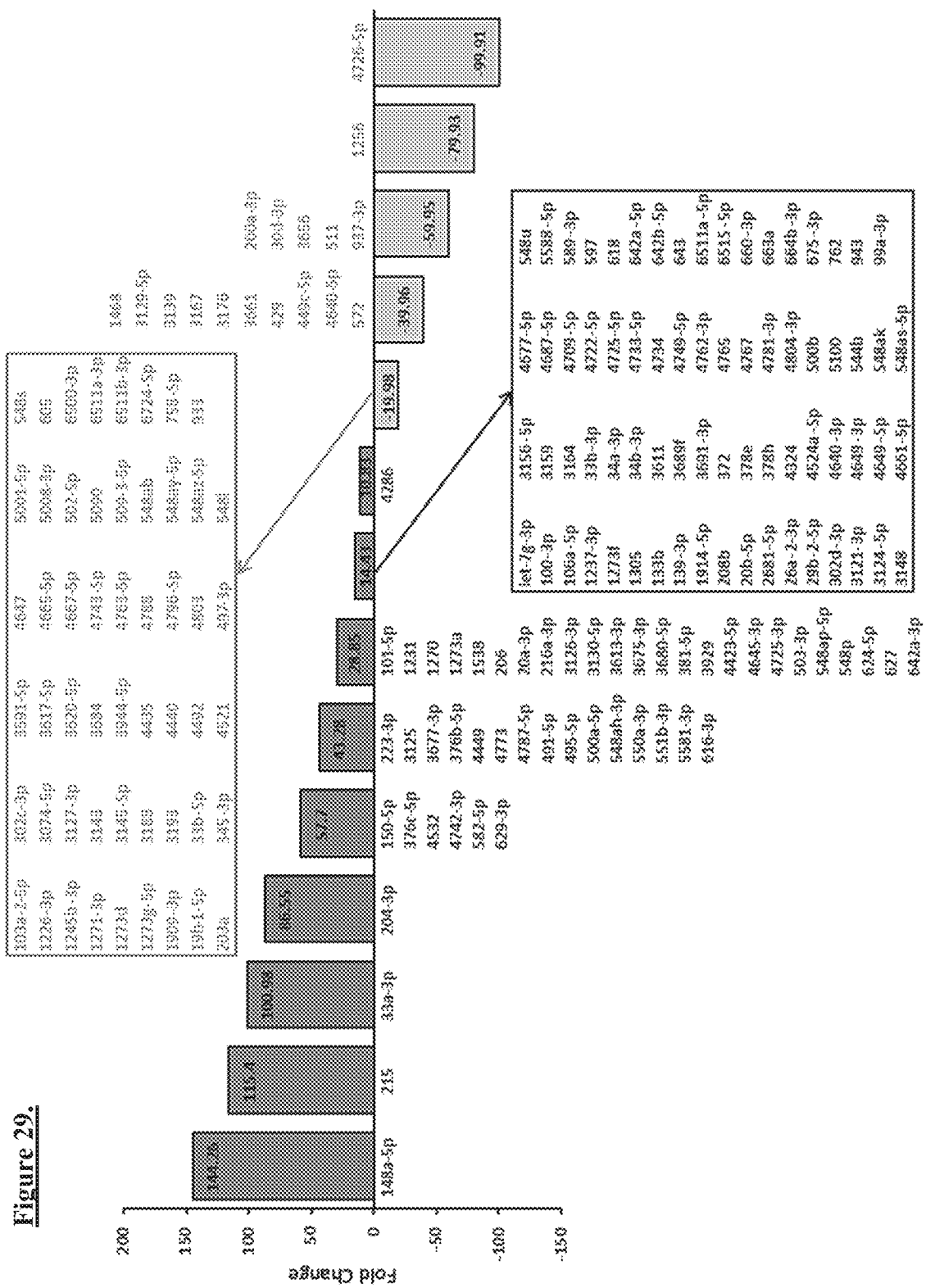
FIG. 29. Fold changes of microRNAs under different culturing conditions. Depicted are properties of CDC-XOs isolated from hypoxic conditioned media (2% $O_2$) compared to CDC-XOs isolated from normoxic conditioned media; fold change >10 and <−20 were included. NEBNext Small RNA Library Prep kit (New England BioLabs, Ipswich, Mass.) was used for miRNA-sec library preparation of extracted small RNAs from the XOs. RN As were extracted from XOs using miRNeasy Serum/Plasma Kit (QIAGEN, Germantown, Md.), FIGS. 30A-B. Physiological properties following CDC-XO and miR-148 administration.
Figure 30:
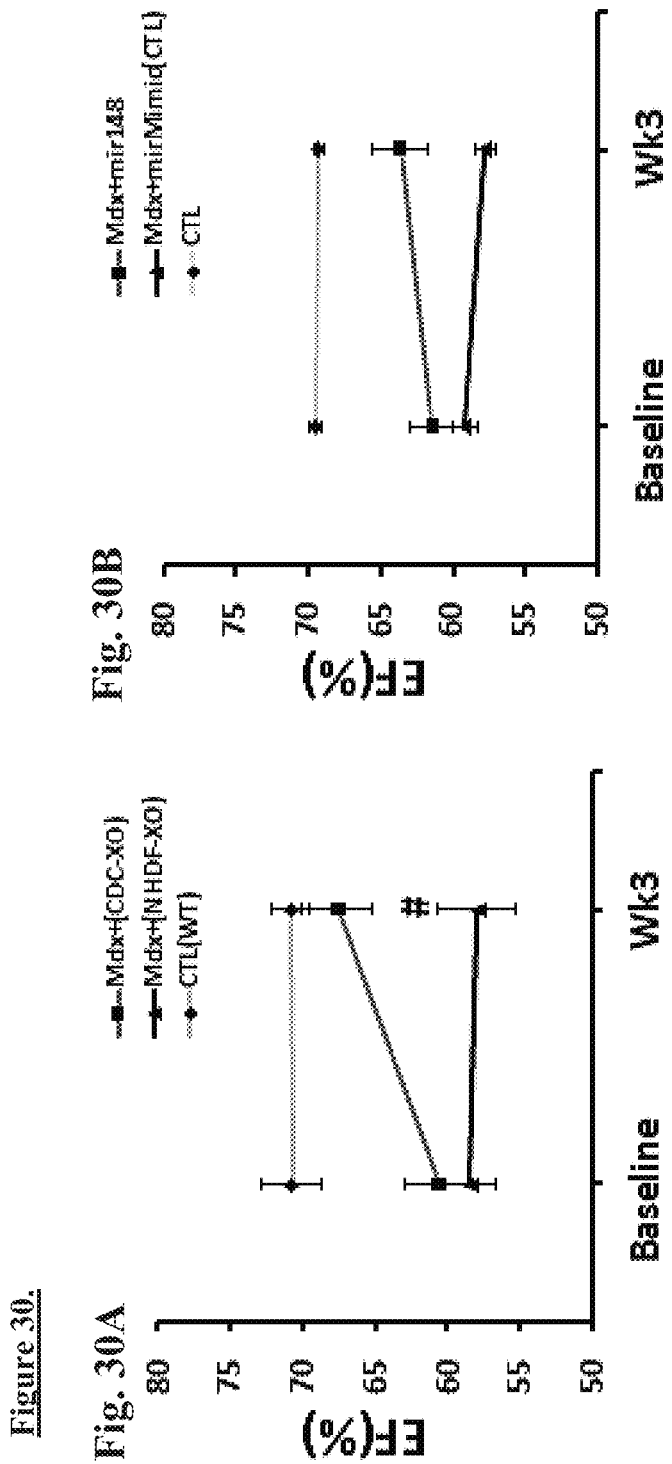
FIG. 30A: LV ejection fraction at baseline and 3 weeks after intramyocardial injection of CDC-XOs and NHDF-XOs in mdx mice.
FIG. 30B: LV ejection fraction at baseline and 3 weeks after intramyocardial injection of miR-148 and microRNA mimic control in mdx mice. Data are means±SEM; n=5 per group.
Figure 33:
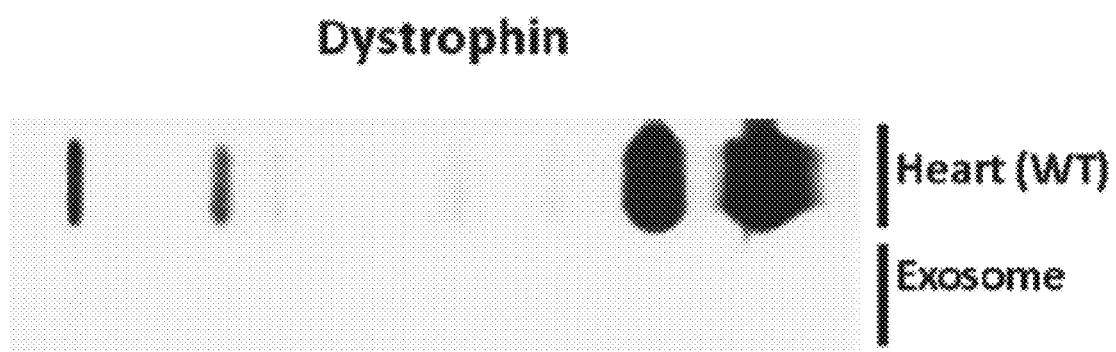
FIG. 33. Dystrophin expression and its consequences. Absence of dystrophin in XOs. Wild type heart lysate was used as a positive control for probing dystrophin.

As shown in FIG. 28, microRNAs in exosomes from hypoxically-cultured CDCs are enriched relative to exosomes from CDCs grown under normoxia. Depicted is 2-Dimensional hierarchical clustering using microRNAs with −6 to 6 times log2 fold change (230 microRNAs. Among 389 detected microRNAs in hypoxic exosomes (derived from CDCs cultured for 24 hours in serum-free hypoxic medium), 248 were previously reported to be mitochondria-related microRNAs. Further depiction of exosomes of interest are shown in FIG. 29. In this aspect, culturing of CDCs under serum-free hypoxic exosomes may heighten potency and improve salutary benefits for exosomes derived therefrom when compared to alternative culturing conditions, such as normoxic conditions.

Example 19

Heterologous Expression System

HEK-293NT cells were grown with 10% FBS in DMEM (without sodium pyruvate) supplemented with MEM-NEAA and 10 mM L-glutamine. Cells were harvested and plated at passage 3 at a density of 3.5×105 cells per well of a 6-well tissue culture-treated plate. The cells were allowed to adhere overnight, then the following day they were transfected using the Roche HP DNA Transfection Reagent according to the manufacturer's protocol. Briefly, all reagents were brought to room temperature. Then, for each well, 1μg of plasmid DNA was suspended in 100 μL of Opti-MEM, and 4 μL of transfection reagent was added to the solution. This reaction was allowed to incubate at room temperature for 30 minutes and then 100 μL was added to each well in a dropwise fashion. The cells were incubated with the transfection solution for 24 hours at 30° C. to stimulate protein translation, and then experimental treatments were added directly to each weft. Treatments consisted of: 1 mg G418 sulfate (Gibco), 125 ng miR-148a mimic or 1.25 μg srDMD reconstituted in UltraPure Distilled Water (DNase and RNase free). Vehicle treatments consisted of equivalent volumes of PBS corresponding to the volume used for each treatment listed above. Following a 24-hour treatment period, the cells were harvested for GFP fluorescence and luciferase activity analysis. Briefly, the 6-well plate was placed on ice and each well was washed twice with ice-cold PBS. Next, 1 mL of ice-cold non-denaturing lysis buffer (20 mM Tris HCl pH 8, 137 mM NaCl, and 1% Triton X-100 in PBS) was added to each well and incubated on ice for 15 minutes. Cell lysates were then transferred to microcentrifuge tubes using cell scrapers and centrifuged at 12,000 RPM for 1 minute at 4° C. Supernatants were transferred to new, pre-chilled microcentrifuge tubes and kept on ice. For each sample, 200 μL of cell lysate was transferred to one well of a black/clear-bottom 96-well plate. This plate was used to measure GFP fluorescence on a SpectraMax M5 plate reader. Then, 20 μL of cell lysate was taken from each of those wells and transferred to a new black/clear bottom 96-well plate. Room temperature-equilibrated luciferase substrate (Sigma-Aldrich: LUC-1) was added to each well according to the manufacturer's protocol and luminescence was measured on the SpectraMax M5 plate reader (top read, is integration time). The luciferase measurements were done in shifts to ensure that no more than 20 seconds elapsed between adding the luciferase substrate and measuring luminescence. For each experiment, the raw GFP fluorescence measurements (in RFUs) for non-transfected controls were subtracted from the fluorescence measurements for all of the transfected samples. These corrected values were then divided by the corresponding luciferase activity measurements (in RLUs). Finally, the normalized values were transformed using the exponential function.

Raw GFP fluorescence measurements were corrected by corresponding luciferase activity and then transformed using the exponential function (Equation 1), On the Y axis, 1 is the fluorescence level of an untransfected well. Raw GFP fluorescence measurements were corrected by corresponding luciferase activity and then transformed using the exponential function (Equation 1). On the Y axis, 1 is the fluorescence level of an untransfected well.

$$\text{Normalized } GFP = e^{\left(\frac{GFP}{LUC} \times 1000\right)}$$

The nonlinear relationship between basal levels of PTC and Exon 50 Δ expression versus WT was best described by a saturating function, consistent with the presumption that degradation of the full-length fusion protein increases with increasing expression (e.g., due to endoplasmic reticulum stress)3. PTC: vehicle (n=15), G418 (n=7), miR-148a-3p (n=4), and srDMD (n=4); Exon 50 Δ: vehicle (n=8), G418 (n=3), miR-148a-3p (n=4), and srDMD (n=3); $P<0.05$ vs vehicle. Wild type: human DMD variant Dp427m [BC111587.2] in mammalian expression vector with CMV promoter+C-eGFP tag+SV40-firefly luc (no neomycin and no stop codon before C-eGFP) PTC: human DMD variant Dp427m [BC111587.2, G to U mutation at pos. 6863 based on transcript sequence to introduce UAA stop codon] in mammalian expression vector with CMV promoter+C-eGFP tag+SV40-firefly luc (no neomycin and no stop codon before C-eGFP) Exon 50 Δ: human DMD variant Dp427m [BC111587.2, del exon 50] in mammalian expression vector with CMV promoter+C-eGFP tag+SV40-firefly luc (no neomycin and no stop codon before C-eGFP).

Example 20 miR-148a-3p and srDMD Transplantation Into mdx Heart

Figures 35, 35A:
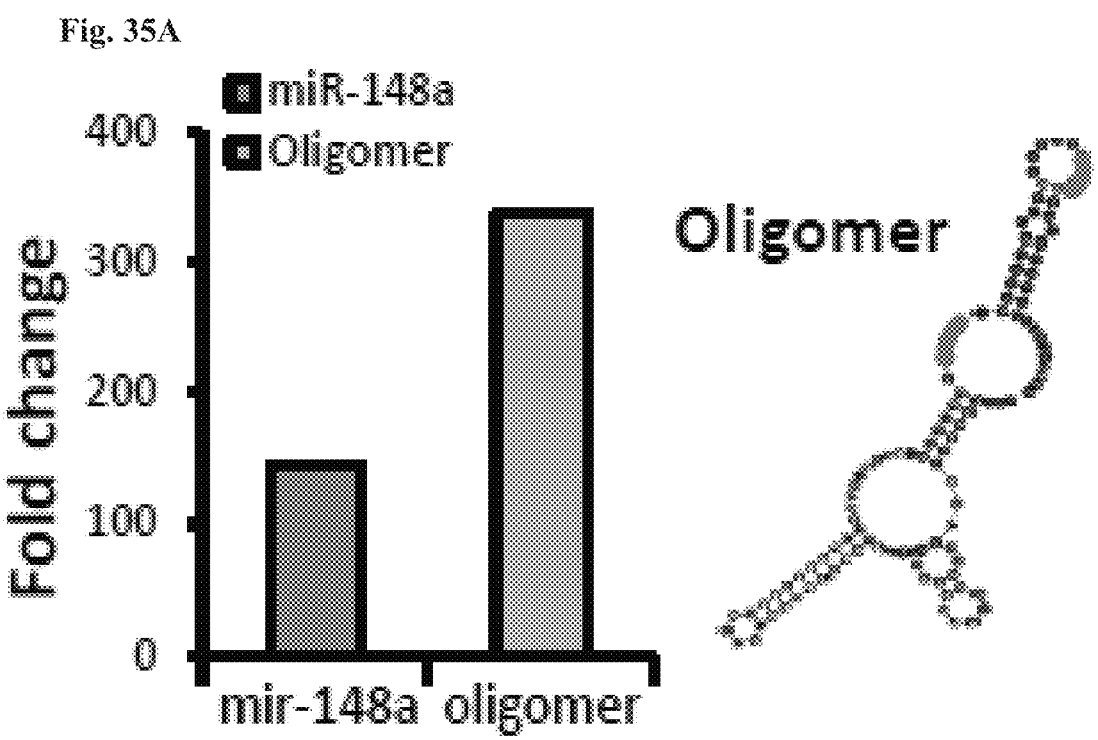
FIGS. 35A-C. miR-148a-3p and srDMD transplantation into mdx heart.
Figure 35:
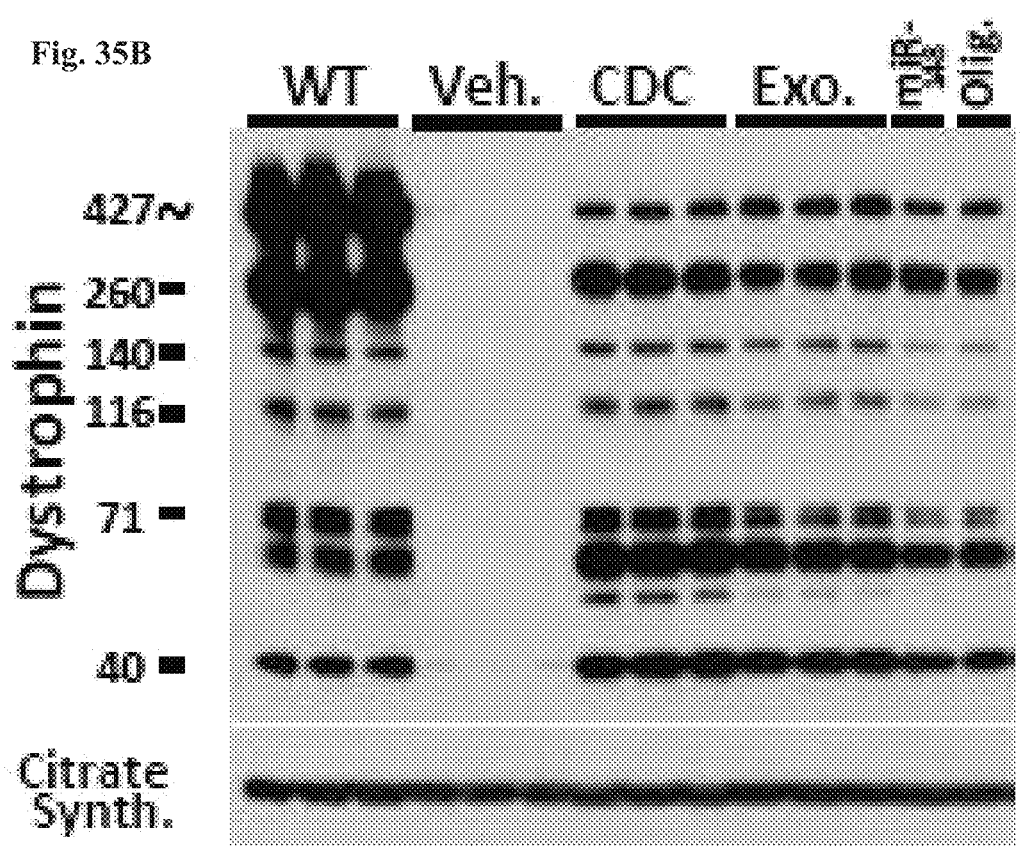
Figures 35, 35C:
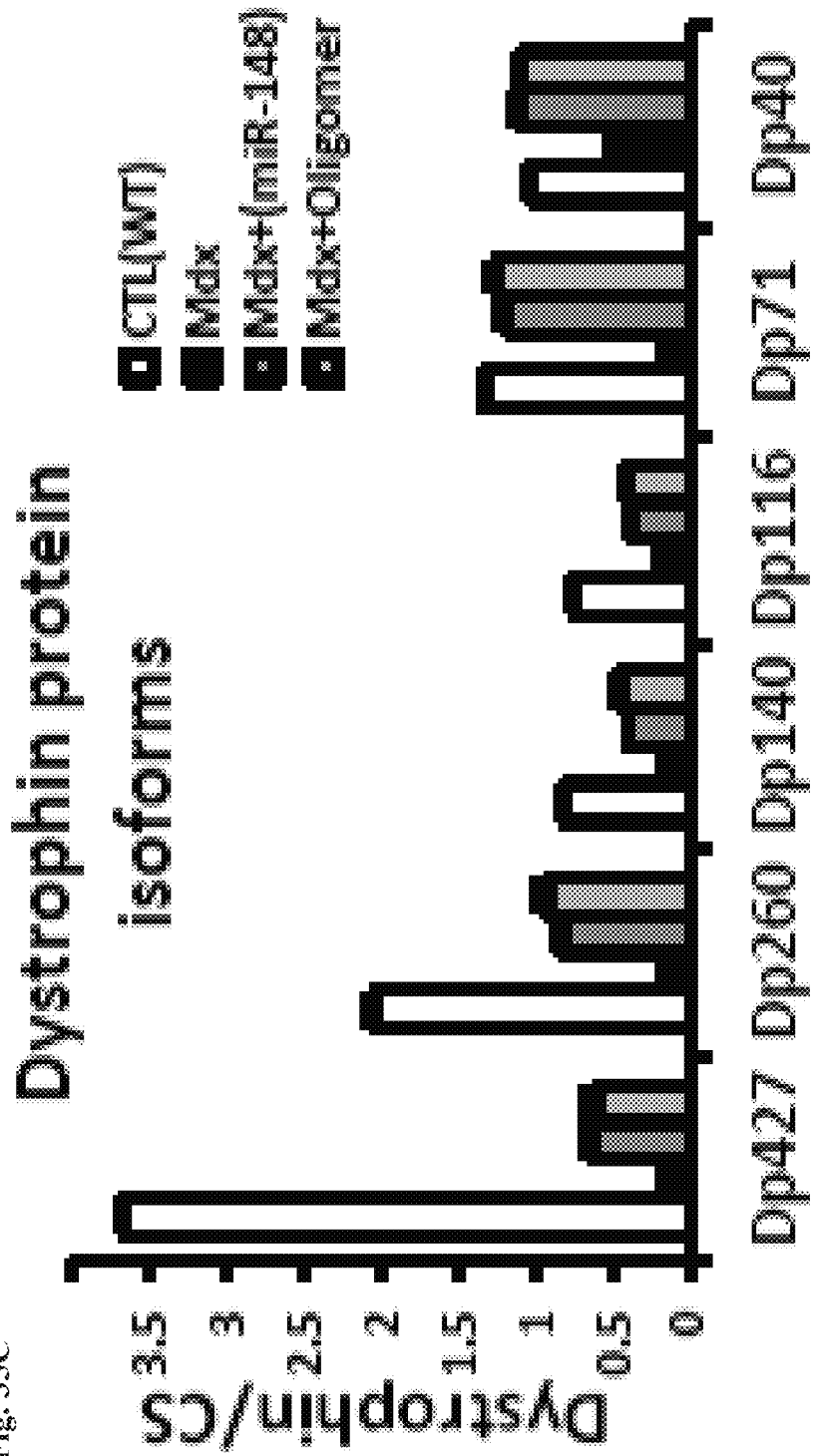

In FIG. 35A, differential expression of miR-148a-3p and srDMD in CDC-derived exosomes isolated from hypoxic conditioned media (2% $O_2$) was observed when compared to CDC-derived exosomes isolated from normoxic conditioned media, along with depiction of apparent secondary structure of srDMD. Further results of changes under culturing conditions as shown in FIGS. 28 and 29. As shown in FIG. 35B, western blots and pooled data for protein abundance of dystrophin isoforms: dp427, dp260, dp140, dp116, dp71, dp40 in mdx mouse hearts 3 weeks after intramyocardial injection of vehicle, or mimics of miR-148a-3p or srDMD, Further, in FIG. 35C, western blots and pooled data for protein abundance of dystrophin isoforms: dp427, dp260, dp140, dp116, dp71, dp40 in mdx mouse hearts 3 weeks after intramyocardial injection of vehicle, mimics of miR-148a-3p or srDMD and levels of dystrophin expression.

Example 21

Exon Skipping/Alternative Splicing Excluded

Figures 36, 36A:
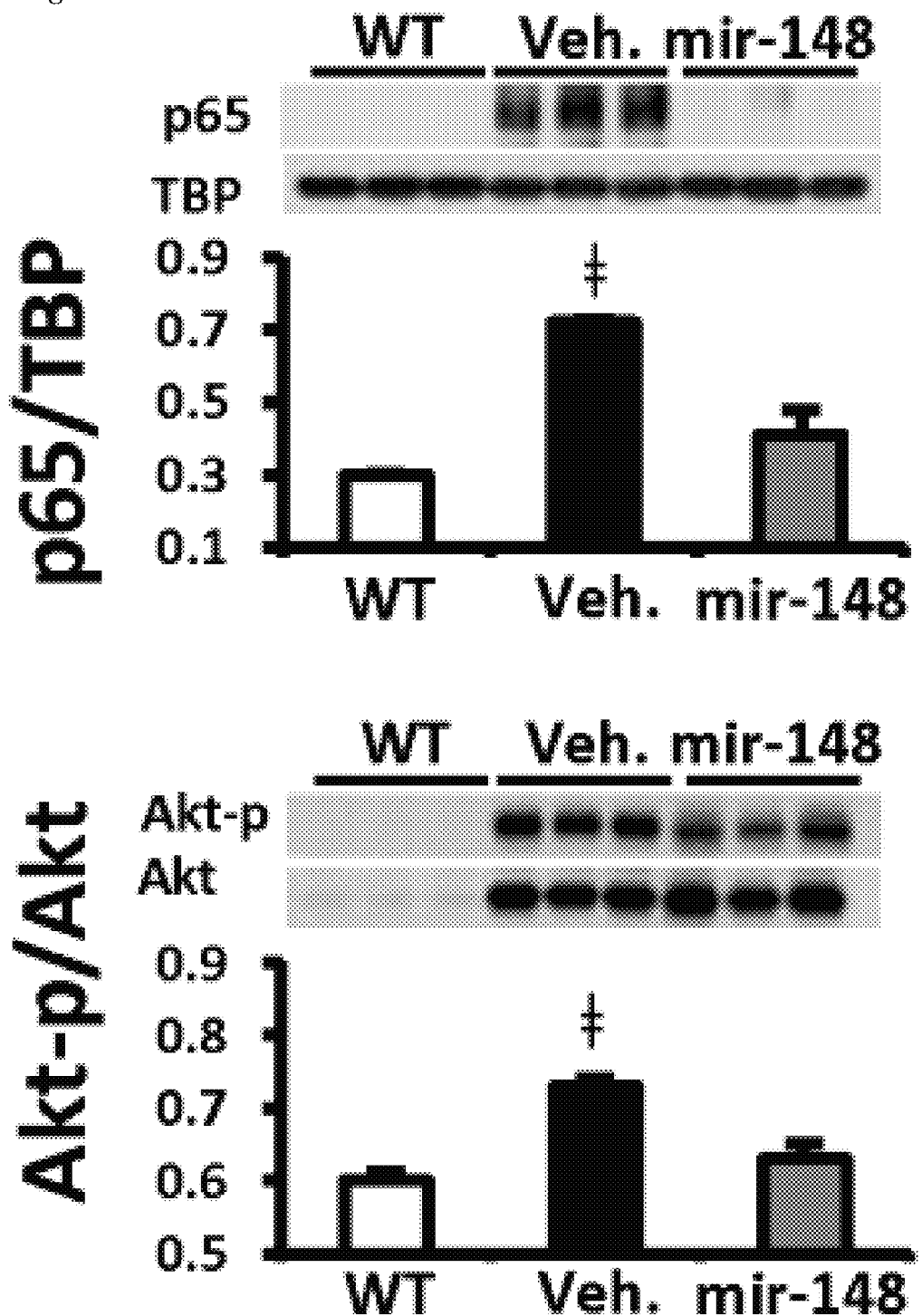
FIGS. 36A-B. Exon skipping/alternative splicing excluded.
Figures 36, 36B:
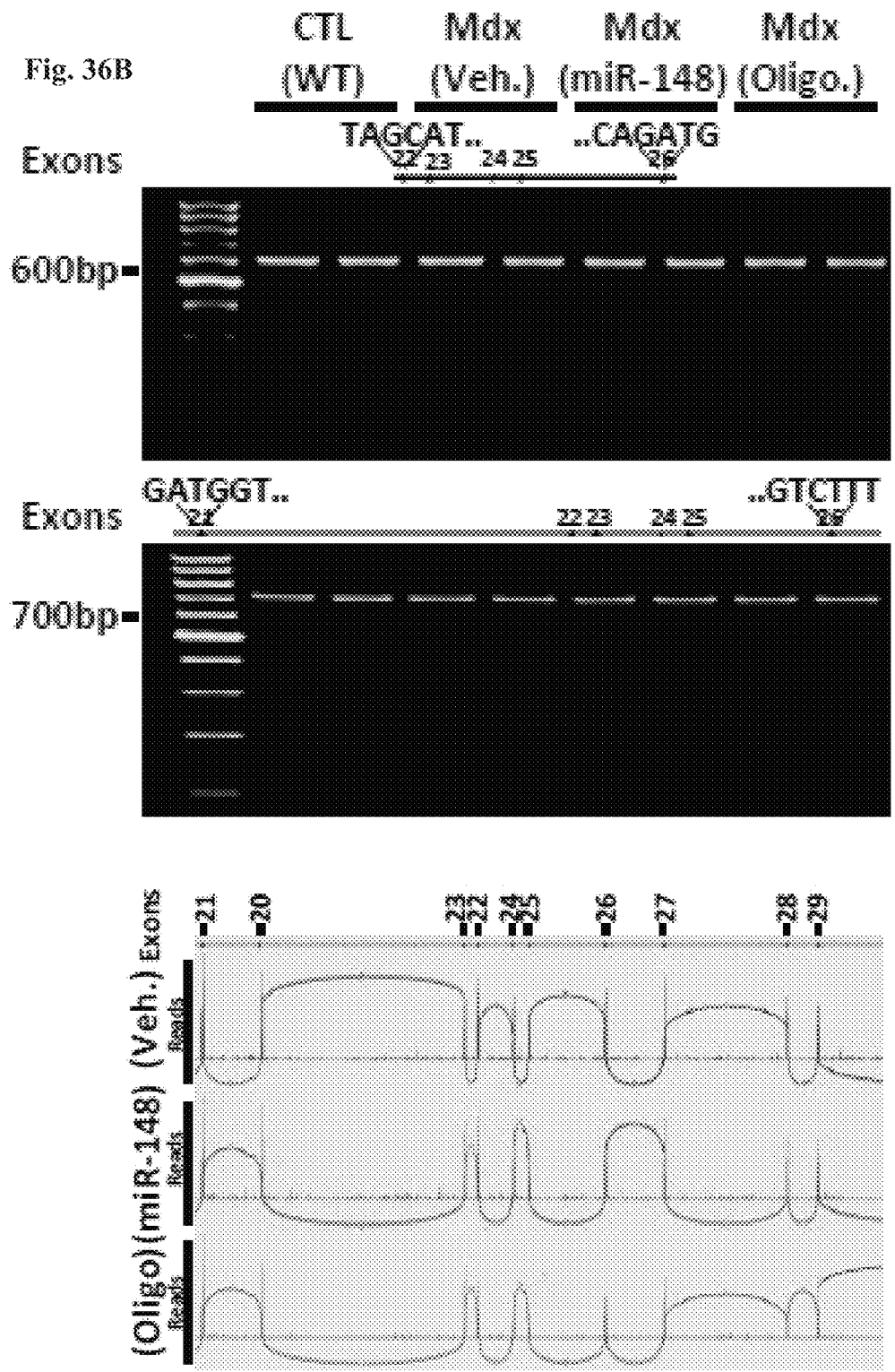

In FIG. 36A, miR-48a-3p results in decreases in both NFκB p65 and phospho-Akt levels. NFκB and Akt are known targets of miR-148a-3p. In FIG. 36B, RT-PCR using primers that flank the exon 23 of dystrophin. It was used to assess exon 23 inclusion in expressed dystrophin in mdx hearts from vehicle, miR-148a-3p or srDMD-treated mice (n=4-6). Sashimi plots of RNA-Seq data for dystrophin from vehicle, miR-148a-3p or srDMD-treated mdx hearts depict no junction read that span exon 23. All data are means±SEM. ‡$P<0.002$ vs. miR-148a-3p and srDMD; †$P<0.03$ vs. miR-148a-3p and CTL (Wild type).

In FIG. 37B, percentage increase [relative to vehicle (PBS)] in dystrophin/eGFP expression after treatment with miR-148a-3p or srDMD in transfected HEK293 NT cells with dual reporter constructs harboring a point mutation in exon 23 of dystrophin gene (PTC) or deletion of exon 50 of dystrophin gene (Exon 50 Δ).

Example 22

Dystrophin Expression and its Consequences

In FIG. 38A, ejection fraction (EF) at baseline and 3 weeks after intramyocardial injection of miR-148a-3p or microRNA mimic control [miRMimic(CTL)] in mdx mice. Wild type (WT) EF values also shown for reference, n=5 per group. In FIG. 38B, western blot depicting protein content of dystrophin in wild type (WT) mouse hearts and in vehicle—(Veh.), mutant srDMD- and srDMD-injected (srDMD) mdx mouse hearts 3 wks after intramyocardial injection.

Example 23

Mechanistic Study Using Heterologous Expression

As shown in FIG. 39A, full length human dystrophin was cloned into the ORF, either as wild-type or as one of two mutants: UAA premature termination codon in exon 23 (PTC), or exon 50 deletion (Exon 50 Δ), The construct creates a fusion protein of full-length dystrophin in frame with eGFP, such that green fluorescence can be taken as a reporter of dystrophin expression. Constitutive luciferase expression (driven independently by an SV40 promoter) was used to normalize for transfection efficiency.

As shown in FIG. 39B, dystrophin/eGFP expression in HEK-293NT cells transfected with full-length (WT), PTC or Exon 50 Δ constructs. Fluorescence and luminescence of total cell lysates were quantified on a well-by-well basis in a 96-well spectrophotometer; fluorescence in each well was also quantified with nontransfected cells at an equivalent seeding density and lysis volume. The responses mimic those to the aminoglycoside G418 and are qualitatively similar for both mutations. Without being bound by any particular theory, these findings support the idea that short non-coding RNAs act on release factors or on the ribosome itself.

Example 24 miR-148a-3p and srDMD as Effectors of Dystrophin Re-Expression

The Inventors utilized heterologous expression of novel dual-reporter constructs (wild-type and mutant dystrophins fused in-frame to eGFP, and independently-expressed luciferase) to explore mechanism. The responses mimic those to the aminoglycoside G418, and are qualitatively similar for both mutations. Given the efficacy on both types of mutations, short non-coding RNAs are most likely increase dystrophin expression indirectly, by acting on release factors or on the ribosome itself to enhance recoding.

More specifically, read-through of PTCs and ribosomal frameshifting are natural "recoding" processes which increase translational efficacy in certain genetic errors; both are enhanced by aminoglycoside antibiotics (albeit at concentrations that can be toxic in vivo). To quantify translation. The Inventors created dual-reporter plasmids expressing full-length human dystrophin fused in-frame with eGFP, and luciferase independently coexpressed to assay transfection efficiency. The Inventors compared green fluorescence, seen only when dystrophin-eGFP was translated, in HEK-293NT cells transfected with plasmids encoding wild-type dystrophin or each of two mutants: a point mutation in exon 23 introducing a PTC to mimic the mdx mutation, and another with deletion of exon 50, reproducing the human DMD mutation. Normalized fluorescence, expressed as percent enhancement over vehicle only, showed appropriate increases with the aminoglycoside G418 as a positive control in both mutants. Application of miR-148a-3p mimic or srDMD likewise enhanced dystrophin eGFP expression in both mutants.

There is firm evidence that the effects of exosomes are attributable to their RNA payloads. Dystrophin transcripts were absent by RNA-seq and undetectable by quantitative PCR in CDC-derived exosomes, so dystrophin restoration is not due to cell-cell transfer of its mRNA. Nevertheless, regulatory RNA may act directly or indirectly to increase dystrophin expression, by splicing to remove defective exons or by readthrough of premature stop codons. RNA-seq of CDC-derived exosomes grown under the Inventors' conditions (24 hours of serum-free hypoxic medium) revealed major differences, including 144- and 337-fold augmentation, respectively, of miR-148a-3p and a small RNA from DMD (srDMD) samples of unknown function as compared to normoxic CDC-derived exosomes. Among sequenced small RNAs (25-200 bp) in the exosomes, miR-148a-3p seemed worthy of investigation given its enrichment. In addition to this consideration, srDMD caught the Inventors' attention as it had cognate sequences with UAA (the premature stop codon in exon 23 of dystrophin in the mdx mice), suggesting that it might function as a nonsense suppressor RNA to promote readthrough. Intramyocardial injection of miR-148a-3p or srDMD restored expression of dystrophin in mdx hearts 3 weeks after administration. The unexpected bioactivity of miR-148a-3p on dystrophin protein levels occurred in parallel to known effects of miR-148a-3p (decreases in both NFκB p65 and phosphoAkt levels). The effects of srDMD were striking insofar as this short RNA has no known function. Mutation of srDMD to alter the cognate UAA site rendered srDMD ineffective. While consistent with nonsense suppressor activity, these findings do not suffice to prove that mechanism. The Inventors did, however, exclude exon skipping as a contributory factor: junction read analysis of sequenced dystrophin mRNAs from miR-148a-3p or srDMD-injected Inch hearts revealed no read spanning exon 23. The evidence against alternative splicing leaves, by exclusion, enhanced readthrough as a likely mechanism underlying the increased dystrophin expression seen with miR-148a-3p or srDMD administration. FIGS. 28 and 29 list a variety of other RNA polynucleotides enriched under hypoxic conditions and possible candidates for therapeutic agents.

To compare possible exosome contents responsible for the aforementioned effects, miR-148a-3p was measured as compared to srDMD oligomer, both of which displayed similar levels of activity, and levels of dystrophin expression.

The inventors utilized heterologous expression of novel dual-reporter constructs (wild-type and mutant dystrophins fused in-frame to eGFP, and independently-expressed luciferase) to explore mechanism. The data support the idea that exosomes increase translation of dystrophin mutants, as do their individual constituents miR-148a-3p and srDMD. The responses mimic those to the aminoglycoside (3418, and are qualitatively similar for both mutations. Given the efficacy on both types of mutations, CDC exosomes and their contents most likely increase dystrophin expression indirectly, by acting on release factors or on the ribosome itself to enhance recoding.

More specifically, read-through of PTCs and ribosomal frameshifting are natural "recoding" processes which increase translational efficacy in certain genetic errors; both are enhanced by aminoglycoside antibiotics (albeit at concentrations that can be toxic in vivo). To quantify translation, we created dual-reporter plasmids expressing full-length human dystrophin fused. In-frame with eGFP, and luciferase independently coexpressed to assay transfection efficiency. We compared green fluorescence, seen only when dystrophin-eGFP was translated, in HEK-293NT cells transfected with plasmids encoding wild-type dystrophin or each of two mutants: a point mutation in exon 23 introducing a PTC to mimic the mdx mutation, and another with deletion of exon 50, reproducing the human DMD mutation. Normalized fluorescence, expressed as percent enhancement over vehicle only, showed appropriate increases with the aminoglycoside G418 as a positive control in both mutants. Application of CDC-exosomes (XO), miR-148a-3p mimic or srDMD likewise enhanced dystrophin eGFP expression in both mutants. Given the efficacy on both types of mutations, CDC exosomes and their contents most likely increase dystrophin expression indirectly, by acting on release factors or on the ribosome itself. In contrast, the observed augmentation of dystrophin-eGFP translation in non-dystrophic HEK-293NT cells argues against translational derepression by relief of oxidative stress. The expression vectors here used an open reading frame for dystrophin containing no introns, further excluding splicing as a mechanism of benefit. The data support the idea that exosomes themselves increase translational efficacy in dystrophin mutants, as do their constituents miR-148a-3p and srDMD.

Example 25

Identification of Further Short Non-Coding RNAs of Interest, Validation Platform The creation of a dual-reporter system using eGFP and luciferase provides a robust platform for identifying additional short non-coding RNAs that may possess bioactivity enhancing translation efficiency. In this aspect, RNA profiling of cells possessing therapeutic activity can be compared against inert cells to identify enriched RNAs. Alternatively, the same cells with therapeutic activity can be compared against variable culture conditions enhancing or diminishing therapeutic activity, again to identify enriched RNAs. Short non-coding RNAs identified by these approaches can then be validated by contact with cells expressing the dual-report system. Specifically, by measuring green fluorescence, seen when a fused in-frame protein (e.g., dystrophin-eGFP) is translated, By further comparison to aminoglycoside as control, bioactivity of short non-coding RNAs that enhance translation can be identified.

Example 26

Remote Effects of CDC Transplantation in Max Heart

Intramyocardial injection of CDCs and their exosomes improved Duchenne cardiomyopathy by increasing dystrophin and reversing key pathophysiological processes in the mdx mouse heart. These changes were associated with a substantial increase in exercise capacity which seemed disproportionate to the CDC-related improvement in cardiac function: EF increased by <10%, while ambulatory capacity doubled. To further evaluate the mechanism of enhanced exercise capacity in CDC-treated mdx mice, the Inventors isolated and examined three distinct skeletal muscles: the diaphragm (DIA, a key respiratory muscle), and two limb muscles (soleus and extensor digitorum longus [EDL], representative of slow and fast twitch muscles, respectively) 3 weeks after intramyocardial injection of CDCs or vehicle.

To understand the contribution of CDC-derived exosomes in the above effects, the Inventors assessed skeletal muscles, diaphragm and soleus, 3 weeks after intramyocardial CDC injection. Secondary effect on diaphragm gene expression after intramyocardial CDC injection demonstrated differences in Ca2+. Additional results were observed in inflammatory pathway and response. Intramyocardial CDC-derived exosome injection resulted in decrease of oxidative stress marker, MDA to nearly the same levels as wild-type as shown. Further decreases in inflammatory markers p65 and 1kB were observed. Reduction in fibrosis was observed as well as a reduction in inflammatory cells. Improvements in diaphragm force production and soleus muscle was observed. Similarly, soleus and EDL showed notable improvements at both transcriptomic and functional levels; soleus contractile force was fully normalized. Changes in gene expression were significantly correlated in diaphragm and soleus.

To further evaluate the potential of exosomes to mediate systemic benefits, the Inventors injected CDC-derived exosomes into the left ventricular cavity of mdx hearts. Intraventricular injection of CDC-derived exosomes demonstrated similar beneficial results in the heart as shown in. CDC-derived exosomes were capable of modulating gene expression in a manner mirroring CDCs themselves. Moreover, both ejection fraction and distance improved with CDC-derived exosome injection. These results were further observed in diaphragm and both twitch and specific force improved with CDC-derived exosome injection. These results were further observed in soleus, as shown for gene expression and again both twitch and specific force improved with CDC-derived exosome injection.

Example 27

Animals and Injections

All animal procedures were approved by the Cedars-Sinai Medical Center Institutional Animal Care and Use Committee. Ten twelve-month-old mdx (C57BL10/ScSn-DMD$^{mdx}$/J) and wild-type strain-matched (C57BL10/ScSn/J) animals were used in this study. Mice were housed under pathogen-free conditions in a temperature controlled room with a 12-hour photoperiod. Baseline measurements of maximal exercise capacity and in vivo cardiac function were recorded prior to injection. CDCs ($2.5 \times 1.0^5$) and CDC-exos ($2 \times 10^9$) were suspended in 100 µL of DPBS and injected into the femoral vein of mdx mice. Vehicle-treated mdx mice received an equal volume of DPBS injected into the femoral vein. Mice were reassessed for maximal exercise capacity and in vivo cardiac function 3 weeks post-injection, then tissues were harvested and processed for muscle physiology experiments, histology and immunohistochemistry, or frozen in liquid nitrogen and stored at −80° C.

Cardiosphere-Derived Cell Culture and Exosome Purification

Mouse CDCs were expanded from an 8-week-old strain-matched wild-type donor. The ventricles were cut into fragments <1 mm³, washed, and partially digested with trypsin (0.05%; Gibco). These fragments were individually seeded onto fibronectin (Corning) coated culture dishes and cultured in growth media [Iscove's Modified Dulbecco's Medium (GIBCO), 20% fetal bovine serum (Atlas Biologicals), 1% penicillin/streptomycin (GIBCO), and 1×2-mercaptoethanol (GIBCO)]. After a variable period of growth, a monolayer of cells emerged from the explants, which phase bright cells proliferated. The loosely adherent cells surrounding the explants (termed explant derived cells) were harvested using mild enzymatic digestion (TrypLE; GIBCO) and plated on poly-D-lysine coated culture flasks (ultra-low adherent) for three days. In suspension culture, explant-derived cells spontaneously form three-dimensional clusters termed cardiospheres, which were harvested and plated in fibronectin coated culture flasks. In adherent culture, as disclosed elsewhere herein, cardiospheres form a monolayer of cells termed. CDCs. CDCs were expanded to passage 3-5, which were used for all experiments. To block exosome biosynthesis, confluent CDCs were washed with DPBS and the media was supplanted with serum-free media. CDCs to be used for in vivo experiments were washed, enzymatically dissociated from the adherent culture dishes, counted, and suspended in DPBS. To generate exosomes, human CDCs were cultured until confluency at passage 5. The cells were washed with DPBS, and the media was supplanted to serum-free media. CDCs were then cultured in physiologically low oxygen (2% $O_2$) for 24 hours. The conditioned media was then collected, sterile filtered using a 0.45 µm filter, and frozen for later use. Later, the conditioned media was thawed and the exosomes were purified and concentrated by ultrafiltration via centrifugation using 3 kDa centrifugal filters (EMD Millipore). Exosome concentration of the filtrate was measured by nanoparticle tracking analysis (NanoSight NS300). Exosomes were then aliquoted in ready-to-use tubes, frozen, and stored at −80° C. until later use.

Treadmill Exercise Testing

Mice were placed inside an Exer-3/d rodent treadmill (Columbus Instruments) equipped with a shock plate. During the acclimatization period, the belt speed was set to 10 m/min with the shock plate inactivated, and mice were undisturbed for 20 minutes to acclimate to the environment. After the acclimatization period, the exercise protocol engaged (shock plate activated at 0.15 mA at a frequency of 1 shock/sec). The protocol is intended to induce volitional exhaustion by accelerating the belt speed by 1 m/min per minute. Mice that rest on the shock plate for >10 sec with nudging are considered to have reached their maximal exercise capacity (their accumulated distance traveled is recorded) and the exercise test is terminated.

In Vitro Isolated Skeletal Muscle Physiology

Mice were deeply anesthetized with isoflurane inhalation and the soleus or diaphragm muscles were rapidly excised. Briefly, following a lateral midline skin incision of the lower leg the soleus was dissected and isolated and its tendons of origin and insertion were tightened with silk suture (3-0) and rapidly excised. The soleus muscle was vertically mounted in a tissue bath containing a mammalian Ringer's of the following composition: (in mM) 137 NaCl, 5 KCl, 2 $CaCl_2$, 1 $MgSO_4$, 1 $NaH_2PO_4$, 24 $NaHCO_3$, 11 glucose. The solution was constantly aerated with 95% $O_2$ and 5% $CO_2$ with pH maintained at 7.35 and temperature kept at 24° C. Following a left costal margin skin and muscle incision a section of the midcostal hemidiaphragm was transferred to a preparatory Sylgar-lined dish containing the aerated cold Ringer's and a narrow 3-4 mm wide strip of diaphragm was isolated maintaining fiber attachments to the rib and central tendon intact which were tighten with silk suture and mounted vertically in the tissue bath. One end of the soleus or diaphragm was secured to a clamp at the bottom of the dish and one was attached to a calibrated force transducer (Cambridge Technology Model 300B, Watertown, Mass.). A micromanipulator linked to the system was used to adjust muscle length. Platinum wire electrodes placed on each side of the muscle were used for direct muscle stimulation (Grass Model S88 stimulator; Quincy, Mass.) using 0.2 msec duration monophasic rectangular pulses of constant current (Mayo Engineering, Rochester, Minn.) delivered at supramaximal intensity. Muscle preload was incrementally adjusted until the optimal muscle length for maximum isometric twitch force (Lo) was reached. Lo was measured at 0.1 mm accuracy using a digital caliper (Mitutoyo, Japan). Isometric contractile properties were then determined at this Lo. Peak twitch force (Pt), contraction time (i.e., time to Pt) and half-relaxation time (i.e., time for Pt to fall one-half maximum) were determined from a series of single pulses. Force-frequency relationships were measured at stimulus frequencies ranging from 5 to 180 pulses per second. The stimuli were presented in trains of 1 sec duration with an interval of at least 1 min intervening between each stimulus train. Muscle forces generated, including Pt and maximum tetanic force (Po), were normalized for the estimated physiological cross-sectional area (CSA) of the muscle segment (CSA=muscle weight/1.056×Lo; where 1.056 g/cm$^3$ represents the density of muscle) and expressed in Newtons (N)/cm$^2$. For the soleus muscle, Lo was also normalized for muscle fiber length (0.71 of Lo) in estimating muscle specific force. Absolute muscle maximum forces generating are also reported (mN).

FIG. 40 demonstrates functional improvements to the cardiorespiratory system by a single intravenous dose of syngeneic cardiosphere-derived cells (CDCs) and human CDC-derived exosomes (CDC-XOs) in mdx mice. Ten-twelve-month-old wild-type (WT) and mdx mice were subjected to baseline assessment of maximal exercise capacity and in vivo cardiac function by echocardiography. At this age, mdx: mice have a markedly reduced ability to tolerate exercise concomitant with impaired left ventricular ejection fraction (FIG. 40A). A single intravenous dose of CDCs or CDC-XOs dramatically improved the maximal exercise capacity of mdx mice 3 weeks after treatment. In addition to improving exercise capacity, CDC and CDC-XO treatment boosted left ventricular function (as evidenced by ejection fraction) relative to vehicle treated mdx mice (FIG. 40B). The robust improvements in cardiac function were mirrored by a global decrease in histopathology of mdx hearts (FIG. 40C; vehicle: top panel, CDCs: middle panel, and CDC-XOs: bottom panel) concomitant with a significant reduction in interstitial fibrosis (FIG. 40D).

Example 28

Figure 42A:
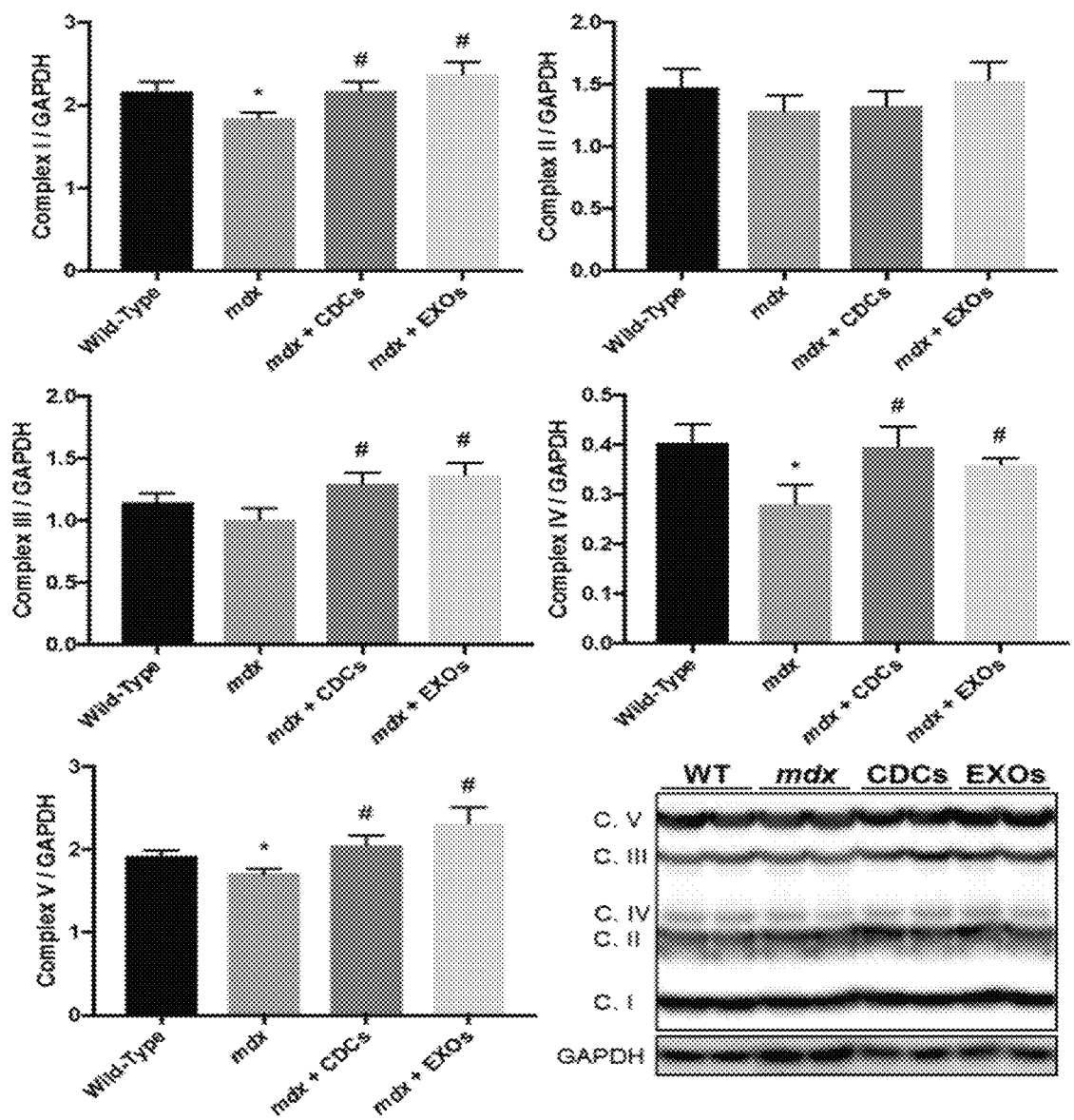
FIGS. 42A-D. Animals were treated as described in FIG. 40.
Figure 42B:
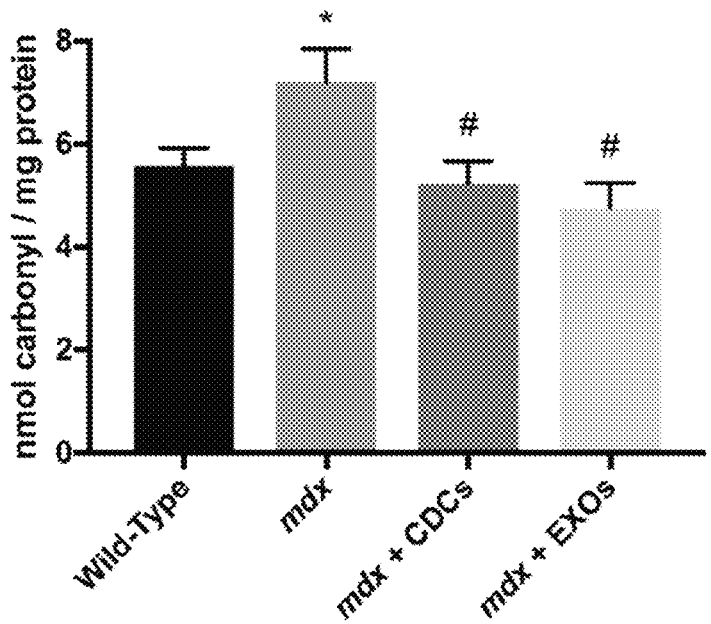
Figure 42C:
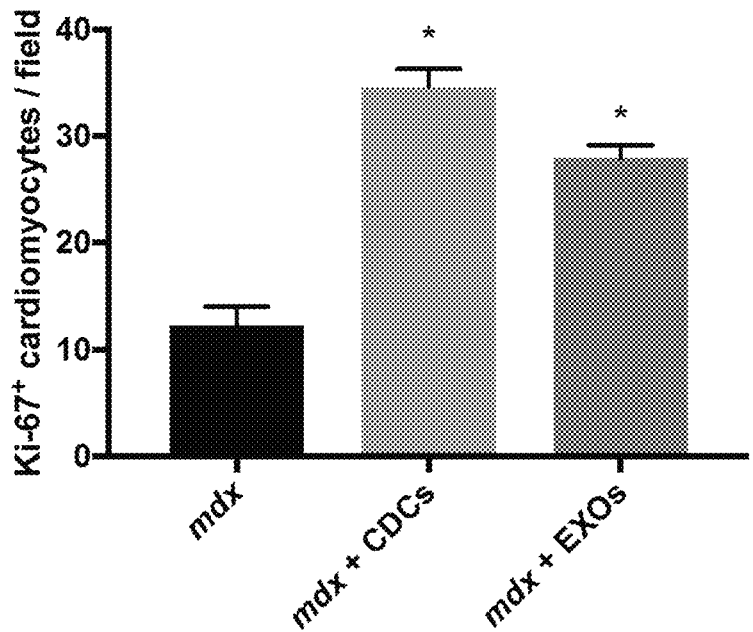
Figure 42D:
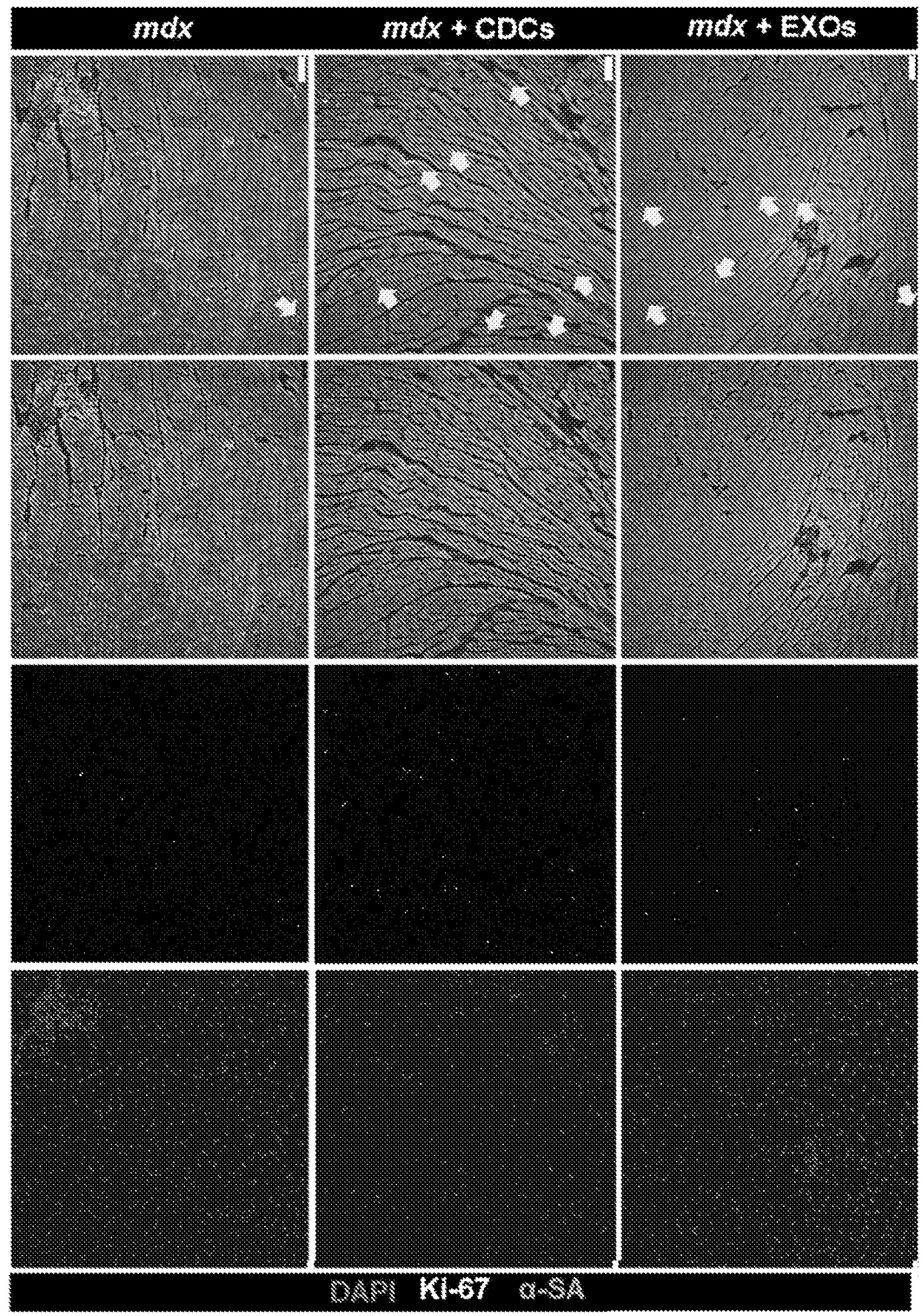

Animals were treated as described in Example 27. FIGS. 41 & 42 reveal the effects of CDCs and CDC-MN on the transcriptome, inflammation, oxidant stress, and regeneration of mdx hearts. Whole transcriptome analysis of RNA-sequencing data demonstrates that CDCs and CDC-XOs partially reverse the transcriptomic profile of max hearts, skewing gene expression toward WT hearts (FIG. 41A). Kyoto Encyclopedia of Genes and Genomes (KEGG) enrichment analysis of the 772 differentially regulated genes show a significant upregulation in cytokine-receptor interaction, complement and coagulation cascades, and several pathways involved in inflammation, such as NF-κB (data not shown). Therefore, the activation (phosphorylation) of NK-κB, a master transcriptional regulator of a host of pro-inflammatory genes, was probed. In mdx hearts, NF-κB is potently activated (FIG. 41B). Conversely, CDC and CDC-XO treatment decreased the protein levels of phosphorylated NF-κB (FIG. 41B), indicating a reduction in pro-inflammatory signaling. To determine if decreased NF-κB signaling had a physiological effect on inflammation in mdx hearts, cryosections of Inch hearts from vehicle (control; labeled mdx), CDC, and CDC-XO treated mice were immunostained for CD68, an activated macrophage marker, and visualized immunofluorescence by confocal microscopy, Relative to vehicle-treated mdx hearts, CDC and CDC-XO-treated mdx hearts contained significantly few CD68$^+$ macrophages (FIGS. 41C&D) demonstrating a direct effect of CDCs and CDC-XOs to modulate inflammation in mdx hearts. Because hearts from mdx mice have been previously described to have mitochondrial dysfunction, assays for the protein expression of complexes involved in electron transport and oxidative phosphorylation were performed. Consistently, a modest, but significant, decrease in most electron transport chain complexes and ATP synthase (complex V) was demonstrated (FIG. 42A). In contrast, CDC and CDC-XO treatment restored protein expression of the electron transport chain complexes and ATP synthase (FIG. 42A). Mitochondrial dysfunction is associated with increases in cellular oxidant stress. The formation of protein-carbonyl adducts, an irreversible oxidative modification to proteins caused by severe oxidant stress, was tested. Treatment with CDCs and CDC-XOs reduced carbonylated protein accumulation to a level consistent with WT hearts (FIG. 42B). Lastly, testing was performed to determine if CDCs or CDC-MN could induce cardiomyocyte proliferation, a marker of cardiac regeneration, when delivered intravenously, Compared to vehicle treated mdx hearts, CDC and CDC-XO-treated mdx hearts 2.5-3-fold more Ki-67$^+$ cardiomyocytes, a protein exclusively expressed during cell division (FIGS. 42C&D).

Example 29

Animals were treated as described in Example 27. FIG. 43 shows the therapeutic benefits of intravenous delivery of CDCs and CDC-XOs are not exclusive to mdx hearts, they are also efficacious at improving skeletal muscle function. Given that skeletal muscles of mdx mice share common pathophysiological processes with mdx hearts, whether systemic delivery of CDCs and CDC-XOs would benefit skeletal muscles of mdx mice was tested. Vehicle-treated mdx mice exhibit a marked reduction isometric twitch and tetanic force of the diaphragm (FIGS. 43A-C) and soleus (FIGS. 43D-F), key respiratory and locomotor muscles respectively. Intravenous delivery of CDCs and CDC-XOs potently boosted isometric force produced by the diaphragm and soleus (FIGS. 43A-F). Like mdx hearts, these improvements were mirrored by a decrease in histopathology (FIG. 43G; vehicle: left panel, CDCs: middle panel, and CDC-XOs: right panel) and related fibrosis (FIG. 43H). In parallel, CDC and CDC-XO treatment boosted the number of myofibers comprising the soleus of mdx mice (FIG. 43I).

Example 30

Figure 44C:
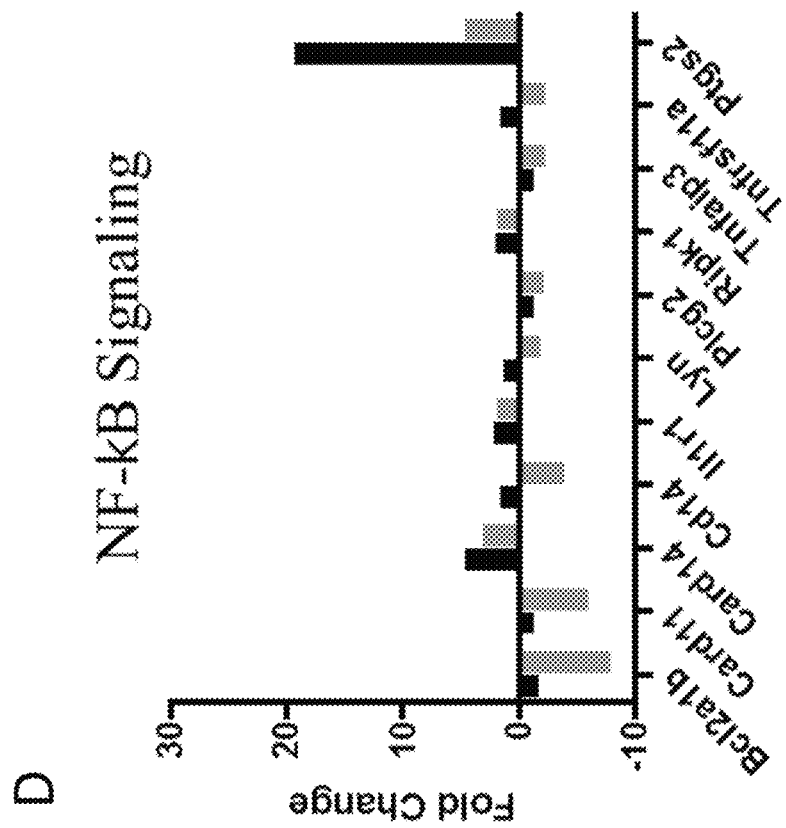
Figure 44D:
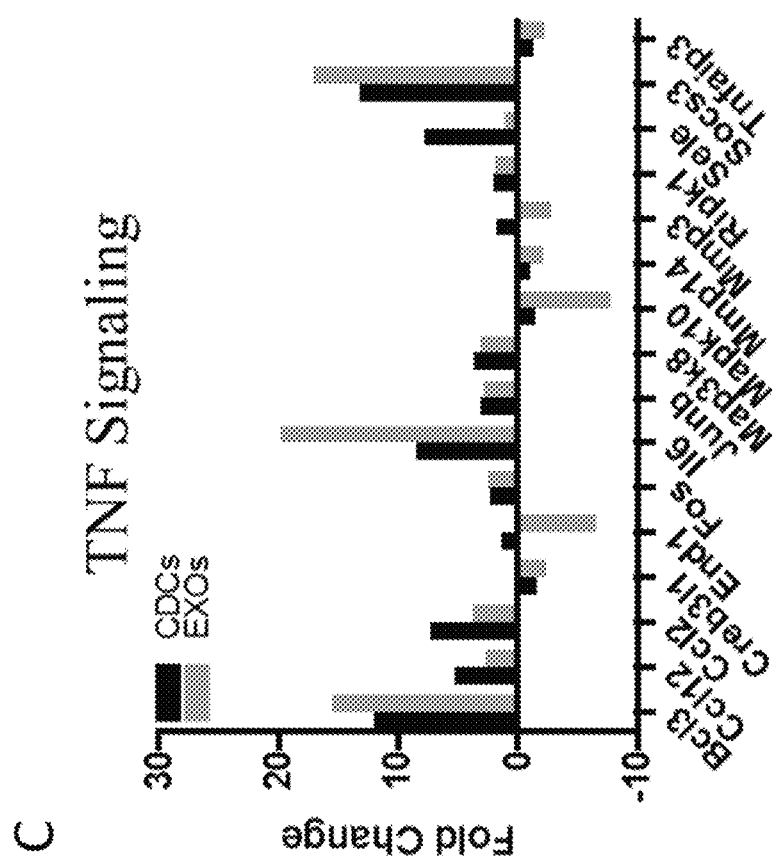
Figure 45C:
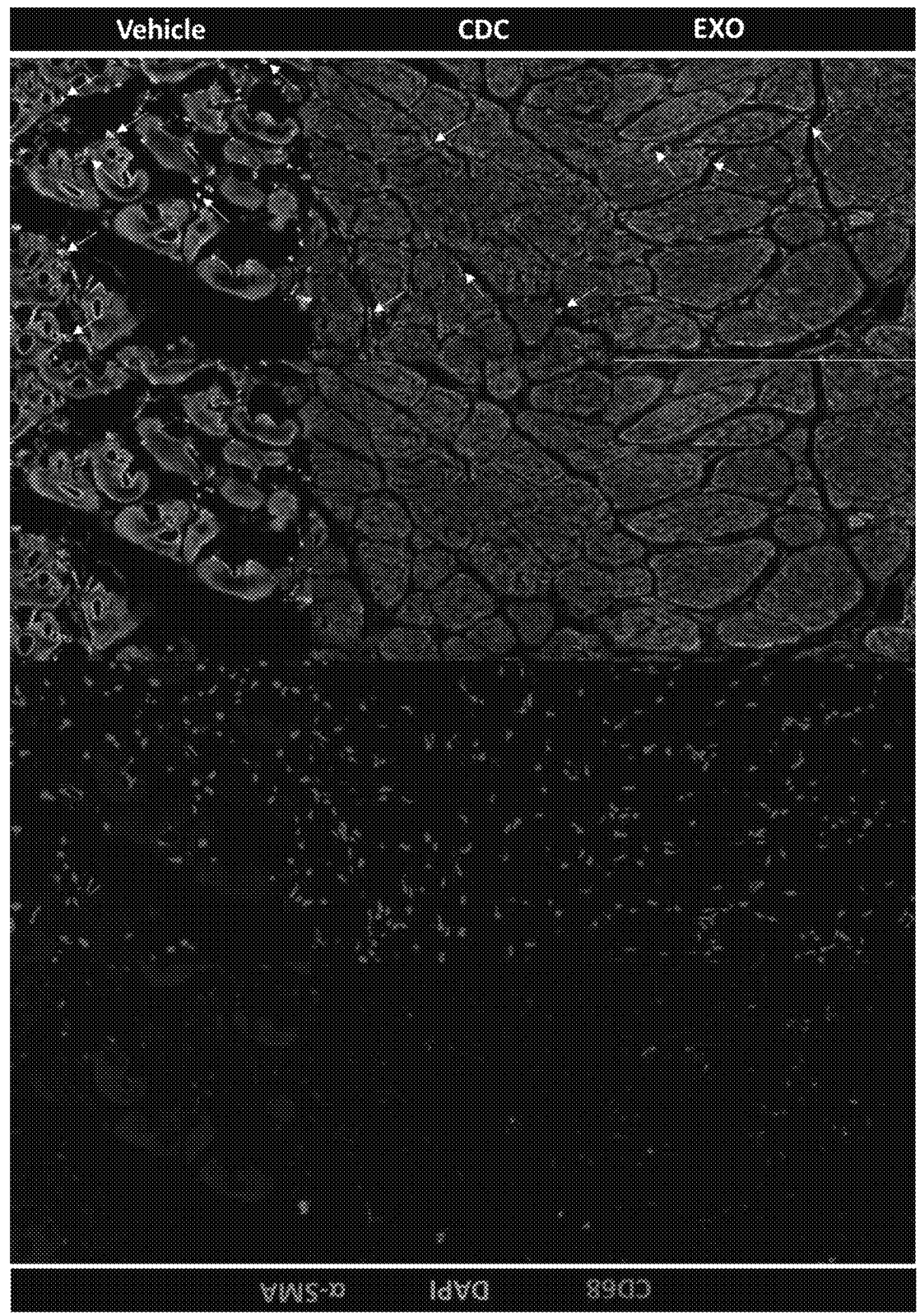

Animals were treated as described in Example 27. FIGS. 44&45 reveal the effects of CDCs and CDC-XOs on the transcriptome, and inflammation in the solei of mdx mice. Like mdx hearts, whole transcriptome analysis demonstrates that CDCs and CDC-XOs partially reverse the transcriptomic profile in the mdx mouse soleus (FIG. 44A). KEGG enrichment show a dramatic upregulation of pathways involved in inflammation in CDC (data not shown) and CDC-XO (FIG. 44B) treated, mdx soleus. Fold change (relative to vehicle treated mdx soleus) of genes due to CDC and CDC-XO treatment involved in TNF and NF-κB signaling are depicted in FIG. 43C and FIG. 43D, respectively. Consistent, with vehicle treated mdx hearts, phosphorylated NF-κB was significant greater in vehicle treated/mix solei than WT solei (FIG. 45A). Next, we probed for CD68 immunohistochemistry on vehicle, CDC, and CDC-XO treated mdx solei cyrosections. Like vehicle treated mdx hearts, their soleus muscles are also infiltrated with CD68+ macrophages. However, unlike CDC and CDC-XO treated mdx hearts, these treatments appear to boost CD68+ macrophage accumulation in the soleus, an observation consistent with RNA-sequencing data (FIGS. 45B&C). A careful inspection of the fascicular arrangement in these muscles (α-sarcomeric actin [green] channel in FIG. 45C) reveal that the increased accumulation of CD68+ macrophages due to CDC and CDC-XO treatment do not appear pathological. Indeed, these treatments boost contractile function of this muscle (FIGS. 43D-F), and attenuate protein-carbonyl adducts (data not shown).

FIG. 46 demonstrates the ability of CDCs and CDC-XOs (when delivered intravenously) to modestly increase the protein expression of the full-length dystrophin isoform in the soleus (FIG. 46A) and diaphragm (FIG. 46B) 3 weeks after a single dose.

Additional Background and Examples

As discussed above, several embodiments of the methods and compositions provided herein are based on the surprising discovery that, despite the finding that intravenous administration of cardiosphere-derived cells (CDCs) to mdx mice resulted in accumulation of the majority of CDCs in their lungs, functional improvements at dystrophic skeletal muscles were achieved as demonstrated by the various data presented herein, thereby enabling an effective treatment of a human subject suffering from muscular dystrophy, e.g., DMD, by administering a therapeutically effective amount of CDCs to a human subject suffering from skeletal muscular dystrophy.

The CDCs accumulated in the lungs may have released extracellular vesicles (EVs) including exosomes and microvesicles, as well as paracrine factors that through direct interactions with dystrophic skeletal muscle at, e.g., the leg, or through an indirect mechanism (e.g., immunomodulatory response and reducing chronic inflammation), reached a therapeutically effective amount to treat a subject in need thereof. As such, in this context and not wishing to be bound by theory, what is meant by "a therapeutically effective amount of CDCs" is a sufficient amount of CDCs administered to a subject to result in delivery of a sufficient amount of EVs to a targeted dystrophic skeletal muscle in a subject to increase and/or restore skeletal muscle function in the subject and to immune-modulate chronic inflammatory immune response.

Accordingly, one aspect of some embodiments provides a method of safely treating skeletal muscular dystrophy in a subject in need thereof, the method comprising administering to the subject a therapeutically effective amount of autologous or allogeneic CDCs and/or EVs, e.g., exosomes and microvesicles. In particular, said therapeutically effective amount of CDCs and/or EVs is sufficient to treat or alleviate a targeted dystrophic skeletal muscle of the subject. What is meant by "a targeted dystrophic skeletal muscle" in this context is that a therapeutically effective amount of CDCs and/or EVs is sufficient to treat or alleviate dystrophinopathy and/or restore skeletal muscle function, of a particular dystrophic skeletal muscle in a subject at the site of a dystrophic skeletal muscle, rather than an accidental or inadvertent delivery of CDCs and/or EVs that might be secreted from CDCs that might not be in a sufficient amount to treat dystrophinopathy at the site of a dystrophic skeletal muscle.

Non limiting examples of said skeletal muscular dystrophy include DMD and Becker muscular dystrophy, wherein one or more skeletal muscles of, e.g., the diaphragm, the arm and/or the leg is; are dystrophic. Non-limiting examples of a means to administer a therapeutically effective amount of CDCs and/or EVs in this context include intramuscular injection or infusion directly at a dystrophic skeletal muscle and systemic administration, in a single dose or multiple doses.

Another aspect provides a method of safely treating dystrophic cardiomyopathy, the method comprising systemically administering to the subject a therapeutically effective amount of CDCs. In particular, said therapeutically effective amount of CDCs is sufficient to treat or alleviate the subject's dystrophic heart muscle. Non-limiting examples of said dystrophic cardiomyopathy include heart failure secondary to, or associated with, an acute or chronic muscular dystrophy, e.g., DMD or Becker muscular dystrophy.

As discussed above, dystrophic tissues includes lack of, or deficient, dystrophin in skeletal and/or heart muscle.

In some embodiments, said subject is a mammal such as a human. Non-limiting examples of said systemic administration of CDCs include intravascular administration (e.g., intravenous or intra-arterial injection or infusion), intra-aortic administration, intraventricular administration (e.g., injection or infusion into the right or left ventricle or atrium), intrathecal administration, and intraperitoneal administration. Non-limiting examples of said intravenous administration of CDCs include jugular and/or femoral vein injection and/or infusion. Non-limiting examples of said administration of CDCs in multiple doses include administration of 2-10 doses at intervals of 1-5 months, e.g., 3 doses at intervals of about 3 months, or 5 doses at interval of about 1 week. Non-limiting examples of said administration of CDCs in multiple doses include three administrations at weeks 0, 6 and 12. Non-limiting examples of said therapeutically effective amount of CDCs include at least about 75-500×10$^6$ CDCs, e.g., about 75×10$^6$ CDCs, about 150×10$^6$ CDCs, about 300×10$^6$ CDCs, 400×10$^6$ CDCs, and 500×10$^6$ CDCs.

Some embodiments provide a formulation comprising CDCs for use in the treatment of skeletal muscular dystrophy and/or dystrophic cardiomyopathy according to the aforementioned methods.

Some embodiments use the aforementioned formulation for treating skeletal muscular dystrophy and/or dystrophic cardiomyopathy according to the aforementioned methods.

Cardiospheres

In some embodiments, cardiospheres are derived from cardiac tissue and include undifferentiated cardiac cells that grow as self-adherent clusters as described in WO 2005/012510, and Messina et al., "Isolation and Expansion of Adult Cardiac Stem Cells From Human and Murine Heart," *Circulation Research*, 95:911-921 (2004), the disclosures of which are herein incorporated by reference in their entirety.

Briefly, heart tissue can be collected from a patient during surgery or cardiac biopsy. The heart tissue can be harvested from the left ventricle, right ventricle, septum, left atrium, right atrium, crista terminalis, right ventricular endocardium, septal, or ventricle wall, atrial appendages, or combinations thereof. A biopsy can be obtained, e.g., by using a percutaneous bioptome as described in, e.g., U.S. Patent Application Publication Nos. 2009/012422 and 2012/0039857, the disclosures of which are herein incorporated by reference in their entirety. The tissue can then be cultured directly, or alternatively, the heart tissue can be frozen, thawed, and then cultured. The tissue can be digested with protease enzymes such as collagenase, trypsin and the like.

The heart tissue can be cultured as an explant such that cells including fibroblast-like cells and cardiosphere-forming cells grow out from the explant. In some instances, an explant is cultured on a culture vessel coated with one or more components of the extracellular matrix (e.g., fibronectin, laminin, collagen, elastin, or other extracellular matrix proteins). The tissue explant can be cultured for about 1, 2, 3, 4, or more weeks prior to collecting the cardiosphere-forming cells. A layer of fibroblast-like cells can grow from the explant onto which cardiosphere-forming cells appear. Cardiosphere-forming cells can appear as small, round, phase-bright cells under phase contrast microscopy. Cells surrounding the explant including cardiosphere-forming cells can be collected by manual methods or by enzymatic digestion. The collected cardiosphere-forming cells can be cultured under conditions to promote the formation of cardiospheres. In some aspects, the cells are cultured in cardiosphere-growth medium comprising buffered media, amino acids, nutrients, serum or serum replacement, growth factors including but not limited, to EGF and, bFGF, cytokines including but not limited to cardiotrophin, and other cardiosphere promoting factors such as but not limited to thrombin. Cardiosphere-forming cells can be plated at an appropriate density necessary for cardiosphere formation, such as about 20,000-100,000 cells/mL. The cells can be cultured on sterile dishes coated with poly-D-lysine, or other natural or synthetic molecules that hinder the cells from attaching to the surface of the dish. Cardiospheres can appear spontaneously about 2-7 days or more after cardiosphere-forming cells are plated.

Cardiosphere-Derived Cells (CDCs)

In some embodiments, CDCs include a population of cells generated by manipulating cardiospheres in the manner as described in, e.g., U.S. Patent Application Publication No. 2012/031525:2, the disclosures of which are herein incorporated by reference in their entirety. For example, CDCs can be generated by plating cardiospheres on a solid surface which is coated with a substance which encourages adherence of cells to a solid surface of a culture vessel, e.g., fibronectin, a hydrogel, a polymer, laminin, serum, collagen, or gelatin, and expanding same as an adherent monolayer culture. CDCs can be repeatedly passaged, e.g., passaged two times or more, according to standard cell culturing methods.

Extracellular Vesicles (EVs)

In some embodiments, EVs, including exosomes and microvesicles, include vesicles formed via a specific intracellular pathway involving multivesicular bodies or endosomal-related regions of the plasma membrane of a cell. EVs can range in size, for example, from approximately 20-150 nm in diameter. In some cases, they have a characteristic buoyant density of approximately 1.1-1.2 g/mL, and a characteristic lipid composition. Their lipid membrane may be rich in cholesterol and contain sphingomyelin, ceramide, lipid rafts and exposed phosphatidylserine. EVs express certain marker proteins, such as integrins and cell adhesion molecules, but generally lack markers of lysosomes, mitochondria, or caveolae. In some embodiments, the EVs contain cell-derived components, such as but not limited to, proteins, DNA and RNA (e.g., microRNA and noncoding RNA). In some embodiments, EVs can be obtained from cells obtained from a source that is allogeneic, autologous, xenogeneic, or syngeneic with respect to the recipient of the exosomes.

In some embodiments, certain types of RNA, e.g., microRNA (miRNA), are carried by EVs, miRNAs function as post-transcriptional regulators, often through binding to complementary sequences on target messenger RNA transcripts (mRNAs), thereby resulting in translational repression, target mRNA degradation and/or gene silencing. For example, as described in WO 2014/028493, miR146a exhibits over a 250-fold increased expression in CDCs, and miR210 is upregulated approximately 30-fold, as compared to the EVs isolated from normal human dermal fibroblasts.

Examples of EVs derived from cardiospheres and CDCs are described in, e.g., WO 2014/028493, the disclosures of which are herein incorporated by reference in their entirety. Methods for preparing EVs can include the steps of: culturing cardiospheres or CDCs in conditioned media, isolating the cells from the conditioned media, purifying the EVs by, e.g., sequential centrifugation, and optionally, clarifying the EVs on a density gradient, e.g., sucrose density gradient. In some instances, the isolated and purified EVs are essentially free of non-exosome components, such as components of cardiospheres or CDCs. EVs can be resuspended in a buffer such as a sterile PBS buffer containing 0.01-1% human serum albumin. The EVs may be frozen and stored for future use.

Example 31

Mouse CDC Preparation

Some embodiments of the compositions and methods provided herein include CDCs prepared from a mammal such as a mouse or a human. In examples where mouse CDCs were used, mouse CDCs were expanded from wild-type strain-matched mouse hearts (C57BL/10ScSnJ wild type mouse heart) as described in, Smith, R. R. et al., Regenerative potential of cardiosphere-derived cells expanded from percutaneous endomyocardial biopsy specimens, *Circulation* 115, 896-908 (2007). Briefly, ventricular tissues were minced into 1 mm explants, partially digested enzymatically and plated on adherent (fibronectin-coated) culture dishes. These explants spontaneously yielded outgrowth cells (explant-derived cells) which were harvested once confluent and plated in suspension culture ($10^5$ cells/mL on poly-D-lysine-coated dishes) to enable self-assembly of three-dimensional cardiospheres, Subsequent replating of cardiospheres on adherent culture dishes yielded CDCs which were used at passage 3, 4 or 5.

Example 32

Exercise Capacity of mdx Mice

Figure 47:
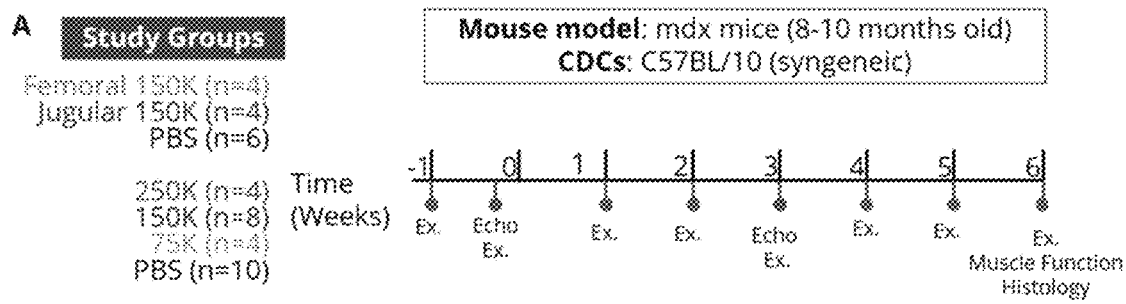
FIG. 47 depicts a schematic protocol that was used for evaluating the efficacy of escalating doses of intravenous administration of CDCs to improve exercise capacity using a mouse model of DMD (may mice), wherein mdx mice received treatment or control vehicle in Week 0, exercised every week, and were sacrificed in Week 6.

As shown in FIG. 47, before treatment, a baseline measure of left ventricular ejection fraction in 8-10 month old mdx mice was obtained by echocardiography, and exercise capacity was measured using treadmill exercise. CDC treatment or vehicle control was given at t=0 weeks. The CDC treatment included one of three doses of CDCs: 75,000 cells (injected intravenously into the jugular vein), 150,000 cells (injected intravenously into the jugular vein unless otherwise indicated), or 250,000 cells (injected intravenously into the femoral vein). The vehicle control included PBS (injected intravenously into the jugular vein). Left ventricular ejection fraction was measured 3 weeks after treatment. Exercise capacity was measured every week for 6 weeks following treatment. At the study conclusion, mice were sacrificed, isolated muscle function was measured on each mouse's soleus and diaphragm, and heart tissue was analyzed by Masson's trichrome staining to measure collagen deposition. The experimental protocol shown in FIG. 47 was used to generate the data in FIGS. 48A, 48B, 49, and 50A-54, and described in Examples 32A-36B.

In one experiment, mdx mice received CDCs intravenously into either the jugular veins or femoral vein, to determine whether the route of administration had an effect on exercise capacity. Mice were treated with 150,000 CDCs in either the jugular (n=4) or femoral (n=4) vein, or received PBS vehicle without CDCs (n=10), at 0 weeks. Exercise capacity was assessed weekly, and is shown in FIG. 48A, Exercise capacity was assessed with an Exer-3/6 open treadmill (Columbus Instruments, Columbus, Ohio), For each mouse, after an acclimation period (10 m/min for 20 min), stepwise increases in average speed (2 m/min) were applied every two minutes during treadmill exercise until the mouse became exhausted (spending >10 seconds on a shocker; continuous nudging was used during treadmill to help mice stay on the track). Subsequently, the mouse was returned to its cage and the total distance traveled on the treadmill was recorded. Both treatment routes (jugular and femoral) resulted in similar increases in exercise capacity during the 6-week study period, *=p<0.05 versus control. Thus, in some embodiments, CDC treatment by systemic administration improves exercise capacity in a subject with a muscular dystrophy, such as DMD or Becker muscular dystrophy, involving dystrophinopathy of a skeletal muscle. A therapeutically effective administration includes intravenous injection into a blood vessel or vein such as the jugular vein or femoral vein.

A set of experiments was performed to determine effects of various CDC doses on exercise capacity, muscle function, body weight, and cardiac fibrosis, structure, and function (described in Examples 32-36B), Mice were treated with IV administration of 75,000 CDCs (n=8), 150,000 (n=8) CDCs, or 250,000 CDCs (n=4), or PBS vehicle (n=12), at 0 weeks and exercise capacity was assessed weekly with Exer-3/6 open treadmill. For each mouse, after an acclimation period (10 m/min for 20 min), stepwise increases in average speed (2 m/min) were applied every two minutes during treadmill exercise until the mouse became exhausted (spending seconds on shocker; continuous nudging was used during treadmill to help mice stay on the track). Subsequently, the mouse was returned to the cage and the total distance traveled by the mouse was recorded. The results are shown graphically in FIG. 48B. After an initial increase in exercise capacity 1-3 weeks after treatment, the exercise capacity of mice treated with 75K CDCs returned to that of PBS-treated mice. Mice treated with 150K and 250K CDCs showed increased exercise capacity over the course of the 6 week study compared to mice treated with 75K or PBS, indicating a dose response. *=p<0.05 versus control. All of these results indicate that in some embodiments, doses of about 75,000, 100,000, 125,000, 150,000, 200,000, 250,000 CDCs, or more, such as about 500,000 or $1\times10^6$ CDCs are therapeutically effective for improving exercise capacity in a subject with muscular dystrophy, such as DMD or Becker muscular dystrophy, involving dystrophinopathy of a skeletal muscle. These results also indicate that in some embodiments, ranges including and/or spanning the aforementioned, numbers of CDCs, are therapeutically effective for improving exercise capacity in a subject with muscular dystrophy, such as DMD or Becker muscular dystrophy, involving dystrophinopathy of a skeletal muscle. These results also indicate that in some embodiments, a dose of about 150,000, 200,000 250,000, 500,000, or $1\times10^6$ CDCs. or more CDCs may be even more effective than a dose of 75,000 CDCs. Thus, in some embodiments, systemic administration of about 75,000 to about 250,000 CDCs, or of about 150,000 to about 250,000 CDCs may be used to improve a subject's exercise capacity, including running capacity.

The therapeutically effective doses exemplified here and in the other examples may be increased or adjusted in accordance with the size and/or body weight of the subject to be treated. For example, where a dose of about 75,000 to about 250,000 CDCs is therapeutically effective for a mouse, a therapeutically effective dose for a human may also be about 75,000 to about 250,000 CDCs, but may also be adjusted in accordance with the body weight of an average human to include a dose such as about $1.86\times10^8$ to about $6.2\times10^8$ CDCs (to adjust from a typical mouse weight of 2.5 g to an average human body weight of 62 kg).

Example 33

In Vitro Isolated Muscle Function

Effects on muscle function of various doses of CDCs administered systemically were also determined. The same mice that were used to generate the data shown in FIG. 48B were deeply anesthetized with ketamine/xylazine (80 mg/kg and 10 mg/kg body weight IP). For each mouse, the diaphragm muscle was rapidly excised, and the animal was euthanized. Following a left costal margin skin and muscle incision, a section of the midcostal hemidiaphragm was transferred to a preparatory Sylgar lined dish containing cold Ringer's and a narrow 3-4 mm wide strip of diaphragm was isolated maintaining fiber attachments to the rib and central tendon intact which were tightened with a silk suture and mounted vertically in the tissue bath. One end of the diaphragm was secured, to a clamp at the bottom of the dish and one end was attached to a calibrated force transducer (Cambridge Technology Model 300B, Watertown, Mass.). A micromanipulator linked to the system was used to adjust muscle length. Platinum plate electrodes placed on each side of the muscle were used for direct muscle stimulation (Grass Model S88 stimulator; Quincy, Mass.) using 0.2 msec duration monophasic rectangular pulses of constant current delivered at supramaximal intensity. Muscle length was adjusted until maximum isometric twitch force response measurements were obtained. Isometric contractile properties were determined at optimal length (Lo). Peak twitch force (Pt) was determined from a series of single pulses. Force/frequency relationships were measured at stimulus frequencies ranging from 5-150 pulses per second (pps). The stimuli were presented in trains of 1 sec duration with an interval of at least 1 min intervening between each stimulus train. Muscle forces generated, including Pt and maximum tetanic force (Po), were normalized for the estimated physiological cross-sectional areas (CSA) of the muscle segment (CSA=muscle weight/$1.056\times$Lo; where 1.056 g/cm$^3$ represents the density of muscle) and expressed in Newtons (N)/cm$^2$. As shown in FIG. 49, diaphragm muscle function tended to be increased in mice treated with 75K (n=8), 150K (n=8) compared to PBS vehicle (n=6). 250K (n=4) CDCs had a higher impact on diaphragm muscle function compared to 150K CDCs and 75K CDCs, indicating a dose response. The data for the 250K dose was statistically significant versus the PBS control treatment (p<0.05). Thus, in some embodiments, systemic administration of CDCs improves muscle function, including skeletal muscle function, in a subject with muscular dystrophy, such as DMD or Becker muscular dystrophy, involving dystrophinopathy of a skeletal muscle. Therapeutically effective doses for improving muscle function include but are not limited to about 75,000 to about 250,000 CDCs, about 150,000 to about 250,000 CDCs, or about 250,000 or more CDCs.

Example 34

Mdx Mouse Body Weight

Figure 50A:
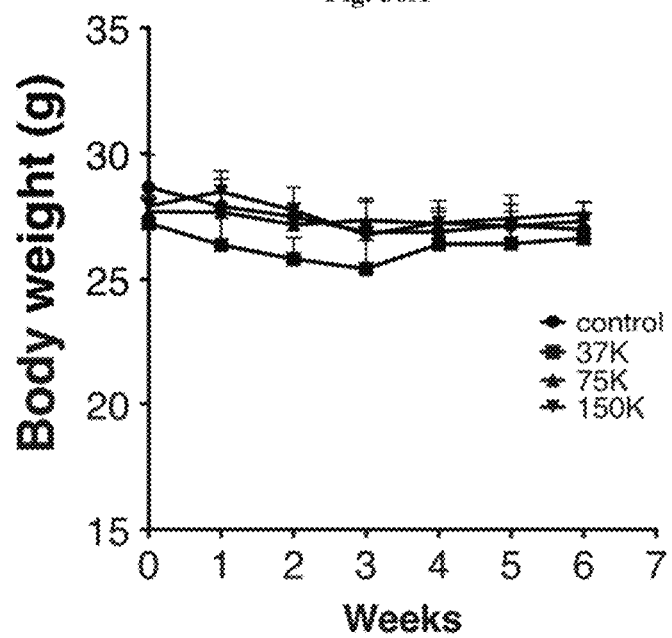
FIGS. 50A and 50B graphically show the effects of jugular IV administration of CDCs on the body weight of mdx mice injected with 37K-150K CDCs versus PBS control.
Figure 50B:
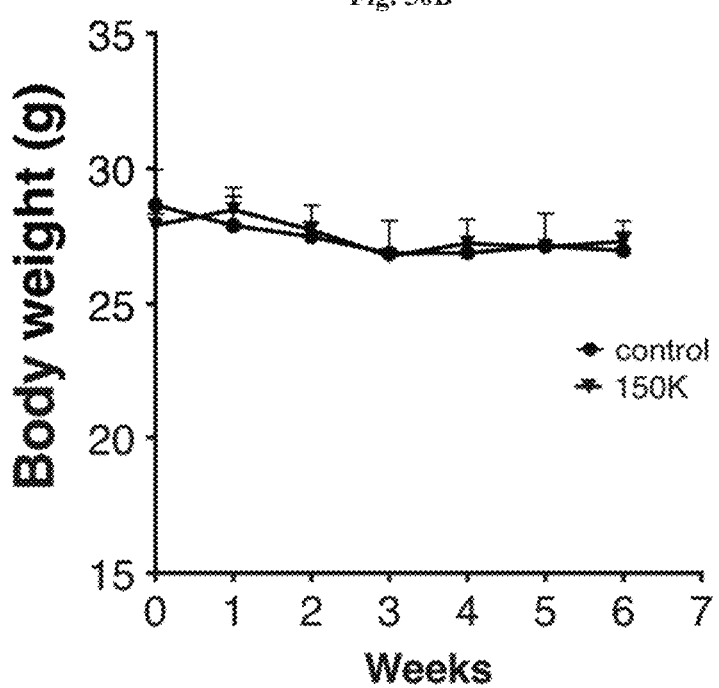

Mice treated with CDCs were weighed weekly immediately after exercise to determine whether CDC treatment had any effect on body mass. Body weight data are shown in FIGS. 50A-50B. No difference in body weight was observed between groups. Thus, in some embodiments, a therapeutically effective dose of CDCs may be systemically administered without affecting a subject's body mass or weight.

Example 35

Masson's Trichrome Stain of mdx Mouse Hearts From PBS or CDC-Treated Mice

As described in Example 31, mice treated with CDCs were sacrificed 6 weeks after treatment. Paraffin-embedded sections of each heart were used for histology to identify the effect of CDC treatment on cardiac fibrosis. Masson's trichrome staining (HT15 Trichrome Stain [Masson] Kit; Sigma-Aldrich, St. Louis, Mo.) was performed for evaluation of fibrosis. As shown in FIG. 51, left ventricular heart tissue from PBS-treated mice exhibited more fibrosis and collagen deposition compared to mice treated with 150K CDCs as shown by the decrease in blue in the CDC-treated mouse heart sections. Thus, in some embodiments, systemically administering CDCs decreases or prevents fibrosis, including cardiac or left ventricular fibrosis in a subject with muscular dystrophy, such as DMD or Becker muscular dystrophy, involving dystrophinopathy of a skeletal muscle. A therapeutically effective dose for decreasing or preventing cardiac fibrosis includes at least 150.000 CDCs.

Figure 53:
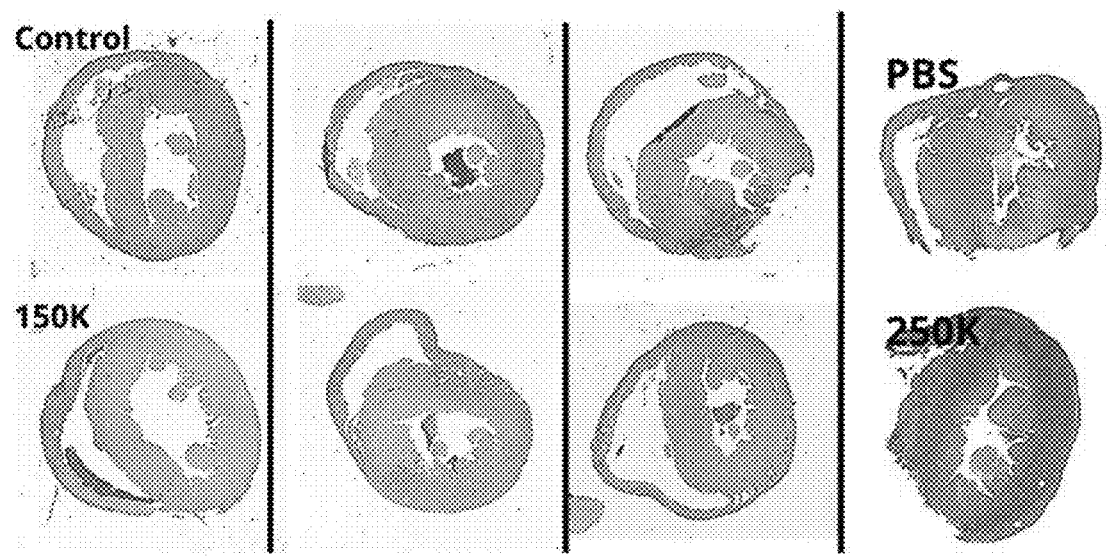
FIG. 53 depicts histology data of Masson's trichrome staining of heart tissue sections of mdx mice injected with 150K CDCs via jugular IV injection, or 250K CDCs via femoral IV injection, versus PBS control.

The histology slides used to generate the images in FIG. 51 were recut and restained with Masson's trichrome. Whole-heart sections of the recut and restained slides are shown in FIG. 53. Similar results were seen in the whole-heart sections shown in FIG. 53 as for the images shown in FIG. 51. Accordingly, in some embodiments, systemic administration of CDCs prevents or decreases fibrosis throughout the whole heart. Therapeutically effective doses for preventing or decreasing fibrosis throughout the whole heart include about 75,000 to about 250,000 CDCs, about 150,000 to about 250,000 CDCs, or about 250,000 CDCs. Additionally, no adverse effects on overall cardiac structure were seen in the hearts of mice treated with CDCs. Accordingly, in some embodiments, a therapeutically effective amount of CDCs does not adversely affect a subject's cardiac structure.

Example 36

Figure 52A:
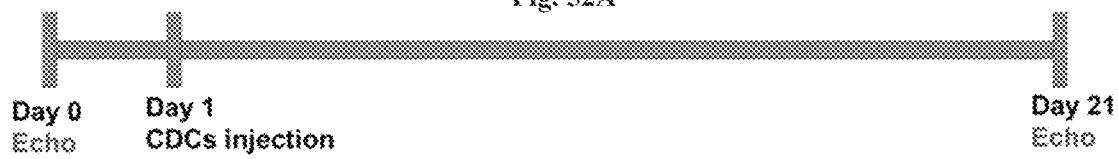
FIG. 52A depicts a schematic protocol that was used for evaluating effects of CDC treatment on cardiac ejection fraction using echocardiography.
Figure 52B:
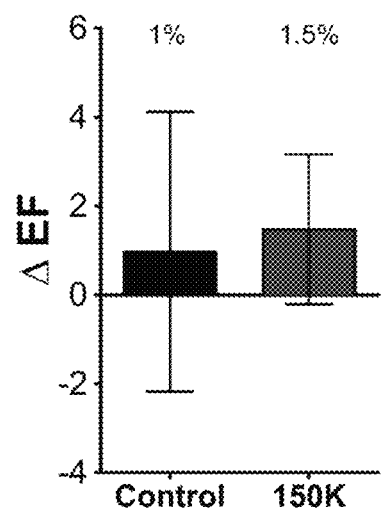
FIG. 52B graphically shows the effects of jugular IV administration of CDCs on the cardiac ejection fraction of mdx mice injected with 150K CDCs versus PBS control.

Change in Ejection Fraction of mdx Mice From Baseline to 3 Weeks After Injection As shown in FIG. 52A (and also FIG. 47), echocardiographic studies were performed 1-3 days before treatment and 3 weeks after treatment using the Vevo 3100 Imaging System (VisualSonics, Toronto, Canada) to determine effects of CDCs on cardiac function. After induction of light general anesthesia, the heart was imaged at the level of the greatest left ventricular (LV) diameter. LV ejection fraction (EF) was measured with VisualSonics version 3.0.0 software from 2-dimensional long-axis views. Treatment with 150,000 CDCs did not decrease the ejection fraction (FIG. 52B). Therefore, in some embodiments, a therapeutically effective dose of CDCs may be administered to a subject with muscular dystrophy, such as DMD or Becker muscular dystrophy, involving dystrophinopathy of a skeletal muscle, without adversely affecting the subject's heart function.

Example 37

Change in Ejection Fraction of SCID Mice With Permanent LAD Ligation

Figure 54:
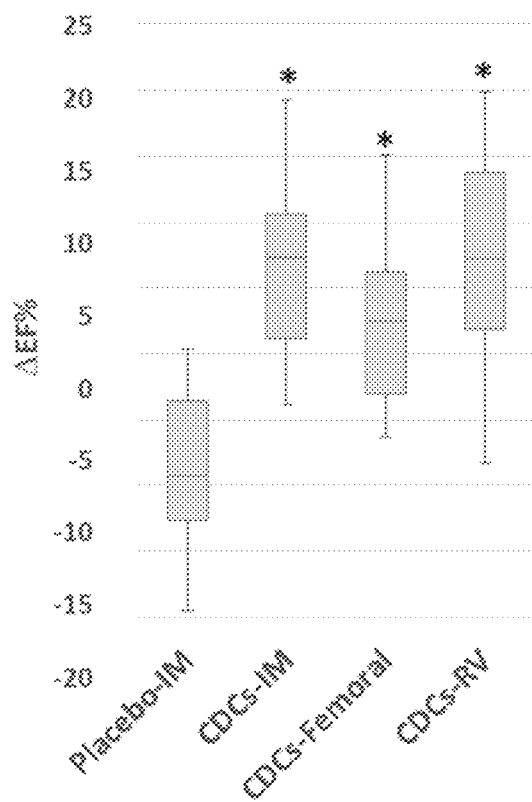
FIG. 54 graphically shows the effects of IV administration on the cardiac (left ventricular) ejection fraction in a mouse model of myocardial infarction with 300K CDCs via systemic injection (femoral IV injection or 100K CDCs via injection into the right ventricle) versus 100K CDCs via intramyocardial injection versus PBS control.

To determine whether various routes of administration could beneficially affect heart function, human CDCs were administered to SCID mice by three separate administration routes: intramuscular (IM), femoral vein, or right ventricle. Administration by all three routes resulted in a positive change in left ventricular ejection fraction (FIG. 54). The change was statistically significant in all three groups compared to mice that received a control treatment. Intramuscular and IV administration routes were equally effective, indicating efficacy with IV administration. Accordingly, in some embodiments, treatment with human CDC improves cardiac function in a subject with SCID. A therapeutically route of administration includes intramuscular injection, systemic intravenous injection into the femoral vein, or cardiac injection such as right ventricular injection.

Example 38

Biodistribution of CDCs After Jugular Vein Administration in Wild Type Mice Evaluated Using Human Alu Sequence qPCR Method One purpose of the study in this example was to determine the biodistribution of CDCs after systemic delivery. Human CDCs were administered systemically to wild-type mice via intravenous injection into the jugular vein. Making the biodistribution determination included measuring the abundance of DNA containing the human Alu sequence, a transposable element abundant in most human DNA and generally absent from mouse DNA. The abundance of DNA containing the human Alu sequence was determined using qPCR on tissues collected 10 minutes and 24 hours after CDC administration.

CDC Preparation

Human CDCs were obtained in a manner similar to mouse CDCs as described hereinabove. After a flask was rinsed with volume of culture medium equal to the amount of culture medium in a cell solution, the cell solution was centrifuged at 1000 rpm (197×g) for 5 minutes to pellet cells in the cell solution. CDCs were resuspended in Iscove's Modified Dulbecco's Media (IMDM) with no phenol red and no additional supplementation, then counted using a iNCYTO C-chip disposable hemocytometer. CDCs were diluted to $1.5 \times 10^6$ cells/mL, in IMDM with no phenol red and no additional supplementation. CDCs were kept on ice prior to injection, or the cell pellet was frozen at −20° C. for tissue spiking studies.

qPCR Method Validation

Genomic DNA was isolated from $1 \times 10^6$ CDCs at passage 5 using a DNeasy Blood and Tissue Kit (Qiagen). Ten-fold serial dilutions of the CDC DNA were prepared in sterile water and qPCR was performed using Taqman Fast Advanced Master Mix (ThermoFisher) with custom Alu primers and a custom Alu probe (from ThermoFisher). The DNA sequences of the probe and primers are as follows:

Forward: 5'-GTCAGGAGATCGAGACCATCCT-3', (SEQ ID NO: 7)

Reverse: 5'-AGTGGCGCAATCTCGGC-3', (SEQ ID NO: 8)

Probe: 5'-6-FAM-AGCTACTCGGGAGGCTGAGGCAGGA-MGB-3' (SEQ ID NO: 9)

The qPCR reactions were performed in a on a QuantStudio 6 Flex Real-Time PCR (RT-PCR) system (ThermoFisher). Ct values were plotted versus the log of the number of CDCs in each qPCR sample. Linear regression analysis was performed using GraphPad Prism 5 and the slope of the line was used to calculate the efficiency of the qPCR using the equation: % efficiency=$-1+10^{(-1/slope)} \times 100$.

Tissue Spiking Curves

Dilutions of DNA isolated from human CDCs were spiked into DNA isolated from nave 8-12 week old C57BL/6J mouse tissue. qPCR was run in triplicate on a QuantStudio 6 Flex RT-PCR system with 1 µL spiked DNA. The qPCR reactions included Taqman Fast Advanced Master Mix and the same primers/probe as described above under "qPCR method validation" for the Alu sequence, and a mouse β-actin (ThermoFisher, Mmn00607939_s1) Taqman primer was used as a housekeeping gene for normalizing Ct values. ΔCt was calculated by subtracting the Ct value for β-actin from the Ct value for Alu from each sample. ΔCt was plotted against the known number of cells in the 1 µL qPCR sample. Linear regression analysis was done using GraphPad Prism 5.

Mouse Injection and Tissue Harvest

C57BL/6J mice (8-12 weeks old, Jackson Laboratory) were injected with 100 µL human CDCs in IMDM ($1.5 \times 10^6$ cells/mL) in the jugular vein under anesthesia with inhaled isofluorane. This dose of CDCs utilized had been effective for Inch mice when administered by jugular vein injection. After 10 minutes (n=8) or 24 hours (n=8), mice were sacrificed by cervical dislocation. Blood was collected from the submandibular vein, followed by removal of the heart, lungs, spleen, liver, diaphragm, and soleus muscle. Tissues were also collected from two control mice that did not undergo cell injection. Tissues were washed in PBS before being frozen at −80° C. EDTA was added to blood as an anticoagulant at a final concentration of 0.05 M prior to freezing at −80° C.

Alu and β-Actin qPCR

Tissue samples were thawed, weighed, and cut into small pieces for homogenization. Average tissue weights, amounts of tissue used for homogenization, and amounts of tissue used for DNA isolation are listed in Table 1. DNA was isolated using a DNeasy Blood and Tissue Kit (Qiagen), per the instructions from the DNeasy Kit manufacturer. DNA was eluted from the DNeasy column with 100 µL elution buffer. qPCR was performed as described above for tissue spiking curves.

Data Analysis

ΔCt was calculated by subtracting the Ct value of β-actin from the Ct value of Alu for each sample. The slope and y-intercept from a standard curve were used to calculate the log of the number of cells in the qPCR sample. The number of cells per gram of tissue was calculated by multiplying the number of cells in the qPCR sample by a factor specific to the tissue, accounting for the amount of tissue used for the DNA isolation and the final volume of eluted DNA (Table 1). Triplicates were averaged and cells per gram of tissue were graphed for each organ at each time point. Significance was determined using a 1-tailed student's T-test with p≤0.05.

Referring to Table 1, the weight of each tissue was measured and the average was taken to approximate tissue weight. In most cases, the whole tissue was homogenized, except for the liver which was larger than the other tissues. From the homogenized tissue, an equivalent of 10-25 mg was taken for DNA isolation. The factor used to calculate CDCs per gram of tissue is based on 1 µL used for qPCR out of 100 µL purified DNA and the amount of tissue used for DNA isolation.

TABLE 1

Tissue weights and DNA isolation information

| Tissue | Approximate tissue weight (mg) | Amount homogenized | Amount used for DNA isolation (mg) | Factor to calculate CDCs per g tissue |
|---|---|---|---|---|
| Lung | 175 | whole tissue | 25 | 4000 |
| Liver | 1300 | 250 mg | 25 | 4000 |
| Heart | 130 | whole tissue | 25 | 4000 |
| Soleus | 10 | whole tissue | whole tissue | 10000 |
| Diaphragm | 40 | whole tissue | 25 | 4000 |
| Spleen | 80 | whole tissue | 15 | 6666 | qPCR Method Validation

Figure 55A:
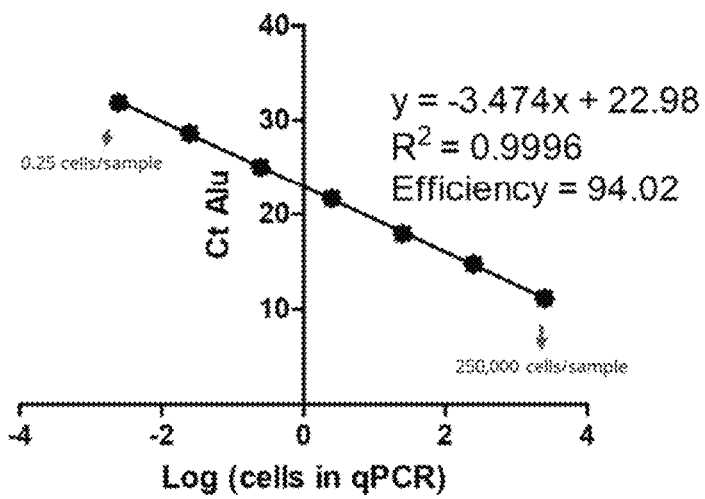
FIG. 55A graphically shows that qPCR performed on purified human CDC DNA was validated.

To validate the qPCR primers and assess the linear range of the assay, human CDC DNA was isolated from a known number of cells. Serial dilutions were prepared and qPCR was performed using the Alu primer. As shown in FIG. 55A, this assay is linear in the range of 0.0025 to 2500 cells per qPCR sample, which can encompass all study samples and can detect DNA from less than 1 cell.

Tissue Spiking Curves—Results

Figure 55B:
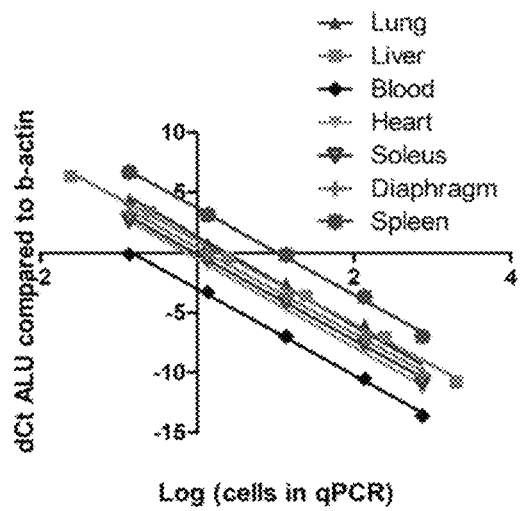
FIG. 55B graphically shows standard curves of human CDC DNA spiked into mouse tissue DNA prepared for each tissue to be tested.

Spiking studies were done in each tissue of interest to remove any tissue-specific variability due to β-actin levels in each tissue. As shown in FIG. 55B, standard curves were prepared in the lungs, liver, heart, spleen, diaphragm, blood, and soleus muscle, by spiking a known amount of CDC DNA into naïve tissue DNA, and Table 2 summarizes the slope, intercept, and $R^2$ for each line. These standard curves were used to calculate the amount of CDC DNA in the qPCR of study samples.

TABLE 2

Summary of tissue spiking curves

| Tissue | Slope | Intercept | $R^2$ |
|---|---|---|---|
| Lung | −3.72 | 1.36 | 0.9932 |
| Liver | −3.471 | 1.02 | 0.9982 |

TABLE 2-continued

Summary of tissue spiking curves

| Tissue | Slope | Intercept | $R^2$ |
|---|---|---|---|
| Blood | −3.601 | −3.011 | 0.9979 |
| Heart | −3.662 | −0.5318 | 0.997 |
| Soleus | −3.582 | −0.1151 | 0.9958 |
| Diaphragm | −3.574 | 0.4034 | 0.9977 |
| Spleen | −3.588 | 3.678 | 0.9975 |

Figure 56A:
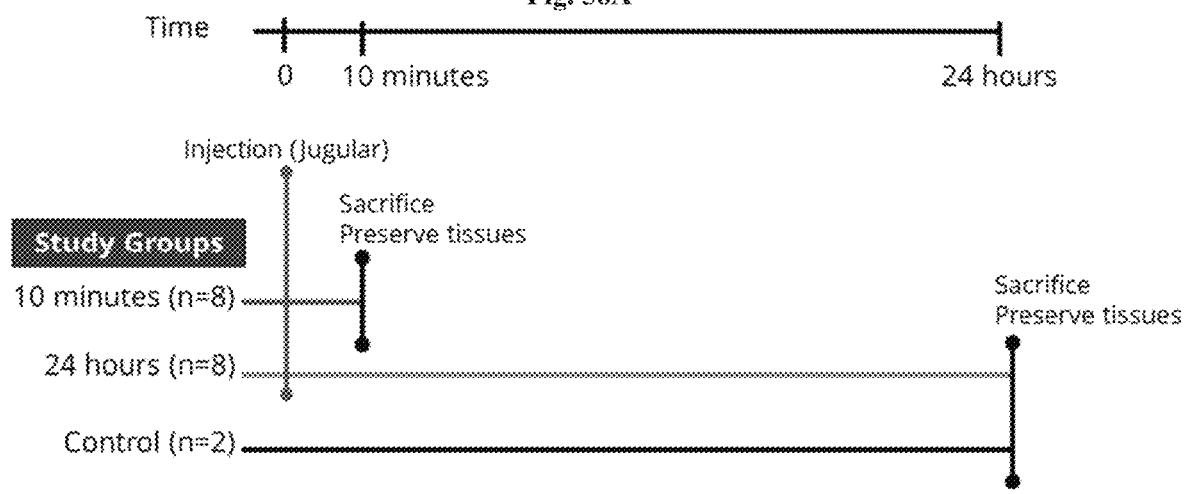
FIG. 56A depicts a schematic protocol for determining the biodistribution of human CDCs in wild type (WT) mice after jugular vein administration by a human Alu sequence qPCR method.

CDC Biodistribution in WT Mice 10 Minutes and 24 Hours After Jugular Vein Administration C57BL/6.1 mice were injected with 150,000 human CDCs by jugular vein administration. At 10 minutes (n=8) or 24 hours (n=8) after injection, each mouse was euthanized, and tissues were removed (FIG. 56A). Tissues were homogenized, DNA was isolated, and qPCR was performed using the Alu sequence and mouse β-actin primers described above.

Figure 56B:
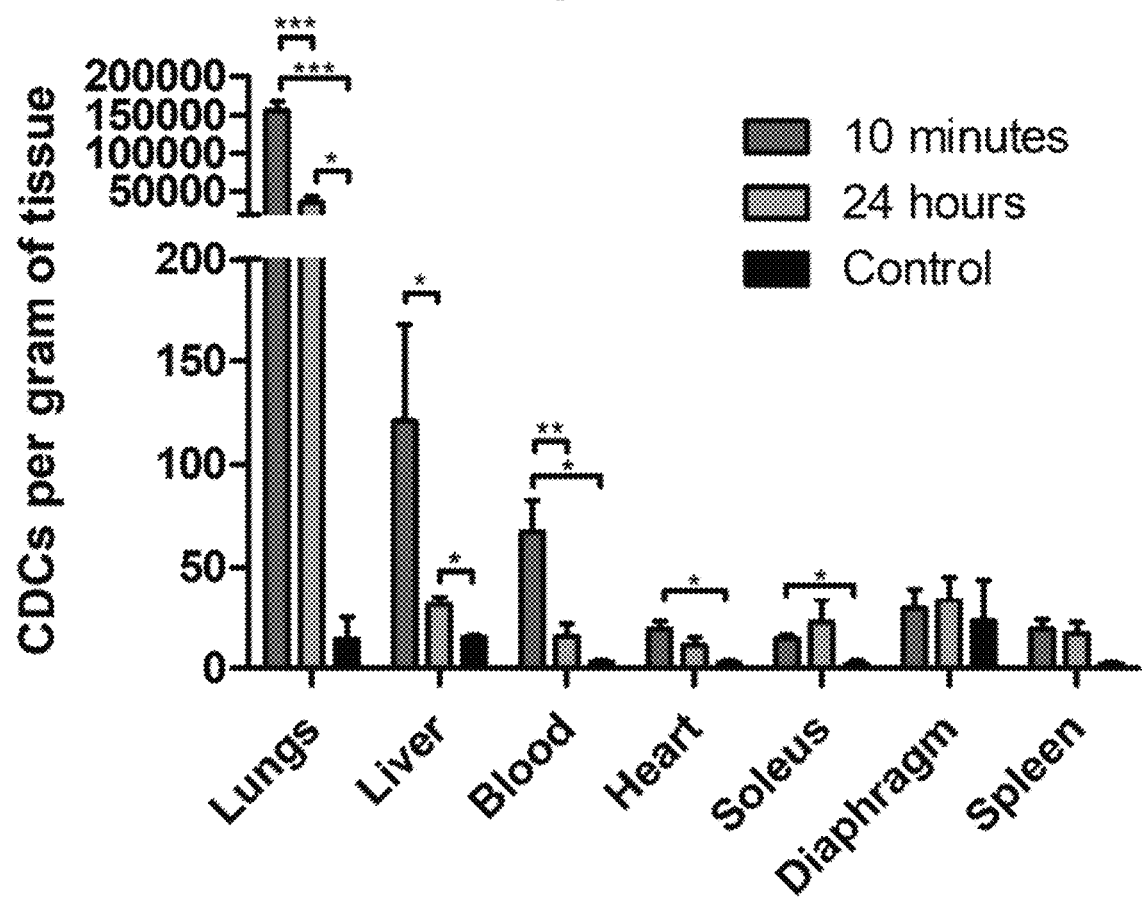
FIG. 56B graphically shows human CDC biodistribution in WT mice 10 minutes and 24 hours alter jugular vein injection, in the lung, liver, blood, heart, soleus, diaphragm, and spleen tissues.

As shown in FIG. 56B, the majority of human CDCs were found in the lungs (155,000±12,500 cells/g tissue in 10 minutes). Less than 1% of infused CDCS were found distributed among all other tissues, with 120±47 CDCs/g, tissue in the liver 10 minutes after CDC infusion. Blood, heart, and soleus muscle also contained CDCS above background levels (67±15, 19±4, 14±2 cells/g tissue, respectively), but were not as high as in the lungs. 24 hours after administration, 23% of the CDCs in the lung remained (36,000±7,900 cells/g tissue). Low levels of CDCs remained in the liver, blood, heart, spleen, and soleus (31±4, 15±6, 11±4, 17±5, and 23±11 cells/g tissue, respectively). Rapid clearance of cells may be due in part to immune system clearance by WT mice, but more studies would be needed to confirm this hypothesis.

After jugular vein administration, human CDCs were rapidly trapped in mouse lungs with less than 1% of injected cells remaining in the rest of the tested tissues. CDCs were cleared rapidly with only 22-26% of the cells in the lungs, liver or blood at 10 minutes remaining after 24 hours. A lower CDC clearance ratio was observed in the heart (58% of the cells found 10 minutes after administration remain 24 hours later) and in the soleus. In fact, more cells per gram of tissue were found in the soleus 24 hours after cell delivery than after 10 minutes. These results indicate that in some embodiments, even though systemic administration of CDCs leads to the majority of the CDCs entering the lungs, some CDCs do arrive at the heart and skeletal muscles such as the soleus and diaphragm. Therefore, in some embodiments, at least some therapeutic effects on the heart and skeletal muscle of systemic CDC administration may be due to direct effects on the heart and skeletal muscle within those tissues.

Example 39

Figure 57A:
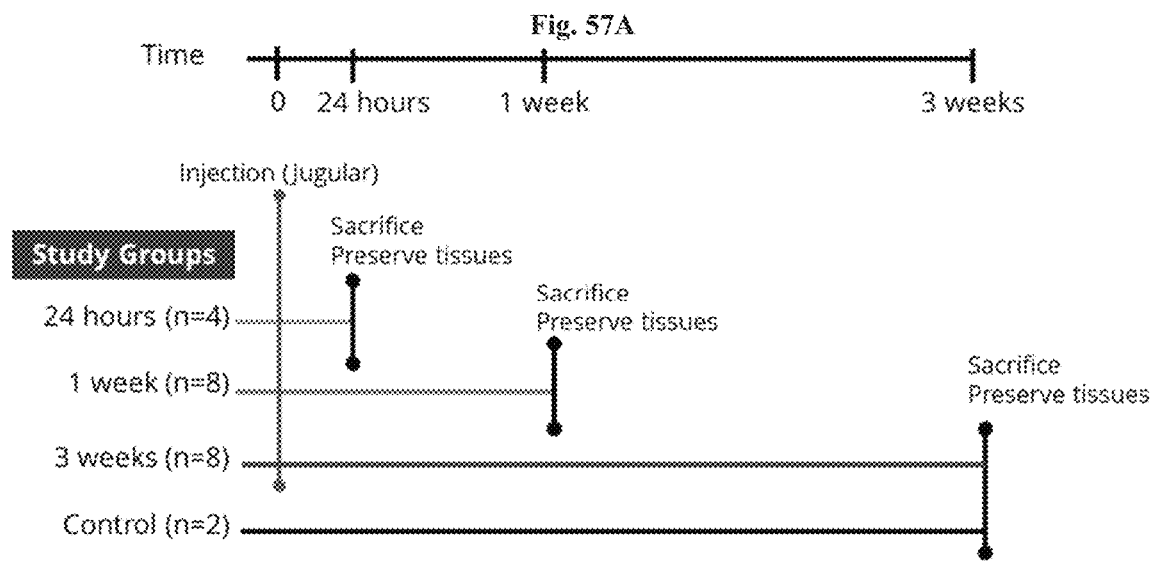
FIG. 57A depicts a schematic protocol for determining the biodistribution and clearance of human CDCs in severe combined immunodeficiency (SCID) mice after jugular vein administration by human Alu sequence qPCR method.

Biodistribution and Clearance of CDCs After Jugular Vein Administration in SCID Mice Evaluated Using Human Alu Sequence qPCR Method One purpose of the study in this example was to determine the biodistribution and clearance of CDCs in severe combined immunodeficiency (SCID) mice after systemic delivery to the jugular vein. The biodistribution of human CDCs was determined by measuring the human Alu sequence. Biodistribution and clearance of CDCs were determined using qPCR on tissues collected 24 hours, 1 week, and 3 weeks after jugular vein administration in the SCID mice (FIG. 57A). SCID mice were chosen for this study because their compromised immune system would limit immune reaction against human CDCs, so longer time points could be studied if an immune response would otherwise have cleared the CDCs from the body sooner.

The methods relating to CDC preparation, qPCR method validation, and tissue spiking curves for this study were performed in the same manner as described in Example 39.

Mouse Injection and Tissue Harvest

Male 8-12-week-old SCID mice (Jackson Laboratory) were injected with 100 CDCs in 1MDM (1.5×10⁶ cells/mL) into the jugular vein under anesthesia with inhaled isoflurane. After 24 hours (n=4), 1 week (n=8), or 3 weeks (n=8), blood was collected from the submandibular vein, followed by removal of the heart, lungs, spleen, liver, diaphragm, soleus muscle, and testes. Tissues were also collected from two control mice that did not undergo cell injection. Tissues were washed in PBS before freezing at −80° C. EDTA was added to blood as an anticoagulant to a final concentration of 0.05 M prior to freezing at −80° C.

The methods relating to Alu and β-actin qPCR and data analysis for this study were performed in the same manner as described in Example 38, FIGS. 55A-55B, and Table 2. Table 3 is the same as Table 1, except that data relating to testes is included in Table 3 but not Table 1.

TABLE 3

Tissue weights and DNA isolation information

| Tissue | Approximate tissue weight (mg) | Amount homogenized | Amount used for DNA isolation (mg) | Factor to calculate CDCs per g tissue |
|---|---|---|---|---|
| Lung | 175 | whole tissue | 25 | 4000 |
| Liver | 1300 | 250 mg | 25 | 4000 |
| Heart | 130 | whole tissue | 25 | 4000 |
| Soleus | 10 | whole tissue | whole tissue | 10000 |
| Diaphragm | 40 | whole tissue | 25 | 4000 |
| Spleen | 80 | whole tissue | 15 | 6666 |
| Testes | 190 | whole tissue | 25 | 4000 |

CDC Biodistribution in SCID Mice 24 Hours, 1 Week, and 3 Weeks After Jugular Vein Administration As described above, SCID mice were injected with 150,000 human CDCs by jugular vein administration. 24 hours (n=4), 1 week (n=8), and 3 weeks (n=8) after injection, mice were sacrificed and their tissues were removed. Tissues were homogenized, DNA was isolated, and qPCR was performed using primers for the Alu sequence and mouse β-actin described in Example 38.

Figure 57B:
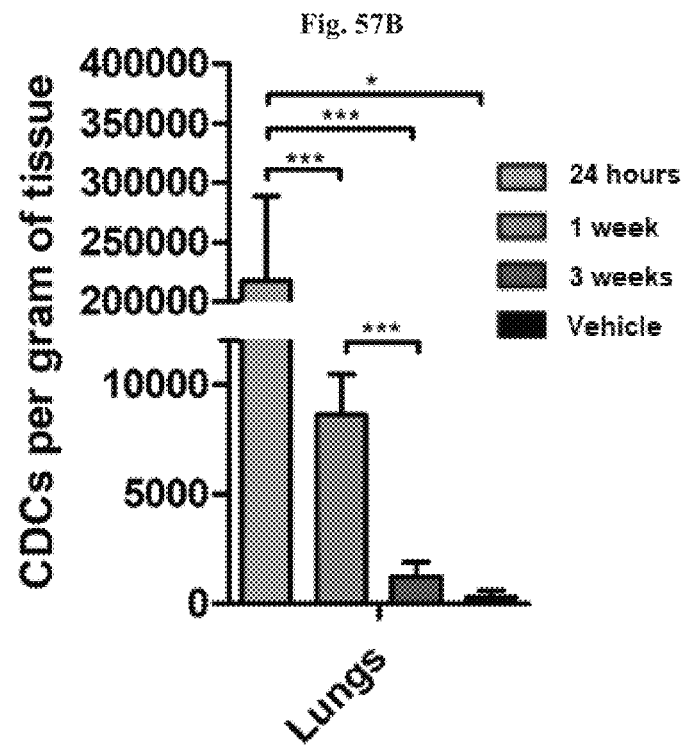
FIG. 57B graphically shows human CDC biodistribution in SCID mice 24 hours. 1 week, and 3 weeks after jugular vein injection, in the lung tissue.
Figure 57C:
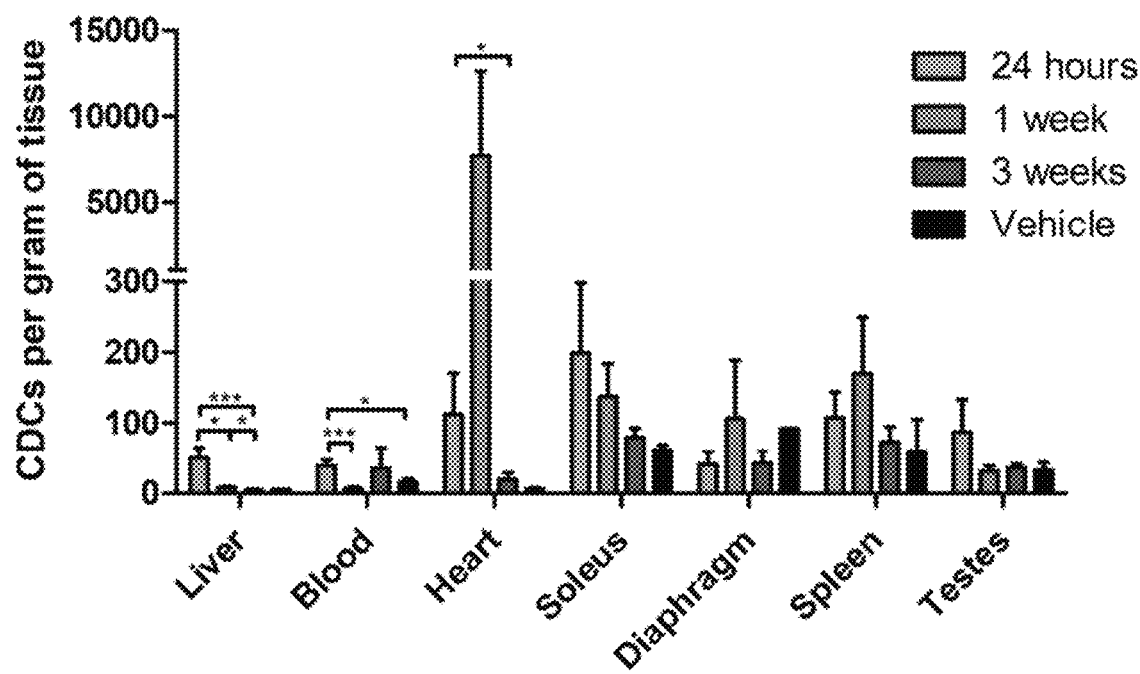
FIG. 57C graphically shows human CDC biodistribution in SCID mice 24 hours. 1 week, and 3 weeks after jugular vein injection, in the liver, blood, heart, soleus, diaphragm, spleen, and testes tissue.

As shown in FIGS. 57B and 57C, the majority of CDCs were found in the lungs (217,000±71,000 CDCs/g tissue in 24 hours). Less than 1% of infused CDCs were found distributed among all other tissues. Liver and blood contained CDCs above background (50±15, 39±8 cells/g tissue, respectively) 24 hours after CDCs administration. 4% of the CDCs found in the lungs at 24 hours remained (8,600±1900 cells/g tissue) 1 week after administration. Interestingly, more CDCs tended to be found in the heart (7,700±5,000 at 1 week vs. 110±58 at 24 hours), diaphragm (107±82 vs. 42±18), and spleen (170±80 vs. 107±37) 1 week after administration than were found in those tissues 24 hours after administration. The increase in CDCs found in those tissues 1 week after administration suggests that in some embodiments, cells are freed from the lungs to redistribute to other tissues, and become notably lodged in the heart, the first organ that would be encountered after exiting the lung via the pulmonary vein. None of the tissues tested had a statistically significant number of cells present 3 weeks after CDC administration compared to vehicle, suggesting most CDCs are cleared within 3 weeks after delivery.

This study confirms the findings of the biodistribution study performed in WT mice (see Example 38), wherein CDCs were trapped in the lungs and relatively few CDCs distributed to other tissues. Compared to 24 hours post administration in WT mice, SCID mice do not clear CDCs as rapidly (36,000±7,900 cells/g tissue in WT mice vs. 218,000±71,000 in SCID mice present at 24 hours), likely due to the immunocompromised nature of SCID mice.

This study shows that CDCs are trapped in the lungs 24 hours after cell administration by the jugular vein. A similar CDC biodistribution was observed in immunodeficient SCID mice and in WT C57BL/6 mice at 24 hours, suggesting that although the immune system could be responsible for the faster clearance observed in immune-competent mice, it does not have a significant impact on cell distribution.

Around 4% of the CDCs found in the lungs 24 hours after jugular vein administration, remained 1 week later. This study shows a possible redistribution within 1 week after cell delivery with more cells found in the heart, spleen, and diaphragm at 1 week versus 24 hours. Thus, the results indicate that in some embodiments, even though systemic administration of CDCs leads to a portion of the CDCs entering the lungs, according to several embodiments, some CDCs arrive at the heart and skeletal muscles (by way of non-limiting example, the soleus and diaphragm). Therefore, in some embodiments, at least some therapeutic effects on the heart and skeletal muscle of systemic CDC administration may be due to effects on the heart and skeletal muscle due to CDCs that are localized within those tissues.

Example 40

Dose-Dependent Safety and Efficacy of CDCs in an Acute Myocardial Infarction (AMI) Porcine Model Using Intravenous Administration The purpose of this study was to investigate a maximum tolerable dose (MTD) for CDCs and a dose efficacy response of CDCs. In this non-limiting example, intravenous administration was used in an AMI pig model, which is a widely used model for AMI.

CDC Preparation

Sinclair mini pig CDCs (pCDCs) were produced and formulated in a manner similar to mouse CDCs and human CDCs (hCDCs) as described hereinabove. Pig hearts were harvested and dissected. Pieces of both the atria and the septum were isolated and minced into explant pieces. These explants were plated on cell hind 1-stacks with 20% growth media. After 3-4 days, explant-derived cells (EDCs) began to grow around each explant. EDCs were harvested and frozen in CS10 in 2 mL cryovials until ready to be used. The EDCs were thawed at 37° C. until only a small amount of ice remained in the vial. The cell solution was added dropwise to a small volume of 20% media (~10 mLs). The cells were centrifuged at ~280 G for 5 minutes to remove any residual CS10. The cells were resuspended, counted, and plated on fibronectin-coated Nunc triple flasks at approximately 3-6× $10^6$ cells per flask. pCDCs were grown in 20% media supplemented with hyclone serum up to P5 and P6. Cells were lifted and frozen in CryoStor CS10. Frozen cells were thawed at 37° C. until only a small amount of ice remained in the vial. The cells were resuspended in the following administration buffer:

CryoStor®CS10 (22.5 mL), heparin (2.5 mL), nitroglycerin (250 µL); and

5% human serum albumin (103 mL), HypoThermosol® (13.5 mL), CS10 (13.5 mL) (This concentration is proportional to the human equivalent dose. The volume was changed after an optimal volume of 130 mL was determined for IV infusion).

Cells were administered over 45 minutes for most doses to keep cell concentrations relatively consistent. Cells delivered in a volume of 130 mL were also delivered over 45 minutes.

Animal Model

Myocardial infarction was induced in Yucatan mini pigs by a 90 minute occlusion of the left anterior descending (LAD) artery using an angioplasty balloon, followed by 30 minutes of reperfusion as previously described (Kanazawa, Tseliou et al. 2015). Animals then underwent a baseline left ventriculogram (LV gram) to assess changes in cardiac function (as indicated by change in ejection fraction), and were then infused with vehicle (CryoStor®CS10, n=10) or allogeneic CDCs (n=18) Three CDC doses were administered sequentially: $50×10^6$ (n=8), $100×10^6$ (n=3), and $200×10^6$ (n=3). Infusions took place using a Swan-Ganz catheter (6-8 French) placed in the right ventricular outflow tract (RVOT). An additional group (n=4) animals were injected with $200×10^6$ CDCs using femoral vein infusion. Two days after infusion, animals underwent a follow-up LV gram. Troponin 1 Jill) levels were assessed by chemiluminescence with an Abbot Architect i2000SR, at baseline and 48 hours to identify any myocardial tissue damage. Briefly, the blood samples were spun down to collect plasma, and once the plasma was collected, it was analyzed with the Abbot Architect i2000SR. Animals underwent physical exams 24 and 48 hours after administration. One animal was administered $200×10^6$ CDCs via femoral vein infusion and then followed up two weeks later. This animal was intended to show the long-term effects of CDCs.

Histopathology Analysis

Figure 58:
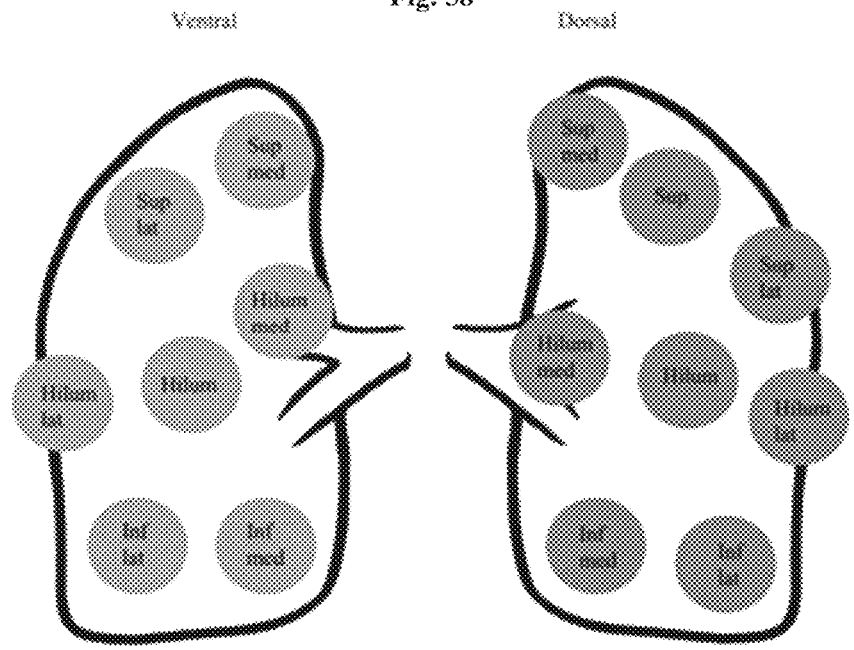
FIG. 58 schematically illustrates lung tissue sample collection for histopathological analysis to evaluate safety of high dose of CDCs in a porcine model of acute myocardial infarction.

Heart and lung tissues were subjected to histology. Gentian Violet and Thioflavin T dyes were injected into the left atrium prior to animal sacrifice to assess area at risk (AAR) and microvascular obstruction (MVO) in the heart. Excised hearts were sliced and stained with triphenyl tetrazolium chloride (TTC) to measure infarct size (IS). Lungs from two pigs RVOT injected with vehicle or 200M CDCs were collected and infused with 4% paraformaldehyde. After 48 hours in 4% PEA, tissue samples were collected from the anterior and posterior areas, as illustrated in FIG. 58).

Fifteen samples were collected from each lung, and paraffin embedded. 5 μm tissue slices on slides were stained with H&E.

Results

Figure 59:
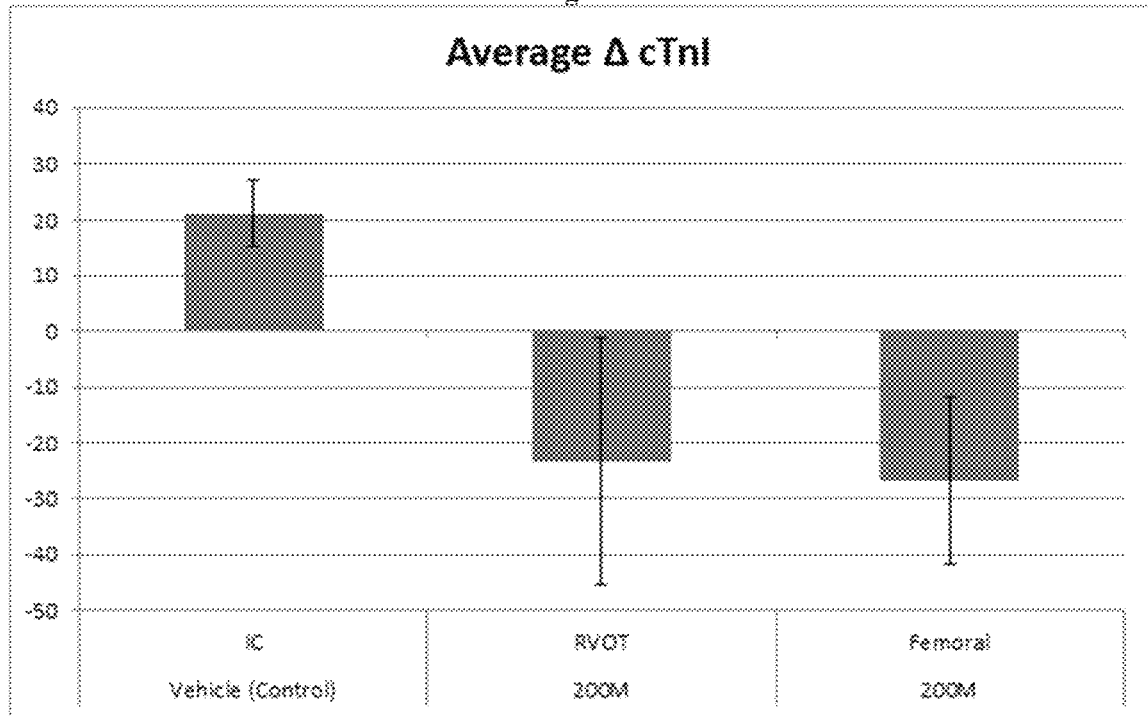
FIG. 59 graphically shows changes in serum troponin I (TnI) levels in pigs treated with 50, 100 or 200 million ("50M." "100M." or "200M." respectively) CDCs.
Figure 60:
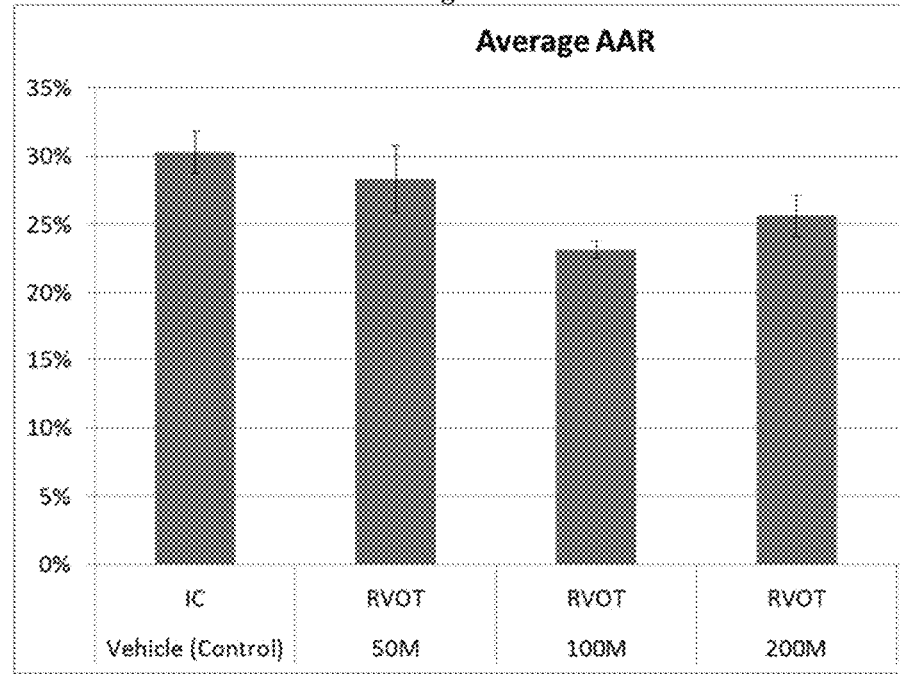
FIG. 60 graphically shows average area at risk (AAR) in pigs treated with 50, 100 or 200 million CDCs.
Figure 61:
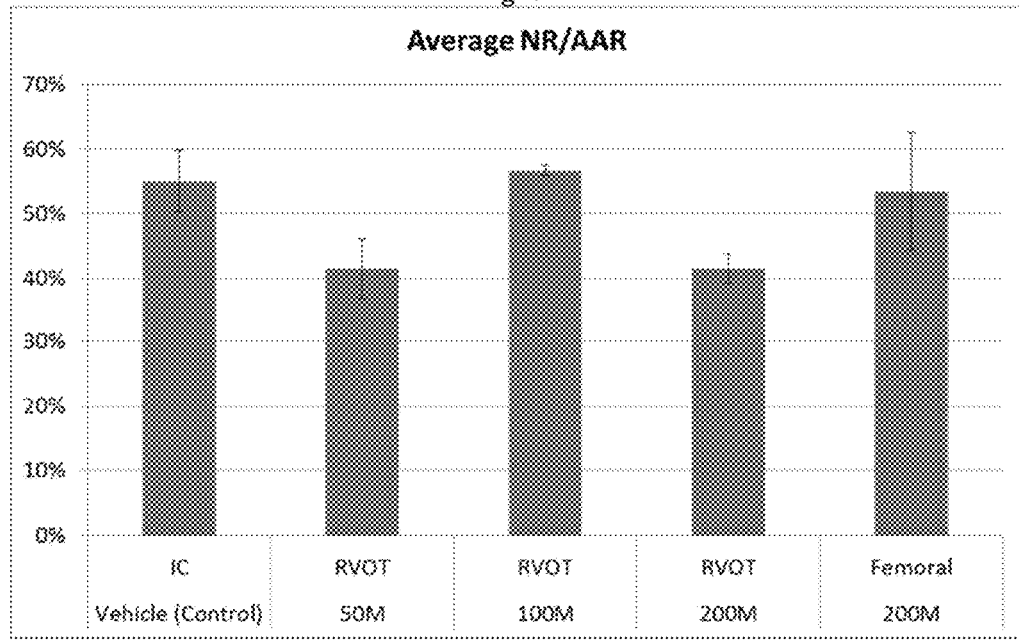
FIG. 61 graphically shows average ratio between no reflow (unstained) and area at risk, indicating myovascular obstruction (MVO) in pigs treated with 50, 100 or 200 million CDCs.
Figure 62:
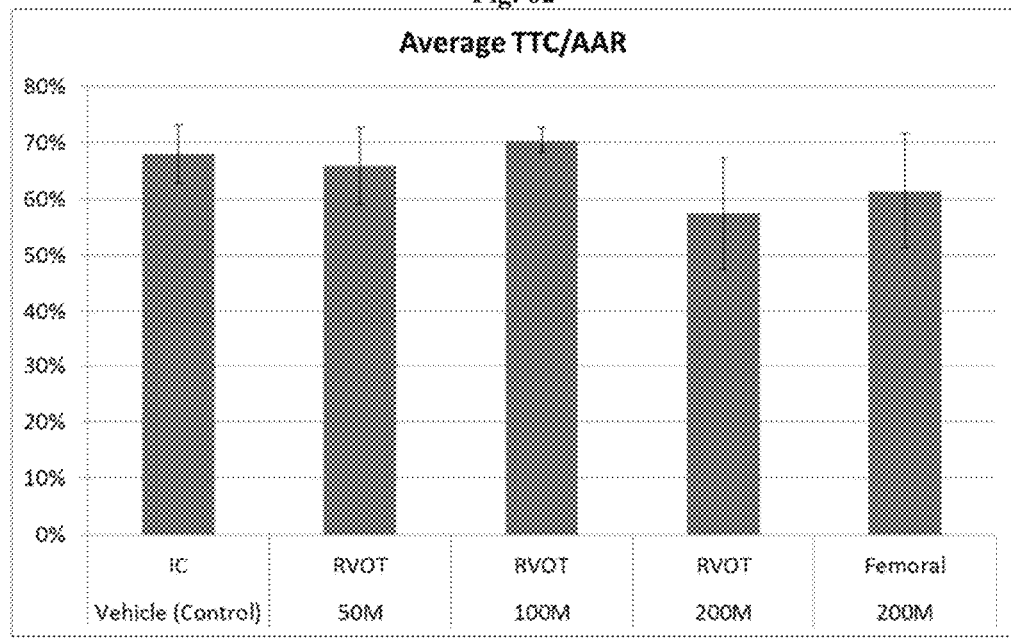
FIG. 62 graphically shows average ratio of triphenyl tetrazolium chloride (TTC) stain and area at risk, indicating scar size, in pigs treated with 50, 100 or 200 million CDCs.
Figure 63:
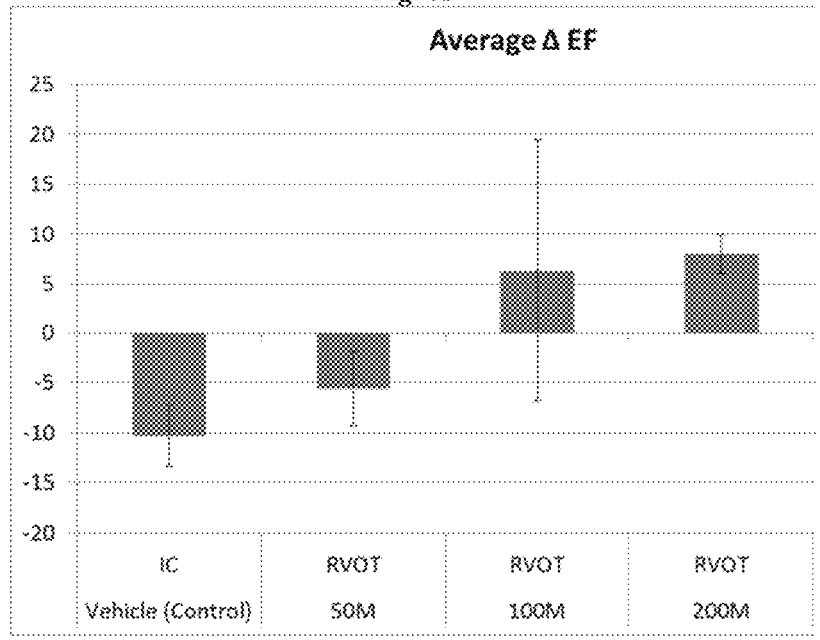
FIG. 63 graphically shows ΔEF calculated for treated and untreated animals, in pigs treated with 50, 100 or 200 million CDCs.

The first animal infused at the $50 \times 10^6$ dose was infused over the course of 15 minutes as opposed to the 45 minutes used for all subsequent animals. This pig experienced a persistent decrease in oxygen saturation during infusion ($SpO_2$ decreased from 100% to 76%). During a physical exam 24 hours post-infusion, thoracic auscultation revealed normal lung sounds. At the 48 hour endpoint, this animal continued to display a decreased $SpO_2$ from baseline (85%). As a result, the infusion time was increased to 45 minutes for all subsequent animals. One animal infused with the $100 \times 10^6$ dose displayed a transient decrease in $SpO_2$ (98% to 81%), which returned to baseline 20 minutes into the infusion. This animal was normal on a follow-up physical exam. One animal infused with the $200 \times 10^6$ dose displayed a slight transient decrease in $SpO_2$ (100% to 94%) but remained within the range of normal for $SpO_2$. Cardiac enzyme (i.e. TnI) increases were moderate and similar for vehicle and CDC treated animals. As shown in FIG. 59, TnI increases did not statistically correlate with CDC dose, Instead, there was a trend for CDC treatment to decrease TnI, indicating that in some embodiments, systemic CDC administration does not cause cardiac tissue damage, and may prevent or decrease cardiac tissue damage. As shown in FIGS. 60-62, AAR, NR/AAR, and TTC/AAR were similar among groups. This provides further evidence that the degree of myocardial damage 48 hours post-infusion was not negatively impacted by CDC treatment in this study. As shown in FIG. 63, EF trended toward improvement when CDCs were administered at the $100 \times 10^6$ and $200 \times 10^6$ doses. However, femoral vein administration of $200 \times 10^6$ cells showed a decrease in EF. Overall, these results indicate that in some embodiments, systemic administration of CDCs into, for example, the RVOT or femoral vein, does not cause cardiac tissue damage or dysfunction, and may prevent or decrease cardiac tissue damage or dysfunction.

Lungs from a pig injected with vehicle or $200 \times 10^6$ CDCs into the RVOT were collected 48 hours after the ischemia/reperfusion event and product administration, and fixed in paraformaldehyde for histological analysis. 32 samples were obtained, paraffin embedded, sliced and analyzed after H&E stain. Lung surfaces as well as section surfaces revealed lack of evident lesions. 68 slides from 2 pigs RVOT injected with vehicle or with $200 \times 10^6$ CDCs were analyzed by an independent pathologist. H&E slides analyzed from pig injected with vehicle or injected with CDCs, displayed normal lung structures without evident histological abnormalities. No CDCs were found in blood vesicles or other lung areas. Thus, in some embodiments, systemic administration of CDCs does not adversely affect lung tissue.

Of the different doses of cells administered, the minimum effective dose when CDCs were delivered through RVOT was $100 \times 10^6$, as a higher dose ($200 \times 10^6$) did not add any apparent additional benefit. Both doses showed similar effects on ejection fraction of the AMI model, Scar size was similar across all conditions. However, pigs that were injected with $200 \times 10^6$ CDCs into the femoral vein showed a limited EF improvement. This suggests that in some embodiments, administration via different routes may have different efficacies.

Histological analysis of the lung samples showed no tissue damage in pigs with $200 \times 10^6$ cells administered via RVOT or using the femoral vein route. Administration of the cells via the RVOT is a more direct path from the heart to the lungs than, for example, the femoral vein, and administration of CDCs by that route would be expected in some embodiments to show a greater effect CDC administration by the femoral vein.

Results from this study illustrate that systemic administration of CDCs is reasonably safe (i.e., not generally associated with more than a few, mild, transient adverse events during infusion) up to a human equivalent dose of at least $400 \times 10^6$ ($200 \times 10^6$ dose in pigs).

This study showed that by systemically delivering $100 \times 10^6$ cells shows an efficacious improvement in EF in an AMI porcine model. No significant differences in terms of efficacy were observed between pigs delivered with $100 \times 10^6$ or $200 \times 10^6$ cells. Accordingly, in some embodiments, a therapeutically effective dose includes $1 \times 10^5$, $1 \times 10^6$, $1 \times 10^7$, $1 \times 10^8$, $2 \times 10^8$, $5 \times 10^8$, $1 \times 10^9$, or $1 \times 10^{10}$ CDCs, and prevents or decreases cardiac dysfunction, and tissue damage in the heart and/or lungs of a subject undergoing a cardiac injury.

The evidence in the studies in this example supports the conclusion that in some embodiments, a maximum effective dose may be between $100 \times 10^6$ and $200 \times 10^6$ CDCs (human equivalent does of between $200 \times 10^6$ and $400 \times 10^6$ CDCs). Further, administering these doses did not result in any toxicological effect on the lung tissue of the subjects to whom the doses were administered.

Example 41

CDC Interaction With Human T Cells

One purpose of the study in this example was to determine the immunological activity of CDCs linked to human allogeneic T cells. The study was conducted with HLA-genotyped human peripheral blood mononuclear cells (PBMC) (n=3) and human $CD3^+$ T cells (n=2) isolated from PBMC. CDCs were prepared in a manner described above.

CDC Immune Phenotype

Figure 64:
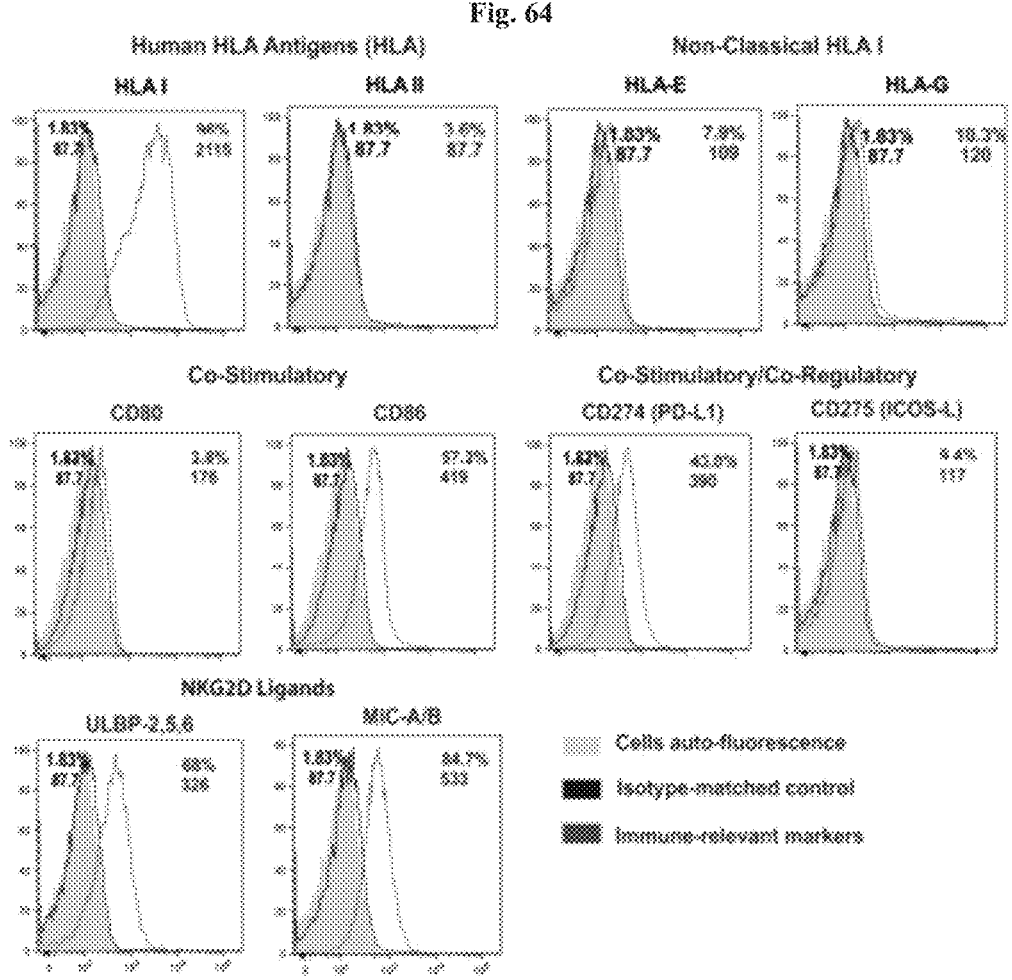
FIG. 64 graphically shows the expression of immune molecules involved in T and natural killer (NK) immune response by steady state CDCs. The percentage of positive cells and geometric mean fluorescence intensity are indicated.
Figure 65:
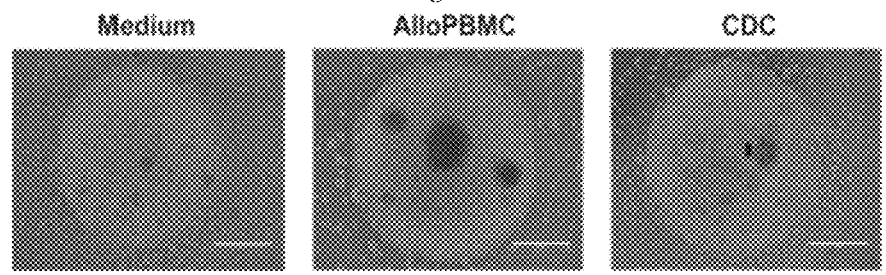
FIG. 65 shows representative images of tailored-MLR cultures.

CDCs ($10^5$ cells) at steady state were stained with antibodies specific for immune relevant molecules or their respective isotype controls. Cells were acquired on a Canto II BD FACS and analyzed by FlowJo software. All of the cells expressed significant levels of HLA class I molecules but were negative for HLA II molecules (FIG. 64).

A modest percentage of cells displayed a dim expression of non-classical HLA I molecules HLA-E and HLA-G. A good proportion of cells expressed moderate levels of co-stimulatory CD86 and co-stimulatory/regulatory CD274 (PD-L1) molecules while few cells displayed dim expression of co-stimulatory CD80 and co-stimulatory/regulatory CD275 (ICOS-L) molecules. Nearly 65% of CDCs also showed considerable expression of NK cells activating receptor NKG2D ligands (ULBP and MIC-A/B). Thus, in some embodiments, at least some immune-stimulatory or immune-modulatory markers may be present in CDCs.

The Capacity of CDCs to Stimulate T Cells in Allogeneic Setting

Tailored one-way mixed lymphocyte cultures was used to investigate the capacity of CDCs to stimulate allogeneic T cells. Briefly, human HLA-mismatched PBMC were prepared from blood samples of 3 different healthy donors by centrifugation on a Ficoll-Hypaque density gradient. Responding unfractionated PBMC ($1 \times 10^5$) labeled with carboxyfluorescein succinimidyl ester (CFSE) (2.5 μM for 10 minutes) were co-cultured in RPMI-10% FBS in U-bottom 96-wells plates with either HLA-mismatched mitomycin-C-treated stimulatory PBMC ($1 \times 10^5$) (AlloPBMC) used as positive-control or mitomycin-C-treated CDCs ($1 \times 10^4$).

Figure 66:
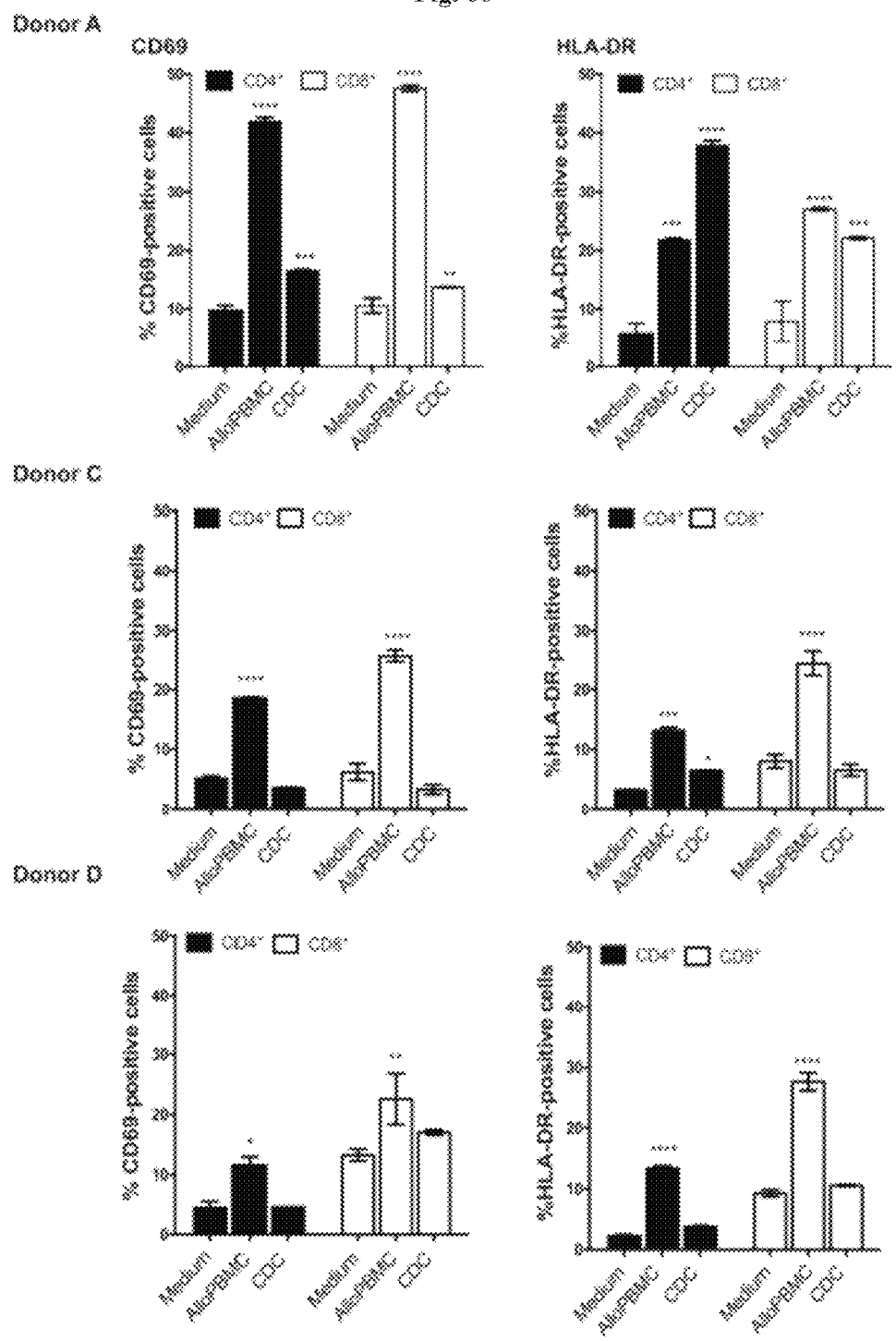
FIG. 66 graphically shows the activation of T cells by CDC. Expression of CD69 (left panel) and HLA-DR (right panel) by CD4+ (black) and CD8+ T (white) cells by three different PBMC (Donor A, C, and D). Results are mean values±SD of triplicates. *$p<0.05$; $p<0.01$; *$p<0.001$ ****$p<0.0001$.

At the end of 5-days co-cultures, the expression of two T-cell activation markers, CD69 and HLA-DR, was monitored by staining with conjugated anti-CD3, anti-CD4, anti-CD8-APC, anti-CD69, anti-HLA-DR; T-cell proliferation by loss of CFSE labeling; and cell death by 7AAD staining. The results in FIG. 66 show slight staining in CDCs, but not as pronounced as for the AlloPBMC positive control. Accordingly, in some embodiments, CDCs may have a slight capacity to stimulate allogeneic T cells.

As seen in FIG. 66, both $CD4^+$ and $CD8^+$ T cells up-regulated, more or less, at least one of the two activation markers in response to allogeneic CDCs. The up-regulation of HLA-DR was more pronounced than CD69. Thus, in some embodiments, CDCs can activate T cells in unfractionated PBMC, However, compared to allogeneic PBMC-induced activation (positive control), the observed up-regulation of these markers is in general very weak albeit for expression of HLA-DR by Donor A.

Figure 67A:
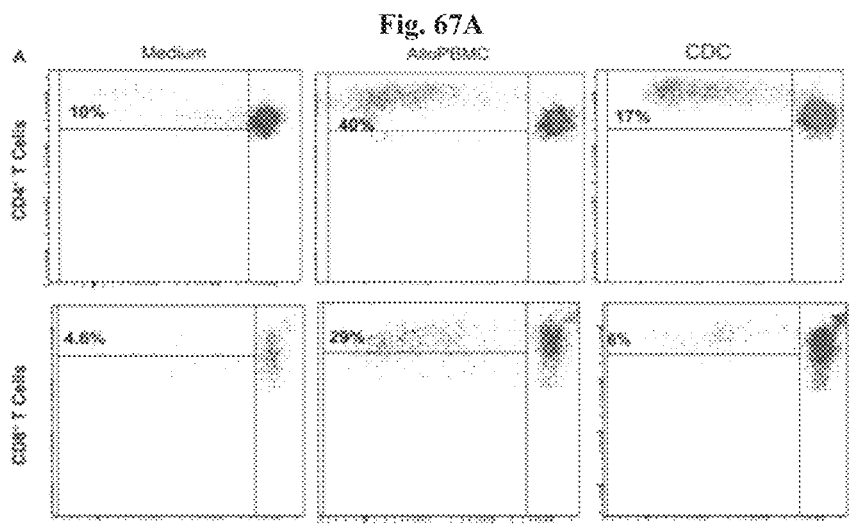
FIGS. 67A-67C graphically show the proliferation of T cells from unfractionated PBMC in response to CDCs.
Figure 67B:
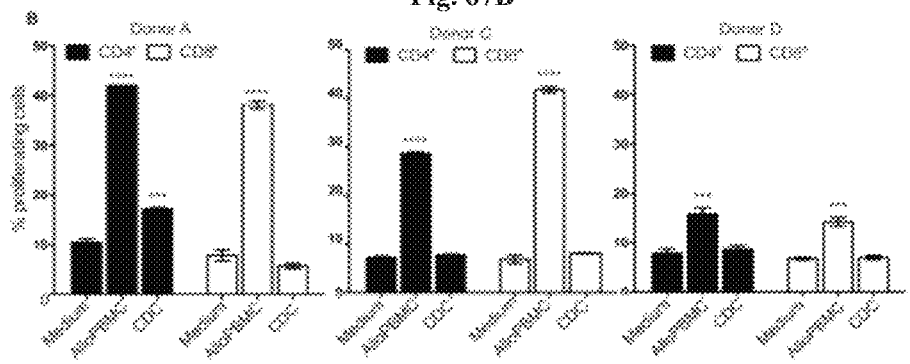
Figure 67C:
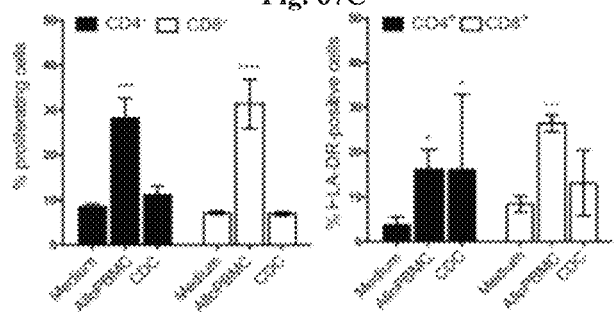

It was then determined whether this activation would be able to result T cell proliferation. By monitoring CFSE, it was observed that CDCs might be able to elicit a weak $CD4^+$ T cells proliferation, however in a donor dependent manner. The observed proliferation seems to be in line with expression of activation markers as shown in FIG. 66. For FIG. 67B, only T cells from unfractionated PBMC Donor A demonstrated significant expression of both CD69 and HLA-DR and were able to proliferate in response to CDC. T cells from unfractionated PBMC Donor C only showed significant expression of HLA-DR, whereas Donor D expressed neither CD69 nor HLA-DR, and both did not demonstrate any significant proliferation in response to CDCs. In contrast, CDCs did not elicit any substantial response in $CD8^+$ T cells, as shown in FIGS. 67A-67B, Taken together, in Wine embodiments, CDCs seem to induce a weak response, much weaker than that observed with an allogeneic PMBC control, in $CD4^+$ T cells. While the response can vary to some degree among donors, as shown in FIG. 67C, according to some embodiments, systemic administration of a therapeutically effective amount of CDCs does not activate $CD4^+$ or $CD8^+$ T cells, or any significant immune response.

The CDC-induced activation and proliferation of purified $CD3^+$ T cells (Donor C and A) were evaluated using the same experimental settings described above. Briefly, responding allogeneic T ($1 \times 10^5$) labeled with CFSE (2.5 µM for 10 minutes) were co-cultured in RPN 10% FBS in U-bottom 96-wells plates with either HLA-mismatched mitomycin-C-treated stimulatory PBMC ($1 \times 10^5$) (AlloPBMC) or CDC ($1 \times 10^4$) and five days later, their activation (expression of CD69 and HLA-DR) and proliferation (CFSE loss) were monitored. $CD4^+$ and $CD8^+$ T cells from both donors up-regulated, more or less, the expression of FILA-DR activation marker rather than CD69, However, this activation did not result in any significant proliferation of either CD4 or CD8 T cells, as shown in FIG. 68. Thus, in some embodiments, the administration of CDCs results in a surprisingly weak or absent immune response, or does not activate an immune response, despite being re-exposed to allogeneic CDCs.

Immune-Modulation by CDCs

Figure 69:
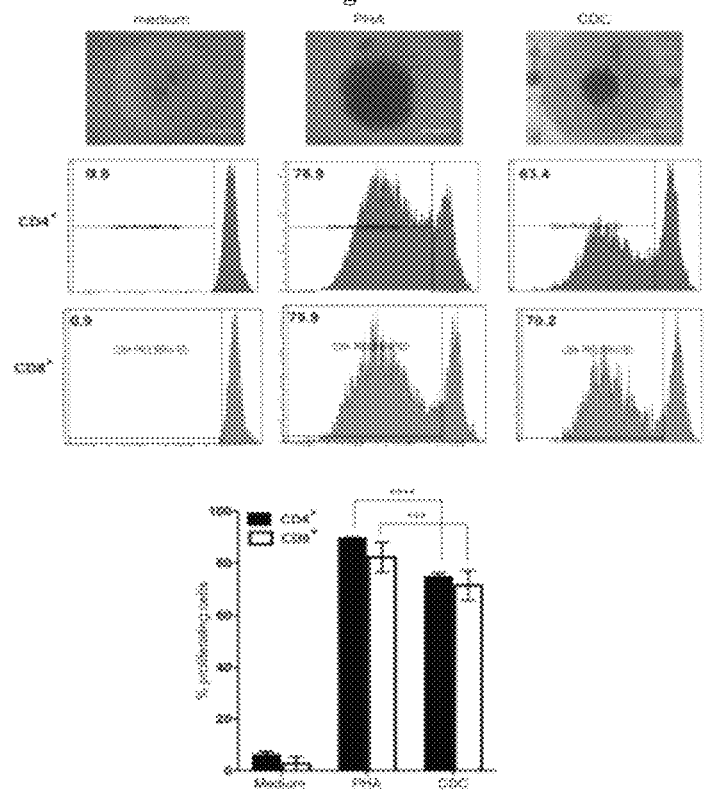
FIG. 69 graphically shows the immune modulation of phytohemagglutinin (PHA)-induced T cells proliferation by CDCs. Representative cultures and histograms (upper panel) and results presented as mean percentage values±SD from 3 different donors each done in triplicates.

The capacity of CDCs to modulate an ongoing immune response in an allogeneic setting was then investigated because a lack of activation of an immune response may indicate an improved safety profile with decreased side effects in response to CDC treatment. To this end, HLA-mismatched unfractionated CFSE-labeled PBMC ($1 \times 10^5$) were stimulated with PHA (1 µg/ml) in the absence or presence of CDCs ($1 \times 10^4$) to see whether the CDCs would enhance the PHA stimulation, in U-bottom 96 well plates and allogeneic T cell proliferation was evaluated by monitoring CFSE. CDC considerably down regulated PHA-induced proliferation of both $CD4^+$ and $CD8^+$ T cells, as shown in FIG. 69. These results indicate that in some embodiments, CDCs surprisingly decrease immune stimulation, and do not enhance it.

Therefore, similar experiments were conducted using purified $CD3^+$ T cells from two donors (Donor C and A). The modulation of PHA-induced CD69 and HLA-DR expression on these HLA-mismatched T cells, as well as the modulation of their PT-TA-induced proliferation, were evaluated.

Figure 70:
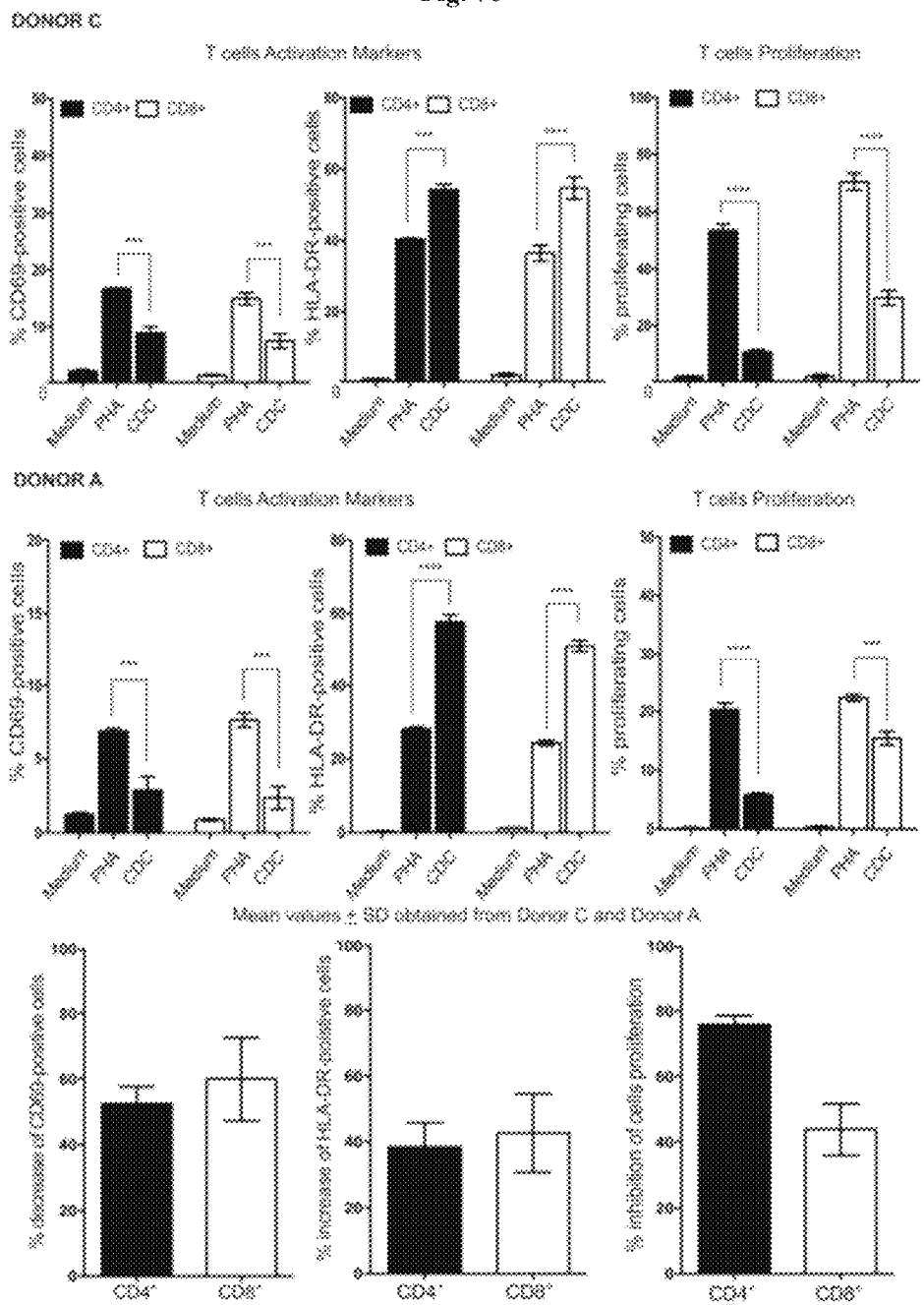
FIG. 70 graphically shows the modulation of PHA-induced CD69 and HLA-DR expression and PHA-induced T cells proliferation by CDCs. Results for each donor are presented as mean values±SD obtained from triplicates. Lower panel presents mean values±SD of the percentages of decrease (CD69) or increase (HLA-DR) in expression of activation markers (left and middle panels) and percentage of proliferation inhibition obtained from both donors each done in triplicates.

While significantly down-regulating the PHA-induced CD69, CDCs significantly increased the expression of HLA-DR on both $CD4^+$ and $CD8^+$ T cells. This modulation of activation markers resulted in strong inhibition of both $CD4^+$ and $CD8^+$ T cell proliferation. The inhibition of T cell proliferation was more pronounced than that observed with $CD8^+$ T cells. Thus, despite the inter-donor variability and within the limit of results obtained Leith two donors only, CDCs appear to be potent immunomodulators. HLA-DR is a marker of effector regulatory T cells (Treg). Therefore the observed increase in FILA-DR expression might suggest an eventual expansion of regulatory T cells induced by the presence of CDC, which might explain the strong inhibition of observed on-going T cells proliferation. These results are in line with the above data analyzing the induction of allogeneic T cells activation and proliferation by CDC, as shown in FIG. 70. Overall, these results indicate that in some embodiments, a therapeutically effective dose of allogeneic CDCs can surprisingly downregulate an immune response.

Example 42

CDC-Derived Extracellular Vesicles (CDC-EVs) Interaction With T Cells

One purpose of the study in this example was to determine the immunological activity of CDC-EVs linked to T cells activation and regulation.

Characterization of CDC-EVs & Immune Phenotype

Figure 71:
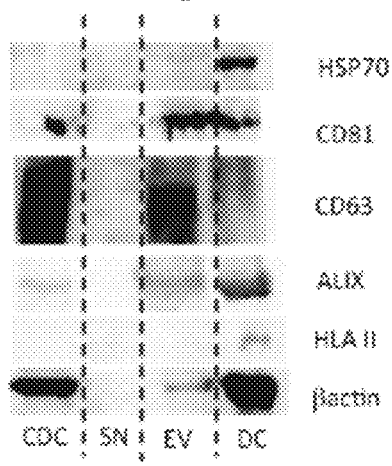
FIG. 71 is a western blot showing CDC-EVs' contents of recognized exosomes markers.

The expression of exosome informative markers was analyzed in CDC-EVs using western blotting. CDC-EVs (20 µl=10 µg) were lysed using RIPA buffer and loaded in 10% SUS-Page gels, then transferred to nitrocellulose membrane. Membranes were blocked with 5% BSA, then hybridized with specific antibodies against HSP70, CD81, CD63, ALIX, HLA II and β-actin. CDCs and dendritic cells (DC) lysates as well as exosome-free supernatant (SN) were used as controls. CDC-EVs expressed expected exosome markers CD81, CD63 and ALIX, while SN was completely negative (FIG. 71).

CDC-EVs were next analyzed for the surface expression of immune relevant markers. CDC-EVs (30 µl=15 µg) were coupled to 5 µl Latex beads (4 µm). CDC-EVs/beads were treated successively with 100 glycine and 2% BSA buffers in order to block any eventual non-specific binding of these EVs/beads with antibodies or with beads. After washing, EVs/heads were stained with specific antibodies against relevant immune molecules acquired on Canto II BD Facs and analyzed by FlowJo software. Beads incubated with the same amount of respective antibodies were used as a control.

Figure 72:
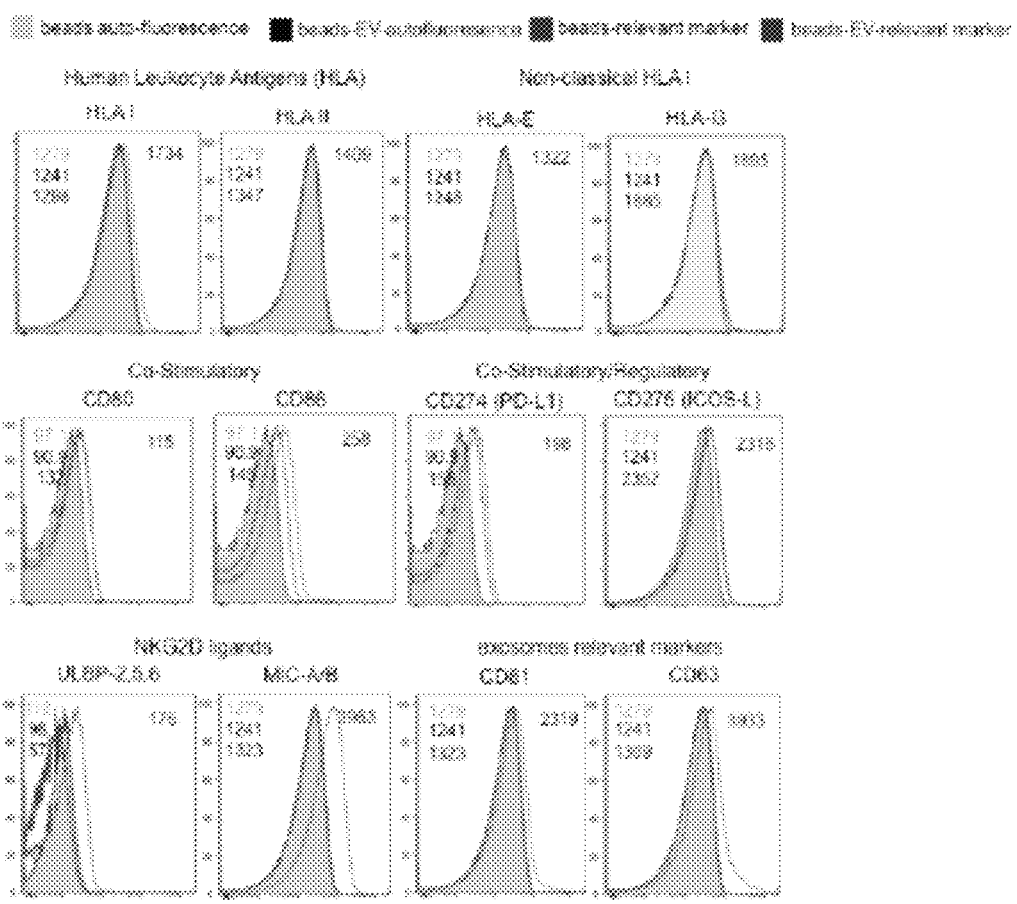
FIG. 72 graphically shows the expression of immune molecules involved in T and natural killer (NK) immune response on CDC-EVs.

Compared to a bead-antibody control, CDC-EVs expressed HLA class I molecules and CD86, but were negative for HLA II and CD80 molecules (FIG. 72). CDC-ECs seem to express the co-stimulatory PD-L1 molecule but not the ICOS-L. NK activating receptor ligands were remarkably expressed on the CDC-EVs. Significant expression of both EV markers CD81 and CD63 was detected. Thus, in some embodiments, at least some immune-stimulatory or immune-modulatory markers may be present in CDC-EVs.

The Capacity of CDCs and CDC-EVs to Activate T Cells in Allogeneic Setting

Figure 73A:
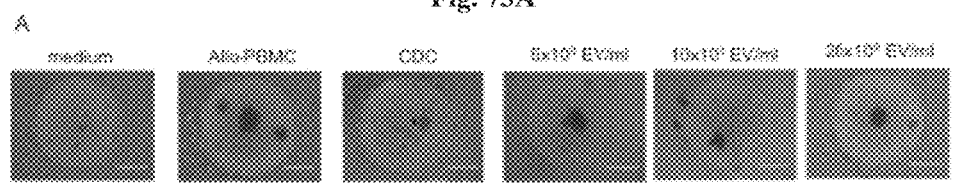
FIGS. 73A-73B show the activation of T cells by CDCs and CDC-EVs.
Figure 73B:
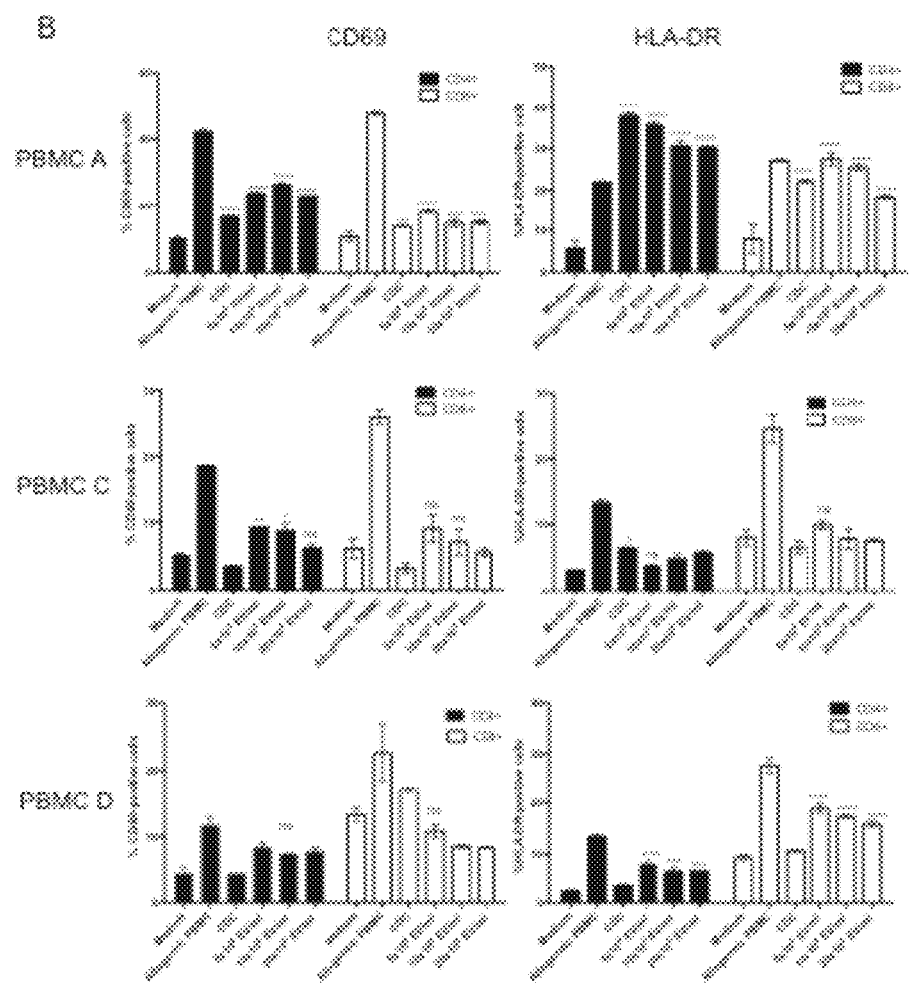

PBMC were prepared from blood samples of 3 different healthy donors by centrifugation on a Ficoll-Hypaque density gradient and cryopreserved for use in different experiments. T cell activation and proliferation in response to CDC and CDC-EVs were investigated by monitoring the expression of two T cells activation markers, CD69 and HLA-DR, and the level of CFSE by flow cytometry, respectively. Briefly, responding PBMC ($1\times10^5$) labeled with CFSE (2.5 µM for 10 minutes) were co-cultured in RPMI-10% FBS in U-bottom 96-wells plates with either HLA-mismatched mitomycin-C-treated stimulatory PBMC ($1\times10^3$) or HLA-mismatched CDC ($1\times10^4$) or with CDC-EVs at different doses as indicated, as shown in FIG. 73A. At the end of 5-days co-cultures staining with conjugated anti-CD3, anti-CD4, anti-CD8-APC, anti-CD69, anti-HLA-DR and 7AAD monitored the activation, proliferation, and cell death of T cells. The results show some staining in CDC-EVs, but not as much as for the AlloPBMC positive control. Accordingly, in some embodiments, CDC-EVs may be capable of stimulating allogeneic T cells.

Figure 74A:
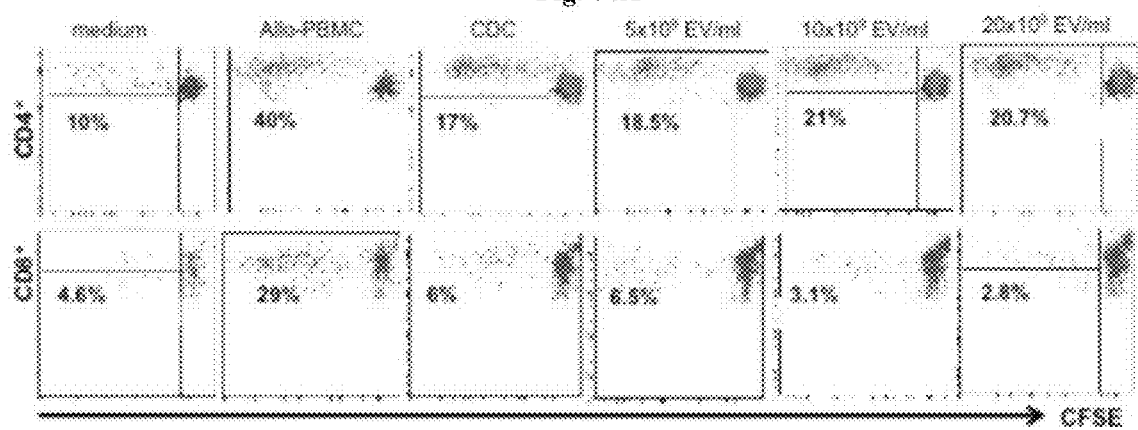
FIGS. 74A-74B graphically show T cells proliferation in response to CDC and EVs.
Figure 74B:
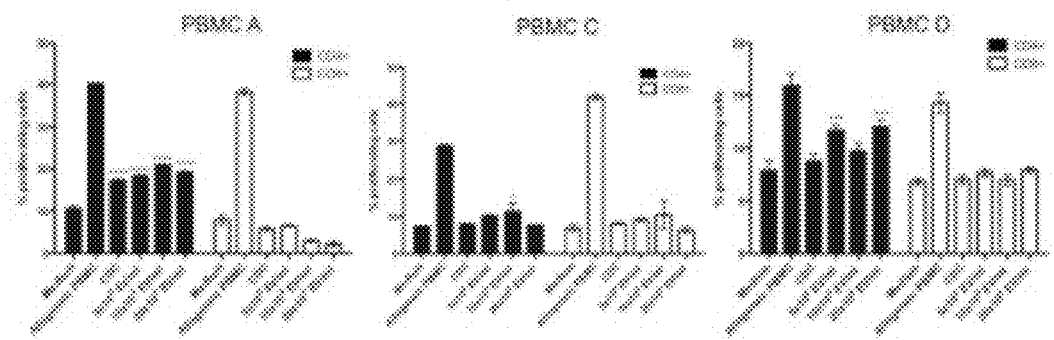

As shown in FIG. 74, compared to control, CDCs and CDC-EVs seem to be able to elicit weak $CD4^+$ T cell proliferation but did not elicit any substantial response in $CD8^+$ T cells. The observed response was much weaker than that observed with allogeneic PMBC control.

Figure 75:
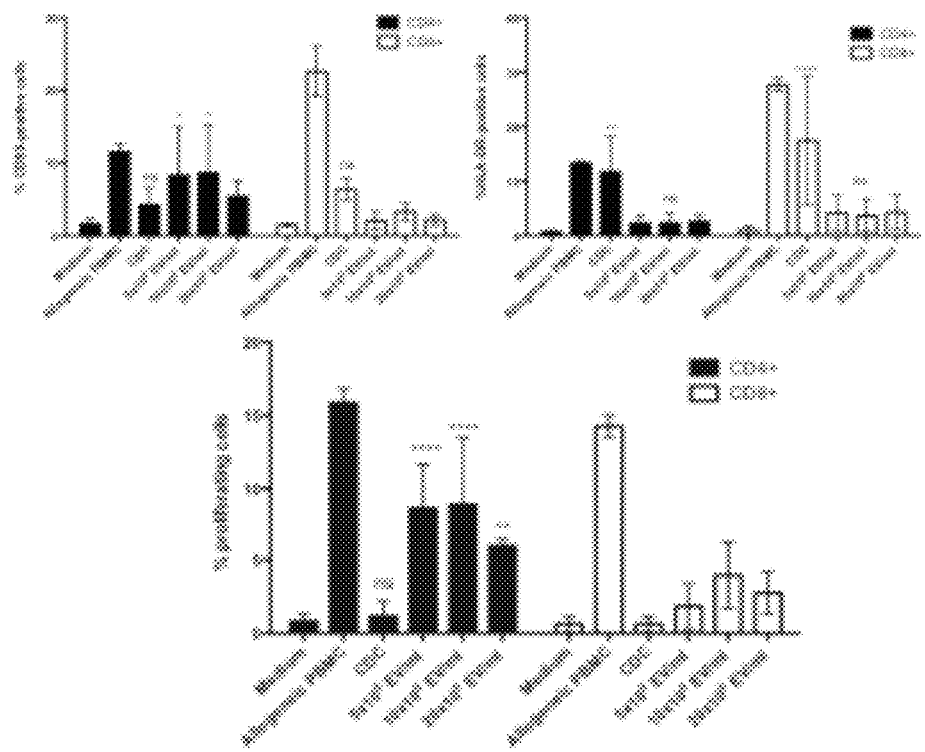
FIG. 75 graphically shows the purified T cells activation and proliferation in response to CDCs and CDC-EVs. Results are presented as mean values±SD obtained from responses (duplicates) from 2 different donors.

Accordingly, the CDC- and CDC-EV-induced activation and proliferation of purified $CD3^+$ T cells (2 different donors) were evaluated using the same experimental settings described above. Briefly, responding allogeneic T ($1\times10^5$) labeled with CFSE (2.5 µM for 10 minutes) were co-cultured in RPMI-10% FBS in 11-bottom 96-wells plates with either HLA-mismatched mitomycin-C-treated stimulatory PBMC ($1\times10^5$) or CDCs ($1\times10^4$) or with CDC-EVs at different doses as indicated. A weak activation and proliferation of $CD4^{4+}$ T cells was only observed with CDC-EVs but not with CDCs, as shown in FIG. 75. However, the magnitude of both activation and proliferation compared to that obtained when unfractionated-PBMC were used was fairly lower. Thus, in some embodiments, the administration of CDCs and/or CDC-EVs results in a surprisingly weak or absent immune response, or does not activate an immune response.

Together these results also indicate that in some embodiments, the observed CDC-EV-induced activation and proliferation of T cells occurs mainly via an indirect pathway that may involve antigen presenting cells such as monocyte/macrophages and dendritic cells (DC).

Indirect T Cells Activation and Proliferation in Response to Allogeneic EVs

Figure 76:
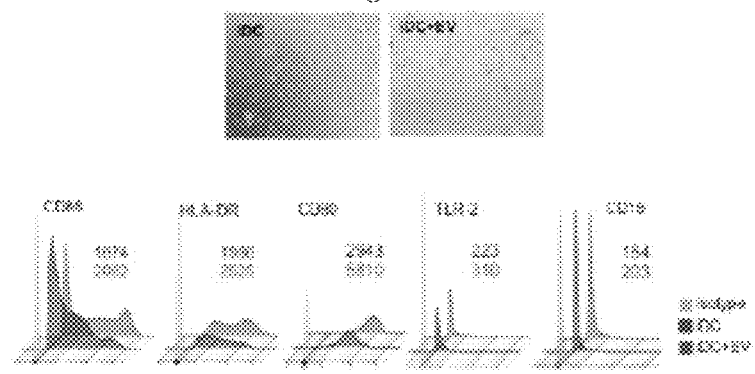
FIG. 76 shows the IDC cultures in the presence and absence of EVs (upper panel) and expression of relevant immune molecules (lower panel).
Figure 77:
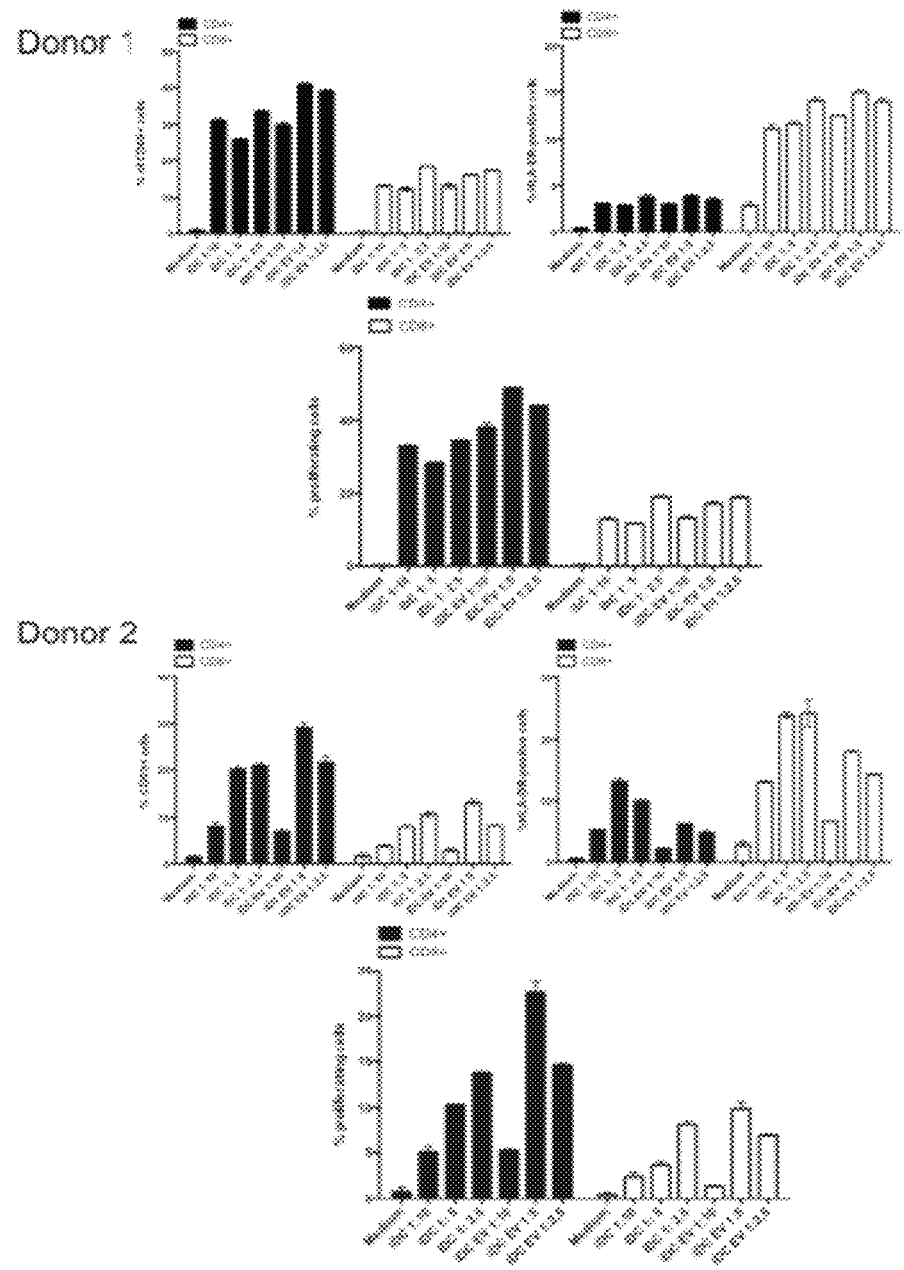
FIG. 77 graphically shows the purified T cells activation and proliferation by CDC-EVs presented by iDC. Results are presented as mean values±from triplicates.

Monocytes were isolated from blood samples obtained from two different healthy donors. Isolated-monocytes were then stimulated for 6 days with a combination of GM-CSF (2.0 ng/ml) and IL4 (20 ng/ml) to allow their differentiation to dendritic cells (DC). Differentiation of monocytes with GM-CSF+IL4 generates immature DCs (iDC) marked by moderate expression of HLA II, CD80, and CD86 molecules, absence of CD16 (marker of monocytes/macrophages), and low expression of TLR-2. These monocyte-derived iDC were then incubated overnight with HLA-mismatched CDC-EVs.

iDC cultured with EVs displayed features of mature DC (mDC); they up-regulated their HLA II, CD80 and CD86 molecules, which is recognized as mDC properties, as shown in FIG. 76. Then $1\times10^4$ of iDCs or iDCs that were in contact with EVs (iDC-EVs) were co-cultured with autologous T cells ($1\times10^5$) in U-bottom 96 wells plates for another 6 days. Autologous T cells co-cultured with iDC or iDC-EVs where analyzed for their expression of CD69 and HLA-DR, and for their proliferation. Although the response of T cells from two different donors was variable, as a whole iDC-EV were more potent in activating and inducing the proliferation of T cells than iDCs alone, as shown in FIG. 77. Compared to direct CDC-EV-induced T cell proliferation, the magnitude of indirect CDC-EV-induced T cells proliferation was fairly higher.

Figure 78:
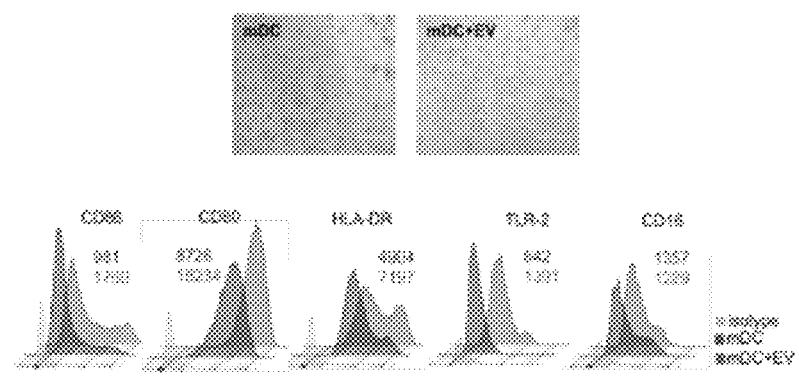
FIG. 78 shows the mDC cultures in the presence and absence of EVs (upper panel) and expression of relevant immune molecules (lower panel).
Figure 79:
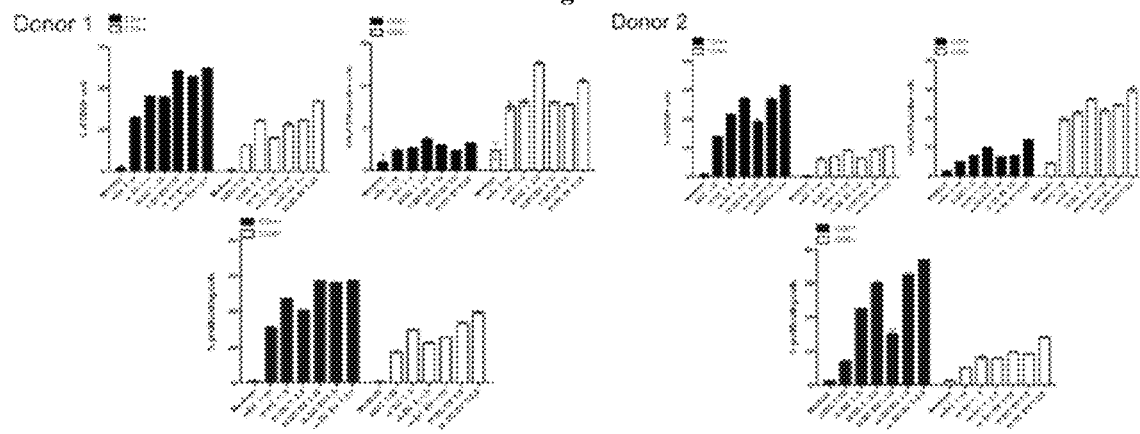
FIG. 79 graphically shows the purified T cells activation and proliferation by mDC and mDC-EVs. Results are presented as mean values±from triplicates.

The capacity of CDC-EVs to stimulate T cells when presented by mature DC (mDC) was evaluated. Given that mDC have a very low phagocytic activity and to ensure appropriate uptake of EVs and based on previous experience of phagocytizing apoptotic bodies, the maturation of DC was induced by treating iDC and iDC-EVs overnight with IFNγ (500 IU/ml), which is a recognized inducer of DC maturation. Compare to iDC, these mDC showed higher expression of HLA II, CD80 and CD86, and higher expression of TLR-2, which are features of mDC. The presence of CDC-EVs during iDC maturation to mDC further up-regulated HLA II, CD86, CD80, and TLR-2 molecules, as shown in FIG. 78, indicating that CDC-EVs may enhance DC maturation.

mDC or mDC-EVs were then co-cultured with autologous T cells ($1\times10^5$) fin U-bottom 96-wells plates or 6 days and their activation (expression of CD69 and HLA-DR), and proliferation was analyzed. Again the responses from two donors, were variable but as a whole mDC-EVs were more potent in activating and inducing the proliferation of T cells than mDCs alone. Compared to iDC-EVs-induced response, mDC-EV-induced T cell activation and proliferation for the same donor was higher.

The ensemble of these results in regards to T cells activation and proliferation suggests that CDC-EVs can activate and induce the proliferation of T cells through the indirect pathway without ruling out at least some activation of the direct pathway. Thus, in several embodiments, an indirect pathway is activated. In other embodiments, the direct pathway is partially activated. In still additional embodiments, a combination of direct and indirect pathways is activated.

Immune-Modulation by CDCs and CDC-EVs

Figure 80:
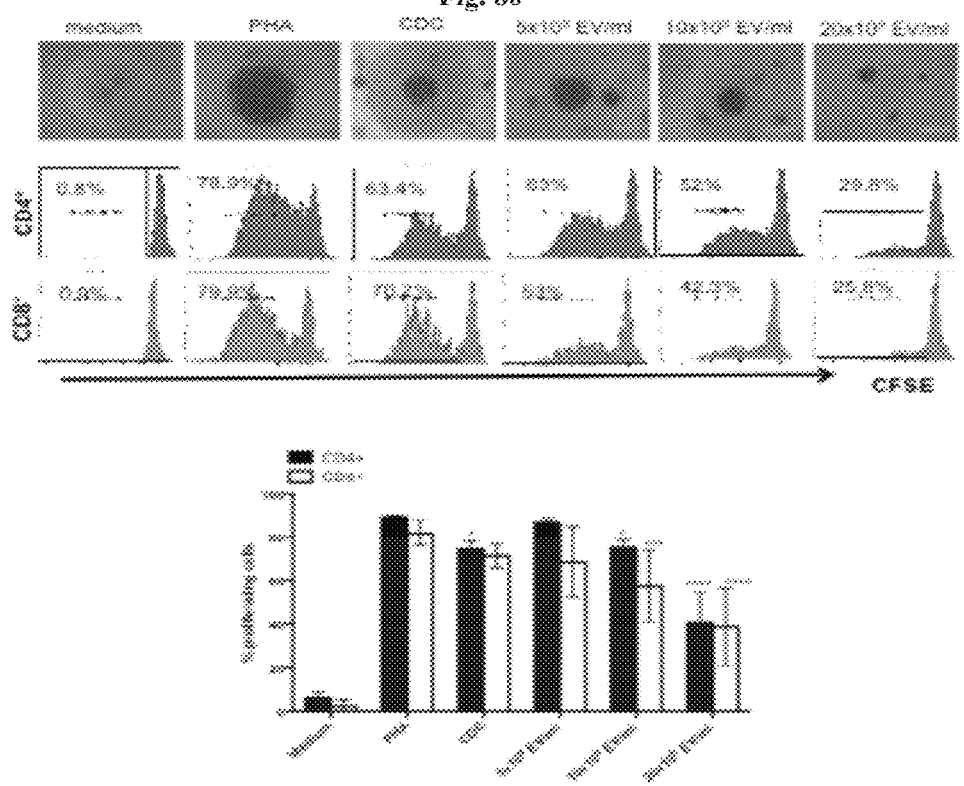
FIG. 80 shows the immune modulation of PHA-induced T cells proliferation by CDCs and CDC-EVs. Results are mean percentage values±SEM from 3 different donors each done in triplicates.

Although CDCs or CDC-EVs may enhance DC maturation, this does not mean that they would necessarily results in an adverse reaction within a subject. To evaluate this, the capacity of CDCs and CDC-EVs to modulate an ongoing immune response in an allogeneic setting was investigated. HLA-mismatched unfractionated CFSE-labeled PBMC ($1\times10^5$) were stimulated with PHA (1 µg/ml) in the absence or presence of CDCs ($1\times10^4$) or various doses of CDC-EVs as shown in the upper panel of FIG. 80. The experiment was conducted in U-bottom 96 well plates, and allogeneic T cell proliferation was evaluated by monitoring CFSE. Both CDCs and CDC-EVs were able to down regulate PHA-induced $CD4^+$ and $CD8^+$ T cell proliferation. CDC-EVs-induced down regulation of T cells proliferation was dose dependent, and at the highest used dose ($20\times10^9$ particles) CDC-EVs were more potent in down regulating ongoing response than their parental cells, as shown in FIG. 80.

Figure 81:
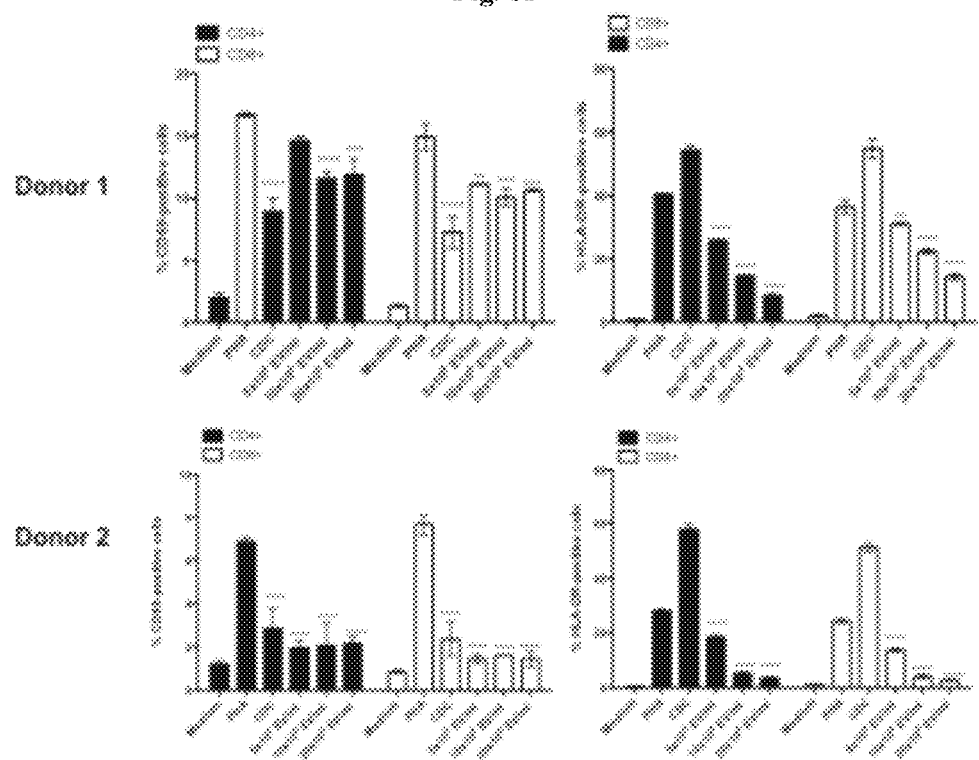
FIG. 81 graphically shows the down-regulation of PHA-induced CD69 and/or HLA-DR expression by CDCs and CDC-EVs. Results are mean percentage values±SD obtained from triplicates.

The CDC- and CDC-EV-induced immune modulation is likely through direct effects since similar results were obtained when purified CD3$^+$ T cells were used instead of PBMC within the same experimental settings. Indeed, CDCs and CDC-EVs were able to down regulate PHA-induced expression of CDC69 and/or HLA-DR on T cells obtained from 2 different donors, as shown in FIG. 81.

As shown FIG. 82, down-modulation of T cells activation markers by CDCs and CDC-EVs resulted in a pronounced down regulation of PHA-induced CD4$^+$ and CD8$^+$ proliferation. Similarly, as shown in FIG. 83, despite inter-donor variability and within the limit of results obtained with two donors only, both CDCs and CDC-EVs are potent immune modulators.

These studies of capacity of CDC-EVs to induce immune-modulation demonstrated that they are potent immune-modulators. Accordingly, in some embodiments, the administration of CDCs and/or CDC-EVs surprisingly suppresses an immune response, overall.

Example 43

Additional Improvement With Multiple Administrations of Allogeneic CDCs Compared With Single Administration In some cases, because CDCs and CDC-EVs may suppress an immune response, they may be administered repeatedly to a subject without an immune response severely dampening their therapeutic effects or resulting in an inflammatory response. One purpose of the study in this example was to evaluate whether multiple systemic administrations of allogeneic CDCs could result in an additive or enhanced effect compared to a single dose. For example, multiple administrations may promote an additional improvement in muscle activity and exercise capabilities in subjects with muscular dystrophy, as is modeled in Inch mice. Thus, a goal was to analyze immune responses after multiple administrations of allogeneic CDCs.

Cells derived from heart explants were cultured in ultra-low adherent plates to obtain cardiospheres, and then seeded in fibronectin coated plates to produce CDCs. Aged mdx mice (8-10 months of age) were IV treated with three doses of CDCs, six weeks apart (systemic administrations via the jugular vein at weeks 0, 6 and 12), and their exercise capacity was analyzed weekly for 14 weeks. The dose used in this experiment was 150,000 syngeneic CDCs (n=8), 150,000 allogeneic CDCs (n=6), or PBS as a control (n=6). The presence or absence of alto-antibodies was also analyzed to determine the extent of immune activation that the CDCs may have caused.

Figure 84A:
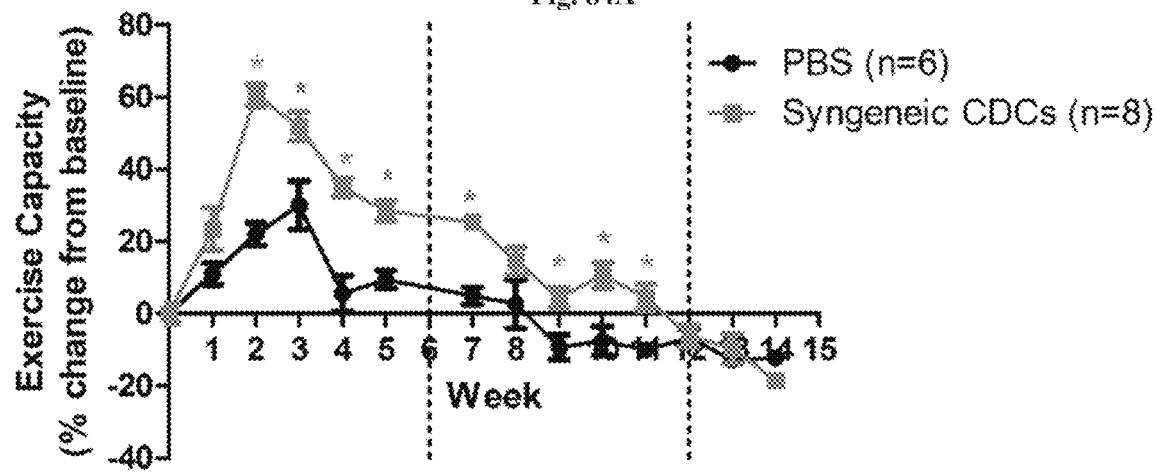
FIG. 84A is a graphical depiction of changes from baseline in exercise capacity with multiple administrations of syngeneic CDCs (from C57BL/10 mice) or a PBS control.
Figure 84B:
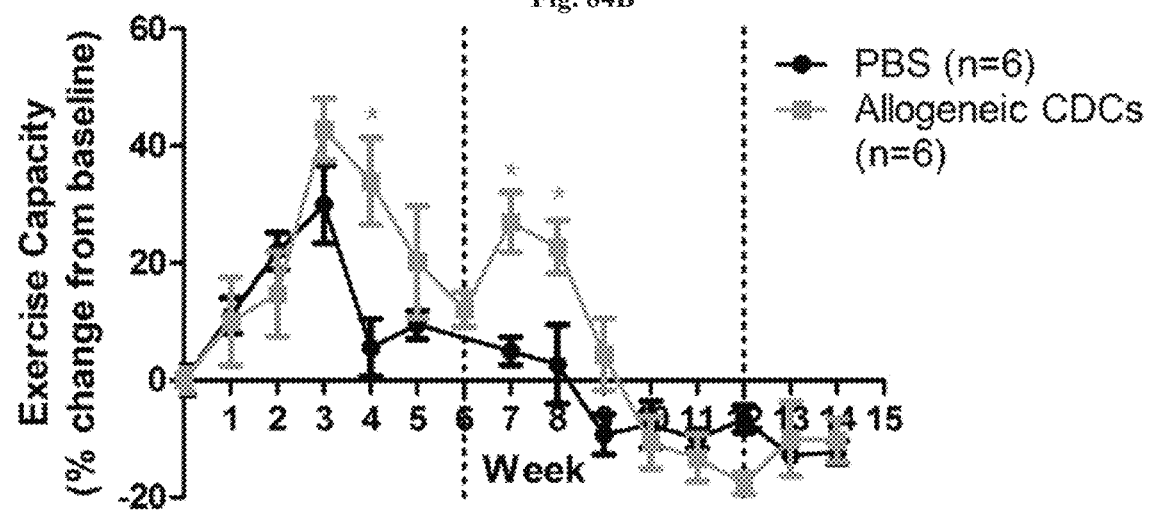
FIG. 84B is a graphical depiction of changes from baseline in exercise capacity after multiple administrations of allogeneic CDCs (from C3H mice) or a PBS control.
Figure 84C:
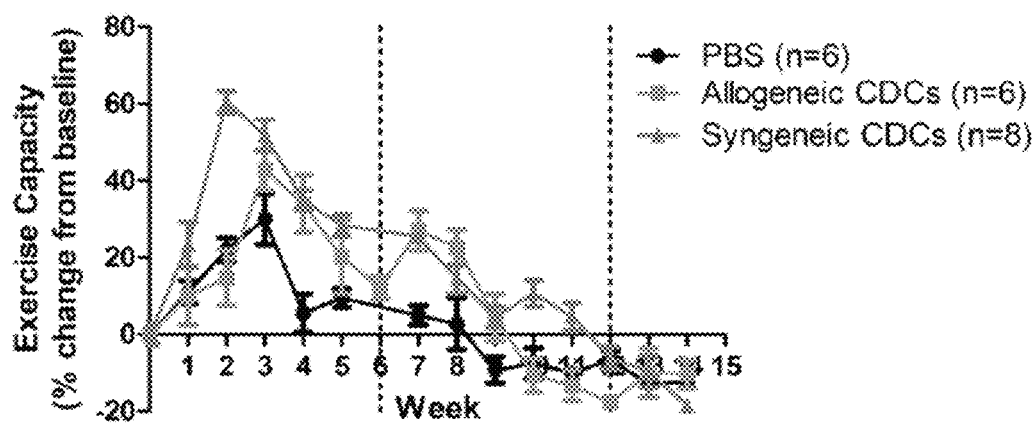
FIG. 84C is a combination of FIG. 84A and FIG. 84B into a single graph.

The repeated systemic dosing of syngeneic or allogeneic. CDCs resulted in an increase in exercise capability after each administration in mdx mice, as shown in FIGS. 84A-84C. These results indicate that in some embodiments, a therapeutically effective dose delivered in multiple systemic administrations enhances the therapeutic benefit when compared to a single administration. Surprisingly, CDC administration resulted in a low immunogenic profile with weak production of allo-antibodies, indicating that in some embodiments, multiple administrations of syngeneic and/or allogeneic CDCs does not result in an immune response. In smile embodiments, the enhanced benefit of multiple administrations compared to a single administration results from the low immunogenic profile and/or weak production of allo-antibodies because the low immunogenic profile and weak production of allo-antibodies allows more CDCs to remain in the body, and/or allows the CDCs to remain in the body longer so the greater number or duration of CDCs can exert their beneficial effects to a greater extent. For example, a strong immune response might have otherwise prevented the second dose from enhancing the therapeutic effect because the immune response might have destroyed the CDCs in the second administration before they could exert their beneficial effects. In some embodiments, several systemic administrations of CDCs are given, where at least one of the additional administrations enhances the benefit of the first administration of CDCs.

In another example, multiple administrations of syngeneic and/or allogeneic CDCs exert a greater beneficial effect on the heart, such as reducing cardiac fibrosis, cardiac tissue damage and cardiac remodeling, and improving cardiac or ventricular function, compared to a single CDC administration, at least partially as a result of lack of or relatively weak immune response to the CDCs.

Figure 85C:
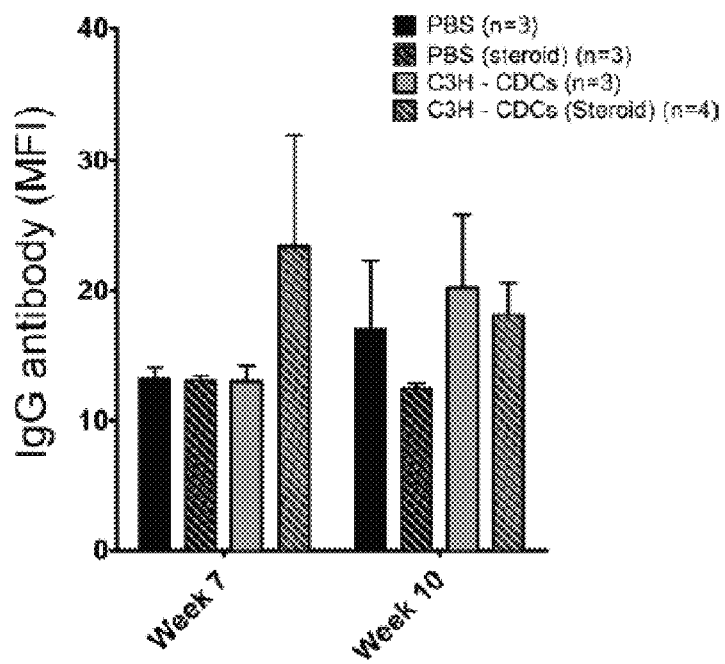
FIG. 85C is a graph indicating the amount of IgG antibodies.
Figure 86:
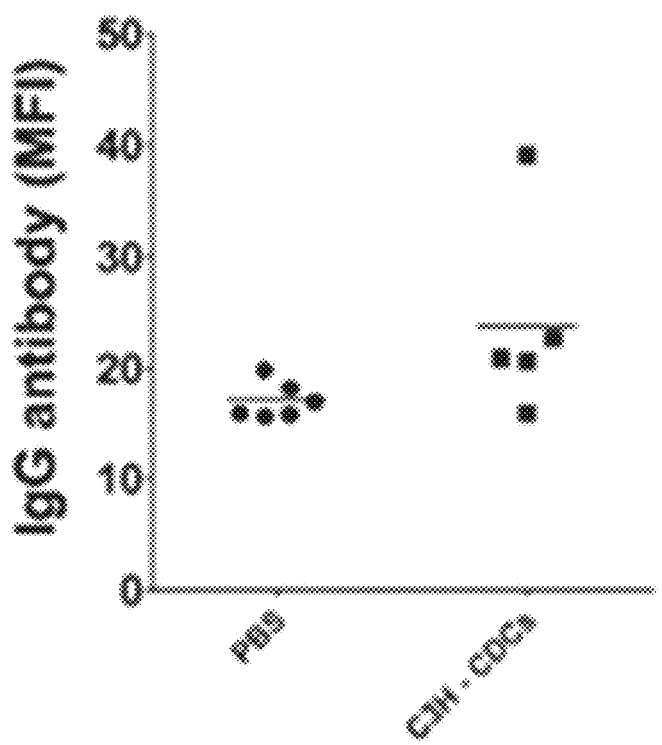
FIG. 86 shows data related to evaluation of antibody production in response to administration of CDCs (as compared to PBS).

To further assess the interaction of an immune response with multiple CDC administrations, another experiment was included in which CDCs were administered with or without a corticosteroid to suppress the immune system and inflammation. 8-10-month-old mdx mice were given PBS vehicle (n=6), PBS vehicle +steroid (n=7), CDCs (n=7), or CDCs+ steroid (n=8). The CDCs were administered at a dose of 150,000 CDCs per mouse per administration. Steroid (prednisone, 1 mg/kg/day) was given for 5 days during each week of CDC and/or PBS administration. The steroid, CDCs, and/or vehicle were administered twice, once at week 0, and the second time at week 6. Each administration included a systemic intravenous injection into the jugular vein. Steroid administration did not impact the CDCs efficacy, and a similar improvement in exercise capability was observed with or without steroids, as shown in FIG. 85A. Allo-antibodies against CDCs in blood were measured by flow cytometry. As shown in FIGS. 85B and 85C, CDCs had a low immunogenic profile with and without steroids (see also FIG. 86). These results are in line with a lack of an immune response to systemic CDC administration because if an immune response prevented or decreased the therapeutic benefits of one or more CDC administrations, then the steroid would have been expected to enhance the CDCs' therapeutic benefits by reducing that iirt mune response. Thus, in some embodiments, a lack of an immune response or a weak immune response enables additional CDCs to be administered multiple times, and thereby exert enhanced therapeutic effects, with a minimized or non-existent immune response to the CDCs, as compared to a single administration.

These data demonstrate that repeat dosing of CDCs is effective in producing additional exercise improvement in mdx mice. Although allogeneic CDCs are recognized by the immune system, their low immunogenic profile and immune-regulatory capabilities allow them to be effectively administered multiple times.

Although the foregoing has been described in some detail by way of illustrations and examples for purposes of clarity and understanding, it will be understood by those of skill in the art that modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the embodiments of the invention(s).

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering an antigen-binding protein" include "instructing the administration of an antigen-binding protein." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 90%" includes "90%." In some embodiments, at least 95% homologous includes 96%, 97%, 98%, 99%, and 100% homologous to the reference sequence. In addition, when a sequence is disclosed as "comprising" a nucleotide or amino acid sequence, such a reference shall also include, unless otherwise indicated, that the sequence "comprises", "consists of" or "consists essentially of" the recited sequence.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like.

The indefinite article "a" or "an" does not exclude a plurality. The term "about" as used herein to, for example, define the values and ranges of molecular weights means that the indicated values and/or range limits can vary within ±20%, e.g., within ±10%. The use of "about" before a number includes the number itself. For example, "about 5" provides express support for "5". Numbers provided in ranges include overlapping ranges and integers in between; for example a range of 1-4 and 5-7 includes for example, 1-7, 1-6, 1-5, 2-5, 2-7, 4-7, 1, 2, 3, 4, 5, 6 and 7.

The invention claimed is:

1. A method of improving skeletal muscle isometric force production in a skeletal muscle of a subject with muscular dystrophy in need of treatment for skeletal muscle myopathy, the method comprising administrating to the subject a therapeutically effective amount of cardiosphere-derived cells (CDCs).

2. The method according to claim 1, wherein said therapeutically effective amount of CDCs is sufficient to treat a dystrophic skeletal muscle of the subject.

3. The method according to claim 2, wherein said muscular dystrophy is Duchenne muscular dystrophy (DMD) involving dystrophinopathy of a skeletal muscle.

4. The method according to claim 2, wherein said dystrophic skeletal muscle is a skeletal muscle of the diaphragm, the arm, or the leg.

5. The method according claim 2, wherein said therapeutically effective amount of CDCs is administered to the subject systemically.

6. The method according to claim 5, wherein said systemic administration of a therapeutically effective amount of CDCs is via intravenous injection.

7. The method according to claim 1, wherein said administration of a therapeutically effective amount of CDCs is via two or more administrations.

8. The method according to claim 7, wherein said two or more administrations of CDCs are given at intervals of about three months to deliver a therapeutically effective amount of CDCs at a targeted skeletal muscle.

9. The method according to claim 1, wherein said therapeutically effective amount of CDCs is, or is at least 150×10$^6$ CDCs.

10. The method according to claim 1, wherein said therapeutically effective amount of CDCs is, or is at least 300×10$^6$ CDCs.

11. The method according to claim 1, wherein said therapeutically effective amount of CDCs is, or is at least 450×10$^6$ CDCs.

12. The method according to claim 1, wherein said CDCs are allogeneic human CDCs, and the subject is a human subject.

13. A method of improving skeletal muscle isometric force production in a skeletal muscle of a subject with muscular dystrophy in need of treatment for skeletal muscle myopathy, the method comprising:
administering to the subject a first dose of a composition comprising a therapeutically effective amount of cardiosphere-derived cells (CDCs),
wherein the therapeutically effective amount of the first dose ranges from about 1×10$^7$ to about 1×10$^9$ CDCs;
waiting a first period of time after administration of said first dose,
wherein said first period of time is between about 1 and 6 months;
administering to the subject a second dose of a composition comprising a therapeutically effective amount of cardiosphere-derived cells (CDCs),
wherein the therapeutically effective amount of the second dose ranges from about 1×10$^7$ to about 1×10$^9$ CDCs;
waiting a second period of time after administration of said second dose,
wherein said second period of time is between about 1 and 6 months;
administering to the subject at least one additional dose of a composition comprising a therapeutically effective amount of cardiosphere-derived cells (CDCs),
wherein the therapeutically effective amount of the at least one additional dose ranges from about 1×10$^7$ to about 1×10$^9$ CDCs;
waiting at least one additional period of time after administration of said at least one additional dose,
wherein said at least one additional period of time is between about 1 and 6 months;
wherein said administrations result in an improvement in exercise capacity or muscle function,
wherein said CDCs are allogeneic with respect to said subject,
wherein said administrations do not induce a significant immune response in the subject, and wherein said administrations comprise systemic administration.

14. The method of claim 13, wherein said systemic administration is via intravenous injection.

15. The method of claim 13, wherein said administrations alter expression of one or more markers of T cell activation or proliferation.

16. The method of claim 13, wherein said skeletal muscular dystrophy is Duchenne muscular dystrophy (DMD) involving dystrophinopathy of a skeletal muscle.

17. The method according to claim 13, wherein said dystrophic skeletal muscle is a skeletal muscle of the diaphragm, the arm, or the leg.

18. A method of improving skeletal muscle isometric force production in a skeletal muscle of a subject with muscular dystrophy in need of treatment for skeletal muscle myopathy, the method comprising:
   administrating to the subject at least two doses of a therapeutically effective amount of cardiosphere-derived cells (CDCs);
   wherein the at least two doses are administered about 1 to 6 months apart from each other; and
   wherein said administrating to the subject at least two doses of a therapeutically effective amount of CDCs does not induce a significant immune response in the subject.

19. The method according to claim 18, wherein said skeletal muscular dystrophy comprises Duchenne muscular dystrophy (DMD) involving dystrophinopathy of a skeletal muscle.

20. The method according to claim 19, wherein said dystrophic skeletal muscle comprises a skeletal muscle of the diaphragm, the arm, or the leg,
   wherein administrating to the subject at least two doses of a therapeutically effective amount of CDCs comprises intramuscular injection at a dystrophic skeletal muscle of the subject, systemic administration, or intravenous injection,
   wherein said systemic administration comprises injection into the right ventricle of the subject's heart, or injection into the left ventricle of the subject's heart,
   wherein the at least two doses are administered about 6 weeks apart from each other, wherein said therapeutically effective amount of CDCs comprises about $1\times10^7$ to about $1\times10^9$ CDCs,
   and wherein said CDCs are allogeneic human CDCs, and the subject is a human.

* * * * *

SEQUENCE LISTING

```
<160> NUMBER OF SEQ ID NOS: 6

<210> SEQ ID NO 1
<211> LENGTH: 68
<212> TYPE: RNA
<213> ORGANISM: Homo sapiens

<400> SEQUENCE: 1
gaggcaaagu ucugagacac uccgacucug aguaugauag aagucagugc acuacagaac    60
uuugucuc                                                            68

<210> SEQ ID NO 2
<211> LENGTH: 22
<212> TYPE: RNA
<213> ORGANISM: Homo sapiens

<400> SEQUENCE: 2
aaaguucuga gacacuccga cu                                             22

<210> SEQ ID NO 3
<211> LENGTH: 22
<212> TYPE: RNA
<213> ORGANISM: Homo sapiens

<400> SEQUENCE: 3
ucagugcacu acagaacuuu gu                                             22

<210> SEQ ID NO 4
<211> LENGTH: 115
<212> TYPE: RNA
<213> ORGANISM: Homo sapiens

<400> SEQUENCE: 4
```

```
uguacacaga ggcugaucga uucucccuga acagccuauu acggaggcac ugcagaucaa        60
gcccgccugg agagguggag uuucaagagu cccuuccugg uucaccgucu ccuuu            115

<210> SEQ ID NO 5
<211> LENGTH: 113
<212> TYPE: RNA
<213> ORGANISM: Homo sapiens

<400> SEQUENCE: 5
uguacacggu ggaguuucaa gagucccuuc cugguucacc gucuccuuua gaggcugauc        60
gauucucccu gaacagccua uuacggaggc acugcagauc aagcccgccu gga             113

<210> SEQ ID NO 6
<211> LENGTH: 115
<212> TYPE: RNA
<213> ORGANISM: Homo sapiens

<400> SEQUENCE: 6
uccccacaga ggcugaucga uucucccuga acagccuccu ccggaggcac ugcagaucaa        60
gcccgccugg agagguggag uuucaagagu cccuuccugg uucaccgucu ccuuu            115
```